(12) United States Patent
Kim et al.

(10) Patent No.: US 11,515,481 B2
(45) Date of Patent: Nov. 29, 2022

(54) COMPOSITION FOR FORMING ORGANIC FILM, DISPLAY DEVICE USING THE COMPOSITION, AND METHOD OF MANUFACTURING THE DISPLAY DEVICE

(71) Applicant: Samsung Display Co., Ltd., Yongin-si (KR)

(72) Inventors: Se Hun Kim, Yongin-si (KR); Chang Woong Chu, Hwaseong-si (KR); Duk Ki Kim, Suwon-si (KR); Dong Woo Shin, Seoul (KR); Jae Kook Ha, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 555 days.

(21) Appl. No.: 15/863,768

(22) Filed: Jan. 5, 2018

(65) Prior Publication Data
US 2019/0019958 A1    Jan. 17, 2019

(30) Foreign Application Priority Data

Jul. 12, 2017 (KR) .......................... 10-2017-0088354

(51) Int. Cl.
*H01L 51/00*    (2006.01)
*G09G 3/3208*   (2016.01)
(Continued)

(52) U.S. Cl.
CPC ....... *H01L 51/0067* (2013.01); *G09G 3/3208* (2013.01); *H01L 51/004* (2013.01); *H01L 51/0015* (2013.01); *H01L 51/0035* (2013.01); *H01L 51/0036* (2013.01); *H01L 51/0068* (2013.01); *H01L 51/0085* (2013.01);
(Continued)

(58) Field of Classification Search
CPC . H01L 27/32; H01L 27/3241; H01L 27/3244; H01L 27/3246; H01L 27/14641; H01L 27/14645; H01L 27/14647
See application file for complete search history.

(56) References Cited

U.S. PATENT DOCUMENTS 6,720,573 B2    4/2004    Son et al.
6,867,243 B2    3/2005    O'Neill et al.
(Continued)

FOREIGN PATENT DOCUMENTS

JP    2004-199935 A    7/2005
JP    4849191 B2       1/2012
(Continued)

OTHER PUBLICATIONS

Yang, X.; Muller, D.C.; Meerholz, K., 2006, Highly efficient Polymeric Electrophsphorescent Diodes, Adv. Mater., 18, 948-954 (Year: 2006).*

(Continued)

*Primary Examiner* — Jay Yang
(74) *Attorney, Agent, or Firm* — Lewis Roca Rothgerber Christie LLP

(57) ABSTRACT

A composition for forming organic film, a display device utilizing the composition, and a method of manufacturing the display device are provided. The composition for forming an organic film includes a solvent; and a compound of Formula 1:

$$Ar-(R)_k \quad \text{Formula 1}$$

20 Claims, 8 Drawing Sheets

(51) Int. Cl.
    *C07D 251/12* (2006.01)
    *C07D 239/24* (2006.01)
    *C07D 209/82* (2006.01)
    *H01L 51/50* (2006.01)

(52) U.S. Cl.
    CPC ......... *C07D 209/82* (2013.01); *C07D 239/24* (2013.01); *C07D 251/12* (2013.01); *H01L 51/5012* (2013.01); *H01L 51/5056* (2013.01); *H01L 51/5088* (2013.01)

(56) References Cited

U.S. PATENT DOCUMENTS

| | | | |
|---|---|---|---|
| 7,166,239 B2 | 1/2007 | O'Neill et al. | |
| 7,538,341 B2 | 5/2009 | Son et al. | |
| 7,901,766 B2 | 3/2011 | Muller et al. | |
| 8,558,013 B2 | 10/2013 | Koch | |
| 8,878,164 B2 | 11/2014 | Gather et al. | |
| 9,029,537 B2 | 5/2015 | Koch | |
| 9,644,070 B2 | 5/2017 | Eckes et al. | |
| 9,745,420 B2 | 8/2017 | Heil et al. | |
| 9,815,940 B2 | 11/2017 | Eckes et al. | |
| 2002/0180369 A1* | 12/2002 | Koyama | H01L 51/5259 315/169.1 |
| 2004/0054152 A1* | 3/2004 | Meerholz | C08G 65/22 534/15 |
| 2004/0169175 A1* | 9/2004 | Son | H01L 51/0072 257/40 |
| 2005/0264715 A1* | 12/2005 | Kahen | G02F 1/133617 349/61 |
| 2007/0272917 A1* | 11/2007 | Cupertino | H01L 51/0035 257/40 |
| 2008/0191617 A1* | 8/2008 | Chae | H01L 51/005 313/504 |
| 2010/0289014 A1* | 11/2010 | Ito | C09K 11/06 257/40 |
| 2015/0090988 A1* | 4/2015 | Oooka | H01L 27/3265 257/40 |
| 2015/0108408 A1* | 4/2015 | Eckes | C08G 61/12 252/500 |
| 2017/0293224 A1* | 10/2017 | Kamemoto | G03F 7/0233 |
| 2018/0019290 A1* | 1/2018 | Arai | H05B 33/22 |

FOREIGN PATENT DOCUMENTS

| | | |
|---|---|---|
| JP | 6032262 B2 | 11/2016 |
| KR | 10-2001-0062711 A | 7/2001 |
| KR | 10-2008-0061673 A | 7/2008 |
| KR | 10-2015-0008119 A | 1/2015 |

OTHER PUBLICATIONS

Schelter, J.; Mielke, G.F.; Kohnen, A.; Wies, J.; Kober, S.; Nuyken, O.; Meerholz, K., 2010, Novel Non-Conjugated Main-Chain Hole-Transporting Polymers for Organic Electronics Application, Macromol. Rapid Commun., 31, 1560-1567 (Year: 2010).*

Jungermann, S.; Riegel, N.; Muller, D.; Meerholz, K.; Nuyken, O., 2006, Novel Photo-Cross-Linkable Hole-Transporting Polymers: Synthesis, Characterization, and Application in Organic Light Emitting Diodes, Macromolecules, 26, 8911-8919 (Year: 2006).*

Zheng, S., and Shi, J., 2001, Novel Blue-Light-Emitting Polymers Containing Dinaphthylanthracene Moiety, Chem. Mater., 13, 4405-4407 (Year: 2001).*

* cited by examiner

COMPOSITION FOR FORMING ORGANIC FILM, DISPLAY DEVICE USING THE COMPOSITION, AND METHOD OF MANUFACTURING THE DISPLAY DEVICE

CROSS-REFERENCE TO RELATED APPLICATION

This application claims priority to and the benefit of Korean Patent Application No. 10-2017-0088354, filed in the Korean Intellectual Property Office on Jul. 12, 2017, the disclosure of which is incorporated herein by reference in its entirety.

BACKGROUND

1. Field

The present disclosure relates to a composition for forming an organic film, a display device utilizing the composition, and a method of manufacturing the display device.

2. Description of the Related Art

Display devices have increasingly become more important in accordance with developments in multimedia technology. Accordingly, various kinds of display devices such as a liquid crystal display (LCD) device, an organic light-emitting display device, etc., have been utilized.

The organic light-emitting display device, which is a self-emissive display device, includes an organic light-emitting element. The organic light-emitting display device has many desired features such as wide viewing angles, excellent contrast, high response speed, superior luminance and driving voltage characteristics, and polychromaticity.

The organic light-emitting element has a structure in which organic films including a hole transfer layer and an emission layer are interposed between an anode electrode injecting holes and a cathode electrode injecting electrons. In response to a voltage applied between the anode electrode and the cathode electrode, holes and electrons recombine in the emission layer, thereby generating excitons. In response to the excitons relaxing from the excited state to the ground, state, light may be emitted.

SUMMARY

The organic films may be formed between the anode electrode and the cathode electrode by a fluid dispensing process such as inkjet printing. The fluid dispensing process can fabricate an organic film at only a particular location by discharging a composition for forming an organic film only to the particular location and drying and baking the composition.

However, the discharging of a composition for forming an organic film only to a desired location is not only very difficult, but may also cause an alignment defect due to a process error, which is a major cause of deterioration of the display quality of a display device. These problems may become more apparent as the resolution of the display device gradually increases. Accordingly, there is a limit in the resolution that can be achieved utilizing the fluid dispensing process.

An aspect according to exemplary embodiments of the present disclosure is directed toward a composition for forming an organic film utilizing a new method.

An aspect according to exemplary embodiments of the present disclosure is also directed toward a display device in which an organic film is formed utilizing a new method.

An aspect according to exemplary embodiments of the present disclosure is also directed toward a method of manufacturing a display device utilizing the composition for forming an organic film.

However, aspects of exemplary embodiments of the present disclosure are not restricted to those set forth herein. The above and other aspects of exemplary embodiments of the present disclosure will become more apparent to one of ordinary skill in the art to which the present disclosure pertains by referencing the detailed description of the present disclosure given below.

According to an exemplary embodiment of the present disclosure, a composition for forming an organic film includes: a solvent; and a compound of Formula 1:

$$Ar\text{-}(\text{-}R)_k \qquad \text{Formula 1}$$

In Formula 1, Ar is

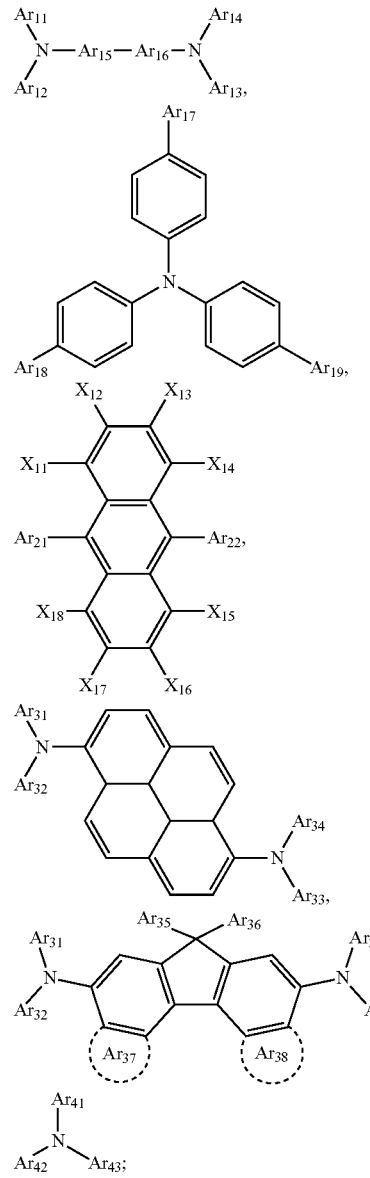

Ar$_{12}$, Ar$_{13}$, and Ar$_{14}$ are each independently a substituted or unsubstituted C$_{6-60}$ aryl, arylene, heteroaryl, or heteroarylene group (e.g., a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group); Ar$_{15}$ and Ar$_{16}$ are each independently a substituted or unsubstituted C$_{6-12}$ arylene or heteroarylene group (e.g., a substituted or unsubstituted C$_{6-12}$ arylene group or a substituted or unsubstituted C$_{1-12}$ heteroarylene group); two or more of Ar$_{11}$, Ar$_{12}$, and Ar$_{15}$ may form a ring together, two or more of Ar$_{13}$, Ar$_{14}$, and Ar$_{16}$ may form a ring together; Ar$_{17}$, Ar$_{18}$, and Ar$_{19}$ are each independently a substituted or unsubstituted C$_{6-60}$ aryl, arylene, heteroaryl, or heteroarylene group (e.g., a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group); Ar$_{21}$ and Ar$_{22}$ are each independently a substituted or unsubstituted C$_{6-60}$ arylene or heteroarylene group (e.g., a substituted or unsubstituted C$_{6-60}$ arylene group or a substituted or unsubstituted C$_{1-60}$ heteroarylene group); X$_{11}$, X$_{12}$, X$_{13}$, X$_{14}$, X$_{15}$, X$_{16}$, X$_{17}$, and X$_{18}$ are each independently a hydrogen atom, a deuterium atom, a fluorine atom, a substituted or unsubstituted C$_{1-10}$ alkyl group, a substituted or unsubstituted C$_{3-10}$ cycloalkyl group, a substituted or unsubstituted C$_{1-20}$ alkoxy group, a substituted or unsubstituted C$_{3-30}$ alkylsilyl group, a substituted or an unsubstituted C$_{6-30}$ aryl group, a substituted or unsubstituted C$_{6-20}$ aryloxy group, a substituted or unsubstituted C$_{8-30}$ arylsilyl group, or a substituted or unsubstituted C$_{5-30}$ heteroaryl group; Ar$_{31}$, Ar$_{32}$, Ar$_{33}$, and Ar$_{34}$ are each independently a substituted or unsubstituted C$_{6-60}$ aryl, arylene, heteroaryl, or heteroarylene group (e.g., a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group); Ar$_{35}$ and Ar$_{36}$ are each independently a hydrogen atom or a substituted or unsubstituted C$_{6-10}$ aryl or heteroaryl group (e.g., a substituted or unsubstituted C$_{8-10}$ aryl group or a substituted or unsubstituted C$_{1-10}$ heteroaryl group), Ar$_{35}$ and Ar$_{36}$ may form a ring together; Ar$_{37}$ and Ar$_{38}$ are each independently a substituted or unsubstituted C$_{6-20}$ fused ring; Ar$_{41}$ is a substituted or unsubstituted C$_{6-60}$ aryl or heteroaryl group (e.g., a substituted or unsubstituted C$_{6-60}$ aryl group or a substituted or unsubstituted C$_{3-60}$ heteroaryl group); Ar$_{42}$ and Ar$_{43}$ are each independently a substituted or unsubstituted C$_{6-60}$ arylene or heteroarylene group (e.g., a substituted or unsubstituted C$_{6-60}$ arylene group or a substituted or unsubstituted C$_{1-60}$ heteroarylene group), Ar$_{42}$ and Ar$_{43}$ may form a ring together; at least one of Ar$_{11}$, Ar$_{12}$, Ar$_{13}$, and Ar$_{14}$, at least one of Ar$_{17}$, Ar$_{18}$, and Ar$_{19}$, at least one of Ar$_{21}$, and Ar$_{22}$, at least one of Ar$_{31}$, Ar$_{32}$, Ar$_{33}$, and Ar$_{34}$, and at least one of Ar$_{42}$, and Ar$_{43}$ are divalent arylene or divalent heteroarylene groups, R is bonded thereto; R is

R$_0$ is a substituted or unsubstituted C$_{1-30}$ alkyl group, a substituted or unsubstituted C$_{3-30}$ cycloalkyl group, a substituted or unsubstituted C$_{3-30}$ heterocycloalkyl group, a substituted or unsubstituted C$_{2-30}$ alkenyl group, a substituted or unsubstituted C$_{2-30}$ alkynyl group, a substituted or unsubstituted C$_{6-30}$ aryl group, or a substituted or unsubstituted C$_{3-30}$ heteroaryl group; j is an integer between 2 and 9, and k is an integer between 2 and 4.

In an exemplary embodiment, the compound of Formula 1 may be a compound of Formula A-1, and the compound for forming the organic film may further include a compound of Formula E-1 or E-2:

Formula A-1

Ar$_1$—(R$_1$)$_{k1}$

Formula E--1

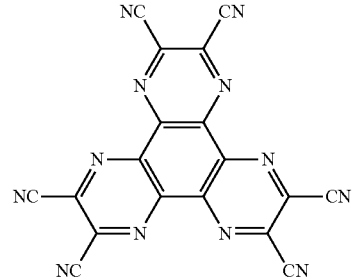

Formula E-2

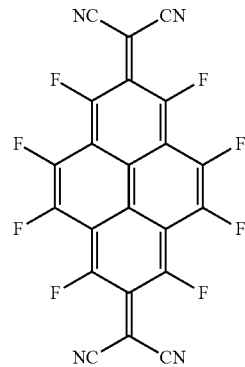

In Formula A-1, Ar$_1$ is

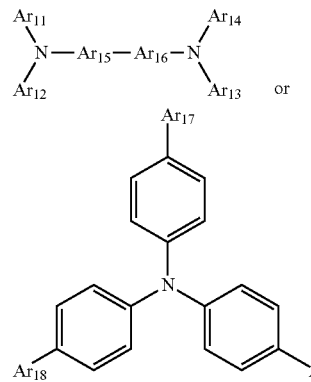

Ar$_{12}$, Ar$_{13}$, and Ar$_{14}$ are each independently a substituted or unsubstituted C$_{6-60}$ arylene, heteroaryl, or heteroarylene group; Ar$_{15}$ and Ar$_{16}$ are each independently a substituted or unsubstituted C$_{6-12}$ arylene or heteroarylene group; two or more of Ar$_{11}$, Ar$_{12}$, and Ar$_{15}$ may form a ring together, two or more of $Ar_{13}$, $Ar_{14}$, and $Ar_{16}$ may form a ring together; $Ar_{17}$, $Ar_{18}$, and $Ar_{19}$ are each independently a substituted or unsubstituted $C_{6-60}$ aryl, arylene, heteroaryl, or heteroarylene group; at least one of $Ar_{11}$, $Ar_{12}$, $Ar_{13}$, and $Ar_{14}$, and at least one of $Ar_{17}$, $Ar_{18}$, and $Ar_{19}$ are divalent arylene or divalent heteroarylene groups, $R_1$ is bonded thereto; $R_1$ is

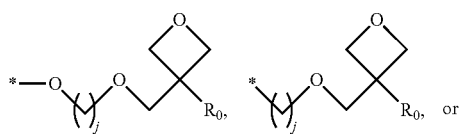

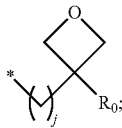

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k1 is an integer between 2 and 4.

In an exemplary embodiment, the compound of Formula A-1 may be a compound of any one of Formulae A-2 through A-8:

Formula A-2

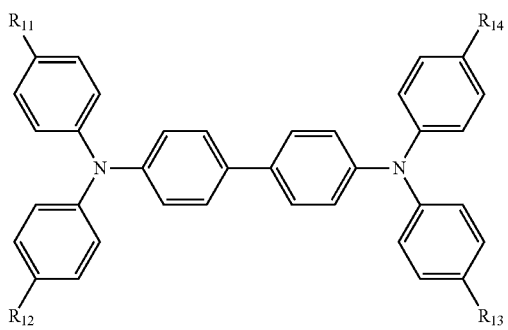

Formula A-3

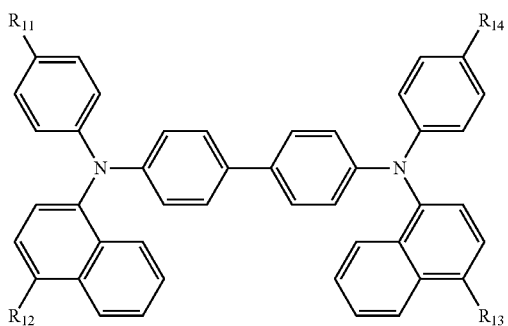

Formula A-4

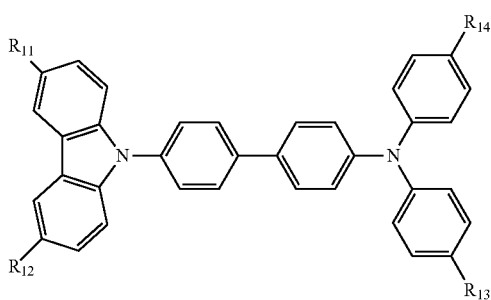

Formula A-5

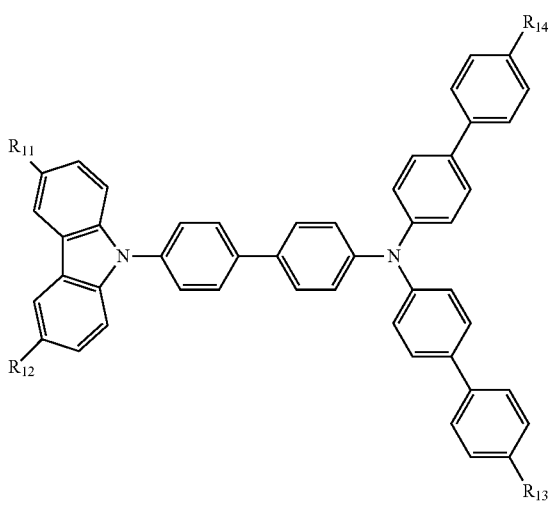

Formula A-6
Formula A-7
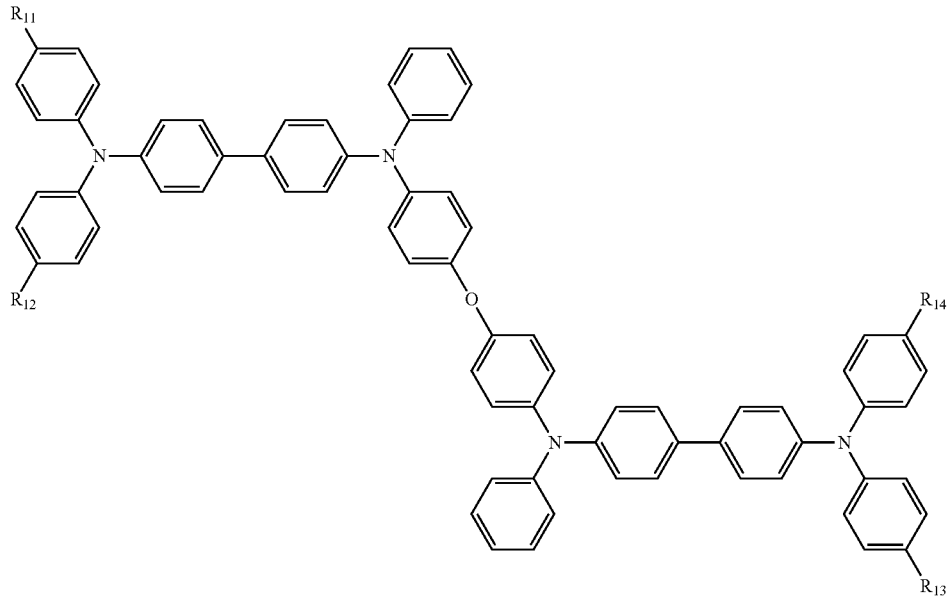
Formula A-8
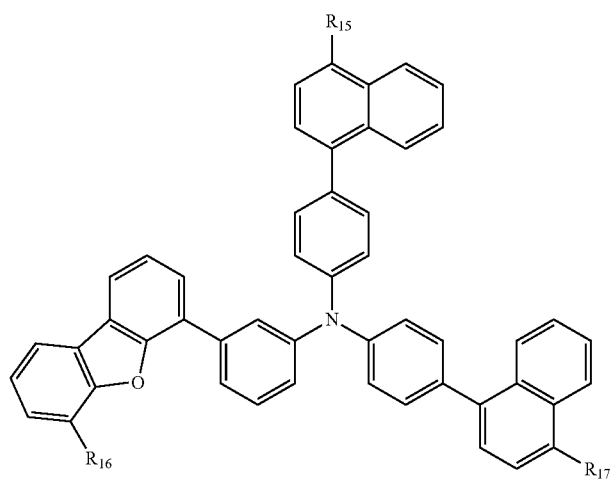

In Formulae A-2 through Formula A-8, $R_{11}$, $R_{12}$, $R_{13}$, $R_{14}$, $R_{15}$, $R_{16}$, and $R_{17}$ are each independently a hydrogen atom,

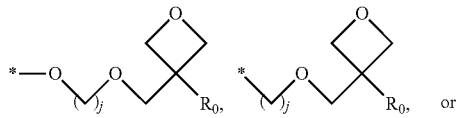

two or more of $R_{11}$, $R_{12}$, $R_{13}$, and $R_{14}$ are each independently

two or more of $R_{15}$, $R_{16}$, and $R_{17}$ are each independently

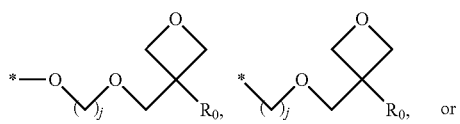

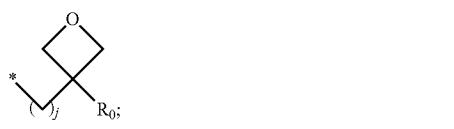

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9.

In an exemplary embodiment, the compound of Formula 1 may be a compound of Formula B-1, and the composition for forming the organic film may include the compound of Formula B-1:

   Formula B-1

In Formula B-1, $Ar_2$ is

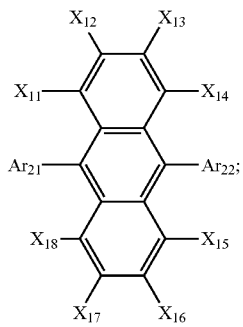

$Ar_{21}$ and $Ar_{22}$ are each independently a substituted or unsubstituted $C_{6-60}$ arylene or heteroarylene group; $R_2$ and $R_2'$ are bonded to $Ar_{21}$ and $Ar_{22}$, respectively; $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group; $R_2$ and $R_2'$ are each independently

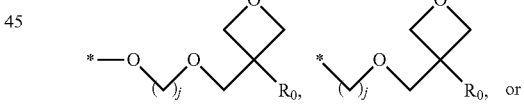

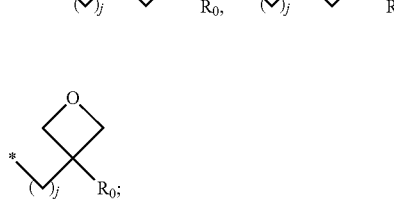

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9.

In an exemplary embodiment, the compound of Formula B-1 may be a compound of any one of Formulae B-2 through B-23:

Formula B-2
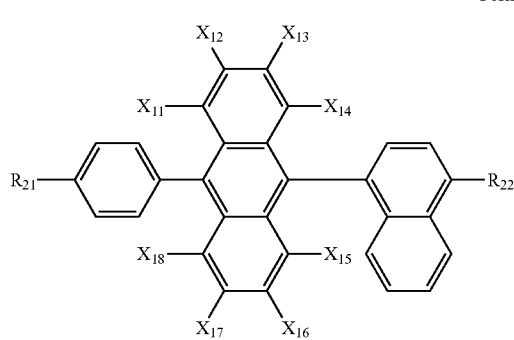
Formula B-3
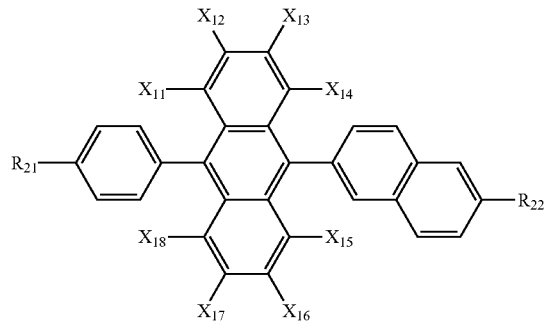
Formula B-4
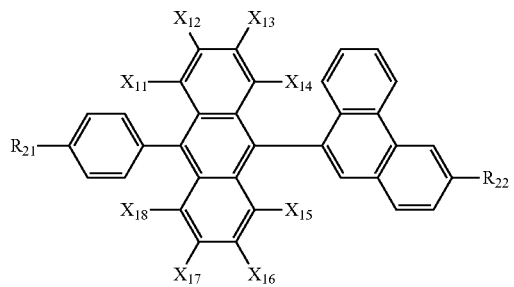
Formula B-5
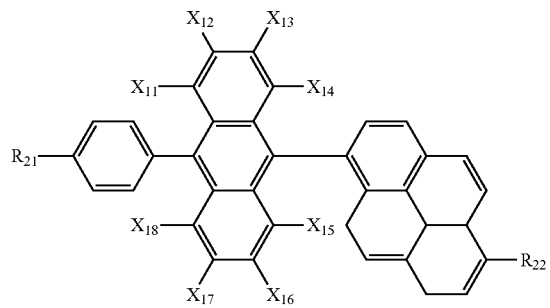
Formula B-6
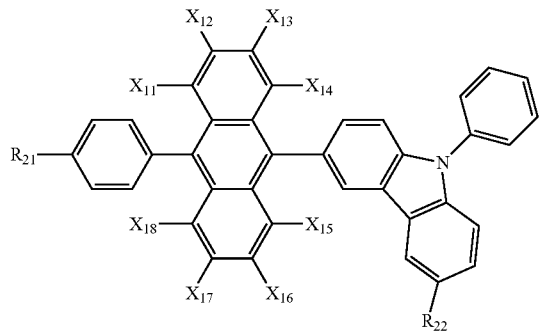
Formula B-7
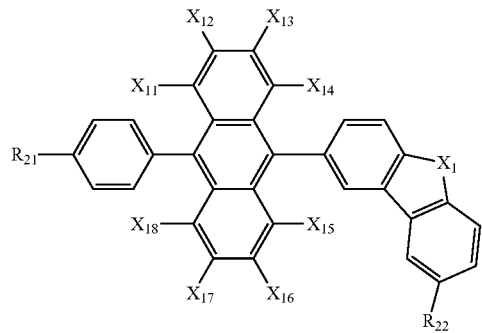
Formula B-8
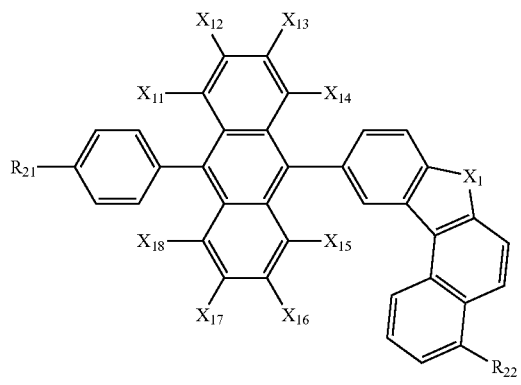
Formula B-9
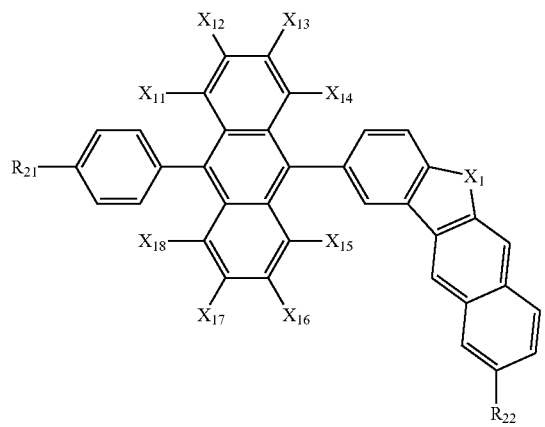

-continued
Formula B-10
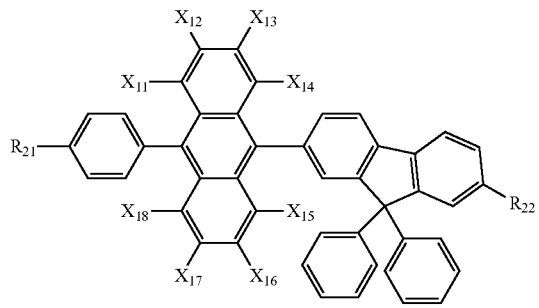
Formula B-11
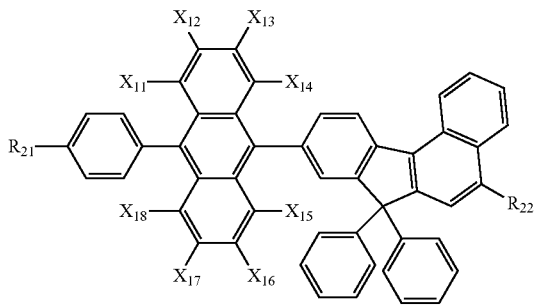
Formula B-12
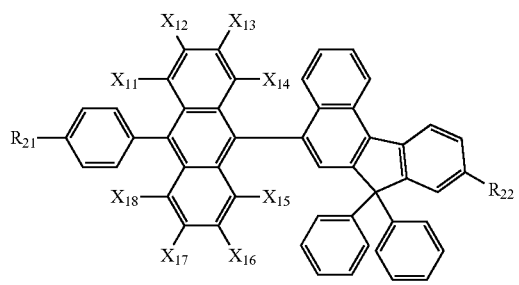
Formula B-13
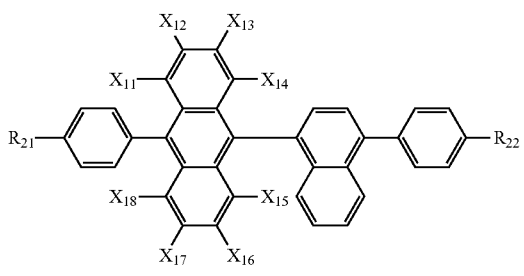
Formula B-14
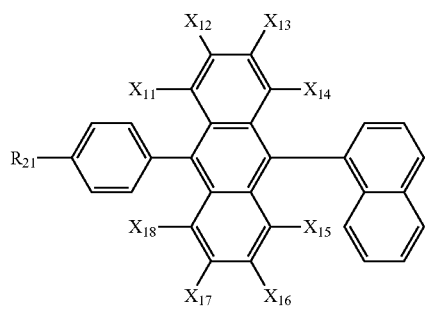
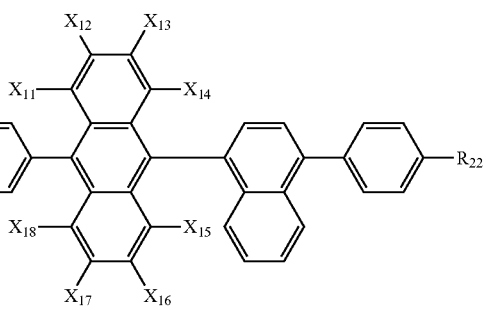
Formula B-15
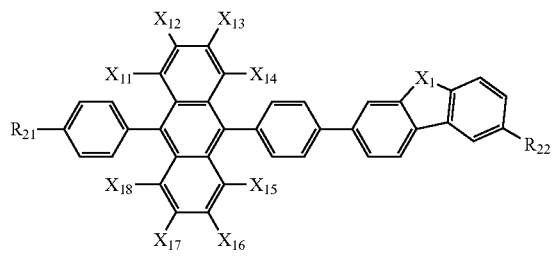
Formula B-16
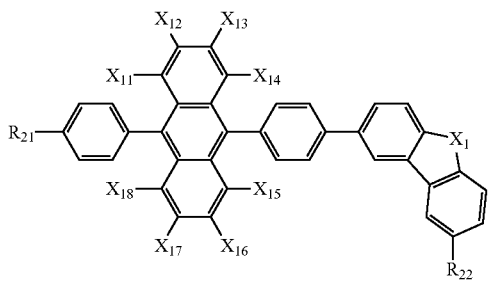
Formula B-17
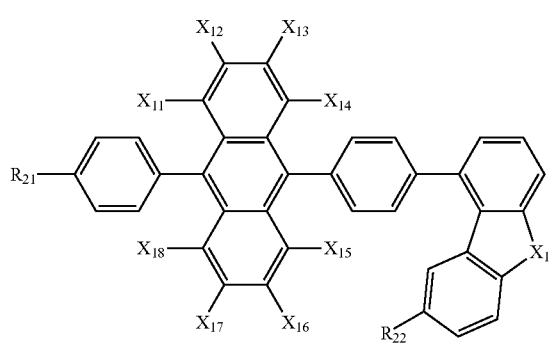

-continued

Formula B-18

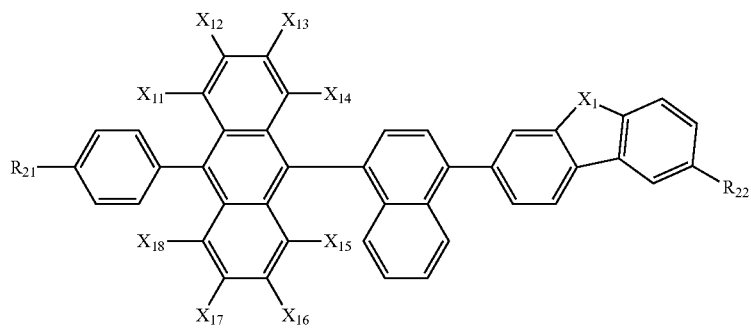

Formula B-19

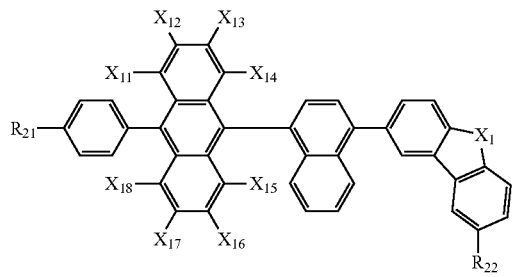

Formula B-20

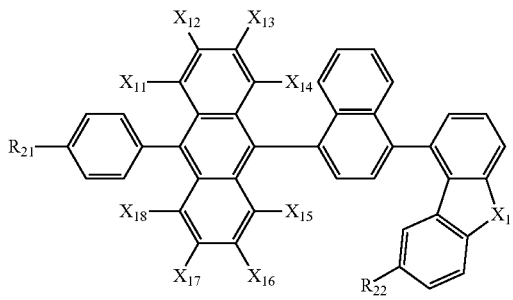

Formula B-21

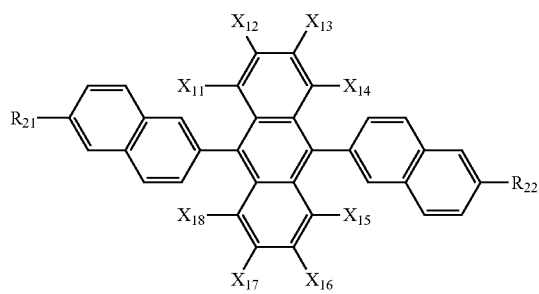

Formula B-22

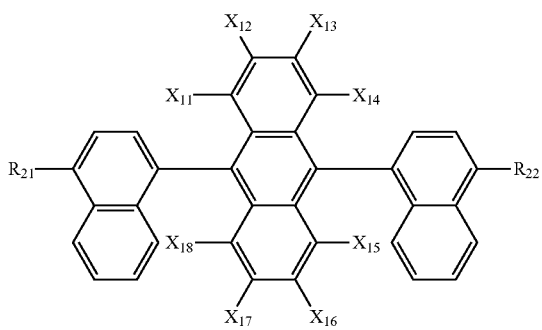

Formula B-23

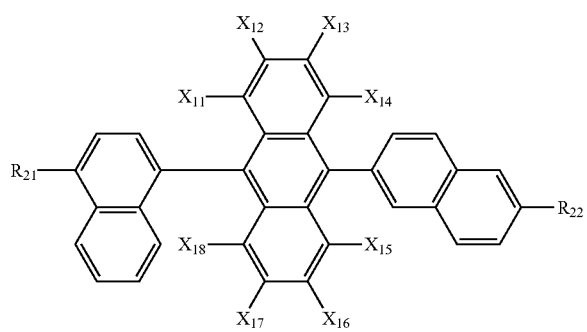

In Formulae B-2 through B-23, $R_{21}$ and $R_{22}$ are each independently

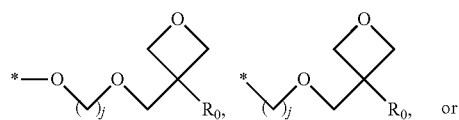

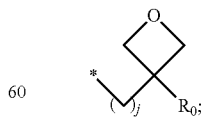

$R_0$ is a substituted or unsubstituted $C_{1-30}$ alkyl group, a substituted or unsubstituted $C_{3-30}$ cycloalkyl group, a substituted or unsubstituted heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9; and $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group. In Formulae B-7 through B-9 and B-15 through B-20, $X_1$ is an oxygen atom or a sulfur atom, and in Formula B-14, $X_{21}$, $X_{22}$, $X_{23}$, $X_{24}$, $X_{25}$, $X_{26}$, $X_{27}$, and $X_{28}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group.

In an exemplary embodiment, the composition may further include: a compound of Formula C-1:

Formula C-1

In Formula C-1, $Ar_3$ is

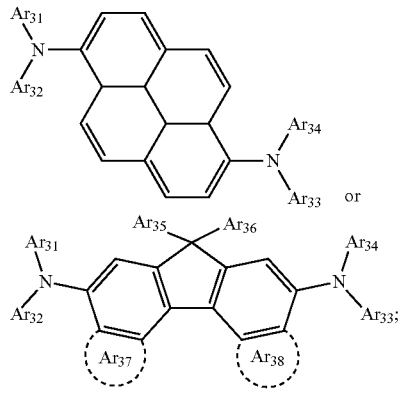

$Ar_{31}$, $Ar_{32}$, $Ar_{33}$, and $Ar_{34}$ are each independently a substituted or unsubstituted $C_{6-60}$ aryl, arylene, heteroaryl, or heteroarylene group; at least one of $Ar_{31}$, $Ar_{32}$, $Ar_{33}$, and $Ar_{34}$ is a divalent arylene or divalent heteroarylene group, $R_3$ is bonded thereto; $Ar_{35}$ and $Ar_{36}$ are each independently a hydrogen atom or a substituted or unsubstituted $C_{6-10}$ aryl or heteroaryl group; $Ar_{35}$ and $Ar_{36}$ may form a ring together; $Ar_{37}$ and $Ar_{38}$ are each independently a substituted or unsubstituted $C_{6-20}$ fused ring; $R_3$ is

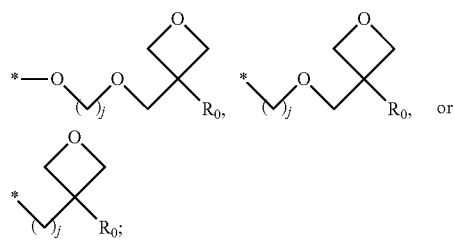

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k3 is an integer between 2 and 4.

In an exemplary embodiment, the compound of Formula C-1 may be a compound of any one of Formulae C-2 through C-16:

Formula C-2

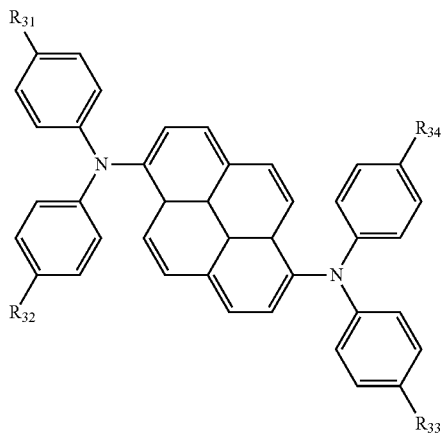

Formula C-3

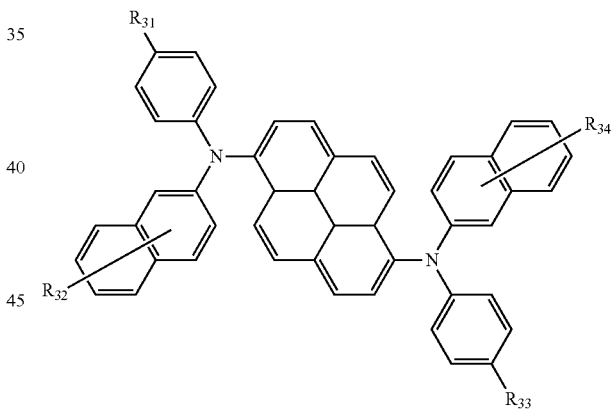

Formula C-4

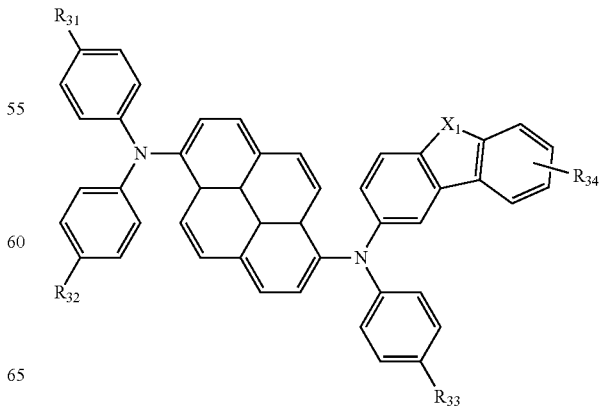

Formula C-5
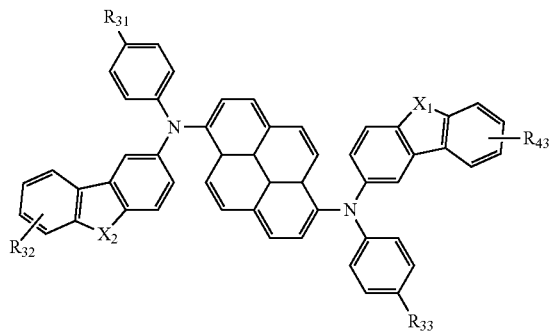
Formula C-6
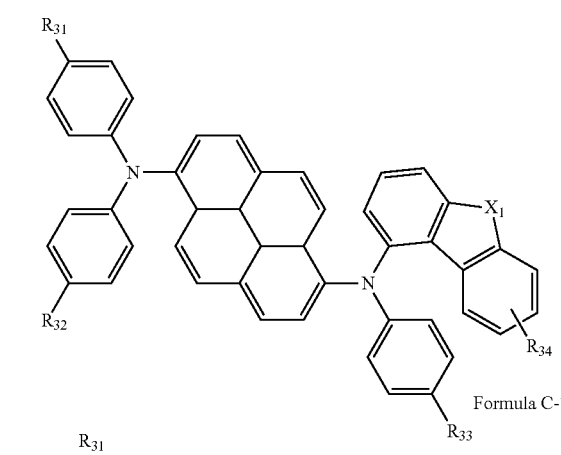
Formula C-7
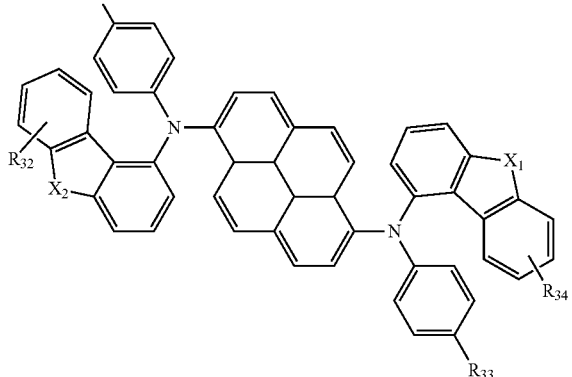
Formula C-8
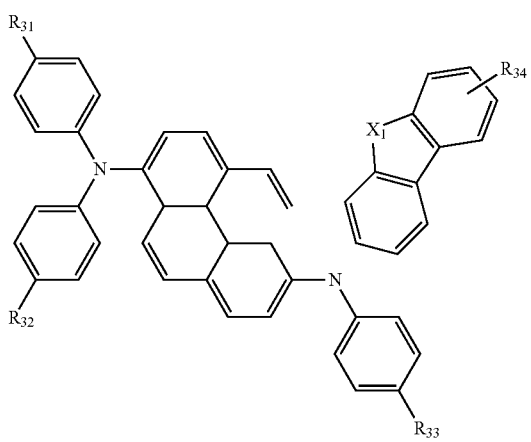
Formula C-9
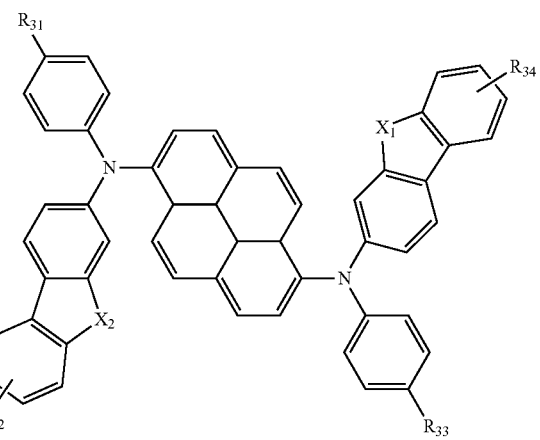
Formula C-10
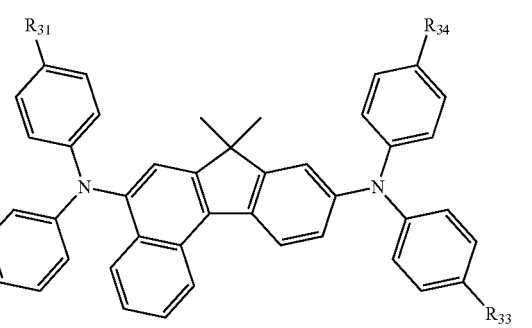
Formula C-11
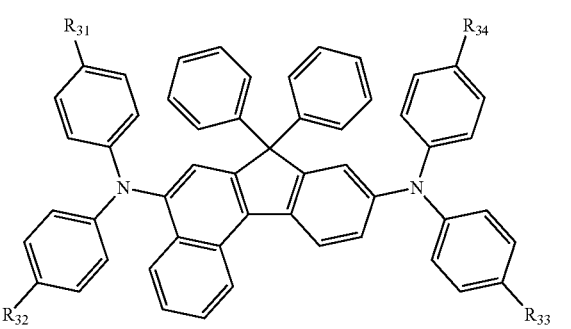
Formula C-12
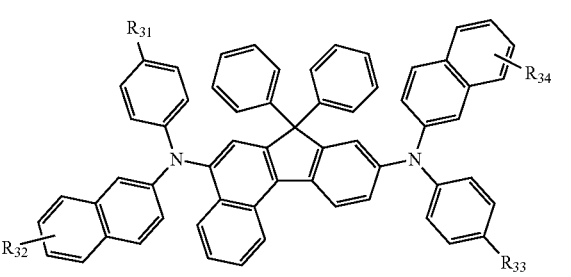

-continued

Formula C-13
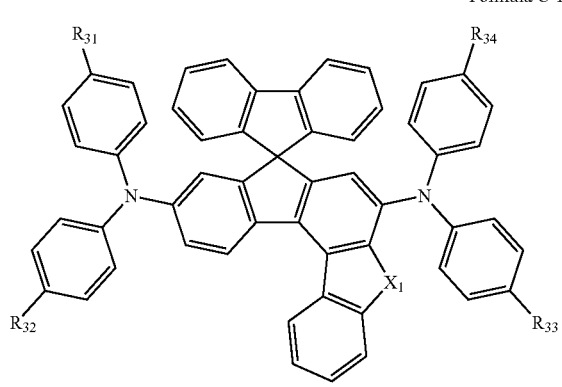

Formula C-14
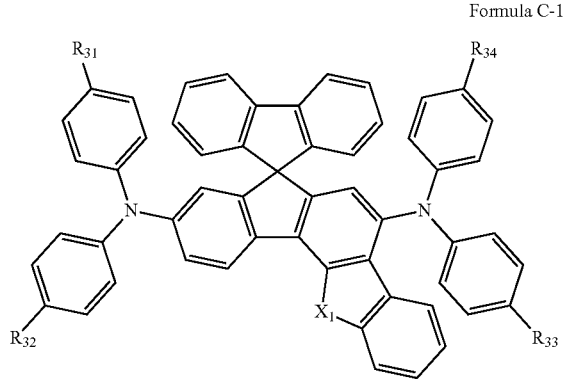

Formula C-15
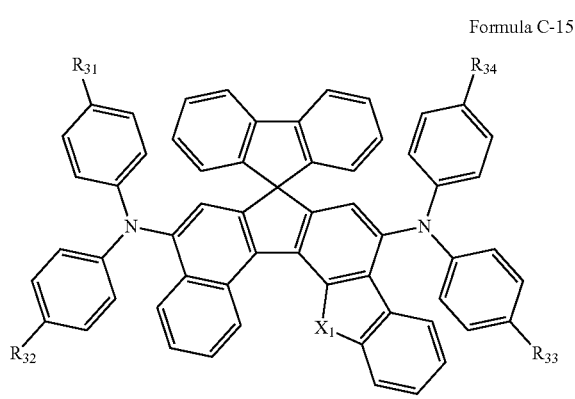

Formula C-16
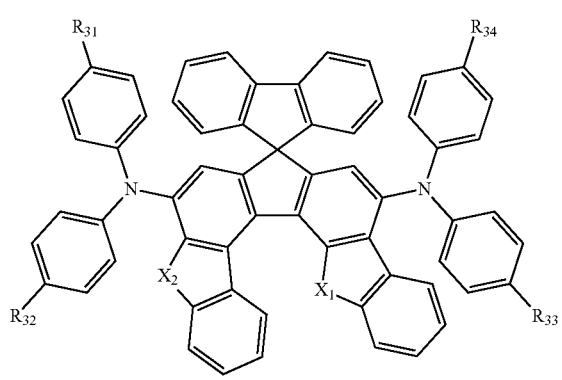

In Formulae C-2 through Formula C-16, $R_{31}$, $R_{32}$, $R_{33}$, and $R_{34}$ are each independently a hydrogen atom,

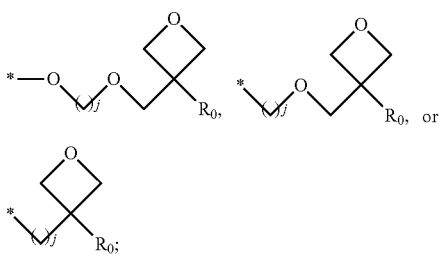

two or more of $R_{31}$, $R_{32}$, $R_{33}$, and $R_{34}$ are each independently

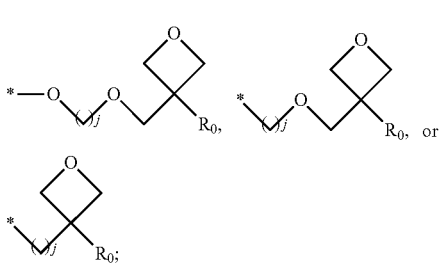

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9; and in Formulae C-4 through C-9 and C-13 through C-16, $X_1$ and $X_2$ are each independently an oxygen atom or a sulfur atom.

In an exemplary embodiment, the compound of Formula 1 may be a compound of Formula D-1, and the composition for forming an organic film may further include a compound of Formula E-3 or E-4:

Formula D-1

Formula E-3
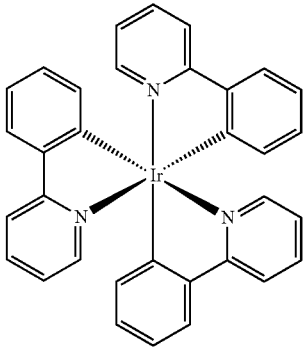

Formula E-4

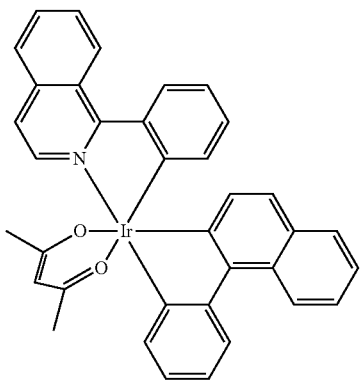

In Formula D-1, Ar$_4$

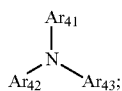

Ar$_{41}$ is a substituted or unsubstituted C$_{6-60}$ aryl or heteroaryl group; Ar$_{42}$ and Ar$_{43}$ are each independently a substituted or unsubstituted C$_{6-60}$ arylene or heteroarylene group; Ar$_{42}$ and Ar$_{43}$ may form a ring together; R$_4$ and R$_4$' are bonded to Ar$_{42}$ and Ar$_{43}$, respectively; R$_4$ and R$_4$' are each independently

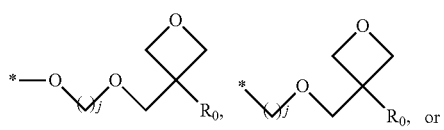

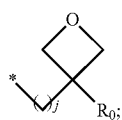

R$_0$ is a substituted or unsubstituted C$_{1-30}$ alkyl group, a substituted or unsubstituted C$_{3-30}$ cycloalkyl group, a substituted or unsubstituted C$_{3-30}$ heterocycloalkyl group, a substituted or unsubstituted C$_{2-30}$ alkenyl group, a substituted or unsubstituted C$_{2-30}$ alkynyl group, a substituted or unsubstituted C$_{6-30}$ aryl group, or a substituted or unsubstituted C$_{3-30}$ heteroaryl group; and j is an integer between 2 and 9.

In an exemplary embodiment, the compound of Formula D-1 may be a compound of any one of Formulae D-2 through D-16:

Formula D-2

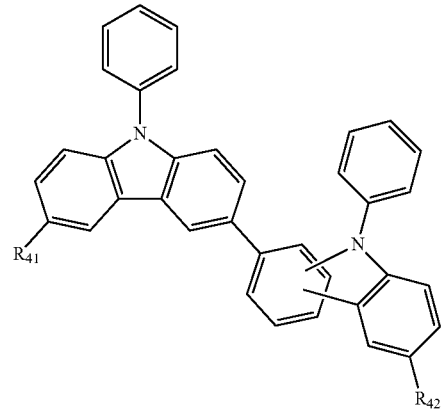

Formula D-3

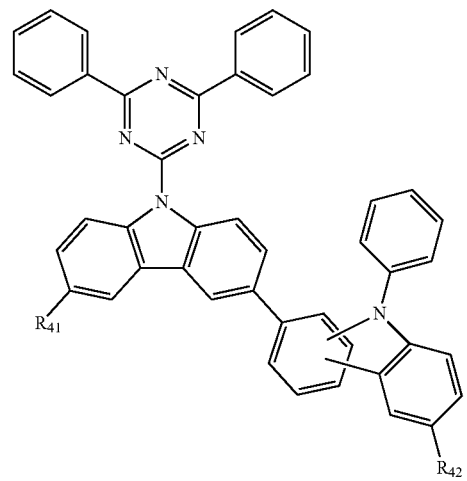

Formula D-4

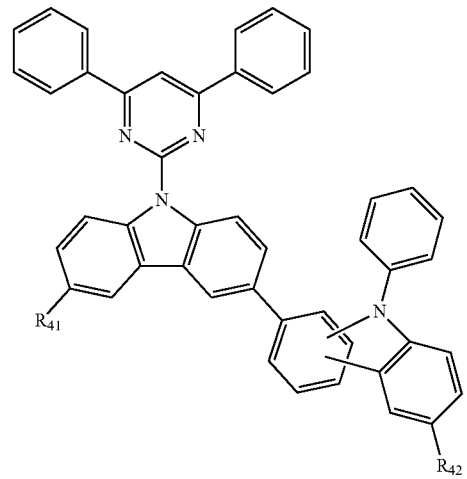

Formula D-5
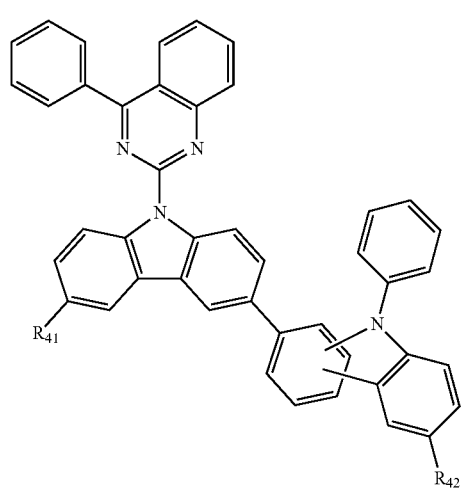
Formula D-6
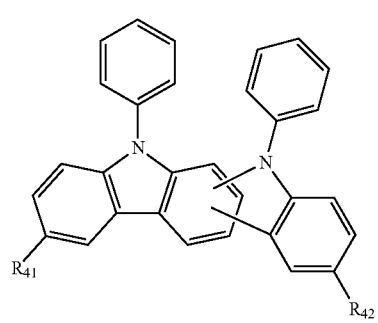
Formula D-7
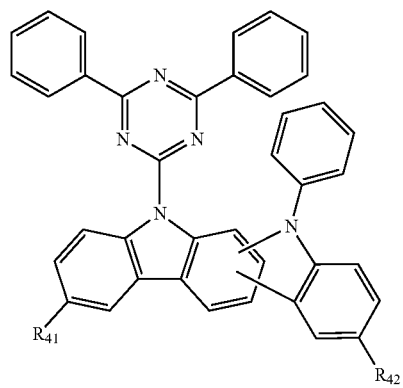
Formula D-8
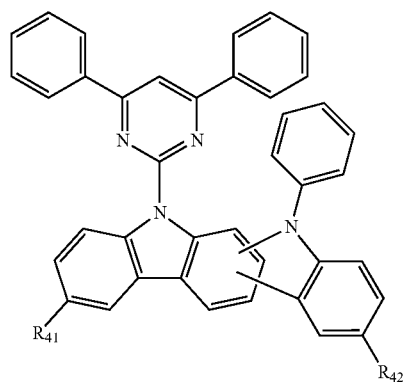
Formula D-9
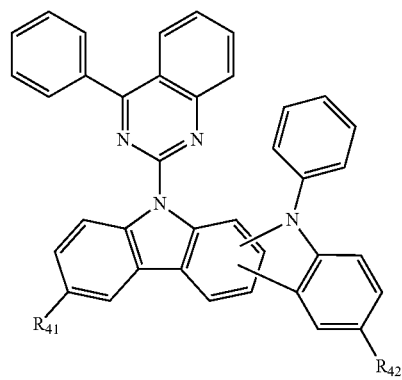
Formula D-10
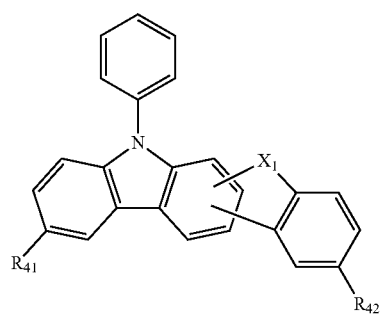
Formula D-11
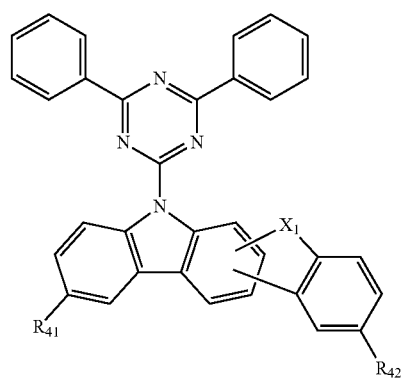
Formula D-12
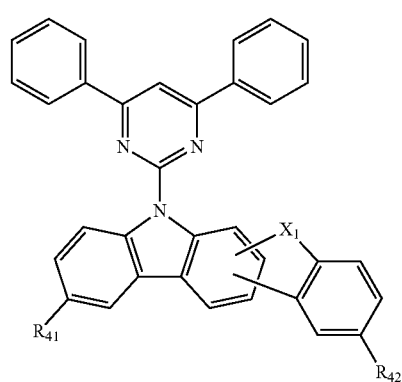

Formula D-13

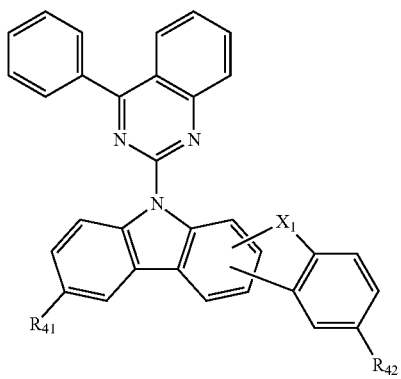

Formula D-14

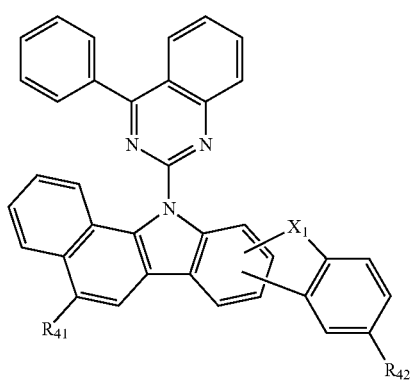

Formula D-15

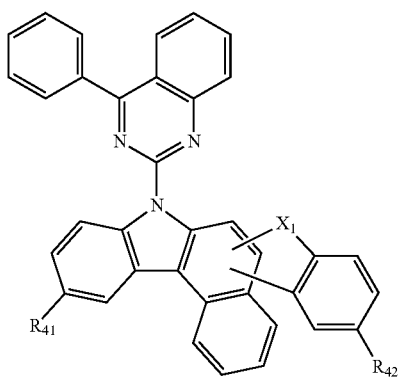

Formula D-16

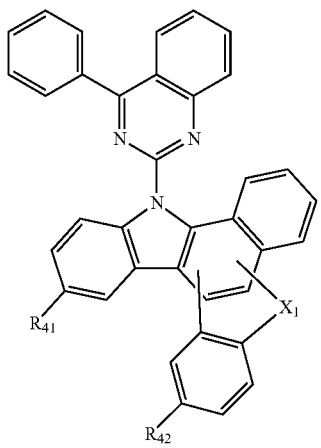

In Formulae D-2 through D-16, $R_{41}$ and $R_{42}$ are each independently

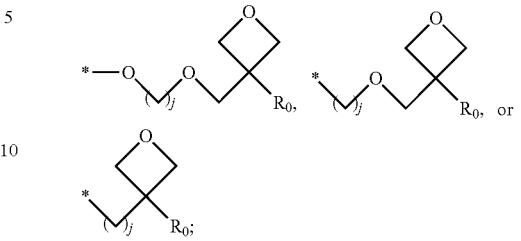

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9; and in Formulae D-10 through D-16, $X_1$ is an oxygen atom or a sulfur atom.

In an exemplary embodiment, the composition may further include: an initiator compound, wherein the solvent may be methyl benzoate, the compound of Formula 1 may be contained in an amount of about 1.0 weight percent (wt %) to 5.0 wt % with respect to the total weight of the composition for forming an organic film, the initiator compound may be contained in an amount of about 0.5 wt % to 4.0 wt % with respect to the total weight of the composition for forming an organic film, and the initiator compound may include a compound of any one of Formulae F-1, F-2, and F-3:

Formula F-1

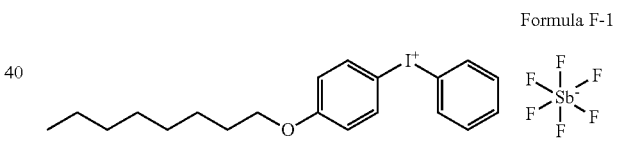

Formula F-2

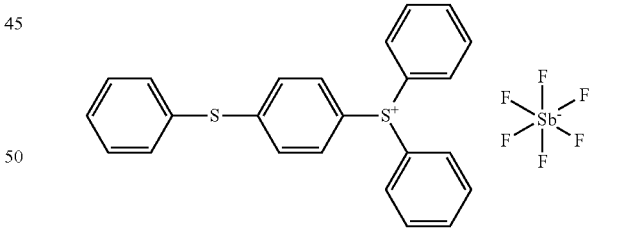

Formula F-3

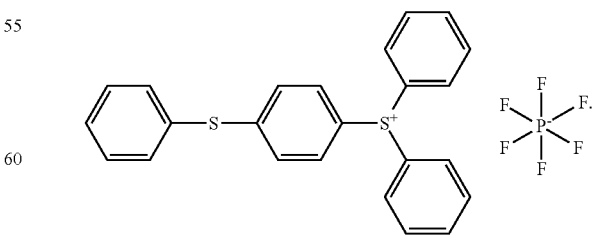

According to an exemplary embodiment of the present disclosure, a display device includes: a base; a plurality of anode electrodes on the base; a cathode electrode on the anode electrodes; and organic layers between the anode electrodes and the cathode electrode, wherein the organic layers include a polymer of a compound of Formula 1:

Ar$+$(R)$_k$    Formula 1

In Formula 1, Ar is

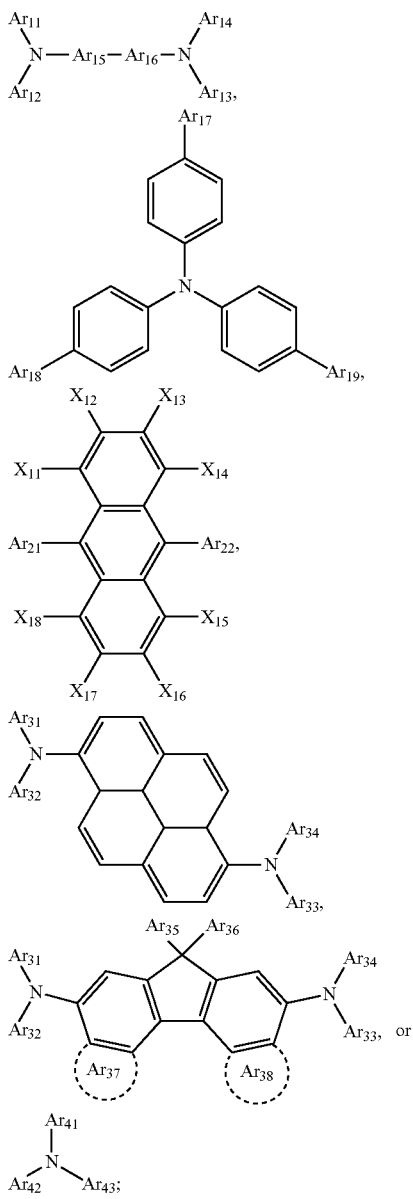

$Ar_{11}$, $Ar_{12}$, $Ar_{13}$, and $Ar_{14}$ are each independently a substituted or unsubstituted $C_{6-60}$ aryl, arylene, heteroaryl, or heteroarylene group; $Ar_{15}$ and $Ar_{16}$ are each independently a substituted or unsubstituted $C_{6-12}$ arylene or heteroarylene group; two or more of $Ar_{11}$, $Ar_{12}$, and $Ar_{15}$ may form a ring together, two or more of $Ar_{13}$, $Ar_{14}$, and $Ar_{16}$ may form a ring together; $Ar_{17}$, $Ar_{18}$, and $Ar_{19}$ are each independently a substituted or unsubstituted $C_{6-60}$ aryl, arylene, heteroaryl, or heteroarylene group; $Ar_{21}$ and $Ar_{22}$ are each independently a substituted or unsubstituted $C_{6-60}$ arylene or heteroarylene group; $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group; $Ar_{31}$, $Ar_{32}$, $Ar_{33}$, and $Ar_{34}$ are each independently a substituted or unsubstituted $C_{6-60}$ aryl, arylene, heteroaryl, or heteroarylene group; $Ar_{35}$ and $Ar_{36}$ are each independently a hydrogen atom or a substituted or unsubstituted $C_{6-10}$ aryl or heteroaryl group; $Ar_{35}$ and $Ar_{36}$ may form a ring together; $Ar_{37}$ and $Ar_{38}$ are each independently a substituted or unsubstituted $C_{6-20}$ fused ring; $Ar_{41}$ is a substituted or unsubstituted $C_{6-60}$ aryl or heteroaryl group; $Ar_{42}$ and $Ar_{43}$ are each independently a substituted or unsubstituted $C_{6-60}$ arylene or heteroarylene group; $Ar_{42}$ and $Ar_{43}$ may form a ring together; at least one of $Ar_{11}$, $Ar_{12}$, $Ar_{13}$, and $Ar_{14}$, at least one of $Ar_{17}$, $Ar_{18}$, and $Ar_{19}$, at least one of $Ar_{21}$, and $Ar_{22}$, at least one of $Ar_{31}$, $Ar_{32}$, $Ar_{33}$, and $Ar_{34}$, and at least one of $Ar_{42}$, and $Ar_{43}$ are divalent arylene or divalent heteroarylene groups, R is bonded thereto; R is

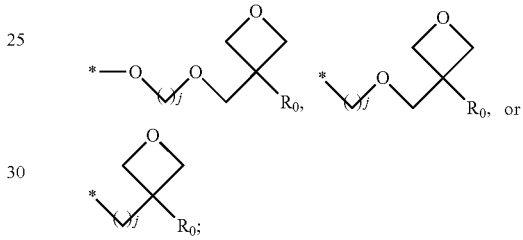

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k is an integer between 2 and 4.

In an exemplary embodiment, the organic layers may include a first organic layer between the anode electrodes and the cathode electrode, and the first organic layer may include a polymer of a compound of Formula A-1:

$Ar_1$$+$($R_1$)$_{k1}$    Formula A-1

In Formula A-1, $Ar_1$ is

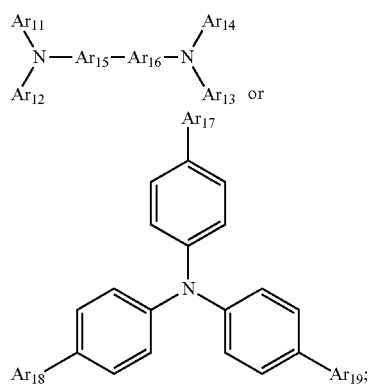

$Ar_{11}$, $Ar_{12}$, $Ar_{13}$, and $Ar_{14}$ are each independently a substituted or unsubstituted $C_{6-60}$ aryl, arylene, heteroaryl, or heteroarylene group; $Ar_{15}$ and $Ar_{16}$ are each independently a substituted or unsubstituted $C_{6-12}$ arylene or heteroarylene group; two or more of $Ar_{11}$, $Ar_{12}$, and $Ar_{15}$ may form a ring together; two or more of $Ar_{13}$, $Ar_{14}$, and $Ar_{16}$ may form a ring together; $Ar_{17}$, $Ar_{18}$, and $Ar_{19}$ are each independently a substituted or unsubstituted $C_{6-60}$ aryl, arylene, heteroaryl, or heteroarylene group; at least one of $Ar_{11}$, $Ar_{12}$, $Ar_{13}$, and $Ar_{14}$, and at least one of $Ar_{17}$, $Ar_{18}$, and $Ar_{19}$ are divalent arylene or divalent heteroarylene groups, $R_1$ is bonded thereto; $R_1$ is

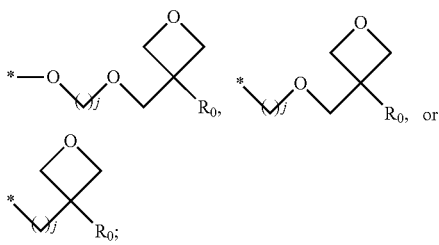

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k1 is an integer between 2 and 4.

In an exemplary embodiment, the display device may include a first pixel configured to display a first color, a second pixel adjacent to the first pixel and configured to display a second color having a longer peak wavelength than the first color, and a third pixel adjacent to the first pixel and configured to display the first color, and the first organic layer in the first pixel may be physically spaced apart from the first organic layer in the third pixel.

In an exemplary embodiment, the organic layers may further include a second organic layer in the first pixel between the first organic layer and the cathode electrode, and the second organic layer may include a polymer of compounds of Formulae B-2 and C-1:

$R_2$—$Ar_2$—$R_2'$      Formula B-1

$Ar_3$—$(R_3)_{k3}$      Formula C-1

In Formula B-1, $Ar_2$ is

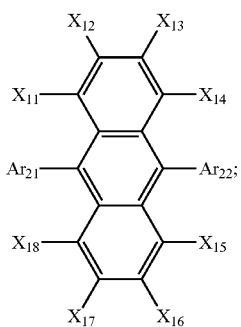

$Ar_{21}$ and $Ar_{22}$ are each independently a substituted or unsubstituted $C_{6-60}$ arylene or heteroarylene group; $R_2$ and $R_2'$ are bonded to $Ar_{21}$ and $Ar_{22}$, respectively; $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group; $R_2$ and $R_2'$ are each independently

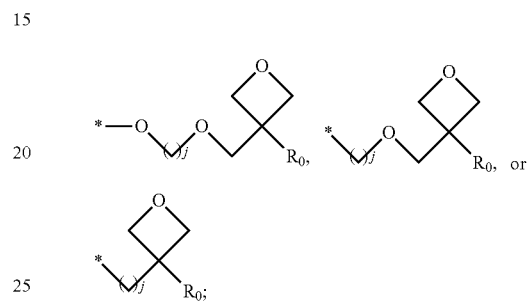

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9. In Formula C-1, $Ar_3$ is

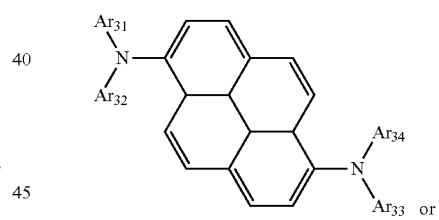

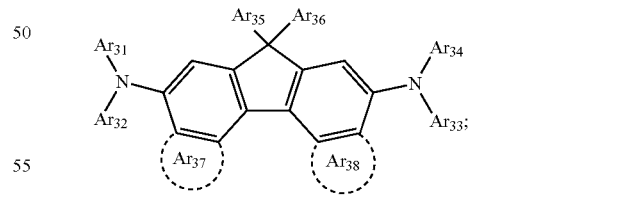

$Ar_{31}$, $Ar_{32}$, $Ar_{33}$, and $Ar_{34}$ are each independently a substituted or unsubstituted $C_{6-60}$ aryl, arylene, heteroaryl, or heteroarylene group; at one of $Ar_{31}$, $Ar_{32}$, $Ar_{33}$, and $Ar_{34}$ is a divalent arylene or divalent heteroarylene group, $R_3$ is bonded thereto; $Ar_{35}$ and $Ar_{36}$ are each independently a hydrogen atom or a substituted or unsubstituted $C_{6-10}$ aryl or heteroaryl group; $Ar_{35}$ and $Ar_{36}$ may form a ring together; $Ar_{37}$ and $Ar_{38}$ are each independently a substituted or unsubstituted $C_{6-20}$ fused ring; $R_3$ is

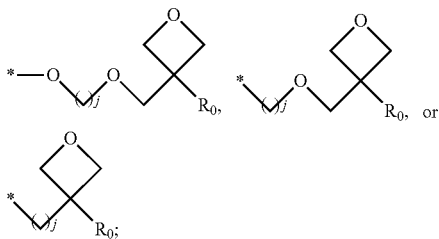

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k3 is an integer between 2 and 4.

In an exemplary embodiment, the organic layers may further include a third organic layer in the second pixel between the first organic layer and the cathode electrode, and the third organic layer may include a polymer of a compound of Formula D-1:

$$R_4\text{—}Ar_4\text{—}R_4' \qquad \text{Formula D-1}$$

In Formula D-1, $Ar_4$ is

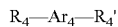
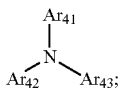

$Ar_{41}$ is a substituted or unsubstituted $C_{6-60}$ aryl or heteroaryl group; $Ar_{42}$ and $Ar_{43}$ are each independently a substituted or unsubstituted $C_{6-60}$ arylene or heteroarylene group; $Ar_{42}$ and $Ar_{43}$ form a ring together; $R_4$ and $R_4'$ are bonded to $Ar_{42}$ and $Ar_{43}$, respectively; $R_4$ and $R_4'$ are each independently

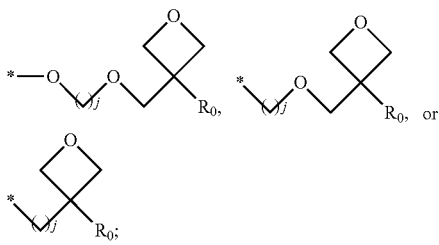

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9.

In an exemplary embodiment, the organic layers may further include a fourth organic layer between the second organic layer and the cathode electrode and between the third organic layer and the cathode electrode, and the fourth organic layer in the first pixel may be physically formed in one integral body with the fourth organic layer in the third pixel.

According to an exemplary embodiment of the present disclosure, a method of manufacturing a display device includes: forming a coating layer by coating a base with a composition for forming an organic film; and forming organic layer patterns by patterning the coating layer, wherein the composition for forming an organic film includes a compound of Formula 1:

$$Ar\text{—}(R)_k \qquad \text{Formula 1}$$

In Formula 1, Ar is

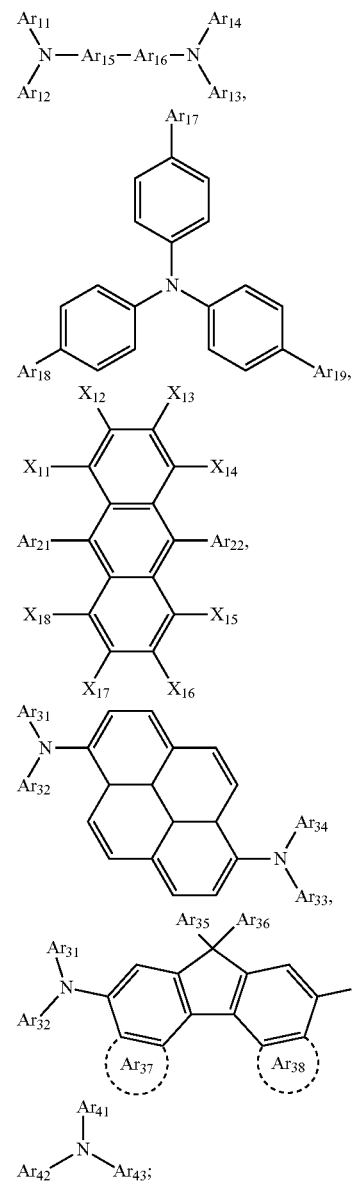

$Ar_{11}$, $Ar_{12}$, $Ar_{13}$, and $Ar_{14}$ are each independently a substituted or unsubstituted $C_{6-60}$ aryl, arylene, heteroaryl, or heteroarylene group; $Ar_{15}$ and $Ar_{16}$ are each independently a substituted or unsubstituted $C_{6-12}$ arylene or heteroarylene group; two or more of $Ar_{11}$, $Ar_{12}$, and $Ar_{15}$ may form a ring together; two or more of $Ar_{13}$, $Ar_{14}$, and $Ar_{16}$ may form a ring together; $Ar_{17}$, $Ar_{18}$, and $Ar_{19}$ are each independently a substituted or unsubstituted $C_{6-60}$ aryl, arylene, heteroaryl, or heteroarylene group; $Ar_{21}$ and $Ar_{22}$ are each independently a substituted or unsubstituted $C_{6-60}$ arylene or heteroarylene group; $X_{11}, X_{12}, X_{13}, X_{14}, X_{15}, X_{16}, X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group; $Ar_{31}, Ar_{32}, Ar_{33}$, and $Ar_{34}$ are each independently a substituted or unsubstituted $C_{6-60}$ aryl, arylene, heteroaryl, or heteroarylene group; $Ar_{35}$ and $Ar_{36}$ are each independently a hydrogen atom or a substituted or unsubstituted $C_{6-10}$ aryl or heteroaryl group; $Ar_{35}$ and $Ar_{36}$ may form a ring together; $Ar_{37}$ and $Ar_{38}$ are each independently a substituted or unsubstituted $C_{6-20}$ fused ring; $Ar_{41}$ is a substituted or unsubstituted $C_{6-60}$ aryl or heteroaryl group; $Ar_{42}$ and $Ar_{43}$ are each independently a substituted or unsubstituted $C_{6-60}$ arylene or heteroarylene group, $Ar_{42}$ and $Ar_{43}$ form a ring together; at least one of $Ar_{11}, Ar_{12}, Ar_{13}$, and $Ar_{14}$, at least one of $Ar_{17}, Ar_{18}$, and $Ar_{19}$, at least one of $Ar_{21}$, and $Ar_{22}$, at least one of $Ar_{31}, Ar_{32}, Ar_{33}$, and $Ar_{34}$, and at least one of $Ar_{42}$, and $Ar_{43}$ are divalent arylene or divalent heteroarylene groups, R is bonded thereto; R is

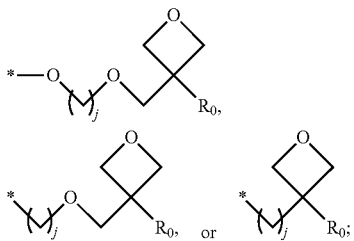

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j is an integer between 2 and 9, and k is an integer between 2 and 4.

In an exemplary embodiment, the forming of the organic layer patterns may include placing a mask having openings over the coating layer, partially exposing and curing the coating layer by applying light, and developing the cured coating layer utilizing a developer.

In an exemplary embodiment, the method may further include, before the forming of the coating layer: forming an electrode layer on the base; and forming a bank having openings to expose the surface of the electrode layer.

In an exemplary embodiment, the method may further include, after the forming of the organic layer patterns: forming a bank having openings to expose the surfaces of the organic layer patterns.

The composition for forming an organic layer according to an exemplary embodiment of the present disclosure includes a photo-polymerizable reacting group and can thus form a patterned organic film through an exposure process. Accordingly, the fabrication of an organic light-emitting element can be relatively simplified, and an organic light-emitting element with high resolution can be realized.

The display device according to an exemplary embodiment of the present disclosure can improve display quality and reliability.

The method of manufacturing a display device according to an exemplary embodiment of the present disclosure can relatively simplify the fabrication of an organic light-emitting element and can realize an organic light-emitting element with high resolution.

Other features and exemplary embodiments may be apparent from the following detailed description, the drawings, and the claims.

BRIEF DESCRIPTION OF THE DRAWINGS

The accompanying drawings, which are included to provide a further understanding of the inventive concepts, and are incorporated in and constitute a part of this specification, illustrate exemplary embodiments of the inventive concepts, and, together with the description, serve to explain principles of the inventive concepts.

DETAILED DESCRIPTION

Figure 1:
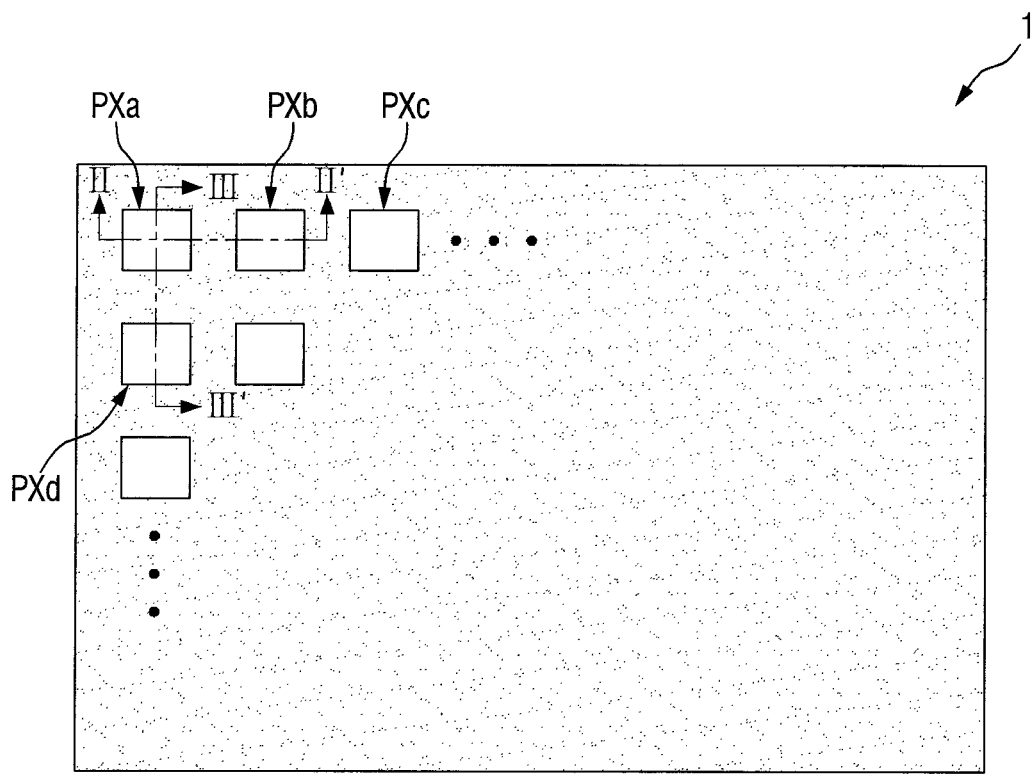
FIG. 1 is a plan view of a display device according to an exemplary embodiment of the present disclosure.

Features of the invention and methods of accomplishing the same may be understood more readily by reference to the following detailed description of preferred embodiments and the accompanying drawings. The invention may, however, be embodied in many different forms and should not be construed as being limited to the embodiments set forth herein. Rather, these embodiments are provided so that this disclosure will be thorough and complete and will fully convey the concept of the invention to those skilled in the art, and the invention will only be defined by the appended claims, and equivalents thereof.

It will be understood that when an element or layer is referred to as being "on," "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Spatially relative terms, such as "below," "lower," "under," "above," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein should be interpreted accordingly.

The terminology used herein is for the purpose of describing particular embodiments only and is not intended to be limiting. As used herein, the singular forms "a," "an" and "the" are intended to include the plural forms as well, including "at least one," unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof. "At least one" is not to be construed as limiting "a" or "an." "Or" means "and/or." As used herein, the term "and/or" includes any and all combinations of one or more of the associated listed items.

In this disclosure, "*" denotes a binding site to which adjacent atoms are covalently bonded, and "$C_{A-B}$" denotes a carbon number of A to B. For example, a $C_{1-5}$ alkyl group refers to an alkyl group having 1 to 5 carbon atoms.

As used herein, the term "alkyl group" denotes a monovalent atomic group obtained by excluding one hydrogen atom from a linear or branched aliphatic saturated hydrocarbon and can be expressed as "*—$C_nH_{2n+1}$ (where n is a natural number)".

As used herein, the term "alkoxy group" denotes a monovalent atomic group having one alkyl group and one oxygen atom bonded thereto and can be expressed as "*—O—$C_nH_{2n+1}$ (where n is a natural number)".

As used herein, unless defined otherwise, the term "alkylene group" denotes a divalent atomic group obtained by excluding two hydrogen atoms from a straight or branched aliphatic saturated hydrocarbon and can be expressed as "*—$C_nH_{2n}$—* (where n is a natural number)".

As used herein, the term "alkenyl group" denotes a monovalent atomic group obtained by excluding one hydrogen atom from an aliphatic unsaturated hydrocarbon having a double bond and can be expressed as "*—$C_nH_{2n-1}$ (where n is a natural number)".

As used herein, the term "alkynyl group" denotes a monovalent atomic group obtained by excluding one hydrogen atom from an aliphatic unsaturated hydrocarbon having a triple bond and can be expressed as "*—$C_nH_{2n-3}$ (where n is a natural number)".

As used herein, the term "alkylsilyl group" denotes a monovalent atomic group having an alkyl group and a silyl group bonded thereto.

As used herein, the term "aryl group" denotes a monovalent atomic group obtained by excluding one hydrogen atom from an aromatic hydrocarbon.

As used herein, the term "heteroaryl group" denotes an aryl group containing at least one atom other than carbon as an atom constituting a ring.

As used herein, the term "arylene group" denotes a divalent atomic group obtained by excluding two hydrogen atoms from an aromatic hydrocarbon.

As used herein, the term "heteroarylene group" denotes an arylene group containing at least one atom other than carbon as an atom constituting a ring.

As used herein, the term "arylsilyl group" denotes a monovalent atomic group having an aryl group and a silyl group bonded thereto.

As used herein, the term "aryloxy group" denotes a monovalent atomic group having an aryl group and an oxygen atom bonded thereto.

As used herein, the term "fused ring" denotes a ring formed by two or more ring groups bonded to share two or more atoms.

Compositions for forming an organic film according to exemplary embodiments of the present disclosure will hereinafter be described.

A composition for forming an organic film according to an exemplary embodiment of the present disclosure includes a compound of Formula 1 (i.e., a compound represented by Formula 1) below and a solvent.

$$Ar\text{—}(R)_k \qquad \text{Formula 1}$$

In Formula 1, Ar, which forms the basic skeleton, is a divalent, trivalent or tetravalent aromatic group. Ar can impart a function to an organic film to be formed. For example, Ar may be expressed as

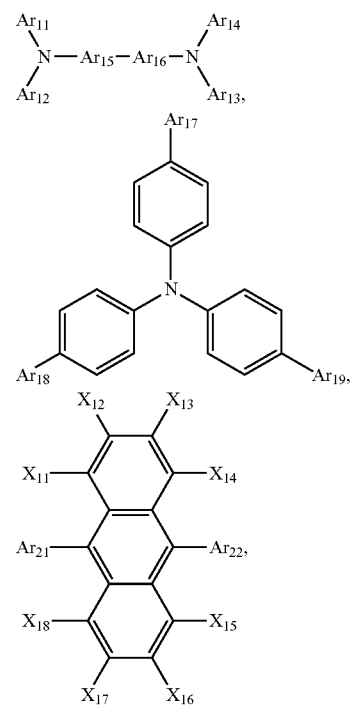

-continued

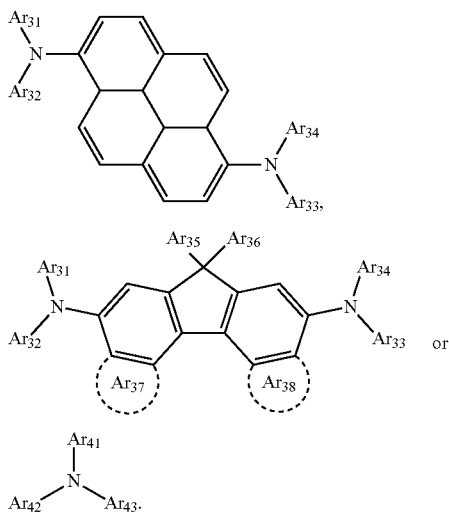

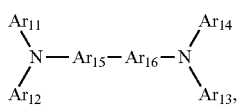

In

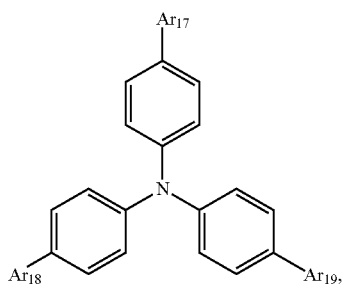

$Ar_{11}$, $Ar_{12}$, $Ar_{13}$, $Ar_{14}$ are each independently a substituted or unsubstituted $C_{6-60}$ aryl, arylene, heteroaryl, or heteroarylene group (e.g., a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group), $Ar_{15}$ and $Ar_m$ are each independently a substituted or unsubstituted $C_{6-12}$ arylene or heteroarylene group (e.g., a substituted or unsubstituted $C_{6-12}$ arylene group or a substituted or unsubstituted $C_{1-12}$ heteroarylene group).

Two or more of $Ar_{11}$, $Ar_{12}$, and $Ar_{15}$ may form a ring together, and two or more of $Ar_{13}$, $Ar_{14}$, and $Ar_{16}$ may form a ring together.

In

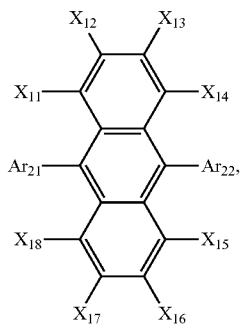

$Ar_{17}$, $Ar_{18}$, and $Ar_{19}$ are each independently a substituted or unsubstituted $C_{6-60}$ aryl, arylene, heteroaryl, or heteroarylene group (e.g., a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group).

In

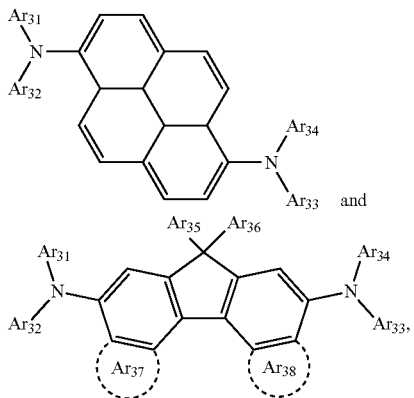

$Ar_{21}$ and $Ar_{22}$ are each independently a substituted or unsubstituted $C_{6-60}$ arylene or heteroarylene group (e.g., a substituted or unsubstituted $C_{6-60}$ arylene group or a substituted or unsubstituted $C_{1-60}$ heteroarylene group), $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group.

In

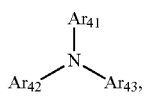

$Ar_{31}$, $Ar_{32}$, $Ar_{33}$, and $Ar_{34}$ are each independently a substituted or unsubstituted $C_{6-60}$ aryl, arylene, heteroaryl, or heteroarylene group (e.g., a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group), $Ar_{35}$ and $Ar_{36}$ are each independently a hydrogen atom or a substituted or unsubstituted $C_{6-10}$ aryl or heteroaryl group (e.g., a substituted or unsubstituted $C_{6-10}$ aryl group or a substituted or unsubstituted $C_{1-10}$ heteroaryl group), $Ar_{35}$ and $Ar_{36}$ may form a ring together, and $Ar_{37}$ and $Ar_{38}$ are each independently a substituted or unsubstituted $C_{6-20}$ fused ring.

In $Ar_{41}$ is a substituted or unsubstituted $C_{6-60}$ aryl or heteroaryl group (e.g., a substituted or unsubstituted $C_{6-60}$ aryl group or a substituted or unsubstituted $C_{1-60}$ heteroaryl group), $Ar_{42}$ and $Ar_{43}$ are each independently a substituted or unsubstituted $C_{6-60}$ arylene or heteroarylene group (e.g., a substituted or unsubstituted $C_{6-60}$ arylene group or a substituted or unsubstituted $C_{3-60}$ heteroarylene group), and $Ar_{42}$ and $Ar_{43}$ may form a ring together.

If $Ar_{11}$, $Ar_{12}$, $Ar_{13}$, $Ar_{14}$, $Ar_{17}$, $Ar_{18}$, $Ar_{19}$, $Ar_{21}$, $Ar_{22}$, $Ar_{31}$, $Ar_{32}$, $Ar_{33}$, $Ar_{34}$, $Ar_{42}$, and $Ar_{43}$ are divalent arylene or heteroarylene groups, R may be bonded thereto. For example, at least one of $Ar_{11}$, $Ar_{12}$, $Ar_{13}$ and $Ar_{14}$, at least one of $Ar_{17}$, $Ar_{18}$ and $Ar_{19}$, at least one of $Ar_{21}$ and $Ar_{22}$, at least one of $Ar_{31}$, $Ar_{32}$, $Ar_{33}$ and $Ar_{34}$, and at least one of $Ar_{42}$ and $Ar_{43}$ are divalent arylene or divalent heteroarylene groups, and R may be bonded thereto.

R may be a photo-polymerizable reacting group. For example, the substituent R is

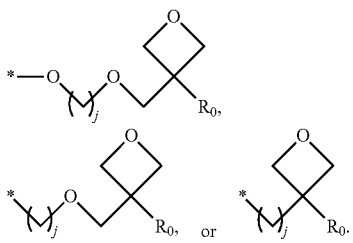

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group, and j is an integer between 2 and 9.

k may define the number of substituents R bonded to Ar. For example, k is an integer between 2 and 4. If k=2, Ar is a divalent aromatic group. If k=3, Ar is a trivalent aromatic group. If k=4, Ar is a tetravalent aromatic group.

In one exemplary embodiment, the composition for forming an organic film may include the compound of Formula 1, and the compound of Formula 1 may be a compound of (i.e., a compound represented by) Formula A-1 below.

 Formula A-1

In Formula A-1, $Ar_1$, which forms the basic skeleton, is a divalent, trivalent or tetravalent aromatic group. For example, $Ar_1$ may be

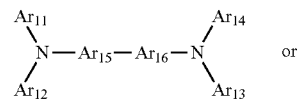

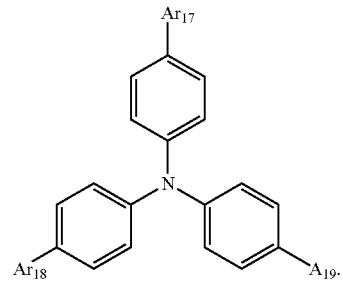

$Ar_{11}$, $Ar_{12}$, $Ar_{13}$, $Ar_{14}$, $Ar_{15}$, $Ar_{16}$, $Ar_{17}$, $Ar_{18}$, and $Ar_{19}$ have already been described above in connection with Formula 1, and detailed descriptions thereof will not be repeated.

If $Ar_{11}$, $Ar_{12}$, $Ar_{13}$, $Ar_{14}$, $Ar_{17}$, $Ar_{18}$, and $Ar_{19}$ are divalent arylene or heteroarylene groups, $R_1$ may be bonded thereto. For example, at least one of $Ar_{11}$, $Ar_{12}$, $Ar_{13}$ and $Ar_{14}$, and at least one of $Ar_{17}$, $Ar_{18}$ and $Ar_{19}$ are divalent arylene or divalent heteroarylene groups, and R may be bonded thereto.

The substituent $R_1$ may be a photo-polymerizable reacting group. For example, $R_1$ may be

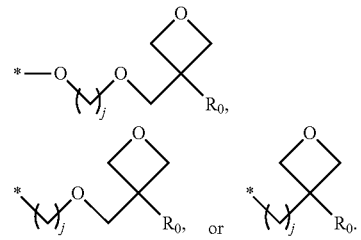

$R_0$ and j have already been described above in connection with Formula 1, and detailed descriptions thereof will not be repeated.

k1 may define the number of substituents $R_1$ bonded to $Ar_1$. For example, k1 may be an integer between 2 and 4.

In a non-limiting example, the compound of Formula A-1 may be a compound of (i.e., a compound represented by) any one of Formulae A-2 through A-8 below.

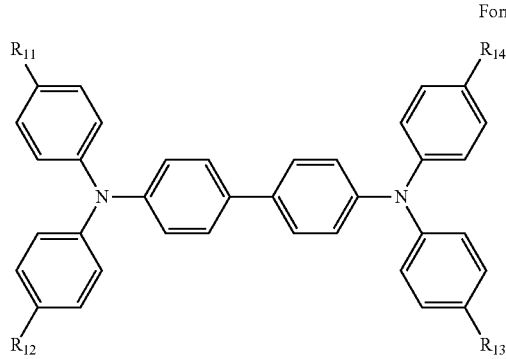

Formula A-2

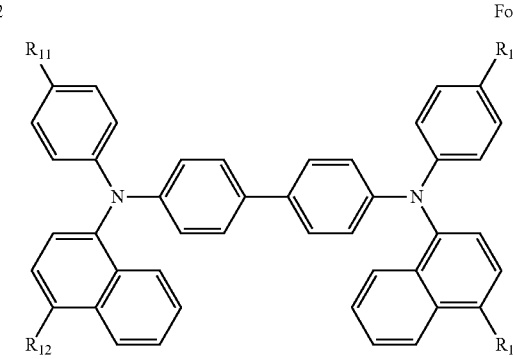

Formula A-3

-continued
Formula A-4
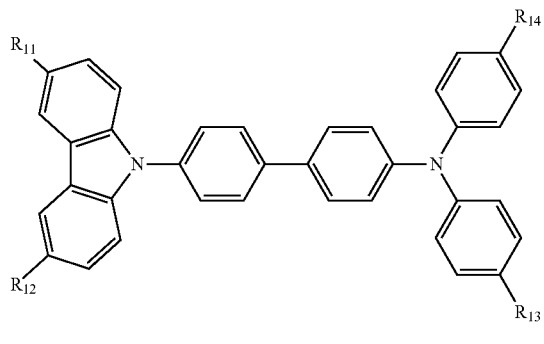
Formula A-5
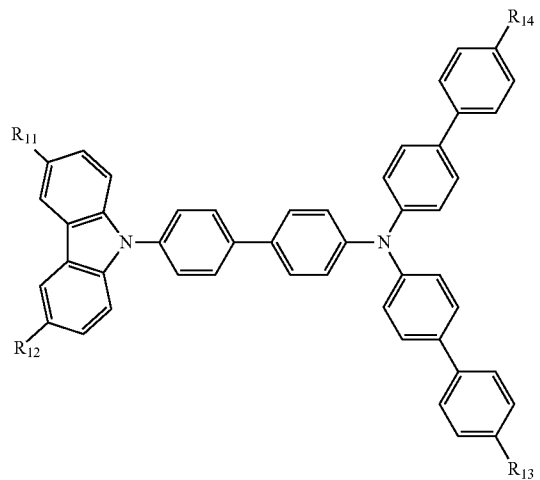
Formula A-6
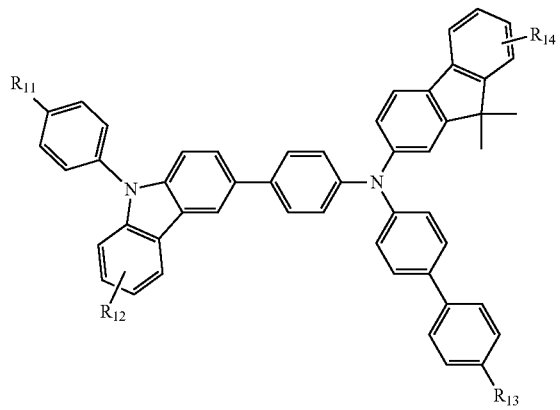
Formula A-7
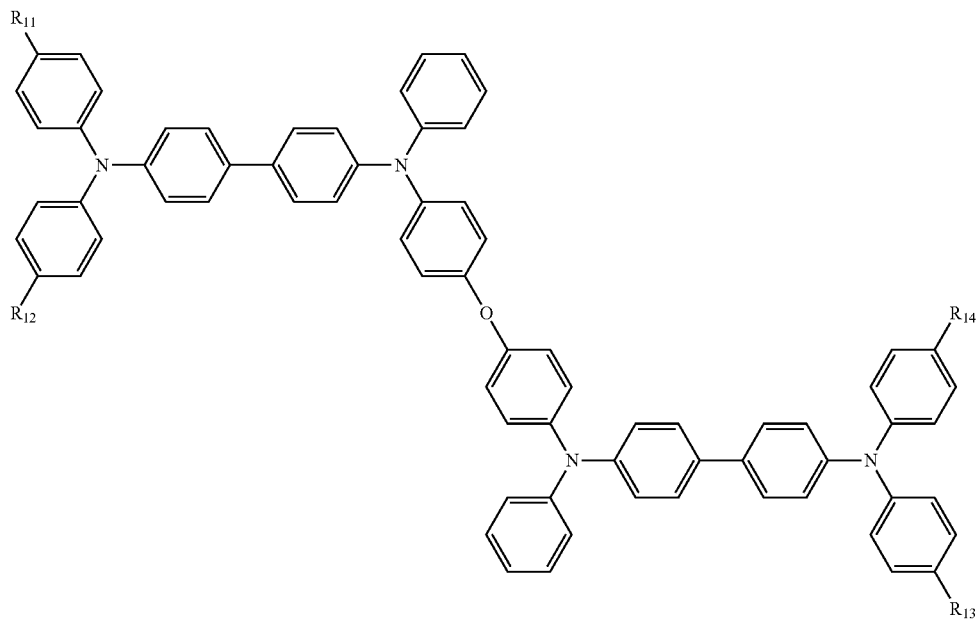

-continued

Formula A-8

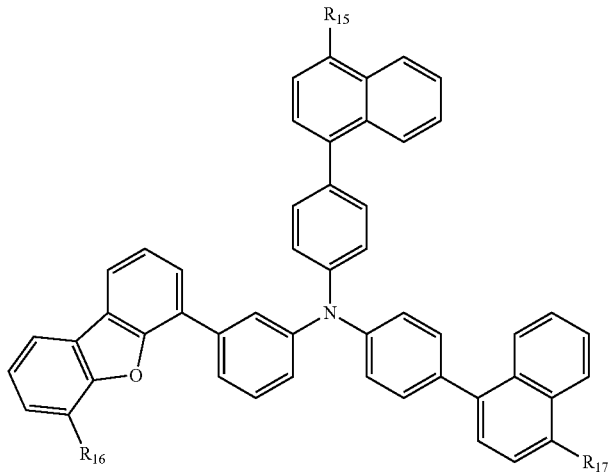

In Formulae A-2 through A-8, $R_{11}$, $R_{12}$, $R_{13}$, $R_{14}$, $R_{15}$, $R_{16}$, and $R_{17}$ are each independently a hydrogen atom,

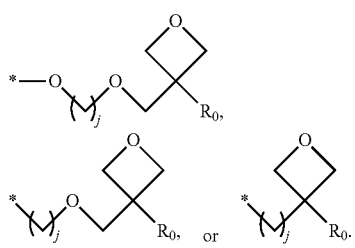

In a non-limiting example, two or more of $R_{11}$, $R_{12}$, $R_{13}$, and $R_{14}$ of Formulae A-2 through Formula A-7 may be each independently

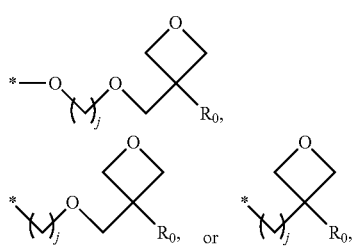

in which case, the compounds of Formulae A-2 through A-7 may exhibit insolubility to a developer, which will be described in more detail later. In Formulae A-2 through A-7, $R_{11}$, $R_{12}$, $R_{13}$, and $R_{14}$ bonded to the benzene ring may be bonded to a carbon atom facing (i.e., in the para position to) the carbon atom bonded to the nitrogen atom. As a result, an anisotropic transition dipole can be allocated.

Two or more of $R_{15}$, $R_{16}$, and $R_{17}$ of Formula A-8 may be each independently

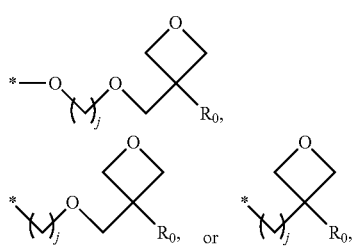

in which case, the compound of Formula A-8 may exhibit insolubility to the developer, which will be described in more later.

$R_0$ and j have already been described above with Formula 1, and detailed descriptions thereof will not be repeated.

The compounds of Formulae A-1 through A-8 may be, but are not limited to, compounds shown below.

A101

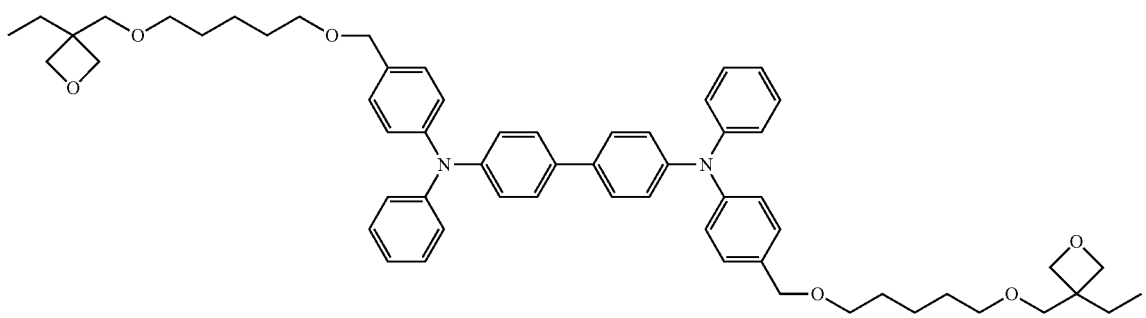

-continued
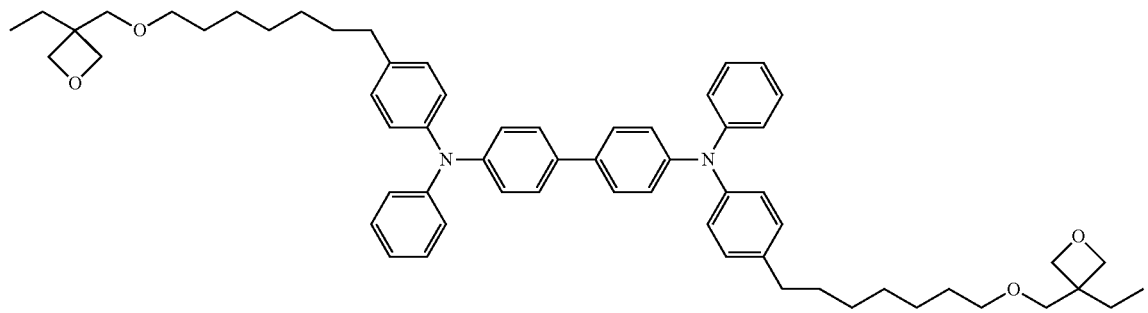
A102
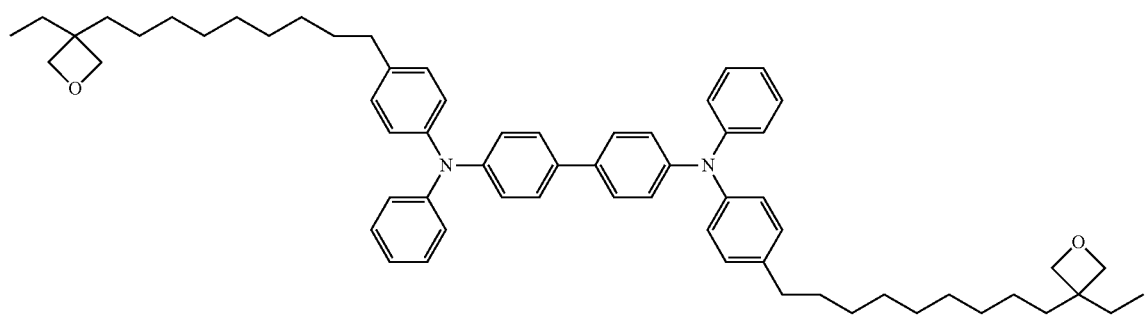
A103
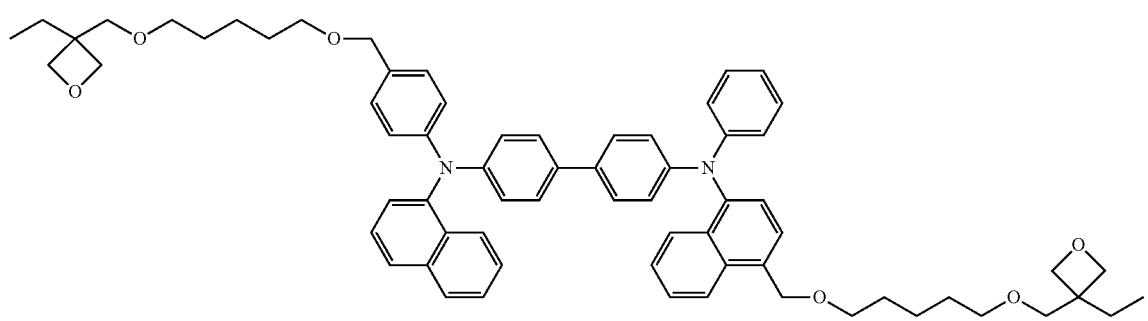
A104
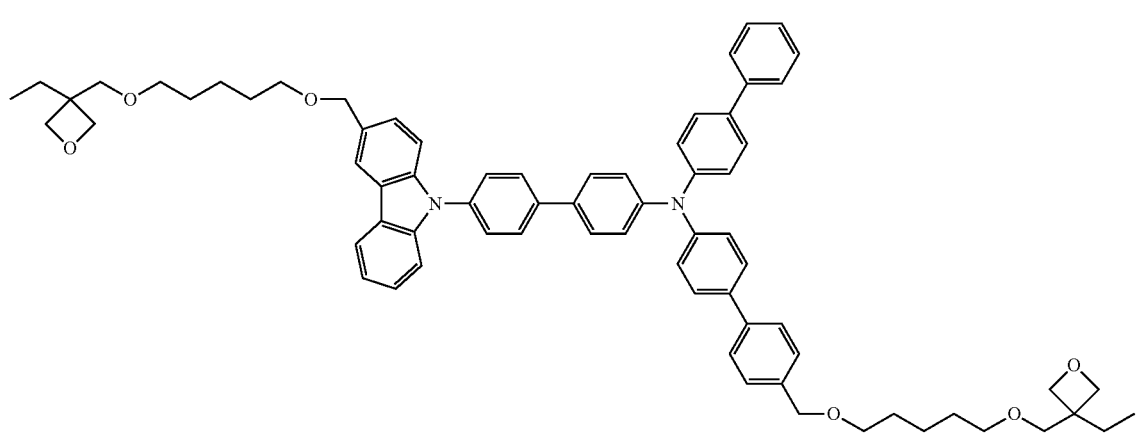
A105

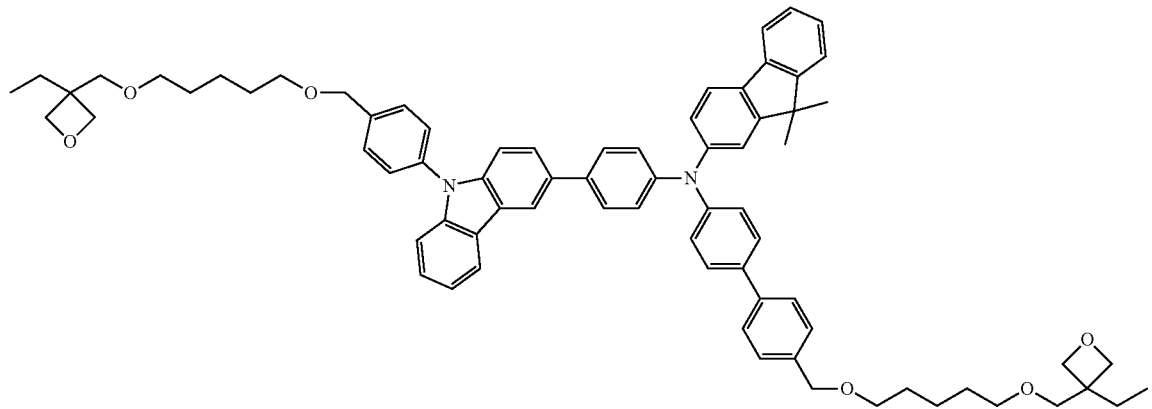
A106
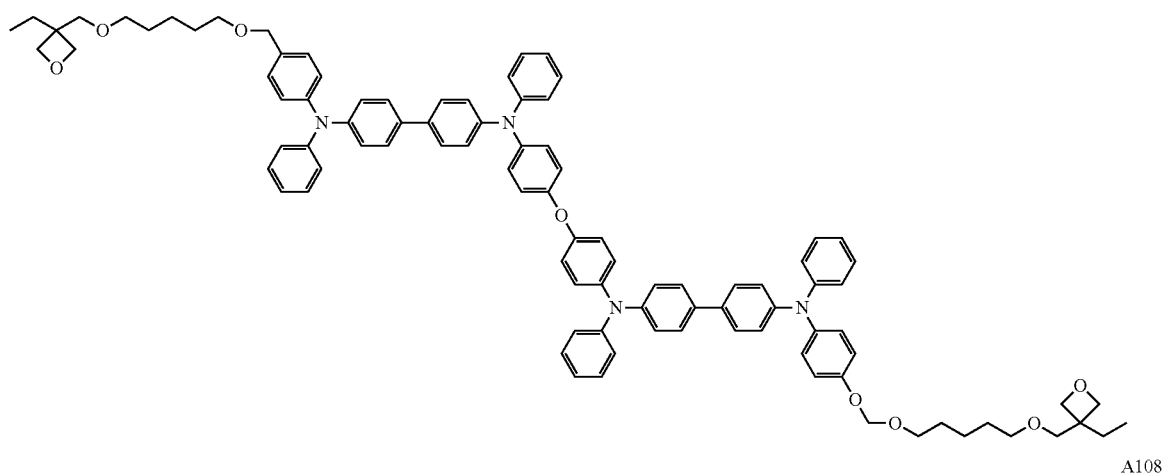
A107
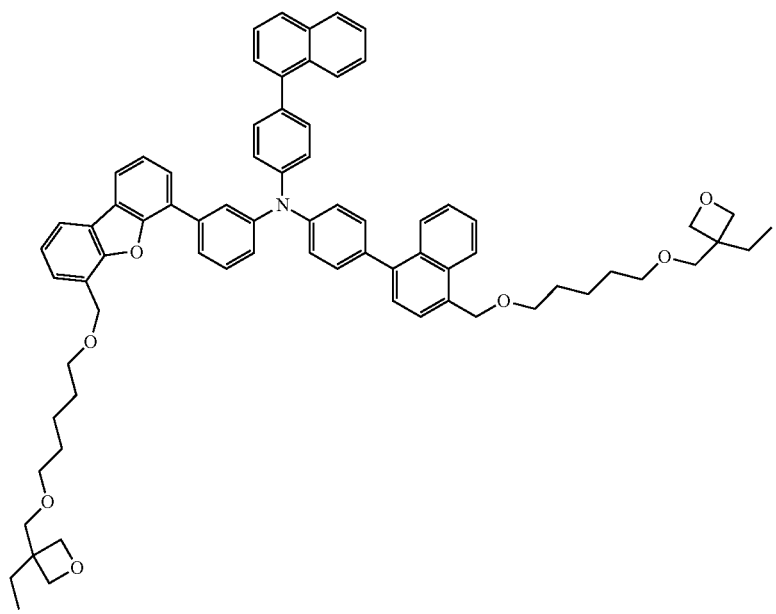
A108

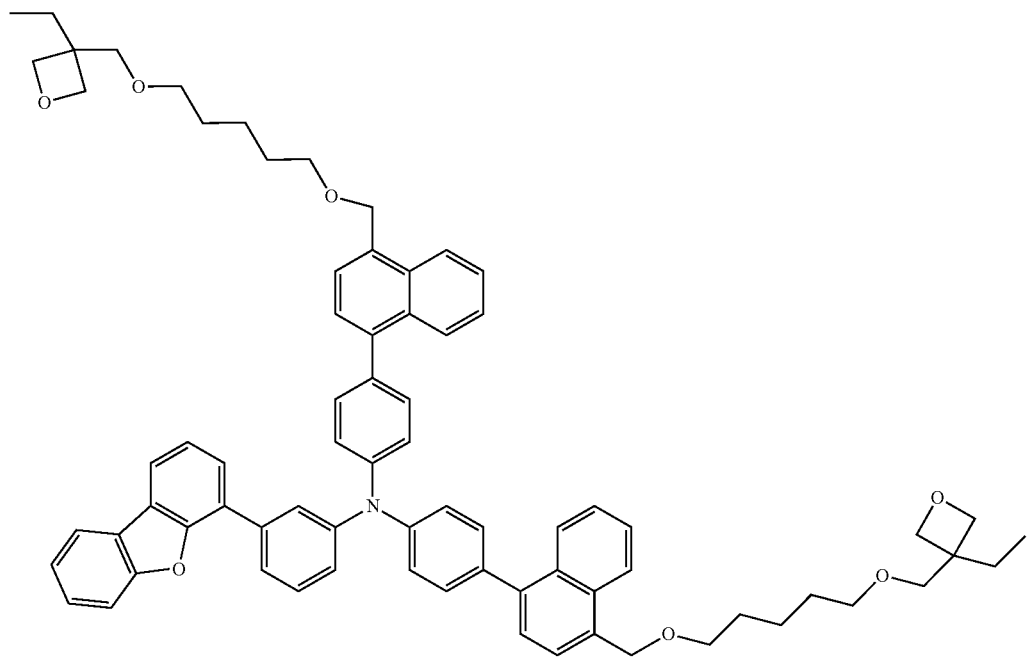
A109
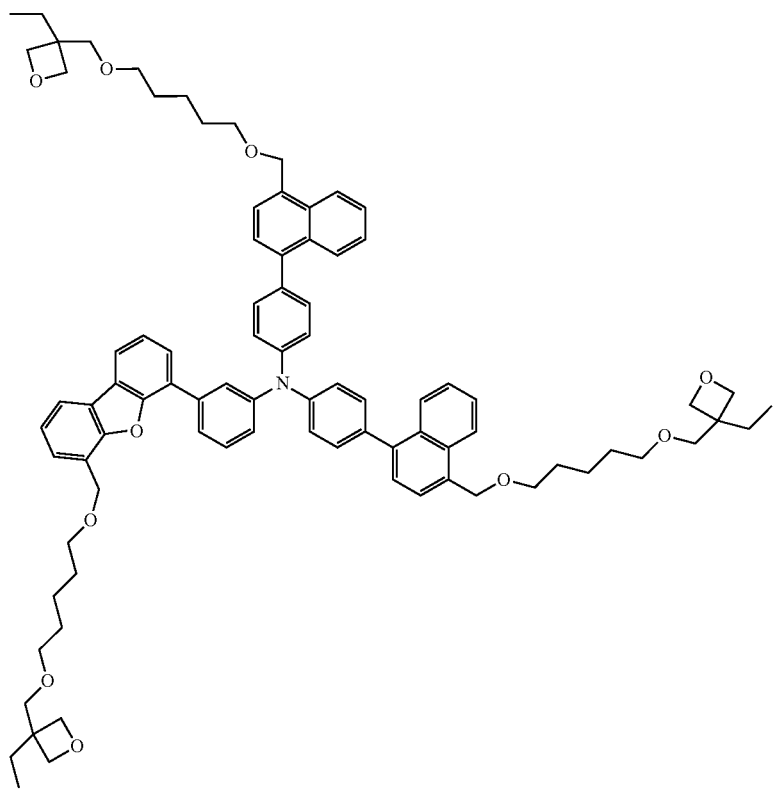
A110

The compounds of Formulae A-1 through A-8 and polymers thereof may have a hole injecting function and/or a hole transporting function. In an exemplary embodiment where the composition for forming an organic film includes the compounds of Formulae A-1 through A-8, the composition for forming the organic film may further include a compound of Formula E-1 or E-2 below.

Formula E-1

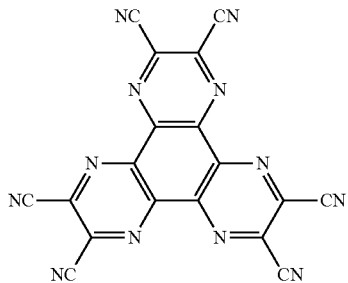

Formula E-2

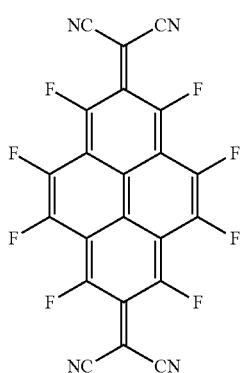

In another exemplary embodiment, the composition for forming an organic film may include the compound of Formula 1, and the compound of Formula 1 may be a compound of (i.e., a compound represented by) Formula B-1.

R$_2$—Ar$_2$—R$_2$'  Formula B-1

In Formula B-1, Ar$_2$, which forms the basic skeleton, is a divalent aromatic group. For example, Ar$_2$ may be

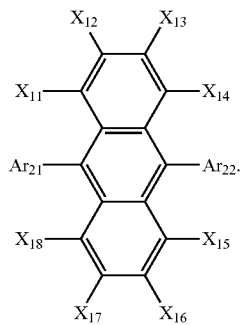

Ar$_{21}$, Ar$_{22}$, X$_{11}$, X$_{12}$, X$_{13}$, X$_{14}$, X$_{15}$, X$_{16}$, X$_{17}$, and X$_{18}$ have already been described above in connection with Formula 1, and detailed descriptions thereof will not be repeated.

Ar$_{21}$ and Ar$_{22}$ are each a divalent arylene or a divalent heteroarylene group, and R$_2$ and R$_2$' may be bonded to Ar$_{21}$ and Ar$_{22}$, respectively. R$_2$ and R$_2$' may each independently be a photo-polymerizable reacting group. For example, R$_2$ and R$_2$' may be each independently

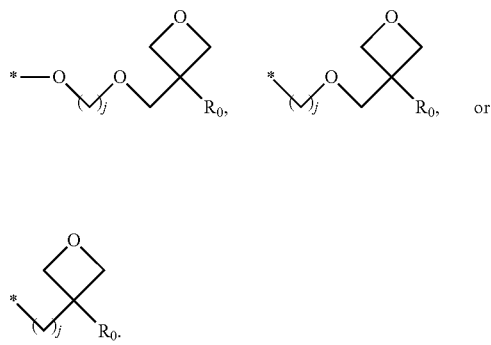

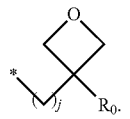

R$_0$ and j have already been described above in connection with Formula 1, and detailed descriptions thereof will not be repeated.

In a non-limiting example, the compound of Formula B-1 may be a compound of (i.e., a compound represented by) any one of Formulae B-2 through B-23.

Formula B-2

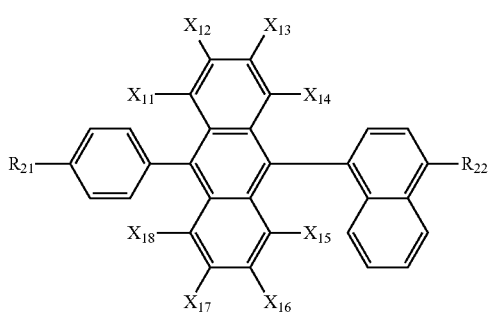

Formula B-3

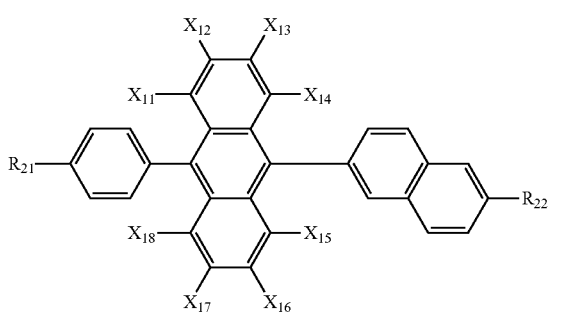

Formula B-4
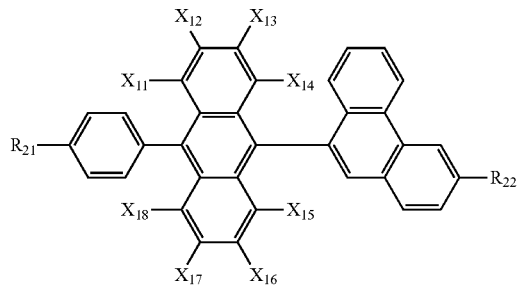
Formula B-5
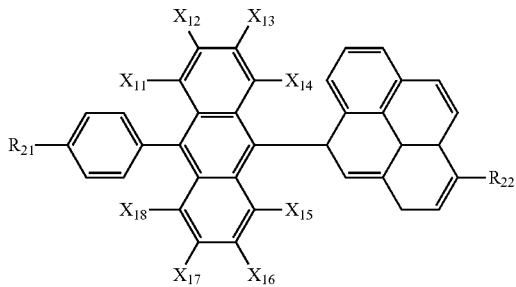
Formula B-6
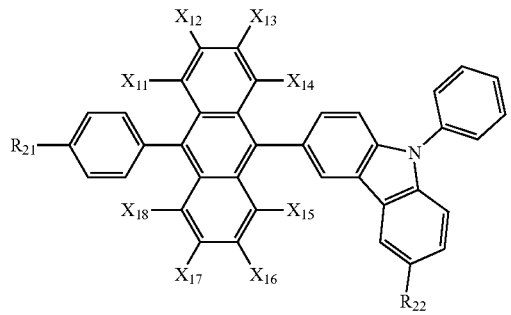
Formula B-7
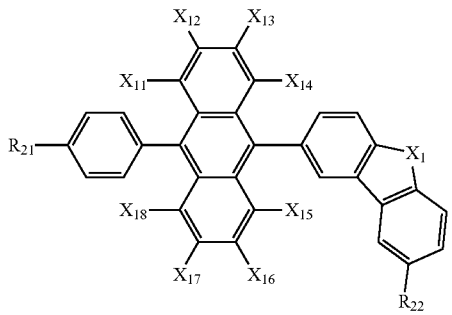
Formula B-8
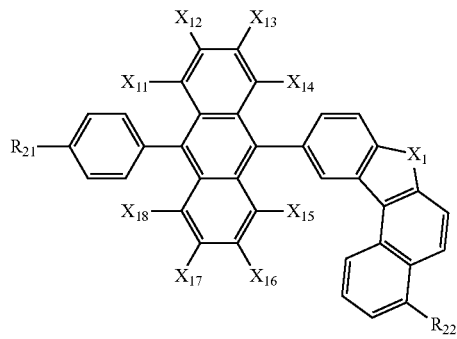
Formula B-9
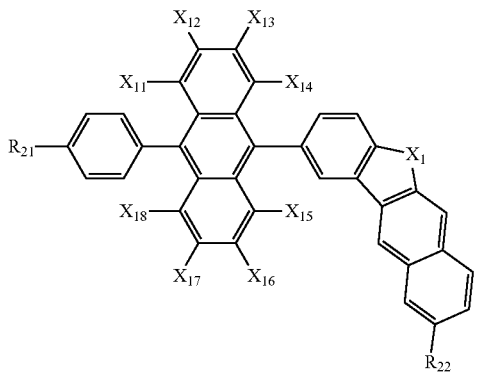
Formula B-10
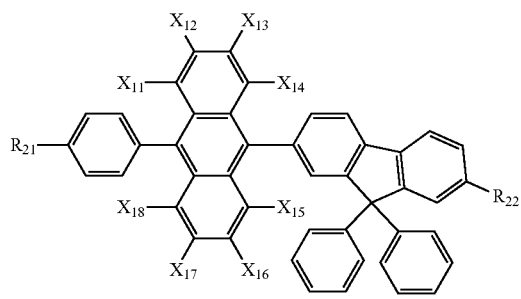
Formula B-11
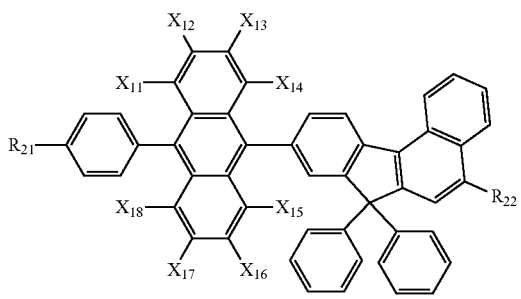

Formula B-12
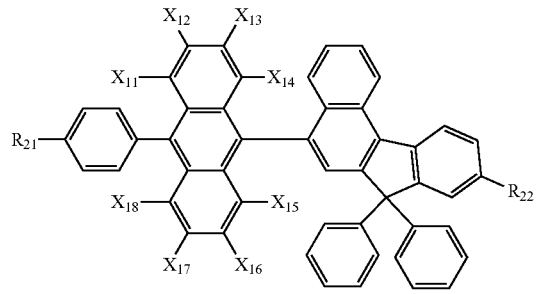
Formula B-13
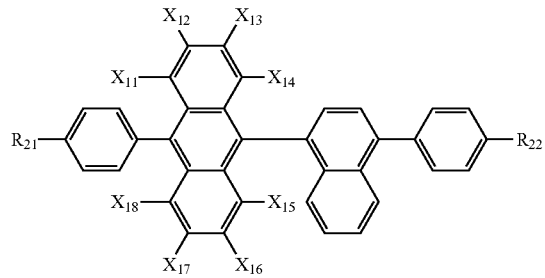
Formula B-14
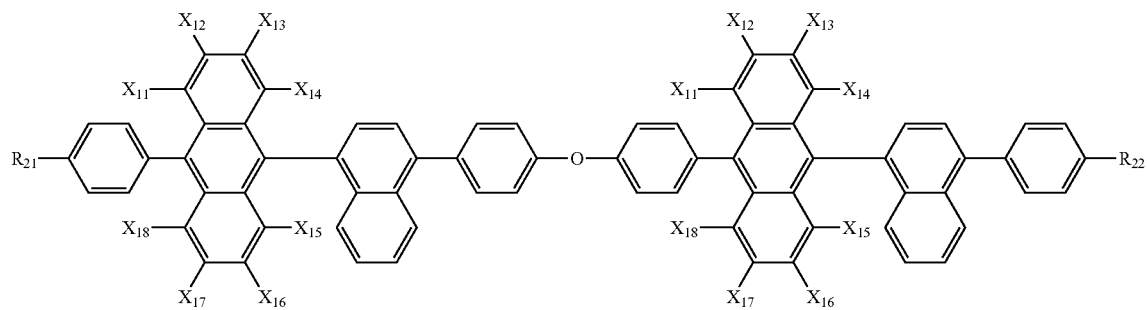
Formula B-15
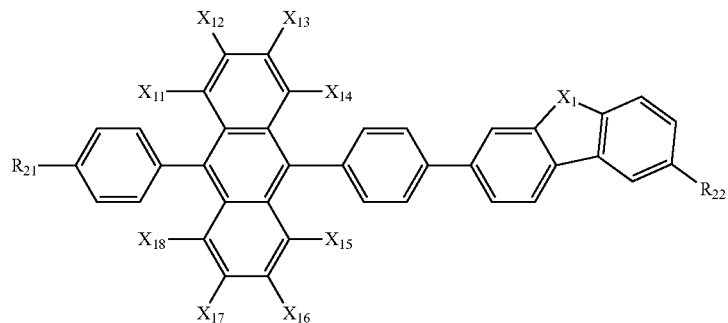
Formula B-16
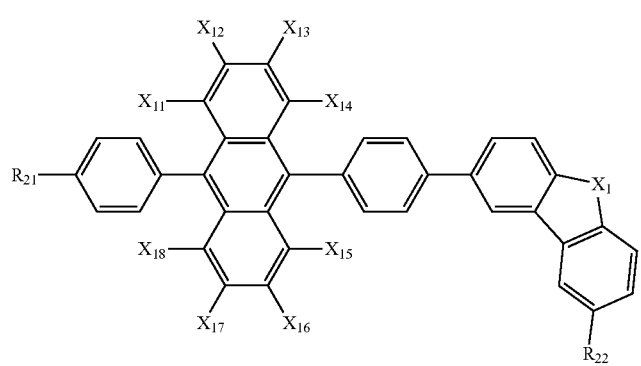

Formula B-17
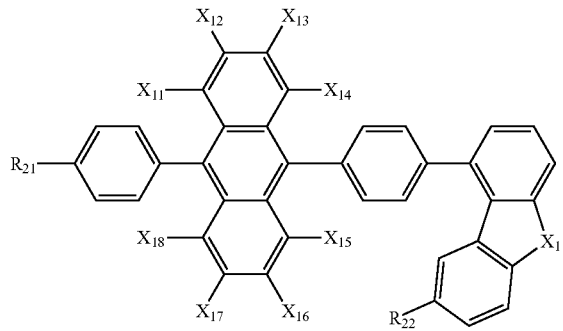
Formula B-18
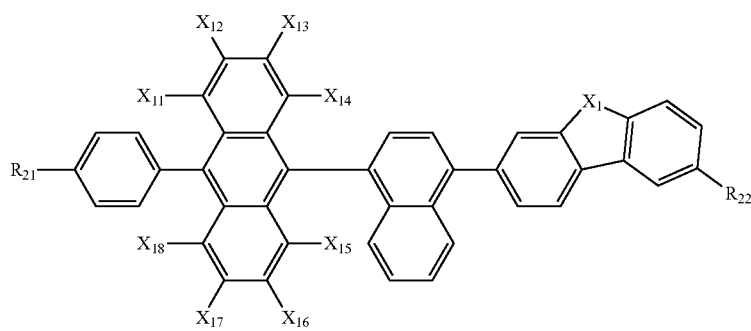
Formula B-19
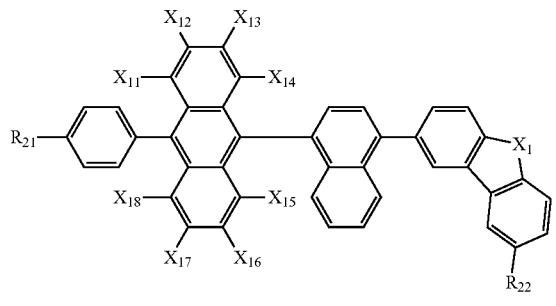
Formula B-20
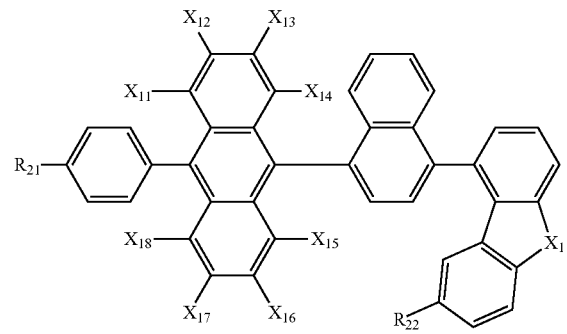
Formula B-21
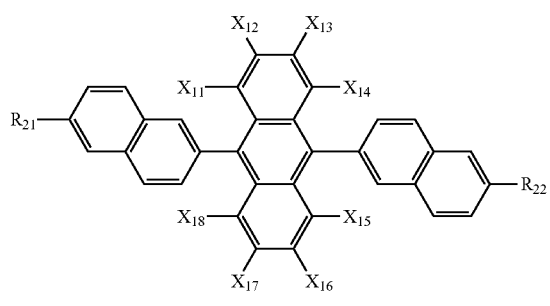
Formula B-22
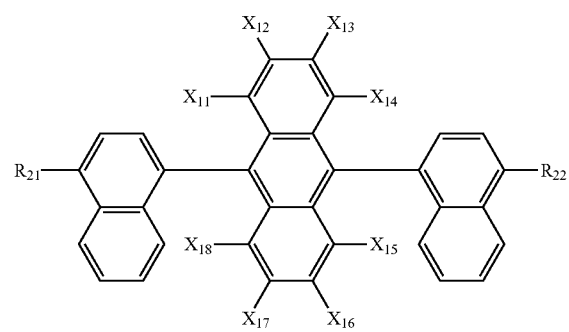

Formula B-23

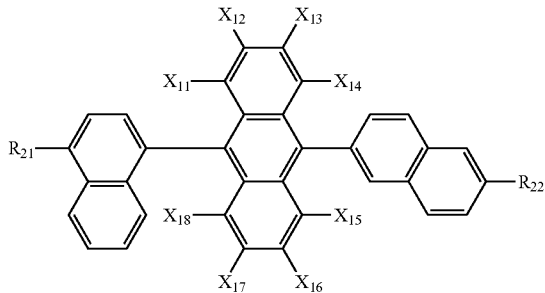

In Formulae B-2 through B-23, $R_{21}$ and $R_{22}$ are each independently

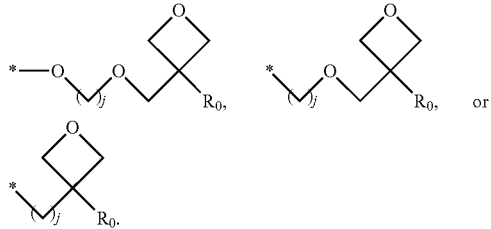

$R_0$ and $j$ have already been described above in connection with Formula 1, and detailed descriptions thereof will not be repeated.

$X_{11}$, $X_{12}$, $X_{13}$, $X_{14}$, $X_{15}$, $X_{16}$, $X_{17}$, $X_{18}$, $X_{21}$, $X_{22}$, $X_{23}$, $X_{24}$, $X_{25}$, $X_{26}$, $X_{27}$, and $X_{28}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group.

In Formulae B-7 through B-9 and B-15 through B-20, $X_1$ is an oxygen atom or a sulfur atom.

The compounds of Formulae B-1 through B-23 and polymers thereof may be utilized as a host material for a blue light-emitting material (e.g., a blue light-emitting layer).

The compounds of Formulae B-1 through B-23 may be, but are not limited to, compounds shown below.

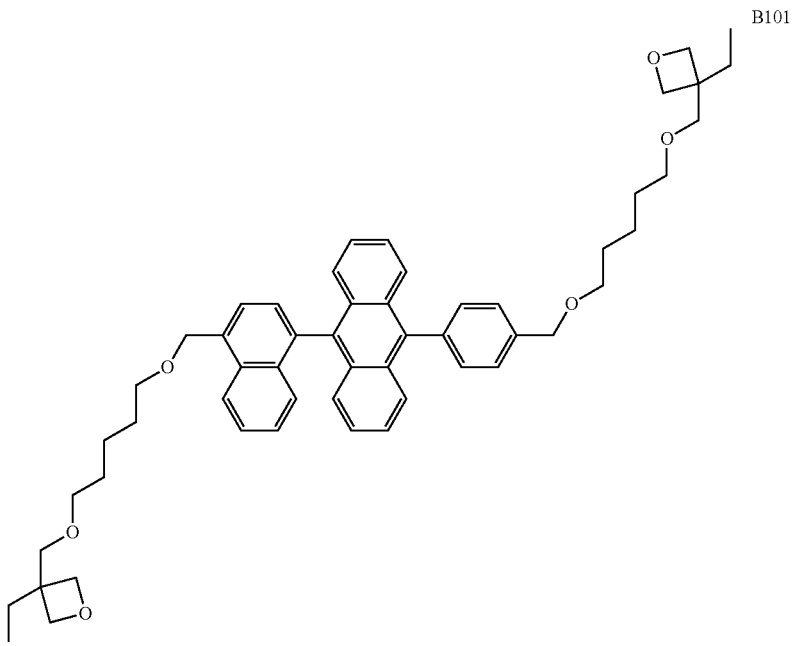

B101

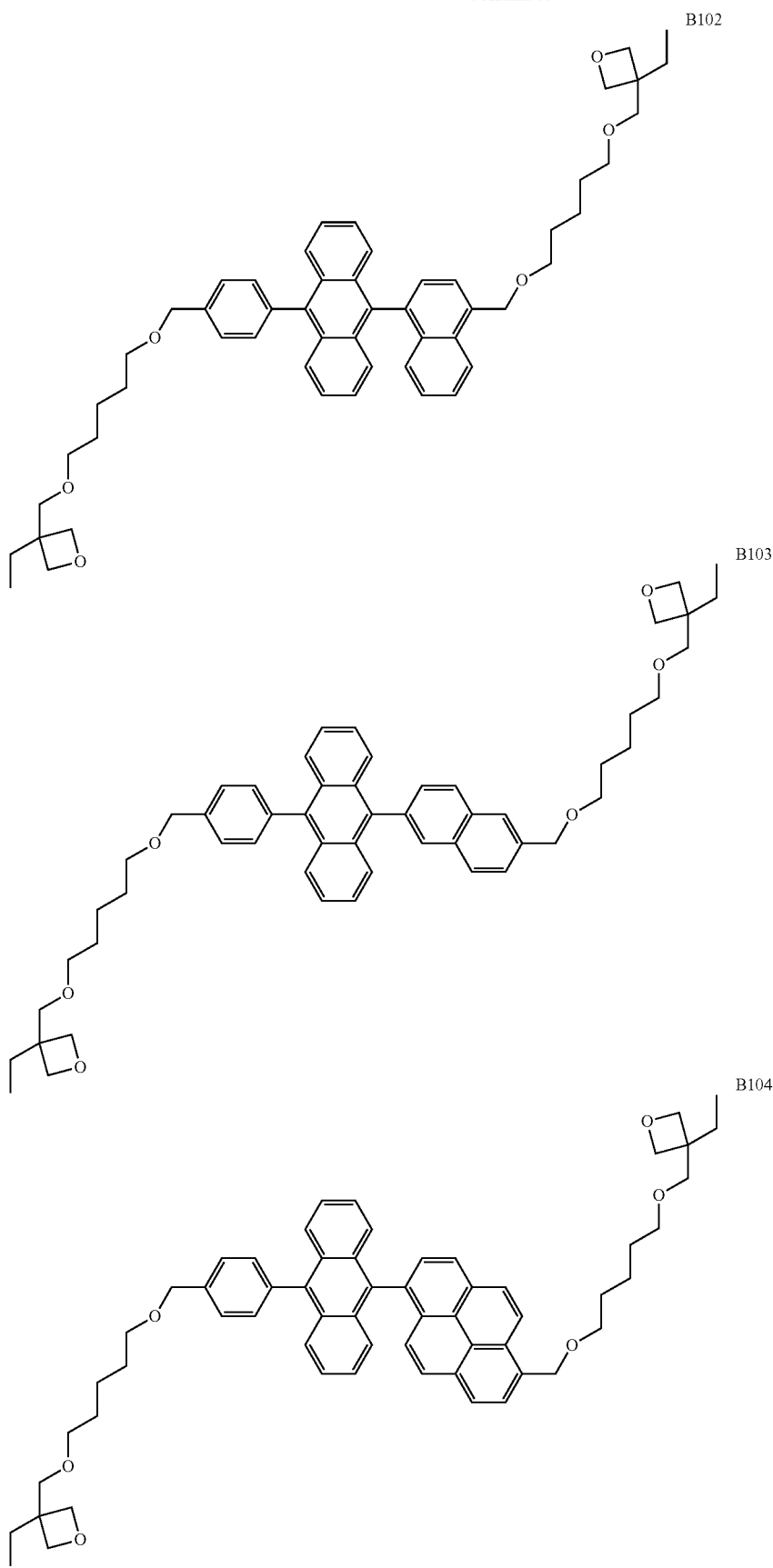

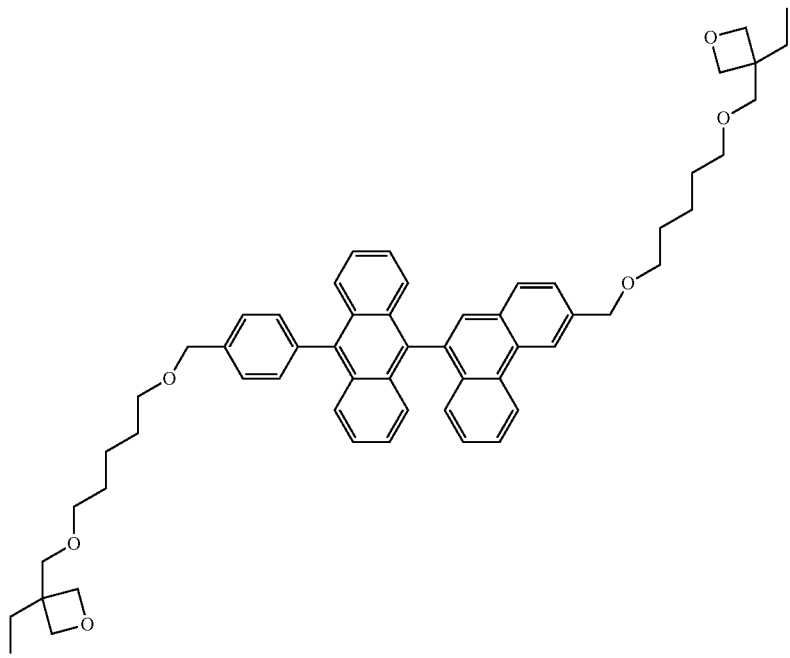
B105
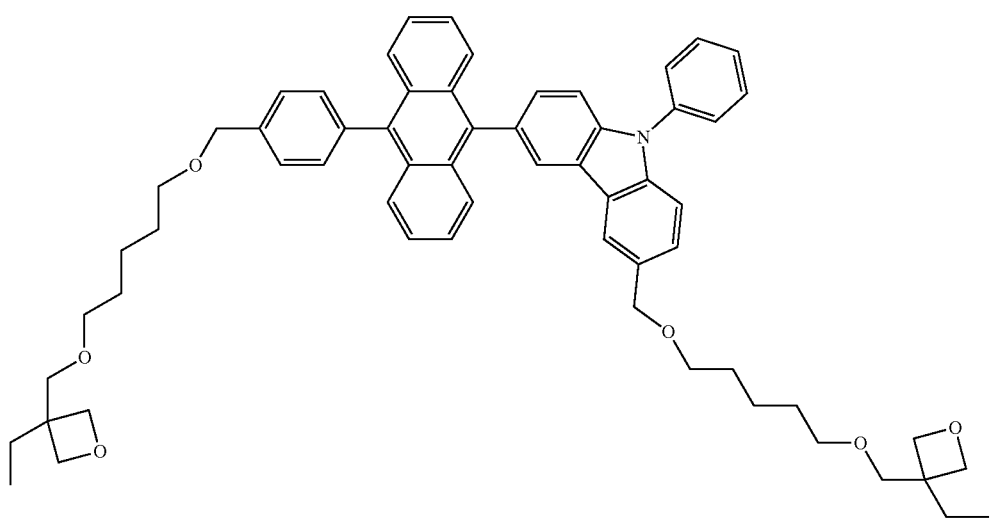
B106

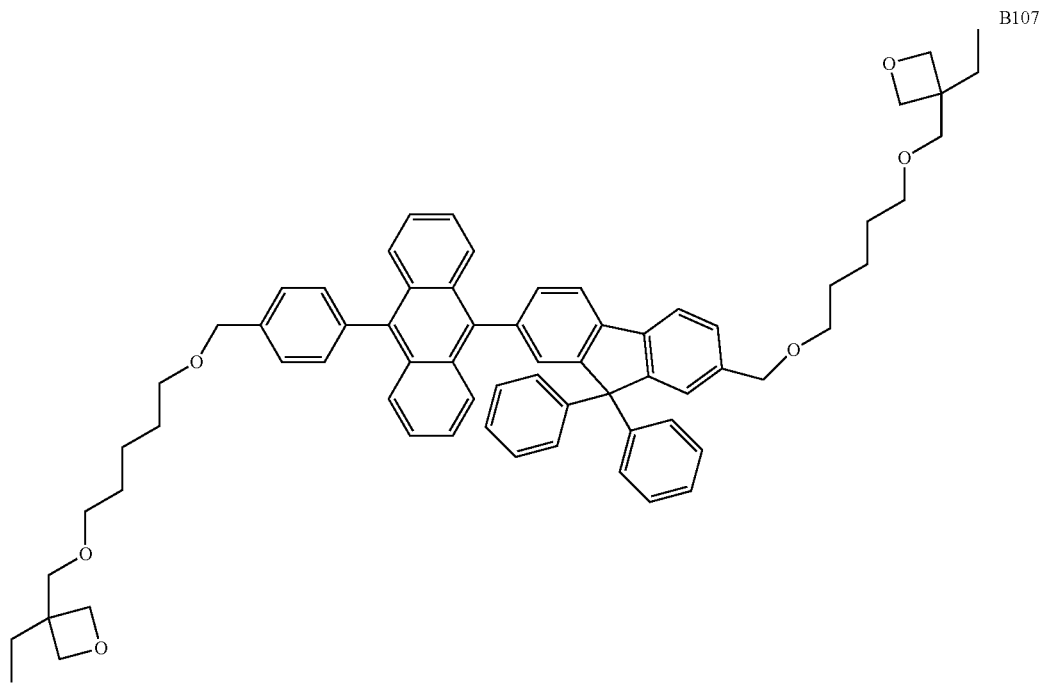
B107
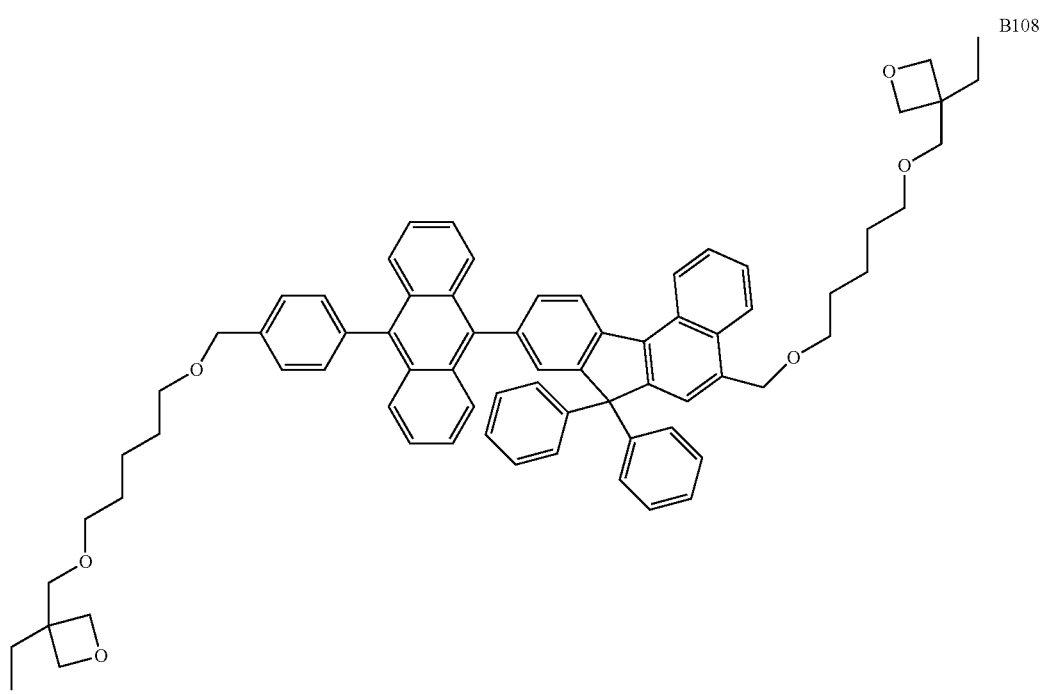
B108

-continued
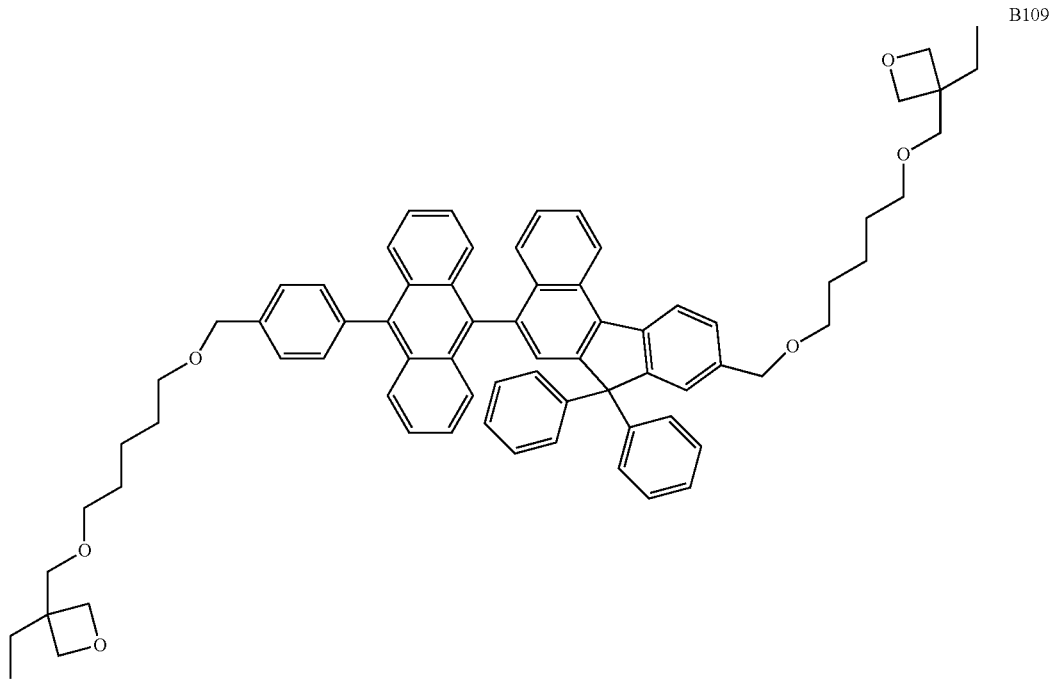
B109
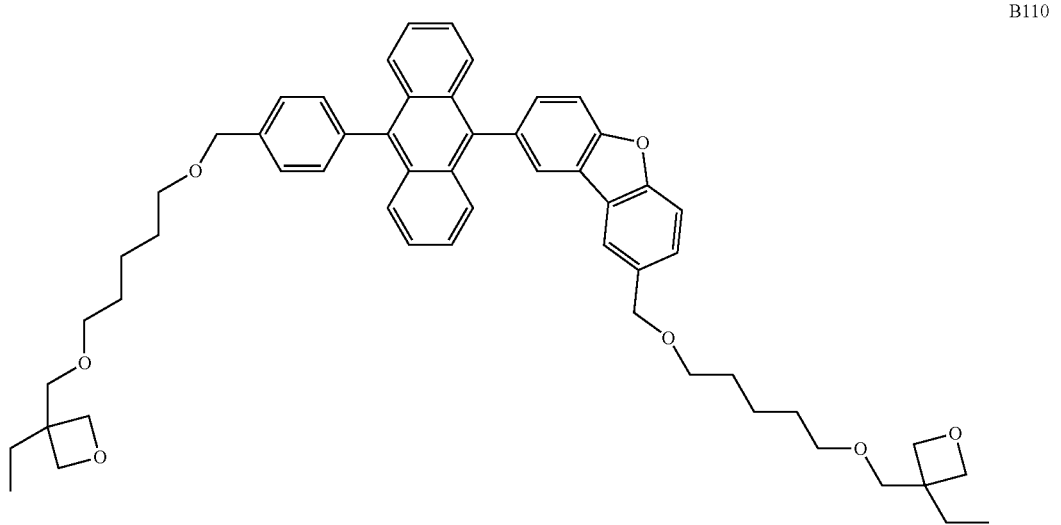
B110
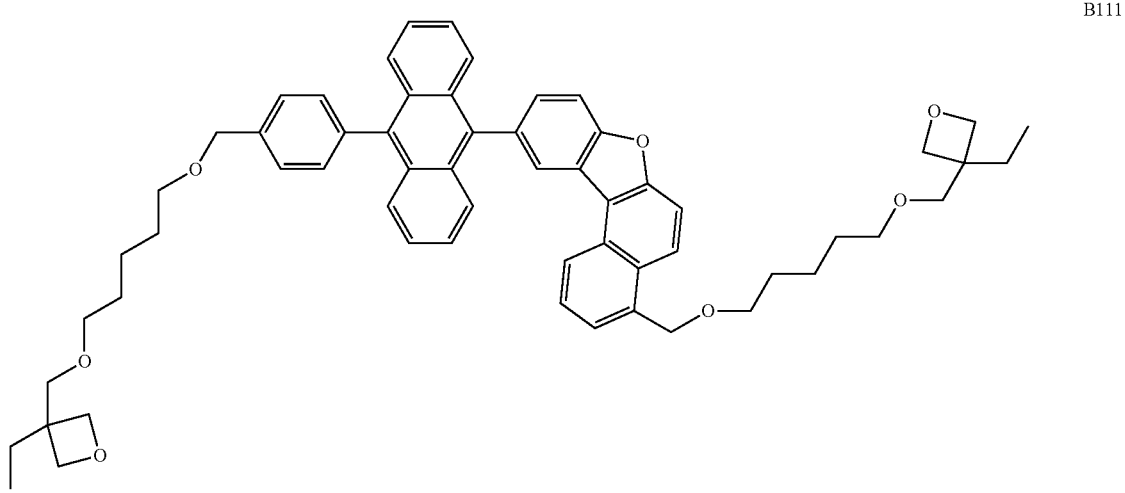
B111

-continued
B112
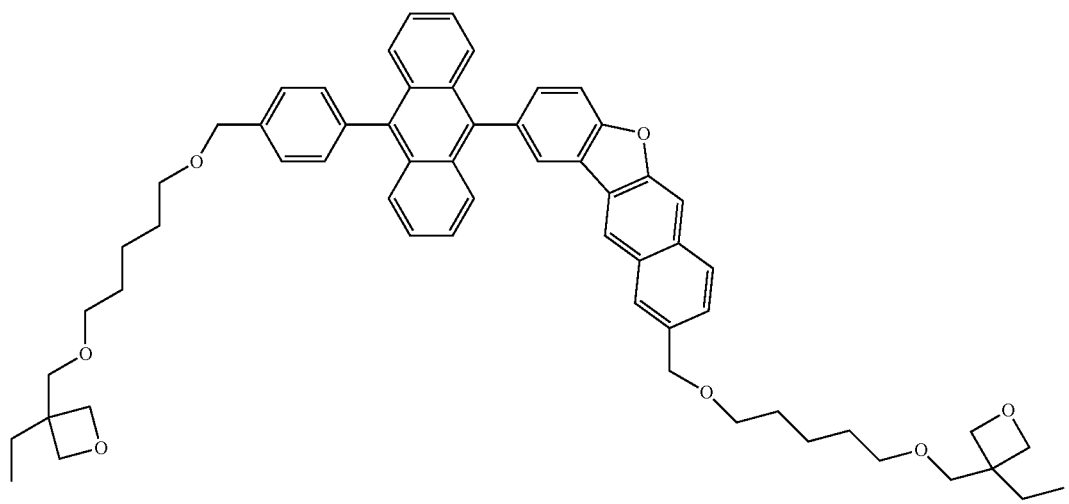
B113
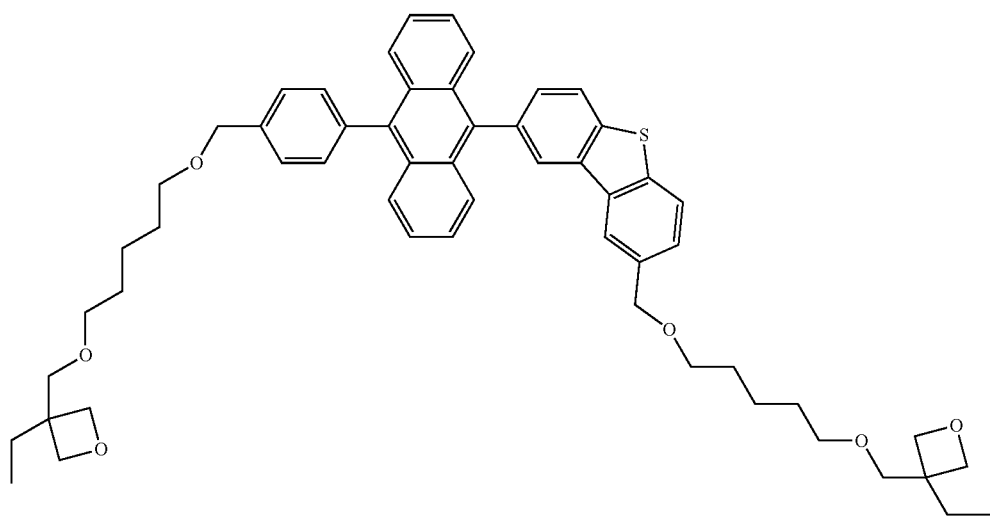
B114
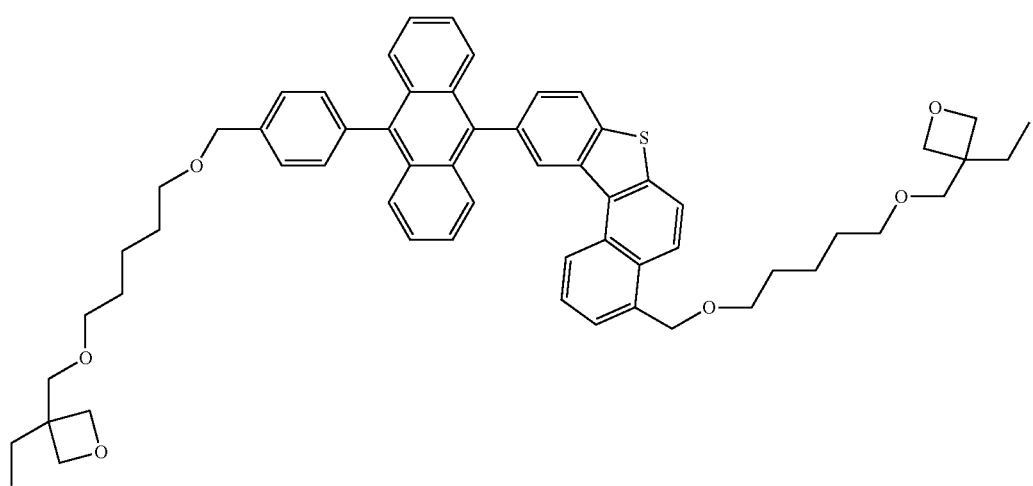

-continued
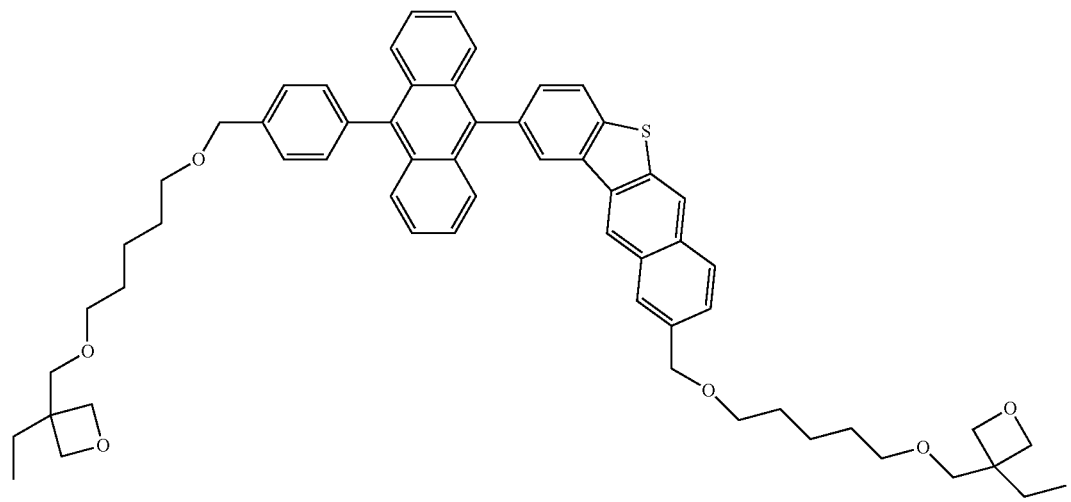
B115
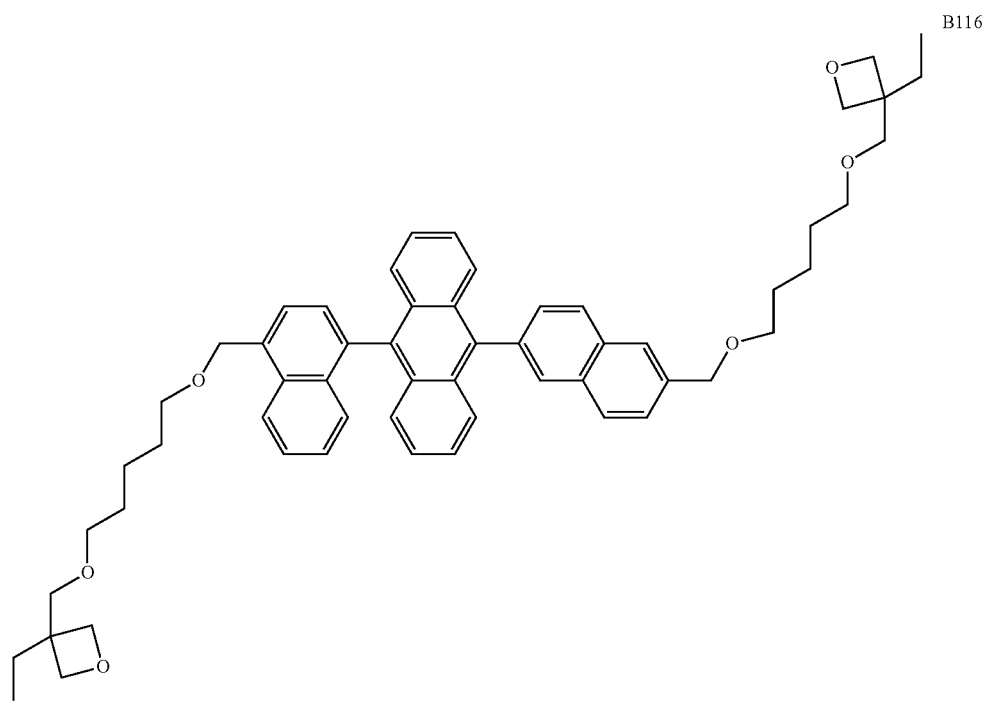
B116

-continued
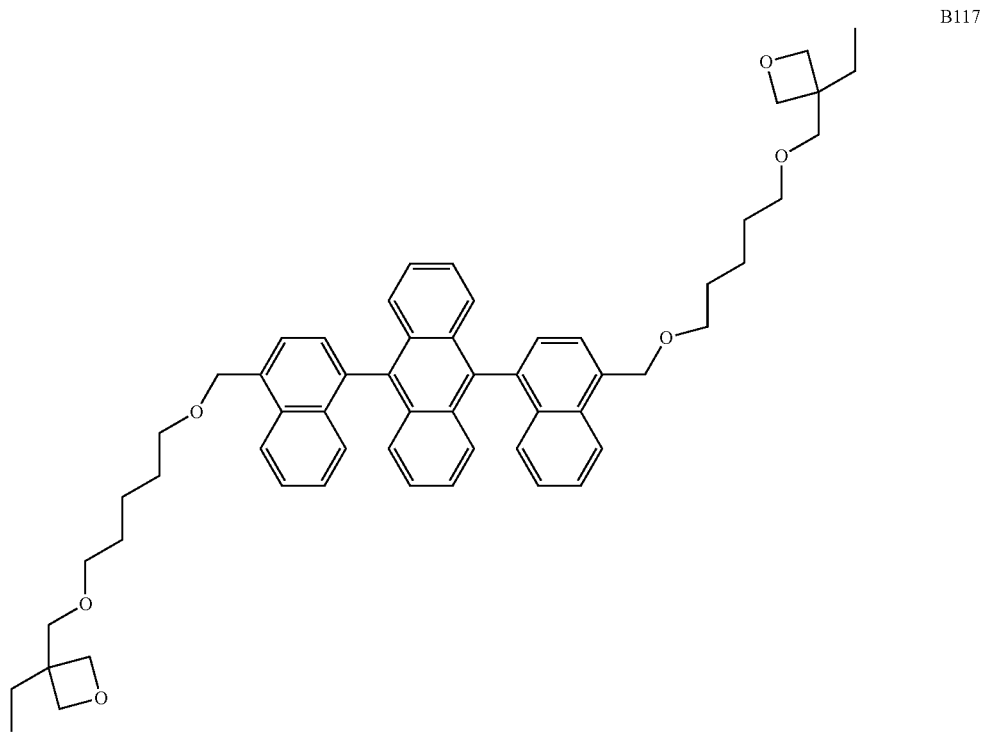
B117
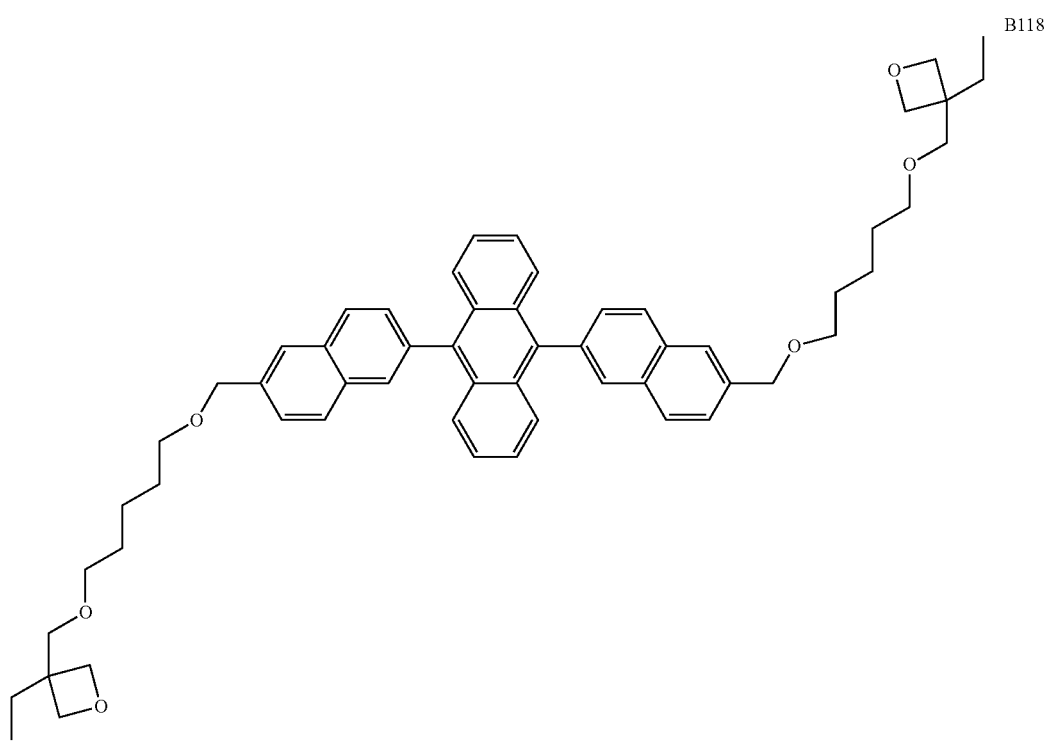
B118

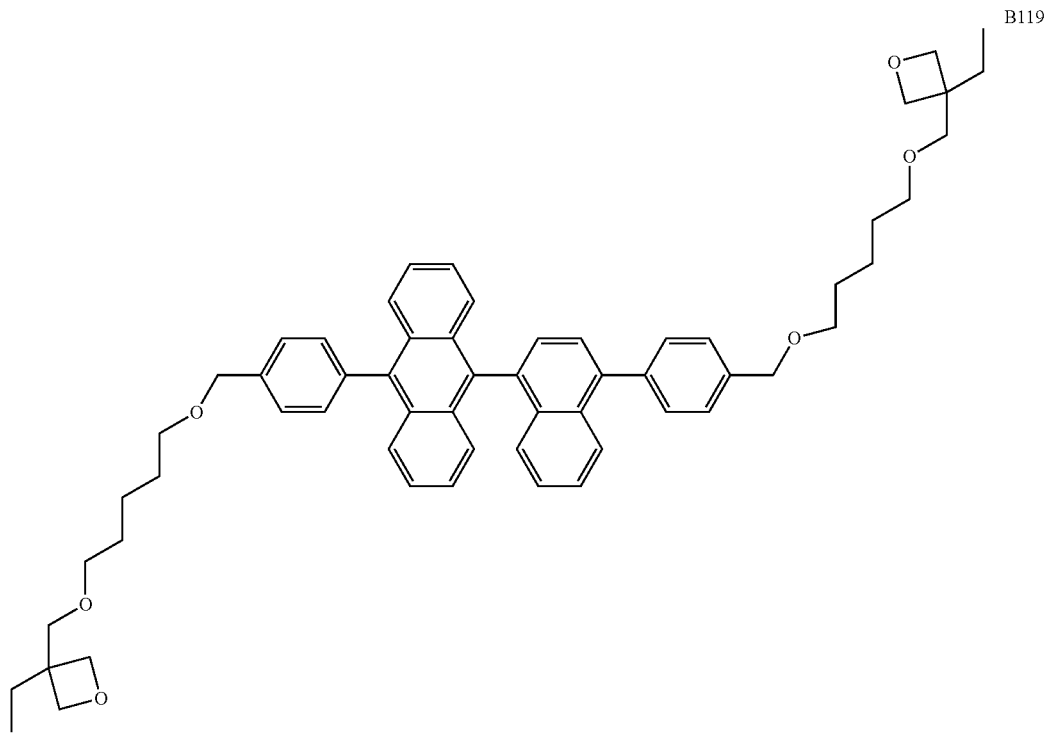
B119
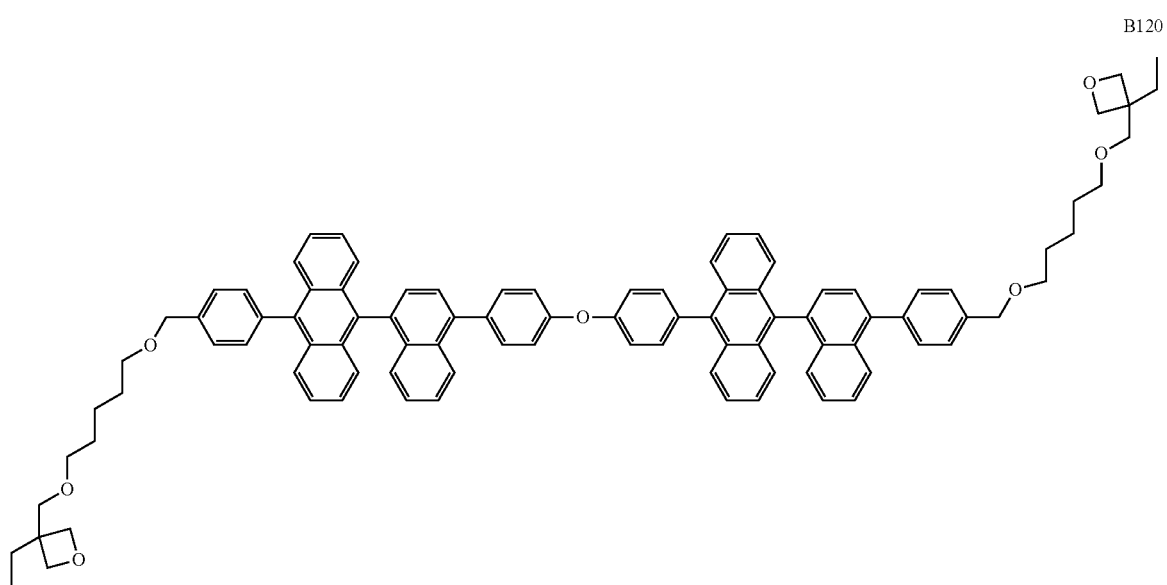
B120

-continued
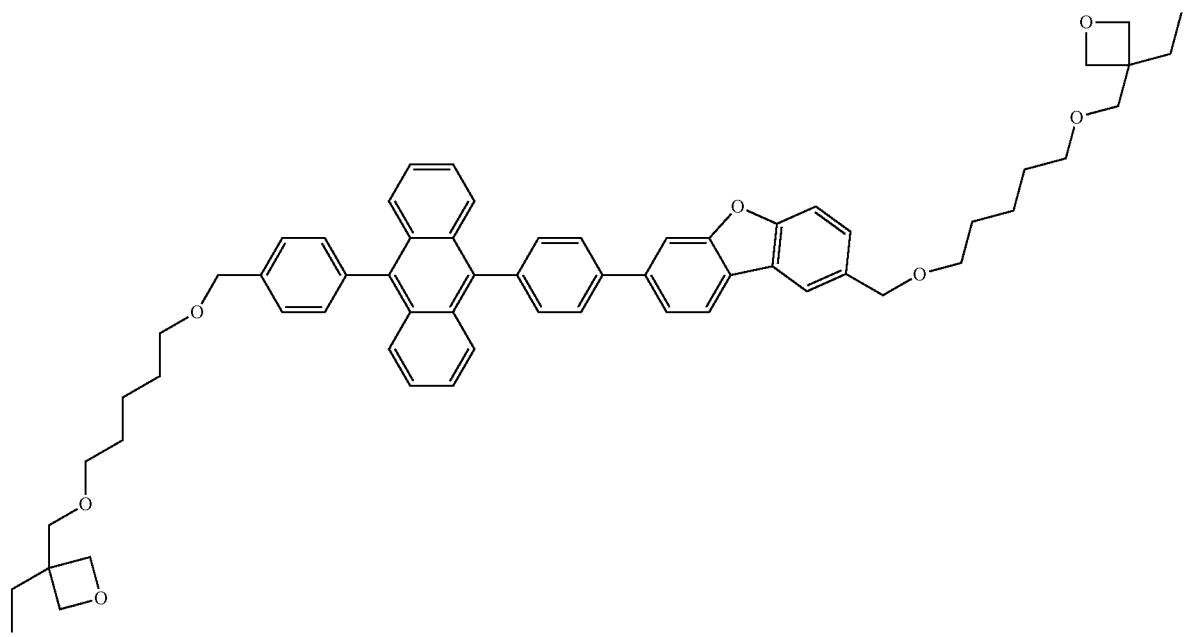
B121
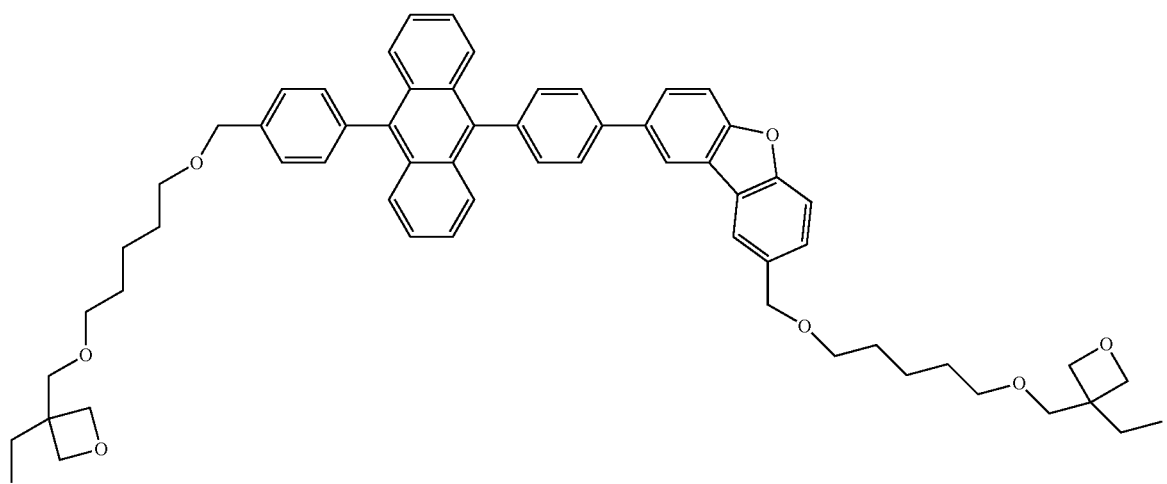
B122

-continued
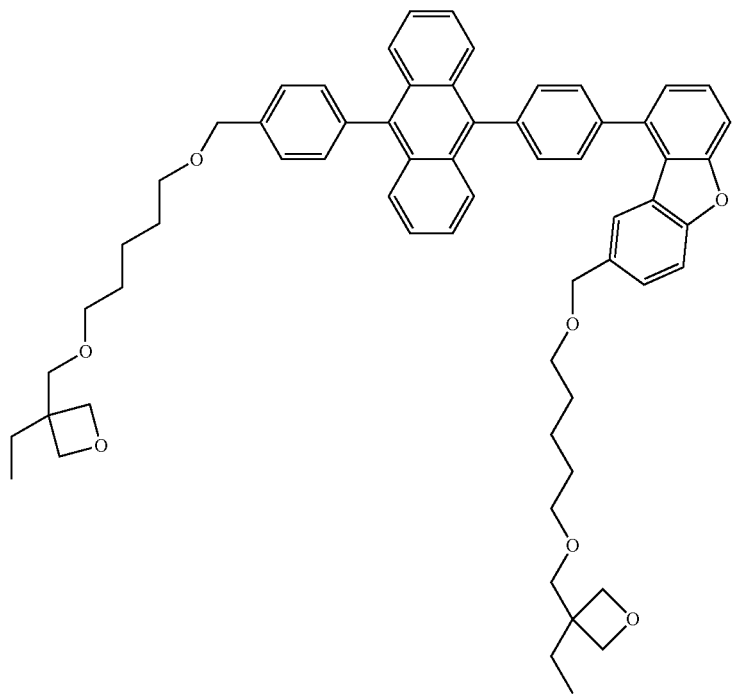
B123
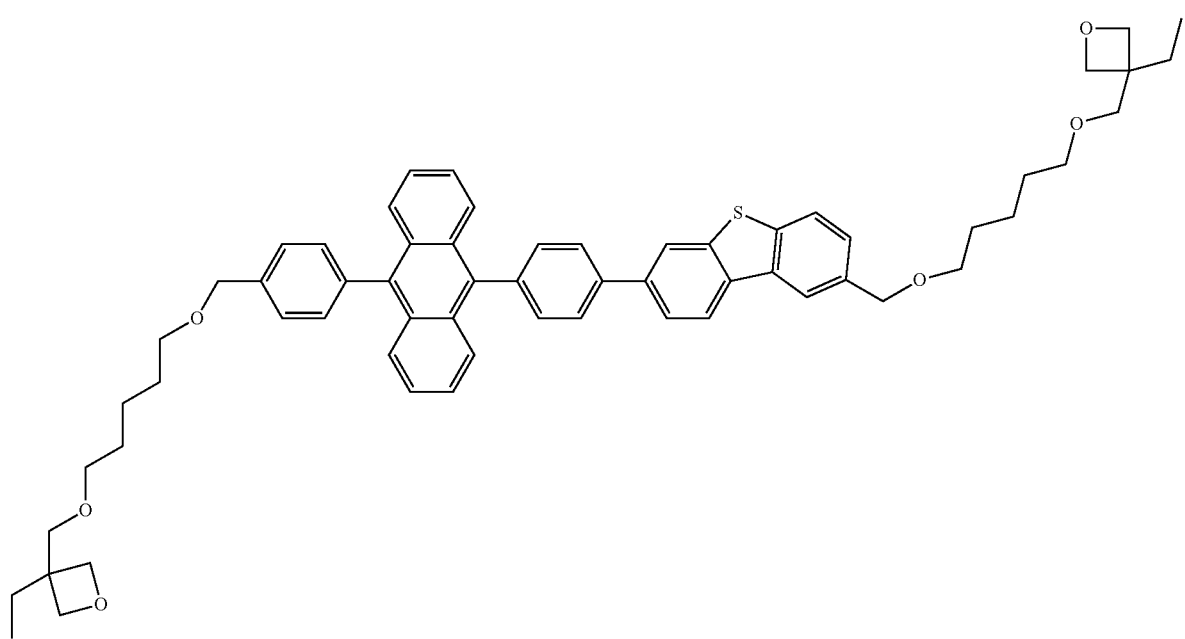
B124

-continued
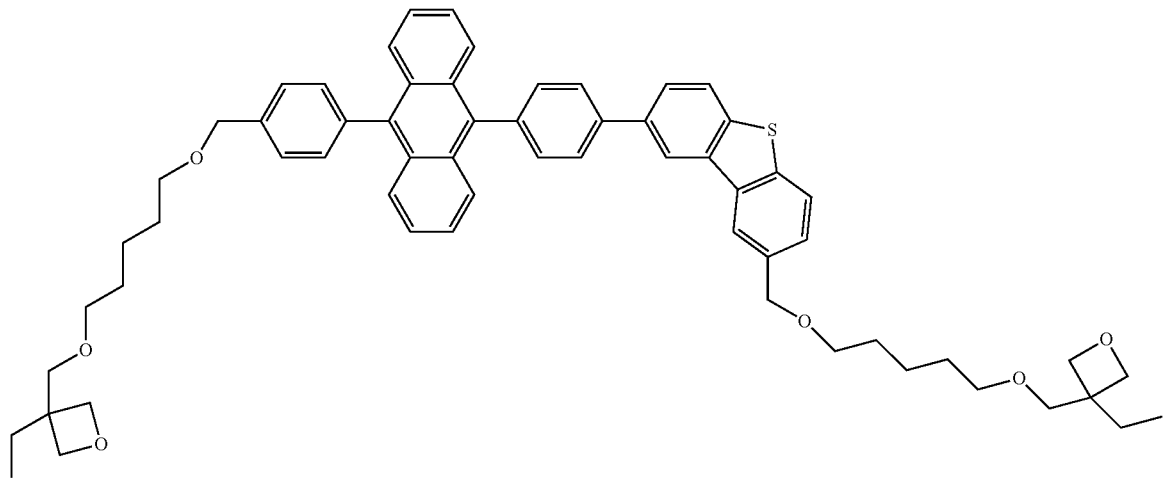
B125
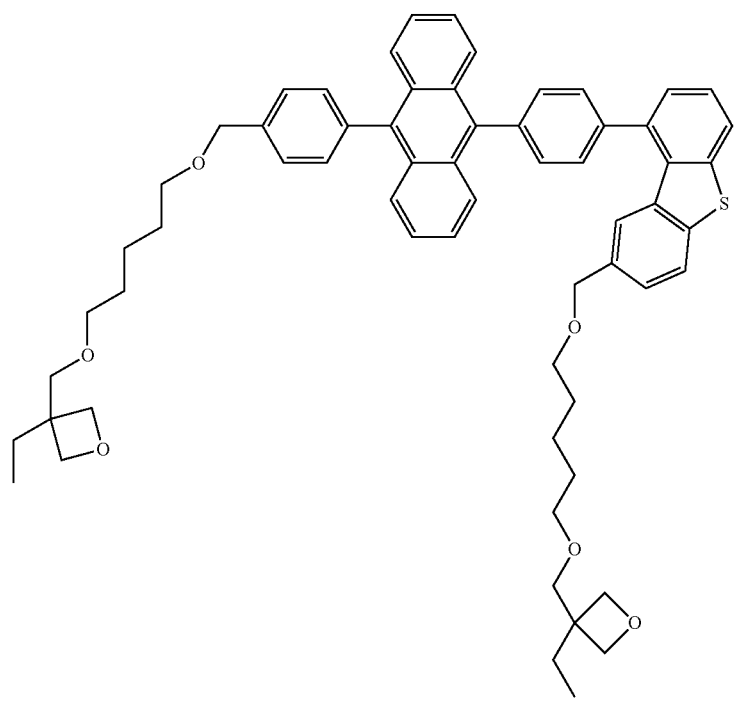
B126

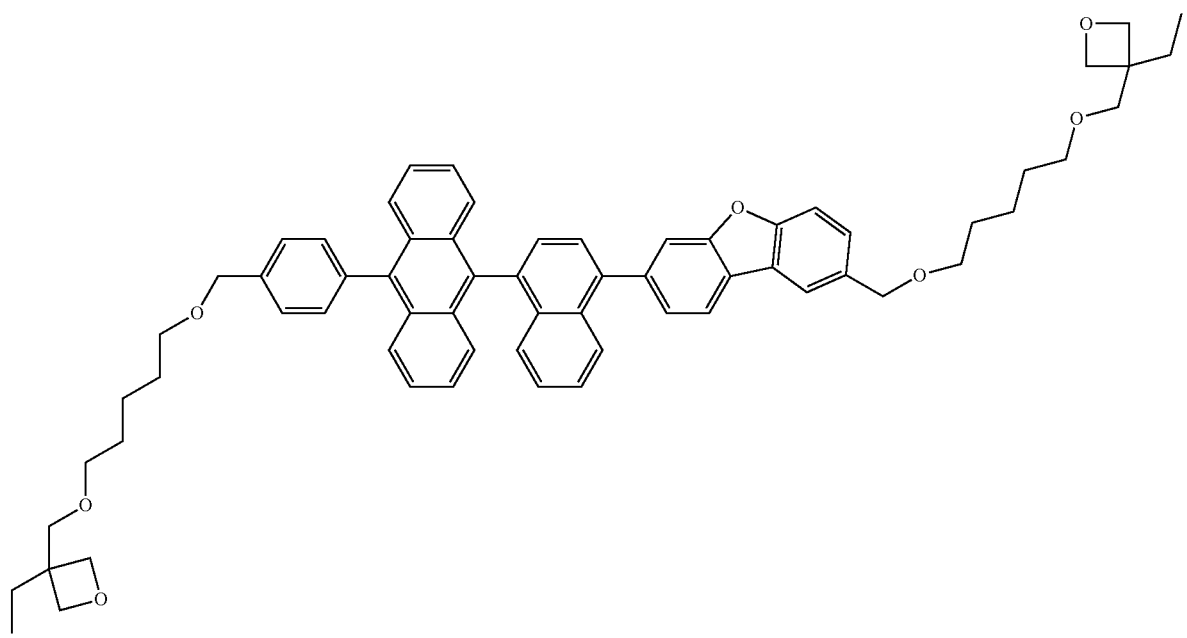
B127
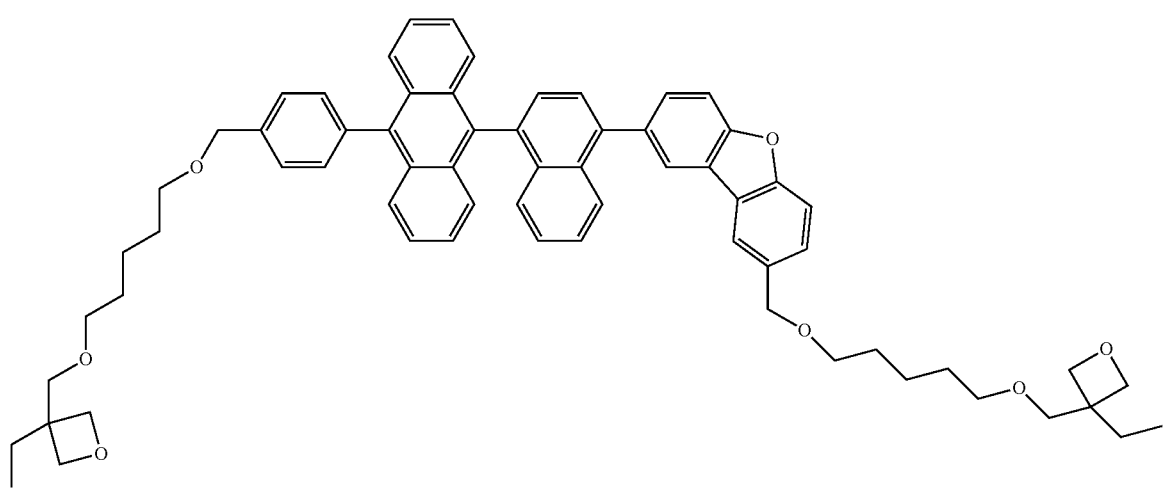
B128

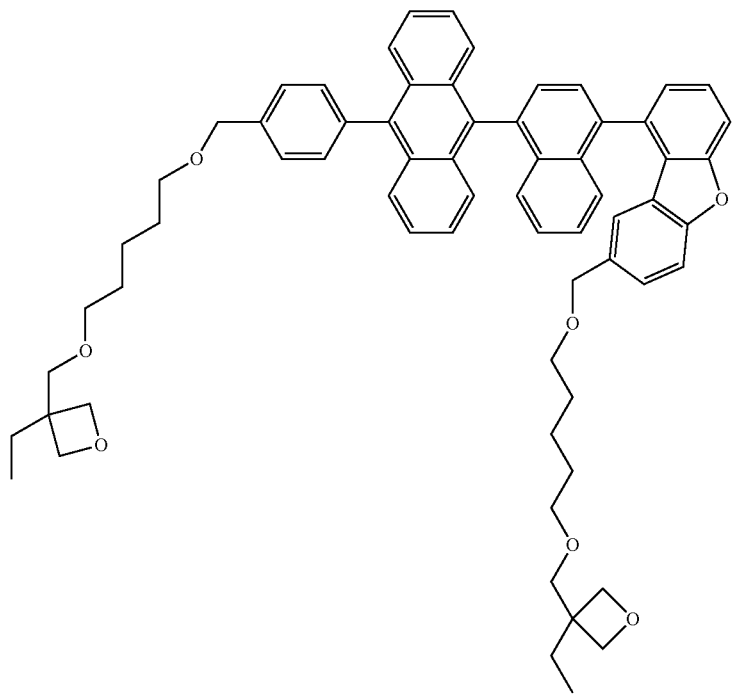
B129
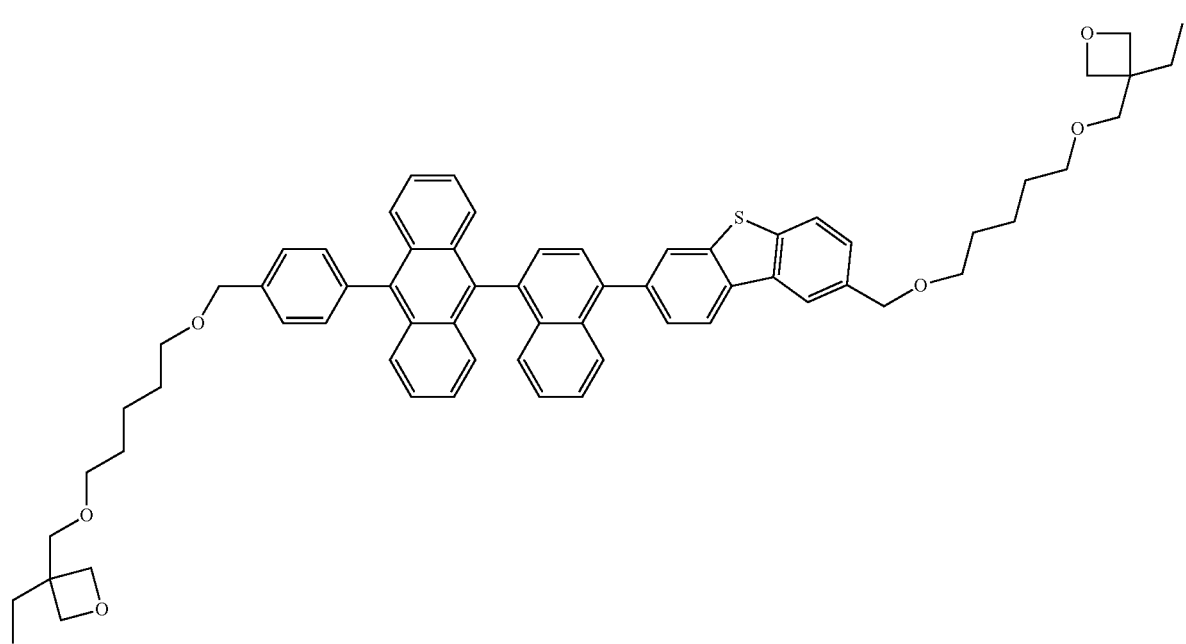
B130

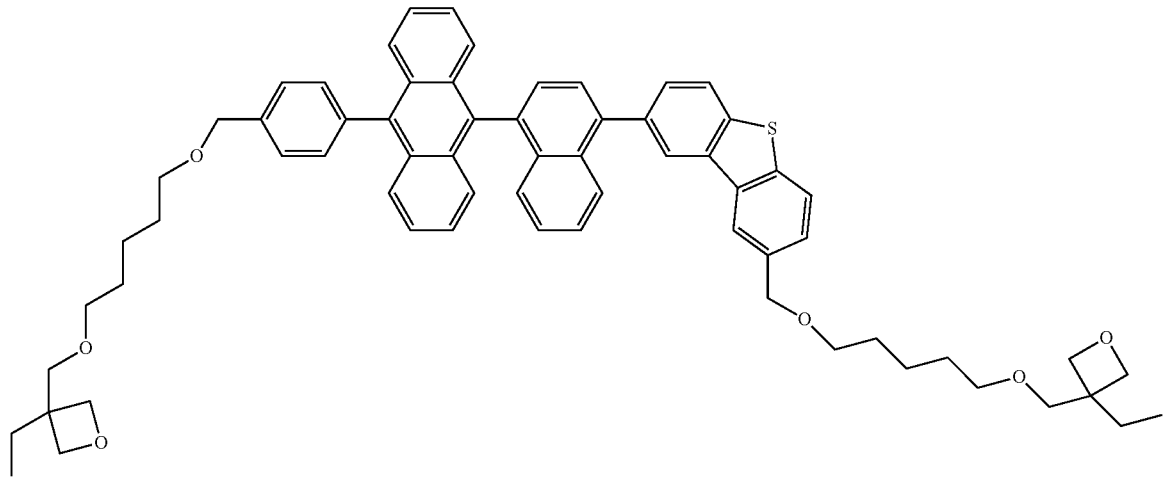

B131

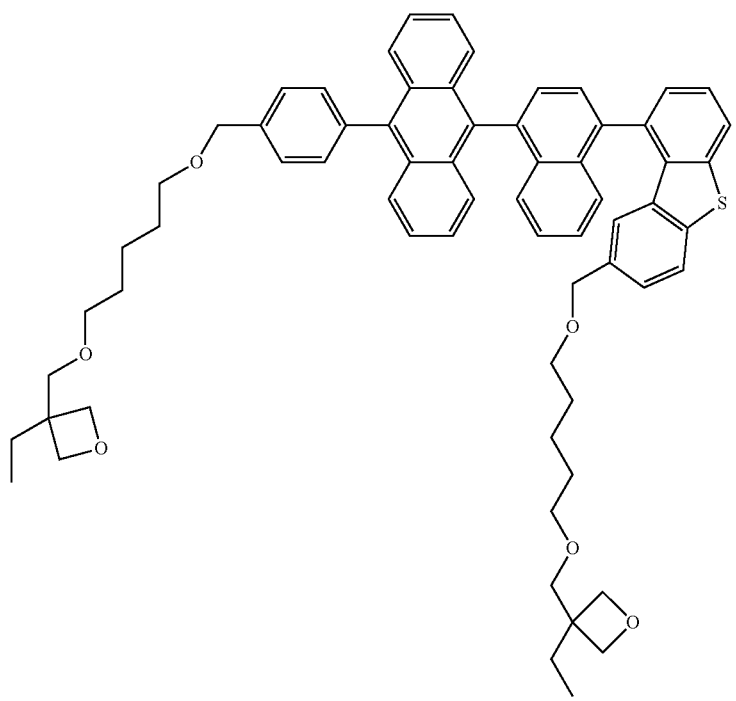

B132

In an exemplary embodiment where the composition for forming an organic film includes the compounds of Formulae B-1 through B-23, the composition for forming the organic film may further include a compound of Formula C-1 below.

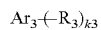

Formula C-1

In Formula C-1, $Ar_3$, which forms the basic skeleton, is a divalent, trivalent or tetravalent aromatic group. For example, $Ar_3$ may be

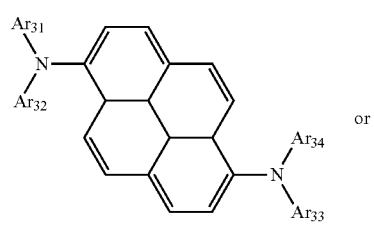

or

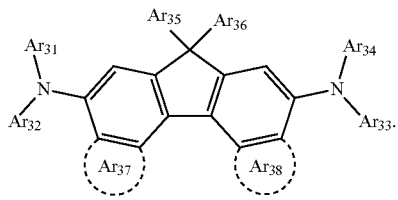

$Ar_{31}$, $Ar_{32}$, $Ar_{33}$, $Ar_{34}$, $Ar_{35}$, $Ar_{36}$, $Ar_{37}$, and $Ar_{38}$ have already been described above in connection with Formula 1, and detailed descriptions thereof will not be repeated.

If $Ar_{31}$, $Ar_{32}$, $Ar_{33}$, and $Ar_{34}$ are divalent arylene or heteroarylene groups, $R_3$ may be bonded thereto. The substituent $R_3$ may be a photo-polymerizable reacting group. For example, $R_3$ may be

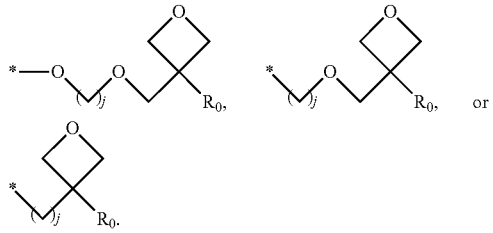

$R_0$ and j have already been described above in connection with Formula 1, and detailed descriptions thereof will not be repeated.

k3 may define the number of substituents $R_3$ bonded to $Ar_3$. For example, k3 may be an integer between 2 and 4.

$Ar_{35}$ and $Ar_{36}$ may form a ring together. $Ar_{37}$ and $Ar_{38}$ are each independently a substituted or unsubstituted $C_{6-20}$ fused ring which may be bonded to an adjacent benzene ring by sharing two or more carbon atoms.

In a non-limiting example, the compound of Formula C-1 may be a compound of any one of Formulae C-2 through C-16 below.

Formula C-2

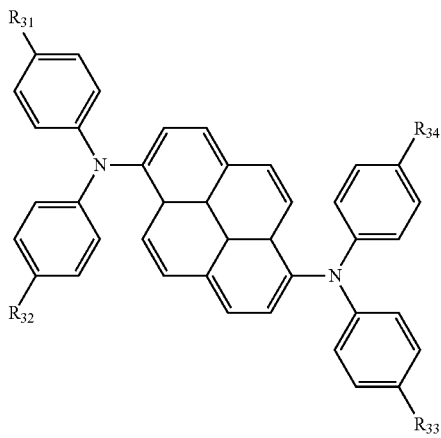

Formula C-3

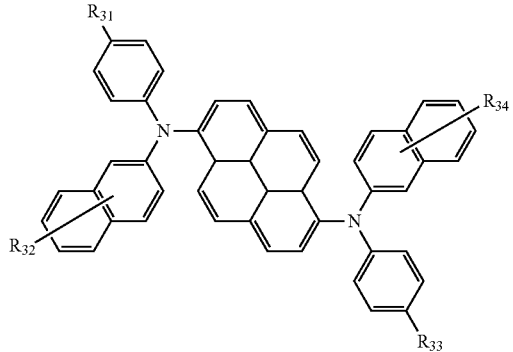

Formula C-4

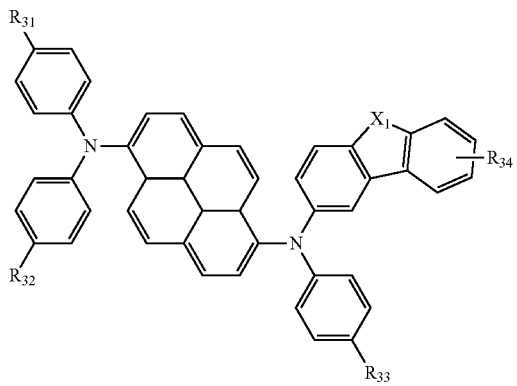

Formula C-5

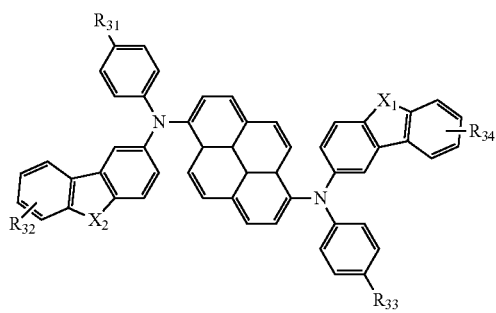

Formula C-6

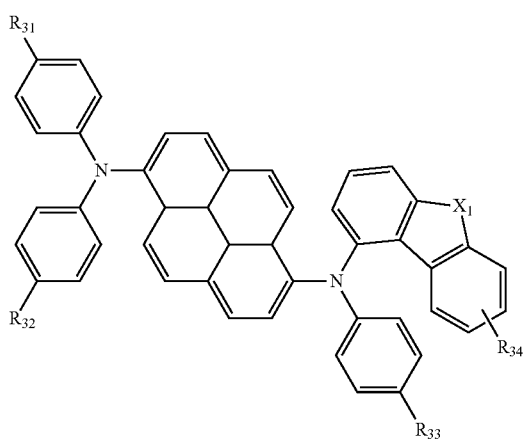

Formula C-7
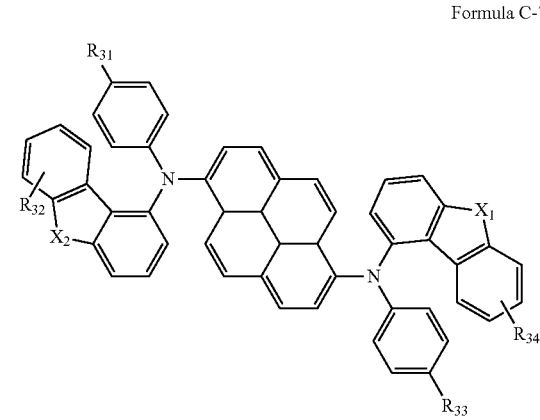
Formula C-8
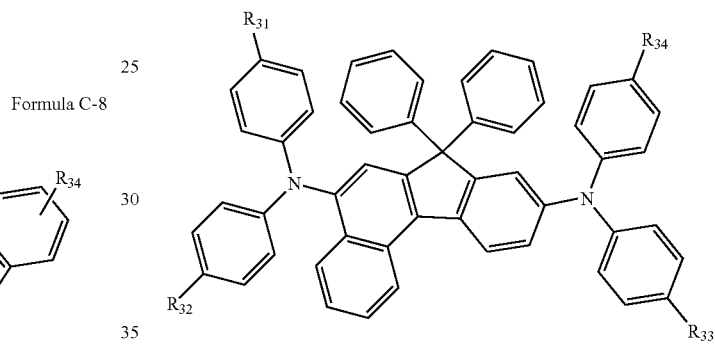
Formula C-9
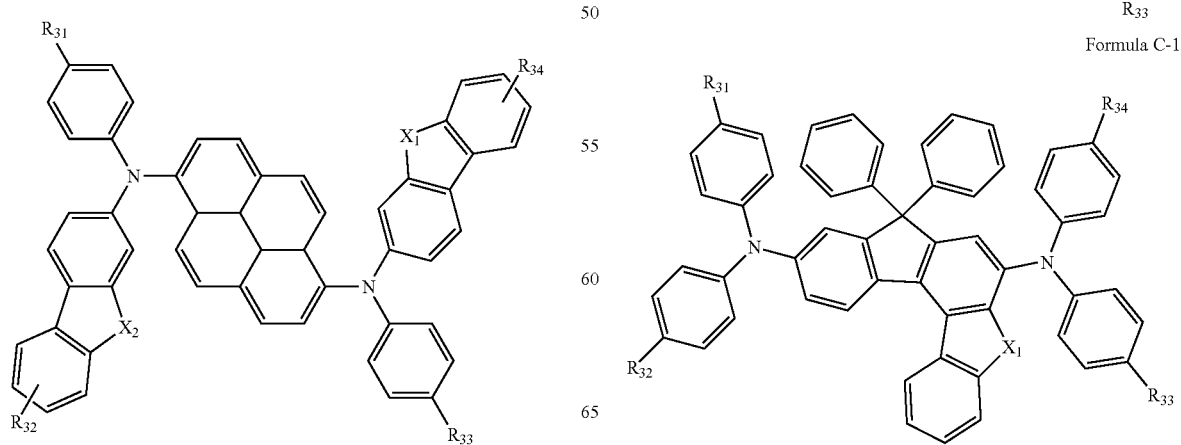
Formula C-10
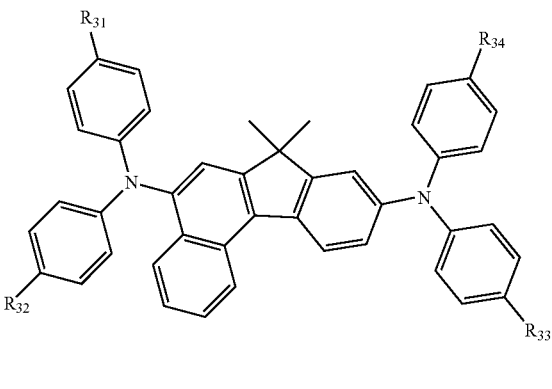
Formula C-11
Formula C-12
Formula C-13

-continued

Formula C-14

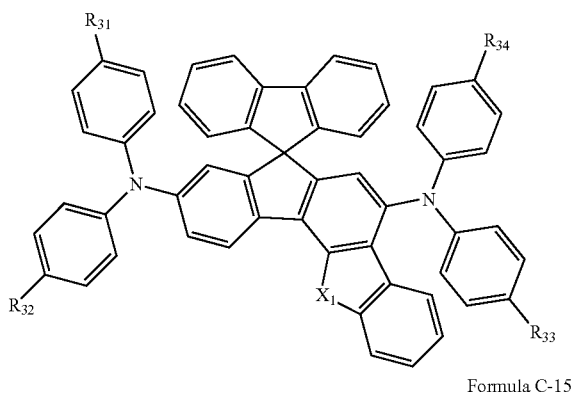

Formula C-15

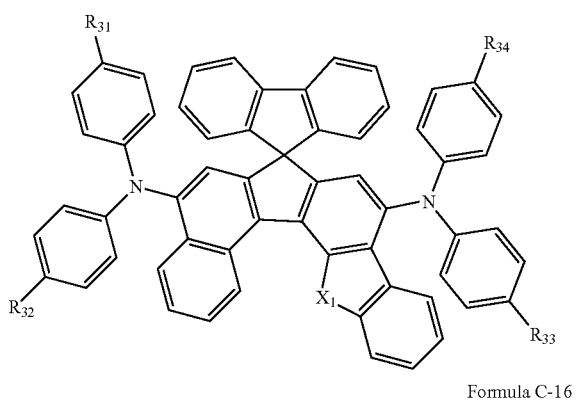

Formula C-16

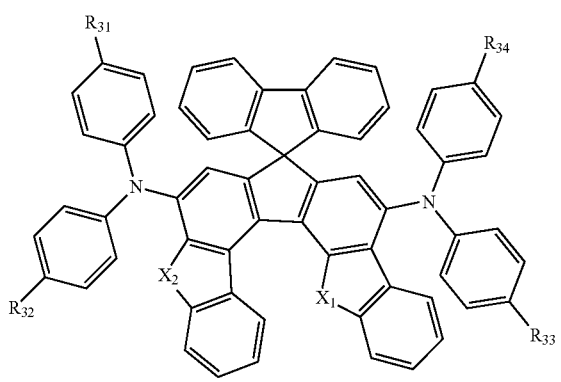

In Formulae C-2 through C-16, $R_{31}$, $R_{32}$, $R_{33}$, and $R_{34}$ may be each independently a hydrogen atom,

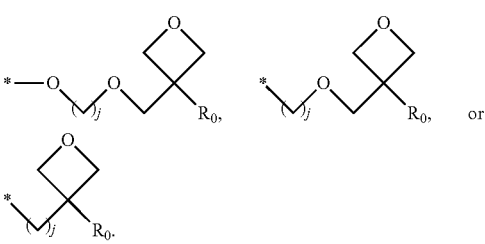

In a non-limiting example, two or more of $R_{31}$, $R_{32}$, $R_{33}$, and $R_{34}$ of Formulae C-2 through C-16 may be each independently

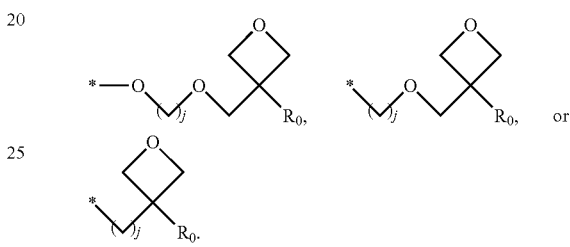

in which case, the compounds of Formulae C-2 through C-16 may exhibit insolubility to the developer, which will be described in more detail later. $R_{31}$, $R_{32}$, $R_{33}$, and $R_{34}$ bonded to the benzene ring may be bonded to a carbon atom facing (i.e., in the para position to) the carbon atom bonded to the nitrogen atom. As a result, an anisotropic transition dipole can be allocated.

$R_0$ and j have already been described above in connection with Formula 1, and detailed descriptions thereof will not be repeated.

In Formulae C-4 through C-9 and C-13 through C-16, $X_1$ and $X_2$ are each independently an oxygen atom or a sulfur atom.

The compounds of Formulae C-1 through C-16 and polymers thereof may be utilized as a dopant material for a blue light-emitting material (e.g., a blue light-emitting layer).

The compounds of Formulae C-1 through C-16 may be, but are not limited to, compounds shown below.

C101

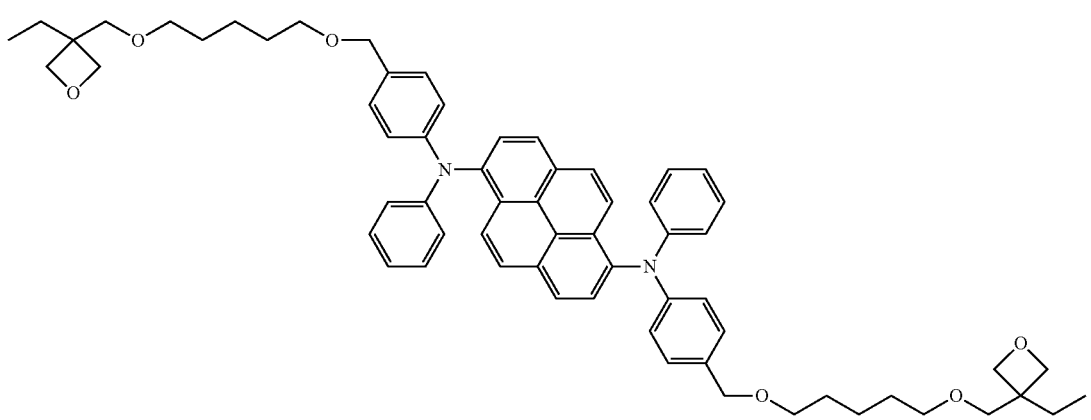

-continued
C102
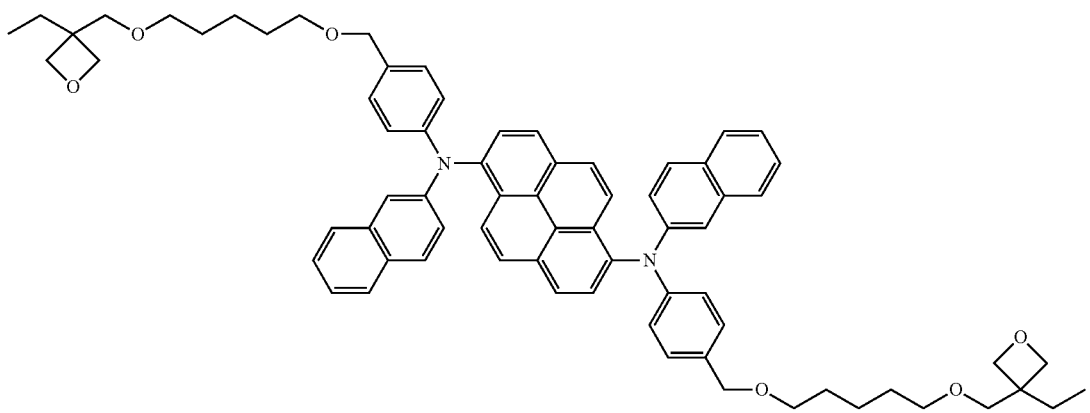
C103
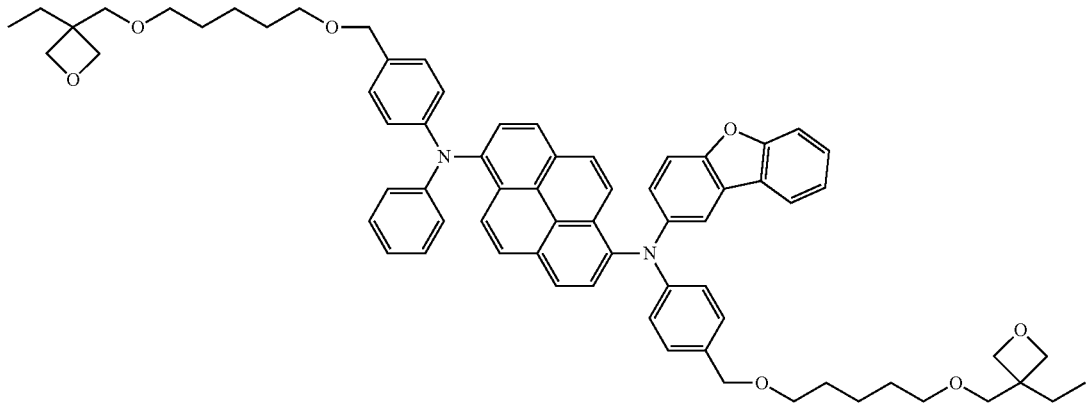
C104
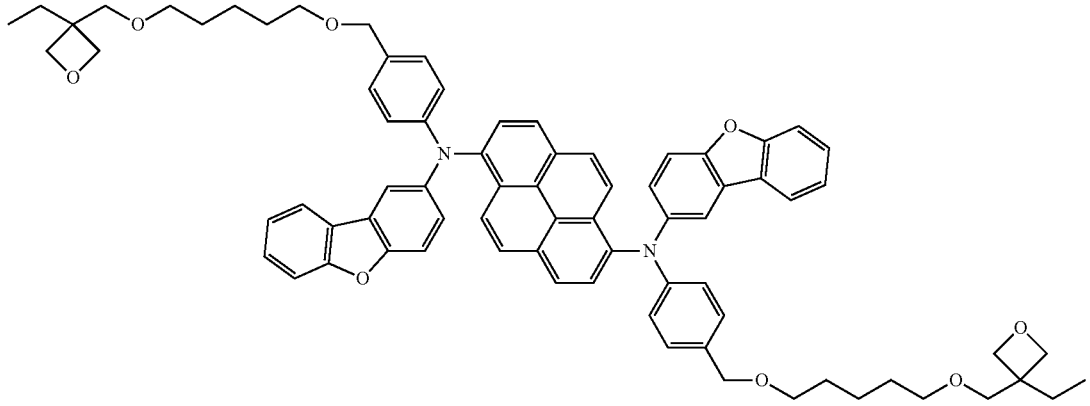
C105
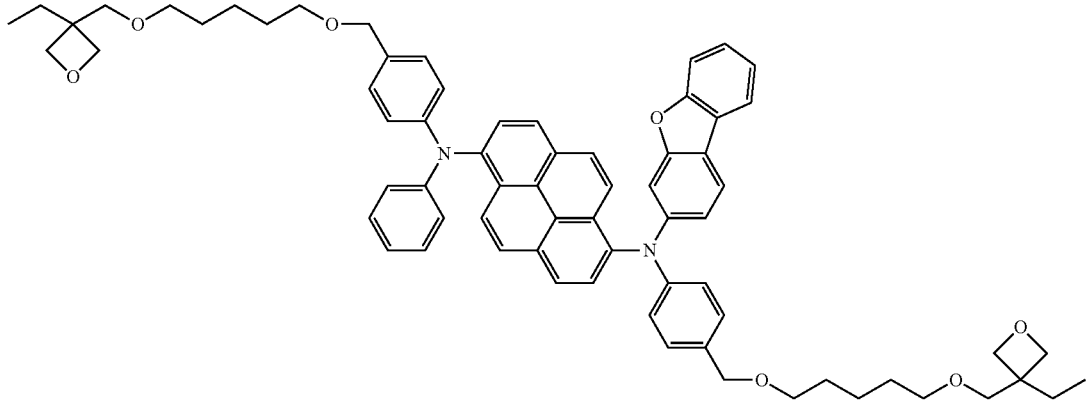

-continued
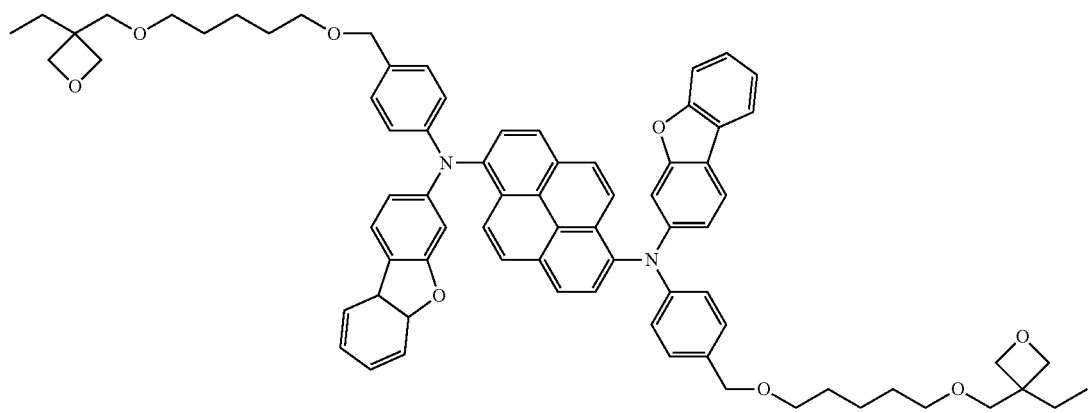
C106
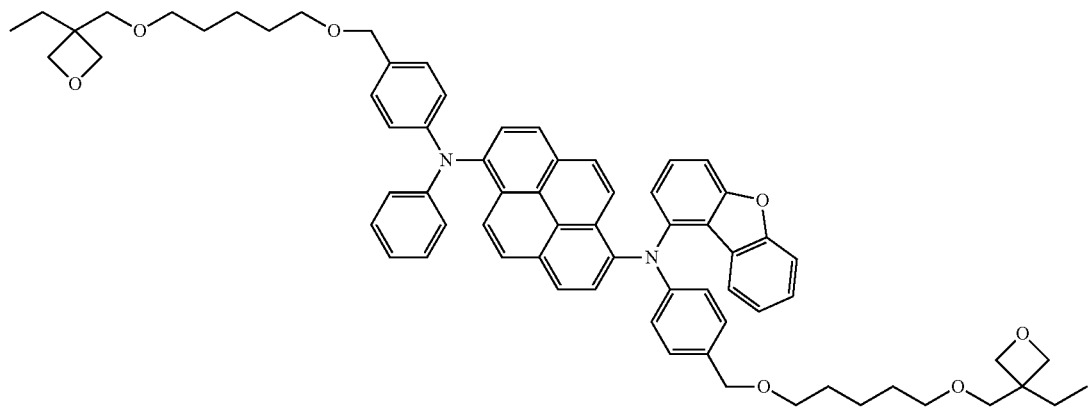
C107
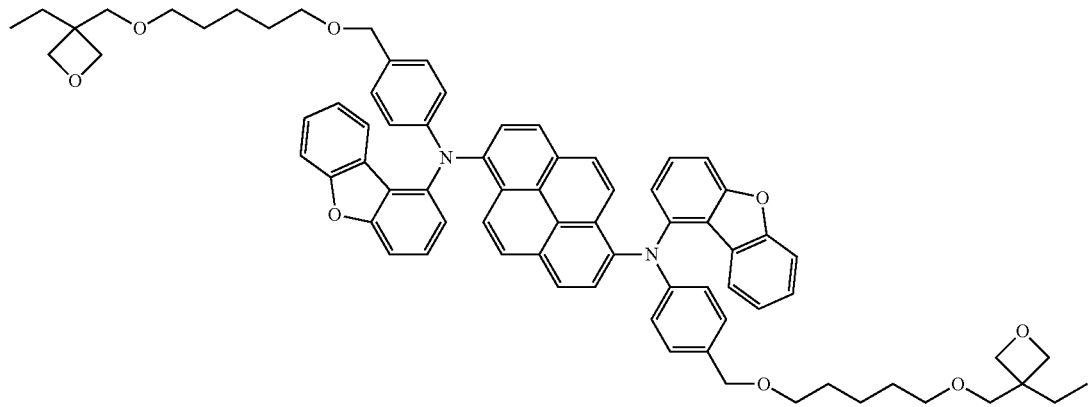
C108
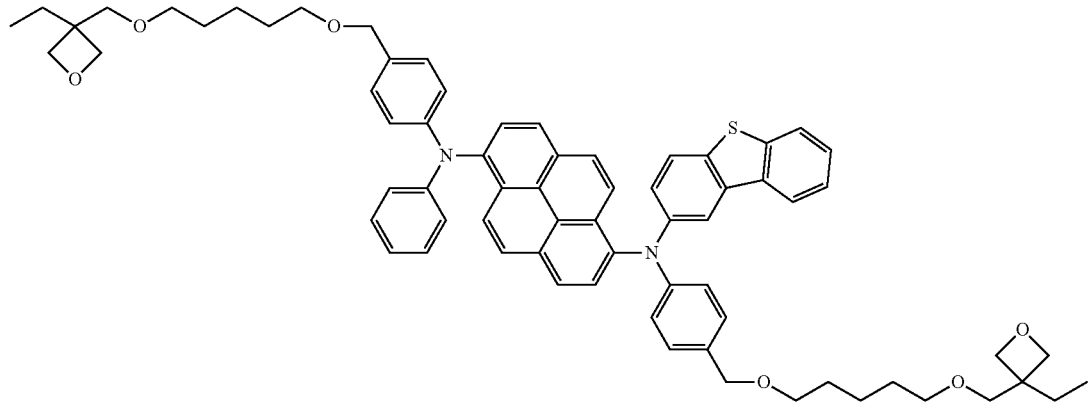
C109

-continued
C110
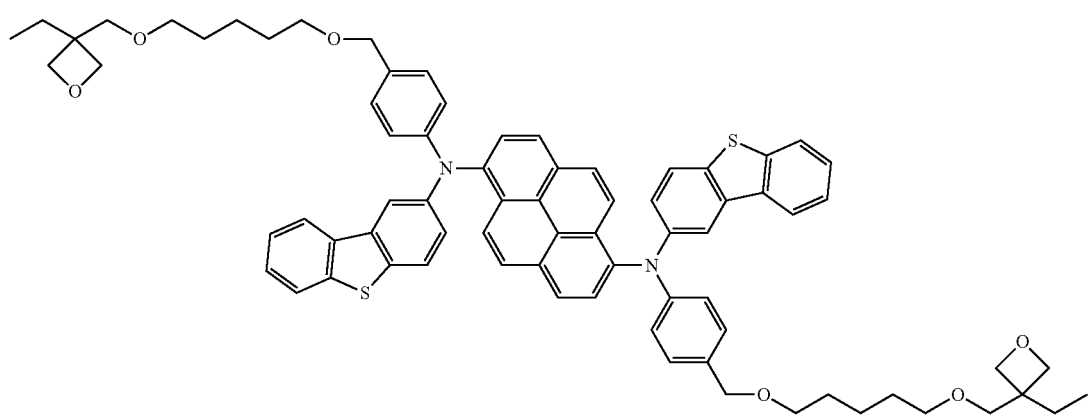
C111
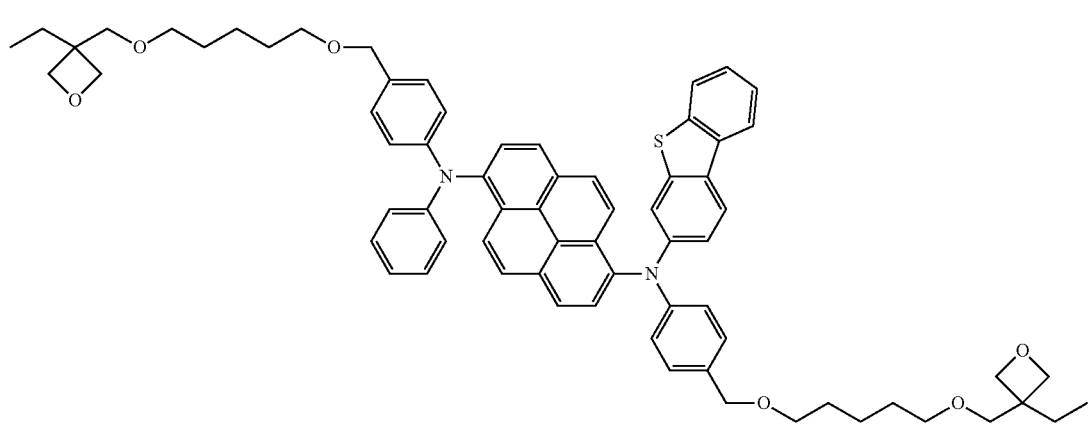
C112
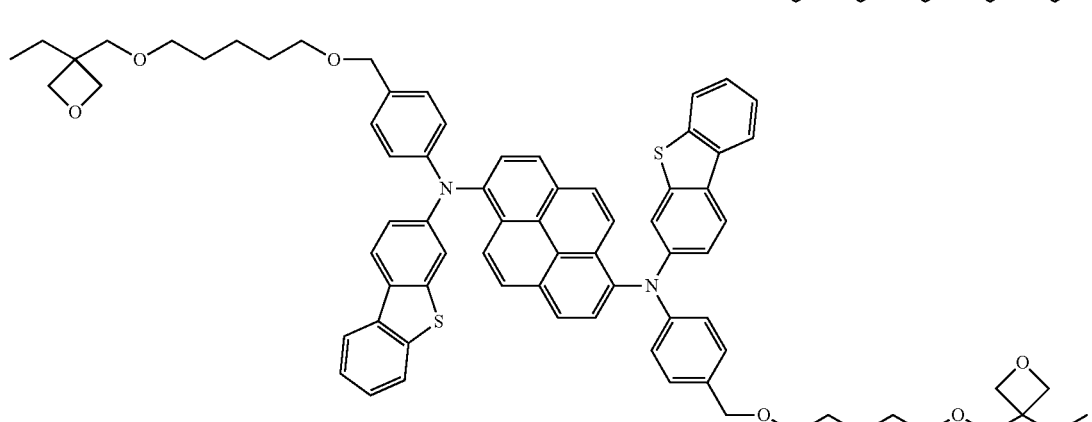
C113
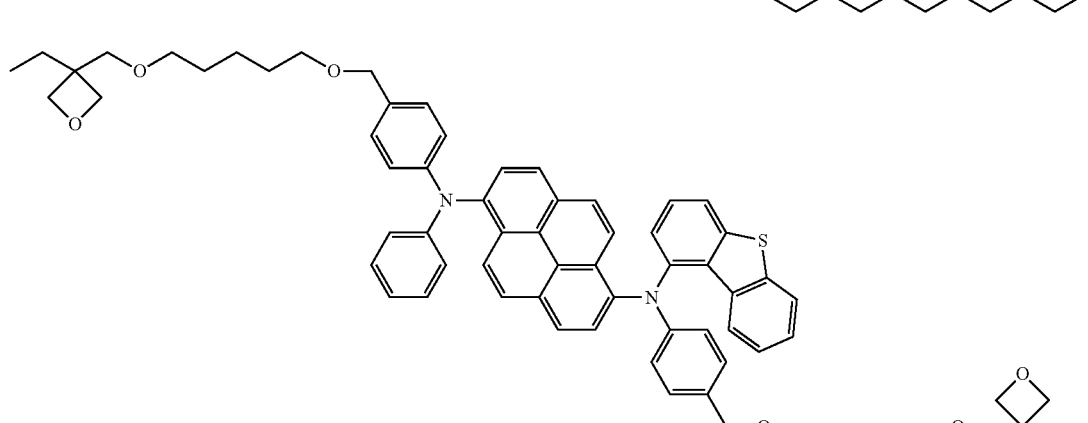

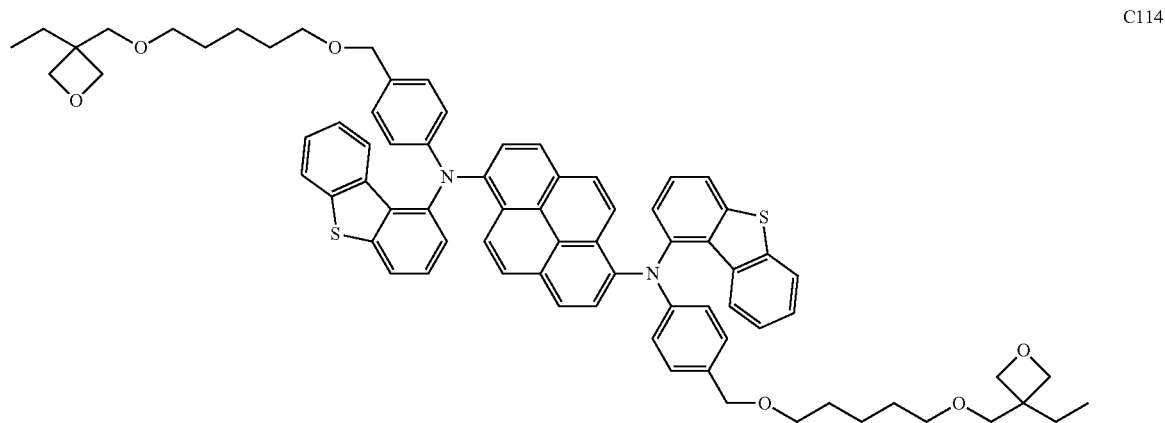
C114
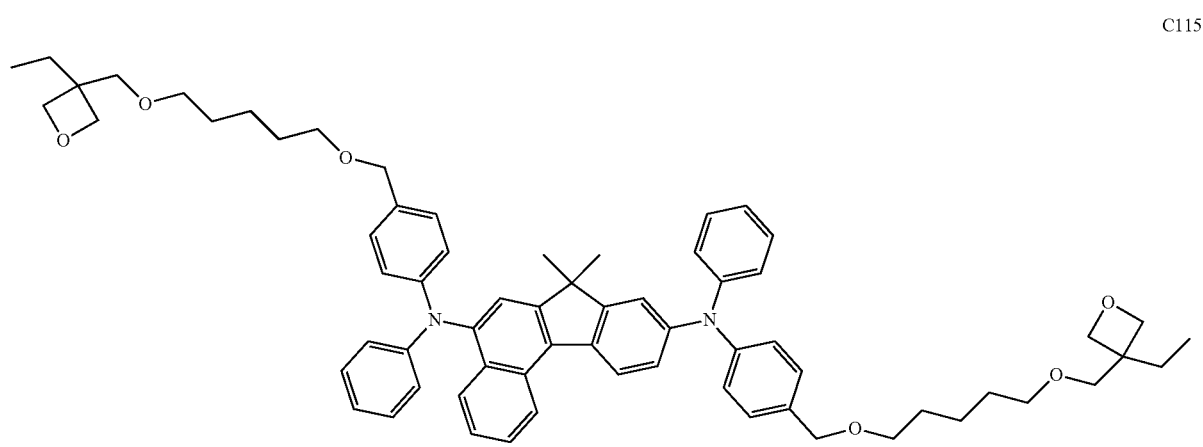
C115
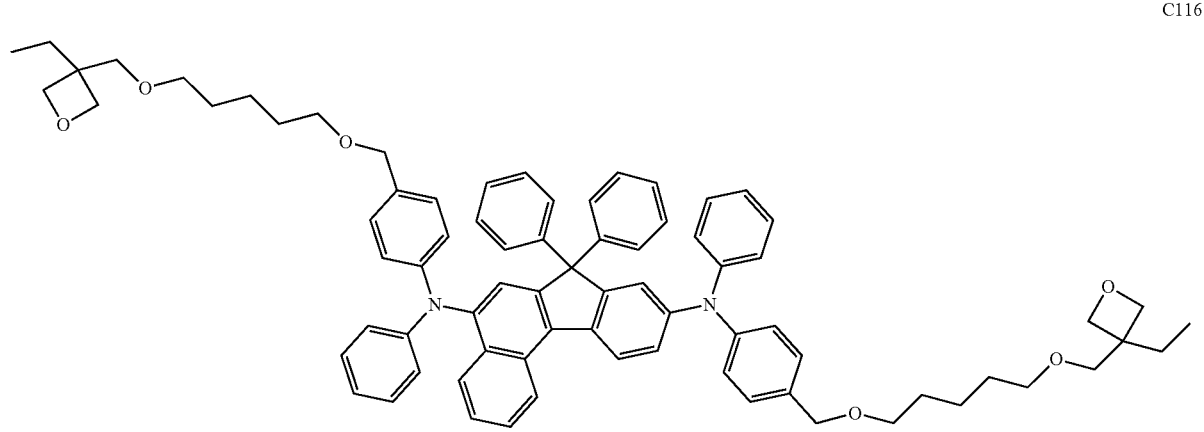
C116

C117
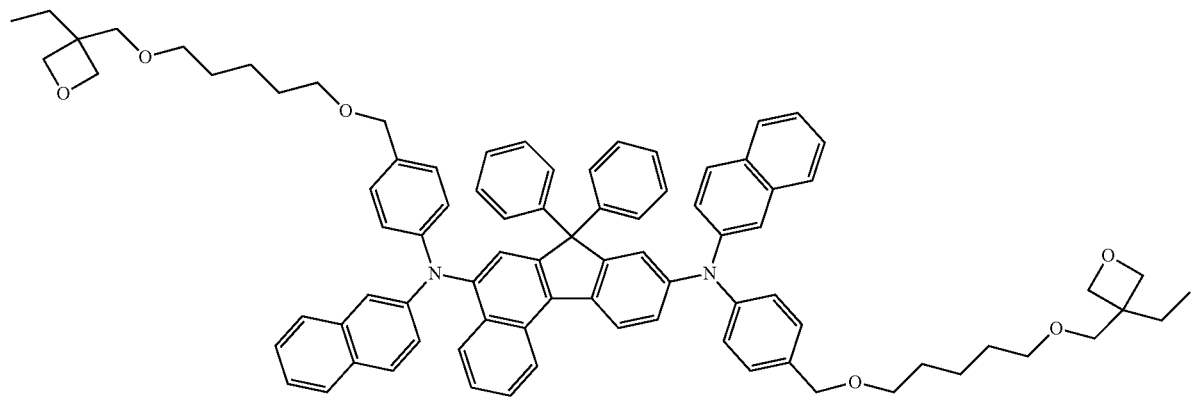
C118
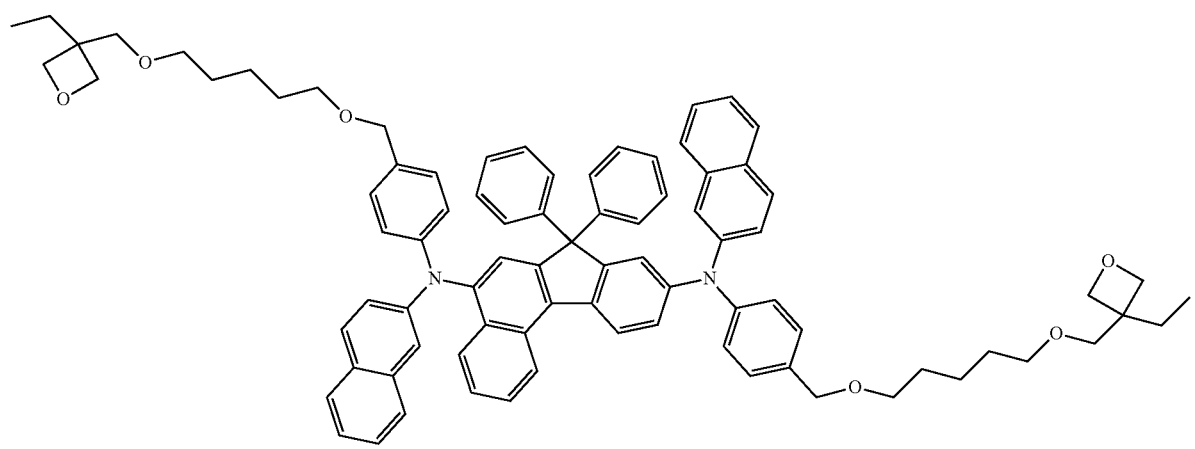
C119
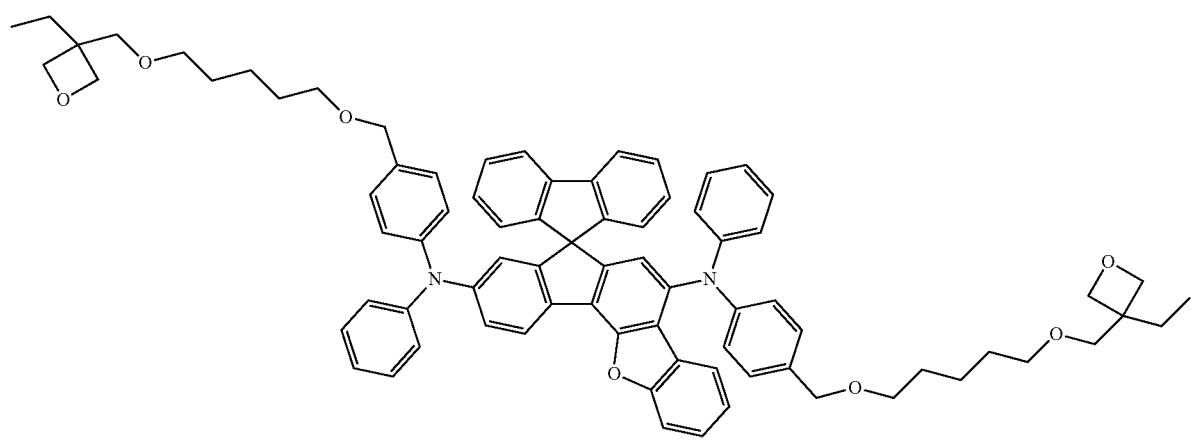

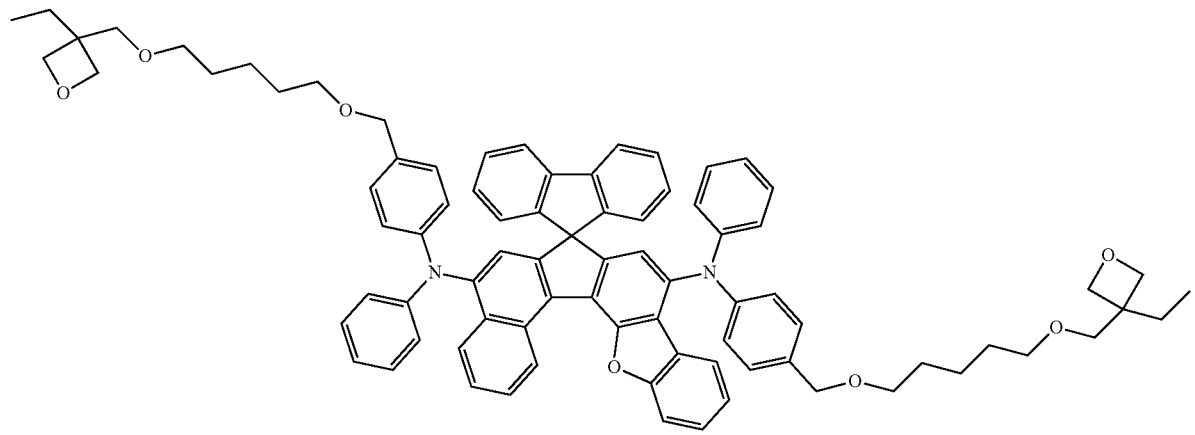
C120
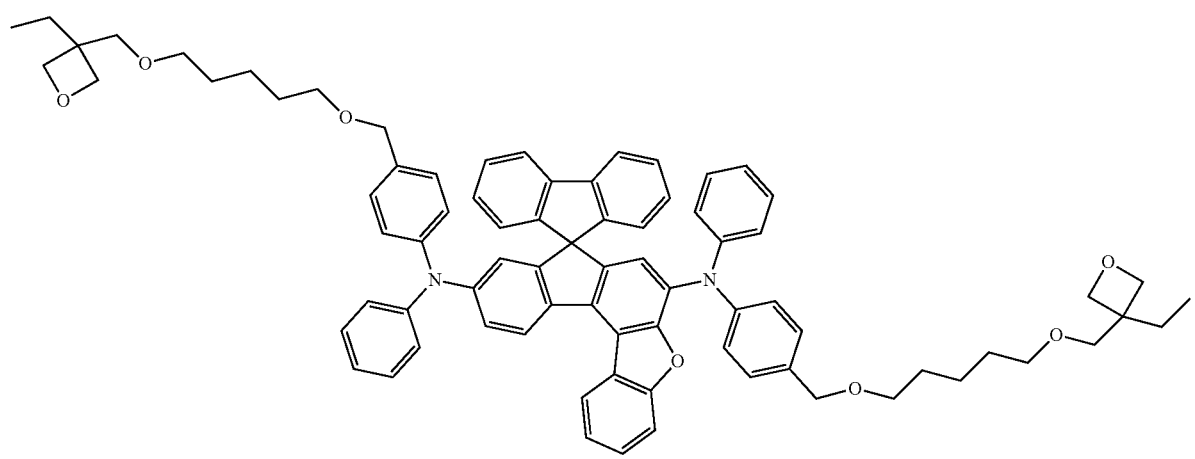
C121
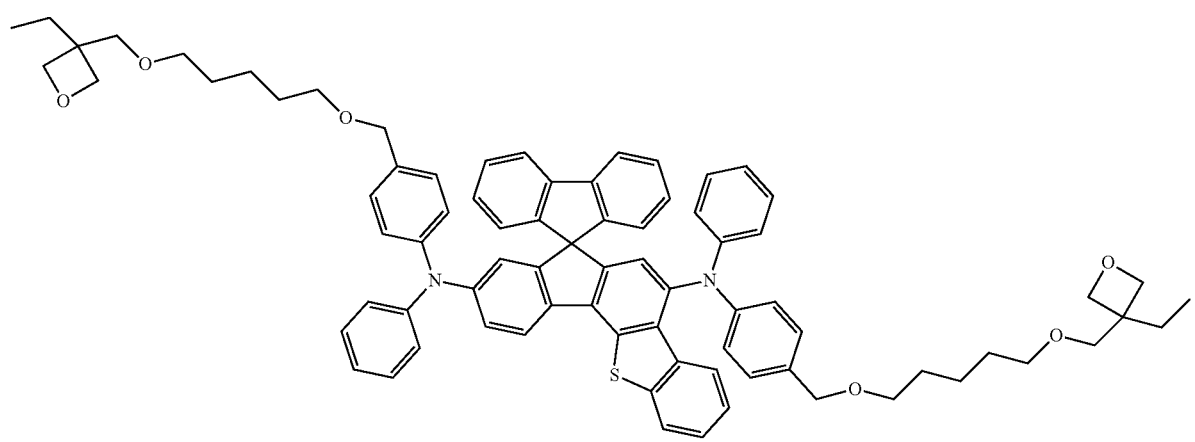
C122

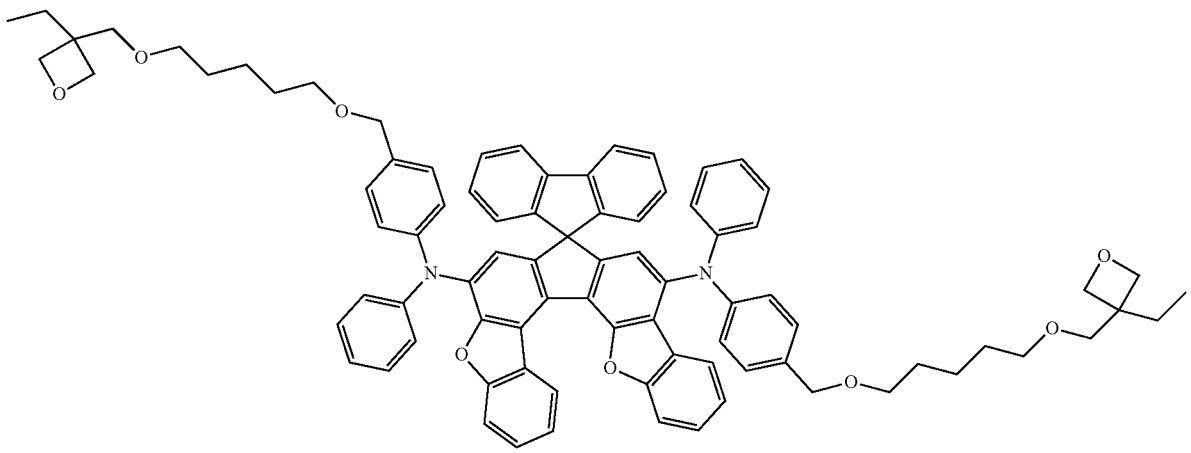

C123

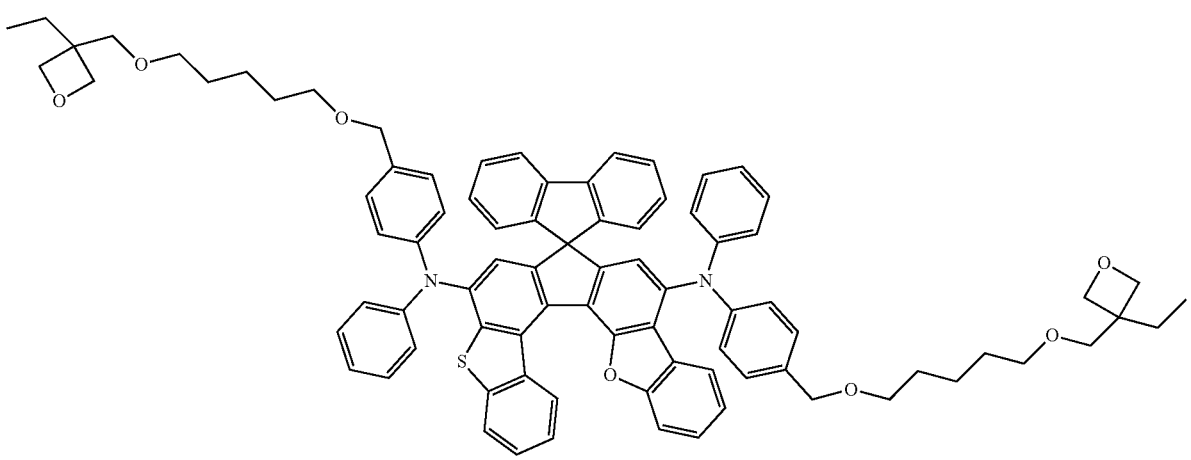

C124

The compounds of Formulae B-1 through B-23 and C-1 through C-16 and polymers thereof may emit blue light.

In another exemplary embodiment, the composition for forming an organic film may include the compound of Formula 1, and the compound of Formula 1 may be a compound of Formula D-1 below.

$R_4$—$Ar_4$—$R_4'$   Formula D-1

In Formula D-1, $Ar_4$, which forms the basic skeleton, is a divalent aromatic group. For example, $Ar_4$ may be

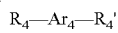

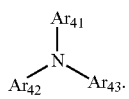

$Ar_{41}$, $Ar_{42}$, and $A_{43}$ have already been described above in connection with Formula 1, and detailed descriptions thereof will not be repeated.

$Ar_{41}$ and $Ar_{42}$ are each a divalent arylene or heteroarylene group and form a ring together. $R_4$ and $R_4'$ may be bonded to $Ar_{21}$ and $Ar_{22}$, respectively. The substituents $R_4$ and $R_4'$ may be photo-polymerizable reacting group. For example, $R_4$ and $R_4'$ may be each independently

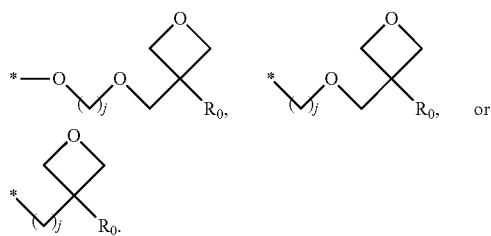

$R_0$ and j have already been described above in connection with Formula 1, and detailed descriptions thereof will not be repeated.

In a non-limiting example, the compound of Formula D-1 may be a compound of any one of Formulae D-2 through D-16.

Formula D-2
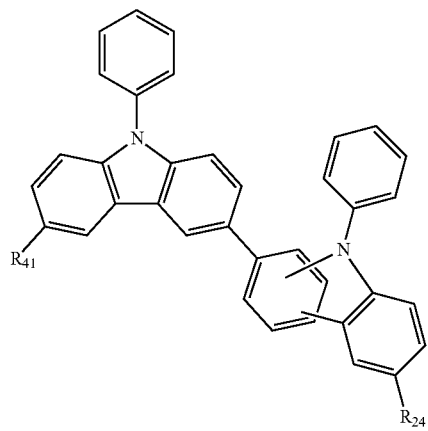
Formula D-3
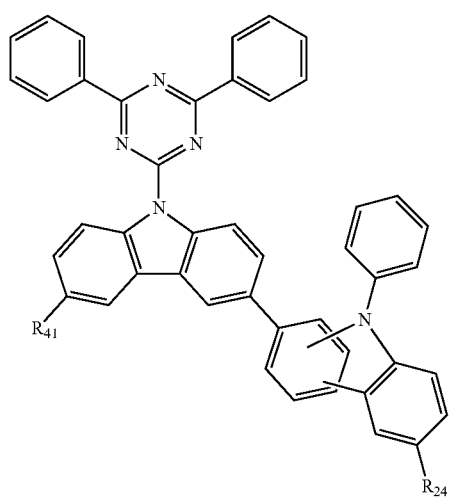
Formula D-4
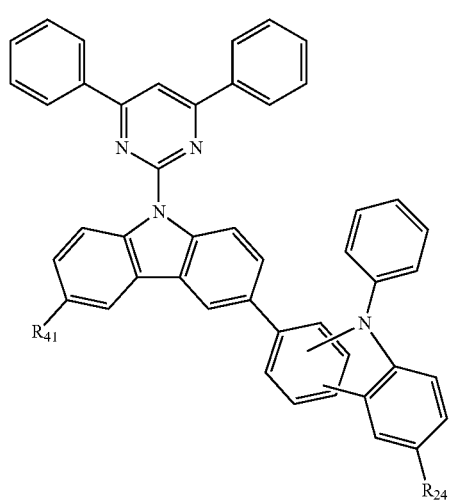
D-5
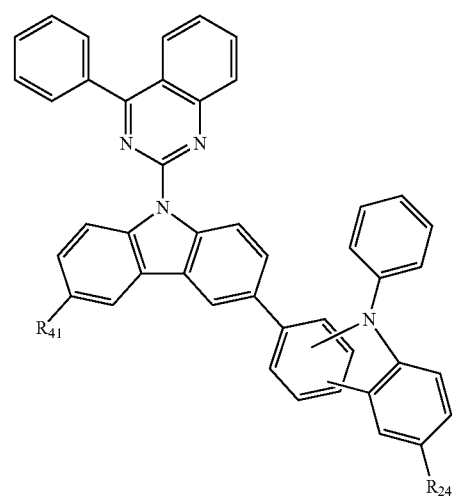
Formula D-6
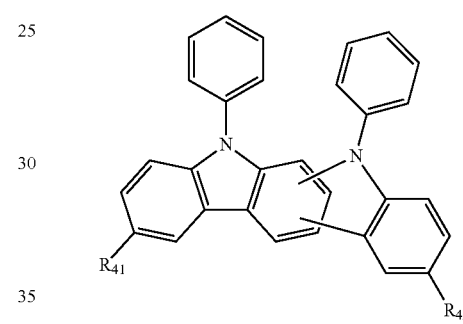
Formula D-7
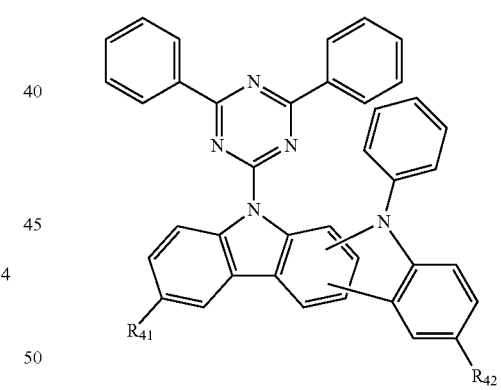
Formula D-8
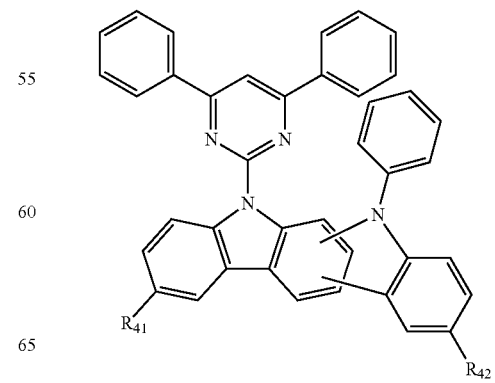

Formula D-9
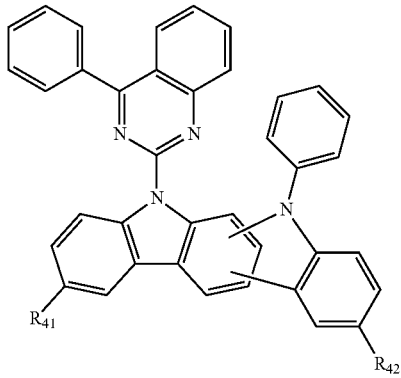
Formula D-10
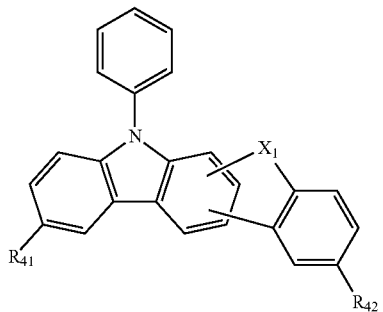
Formula D-11
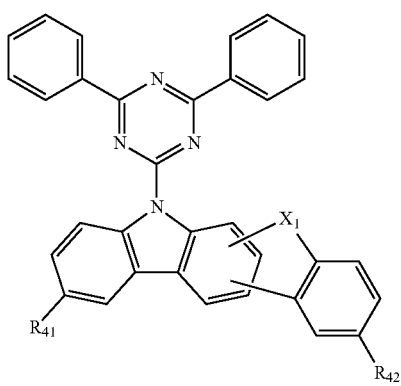
Formula D-12
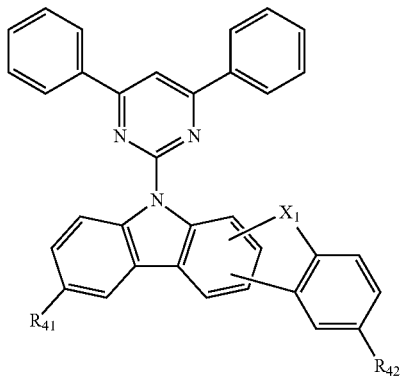
Formula D-13
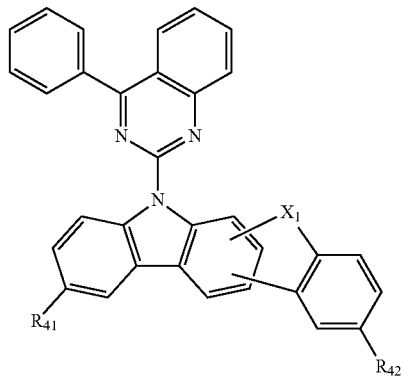
Formula D-14
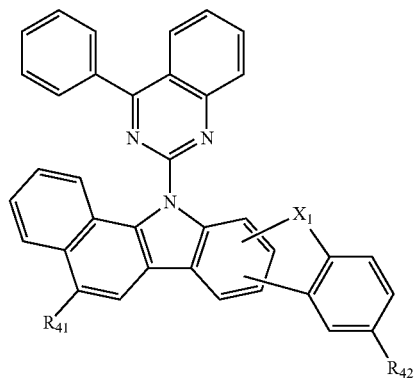
Formula D-15
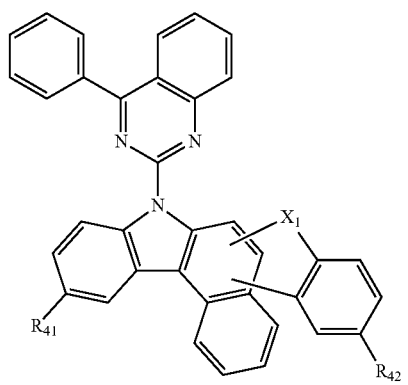
Formula D-16
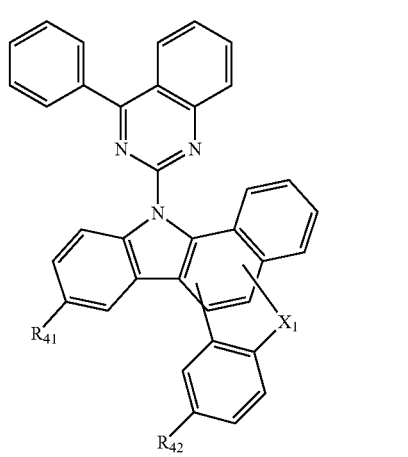

In Formulae D-2 through D-16, $R_{41}$ and $R_{42}$ may be each independently
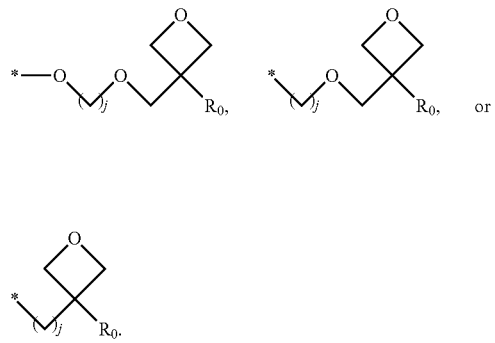
$R_0$ and j have already been described above in connection with Formula 1, and detailed descriptions thereof will not be repeated.
In Formulae D-10 through D-16, $X_1$ may be an oxygen atom or a sulfur atom.
The compounds of Formulae D-1 through D-16 may be, but are not limited to, compounds shown below.
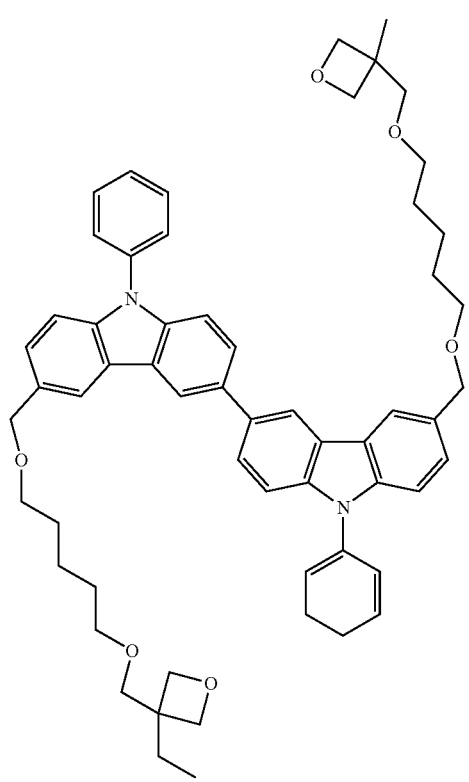
D101
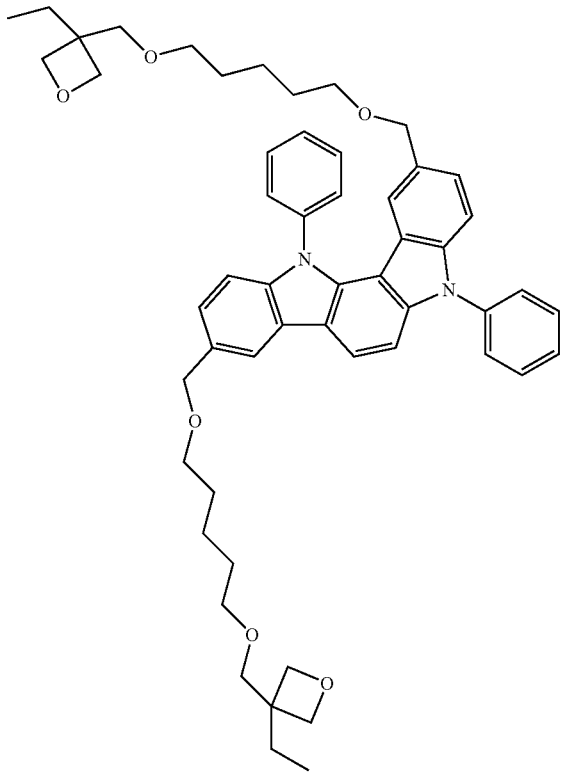
D102
D103

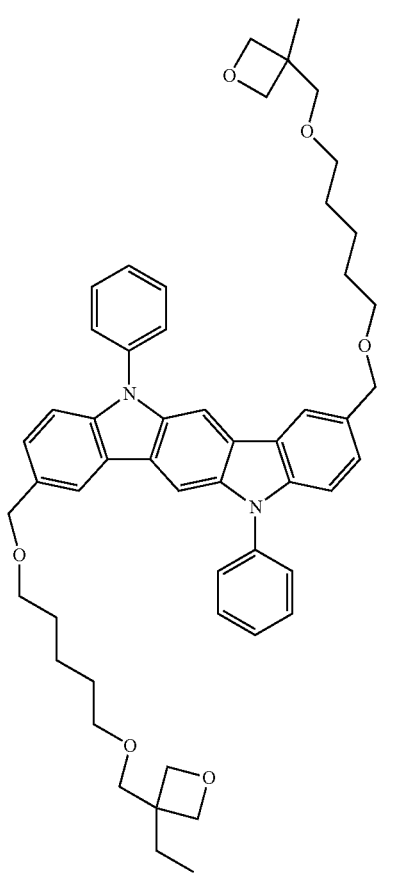
D104
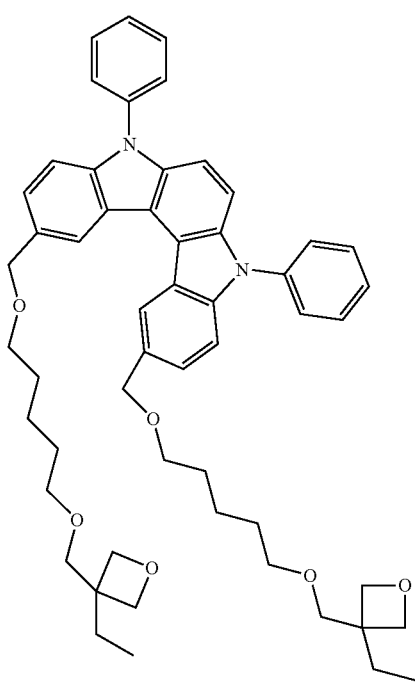
D105
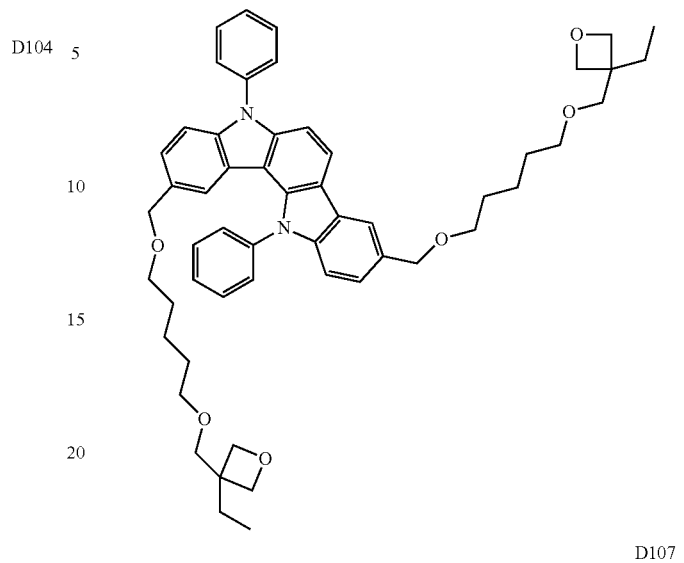
D106
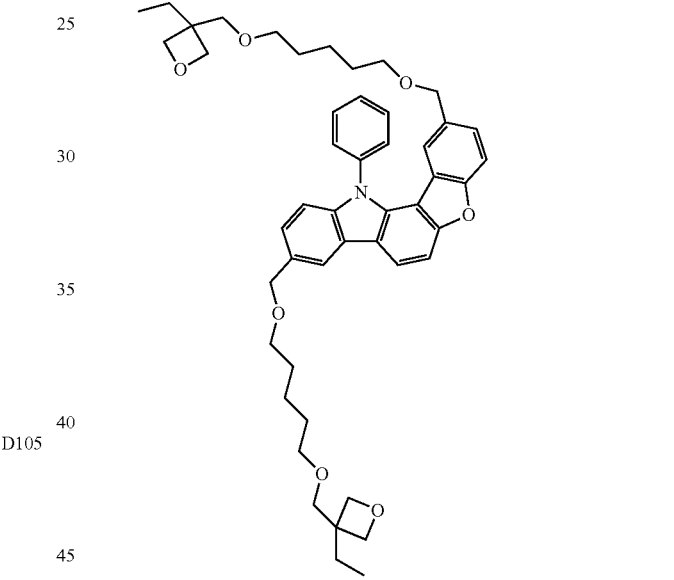
D107
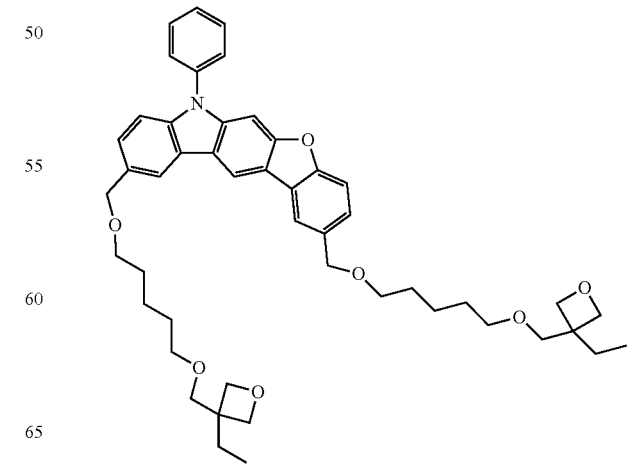
D108

119
-continued
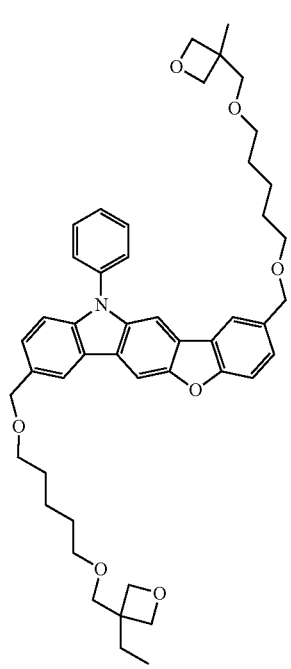
120
-continued
D109
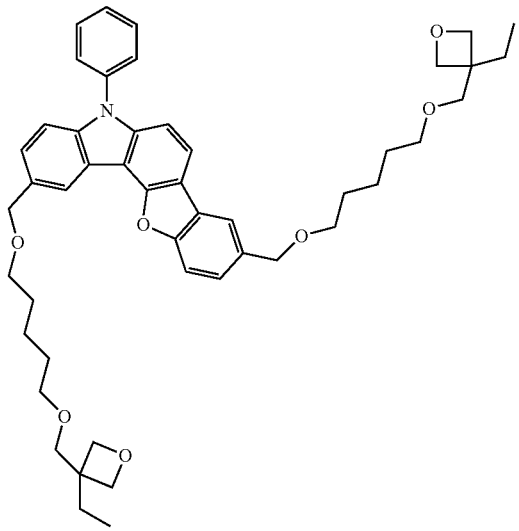
D111
D110
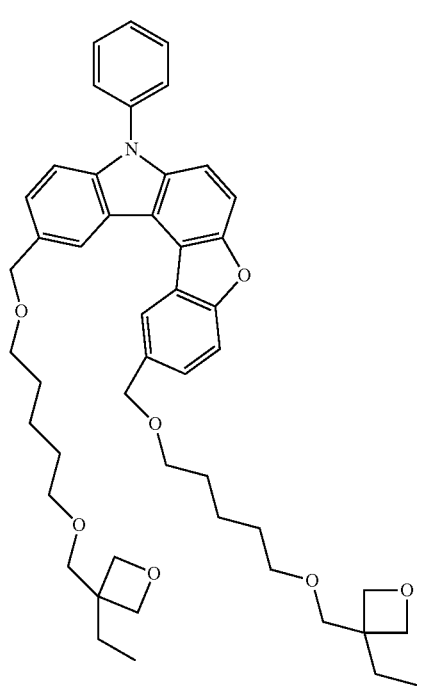
D112
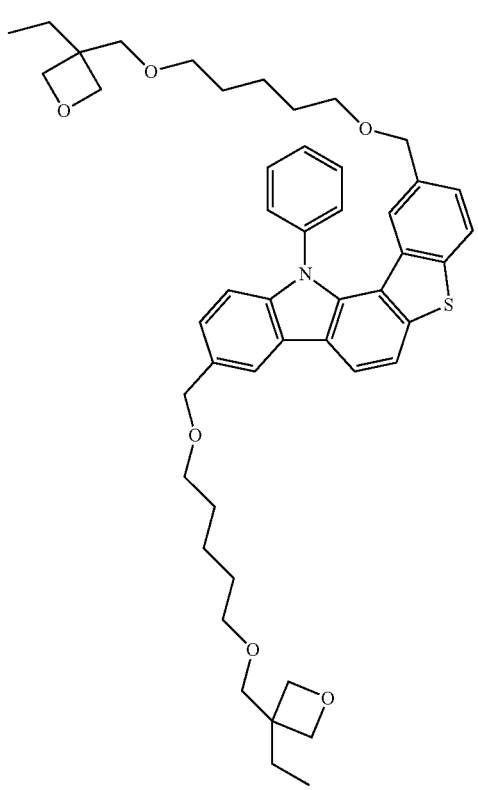

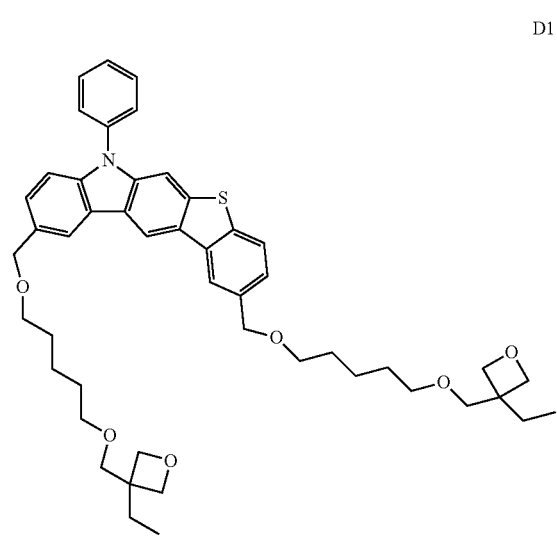
D113
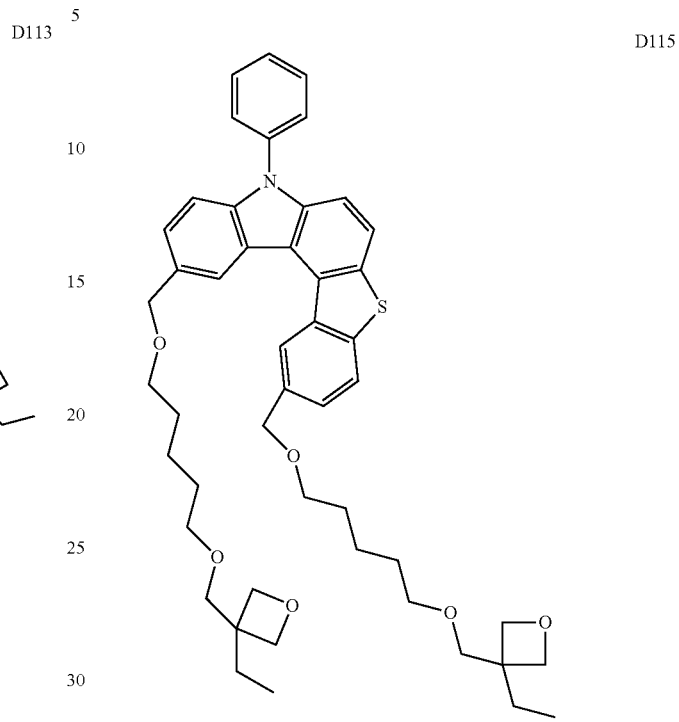
D115
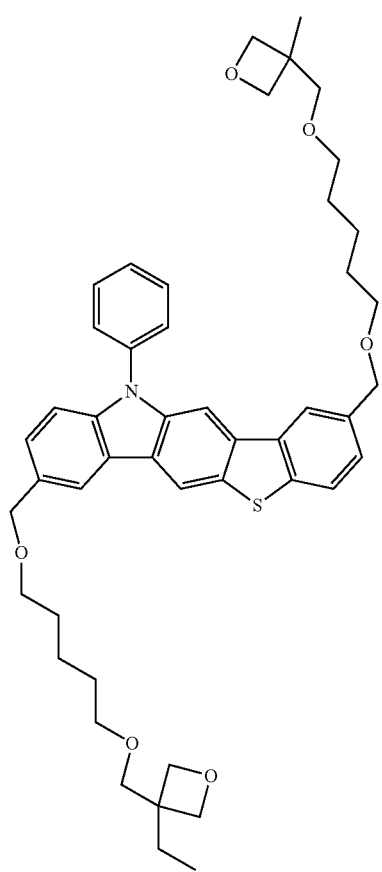
D114
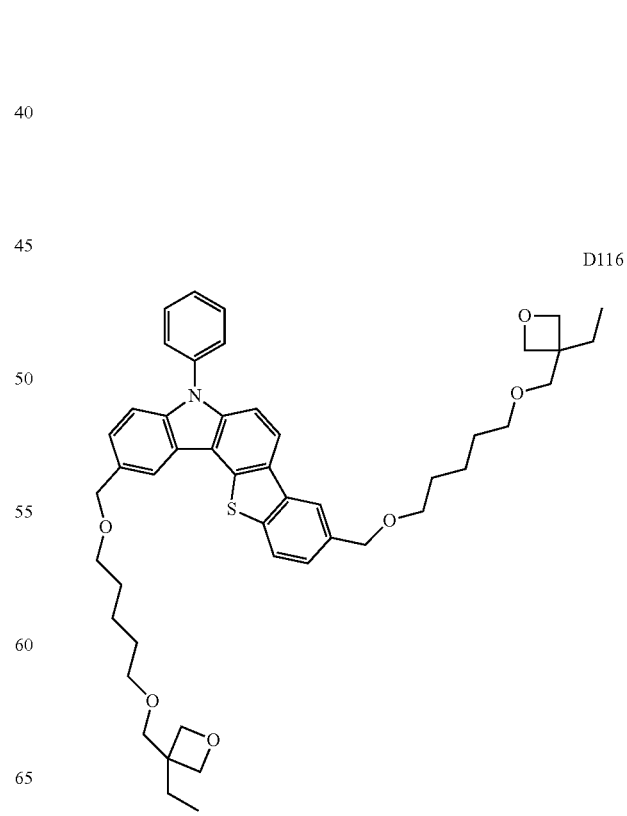
D116

123
-continued
124
-continued
D117
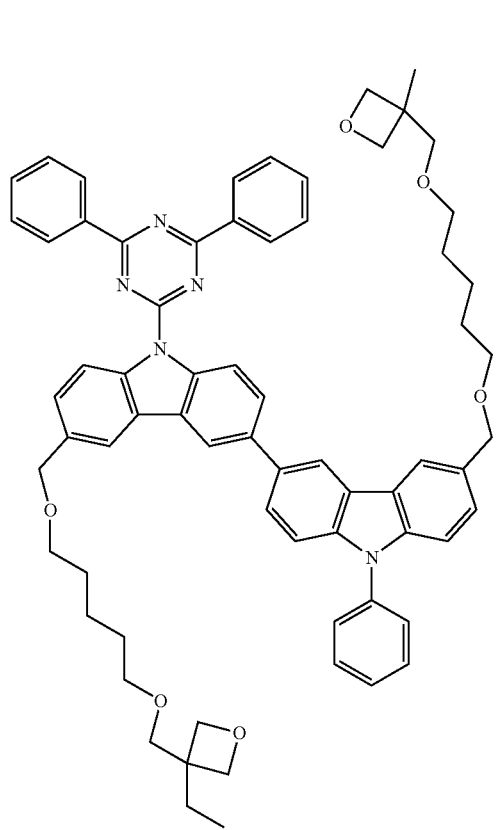
D119
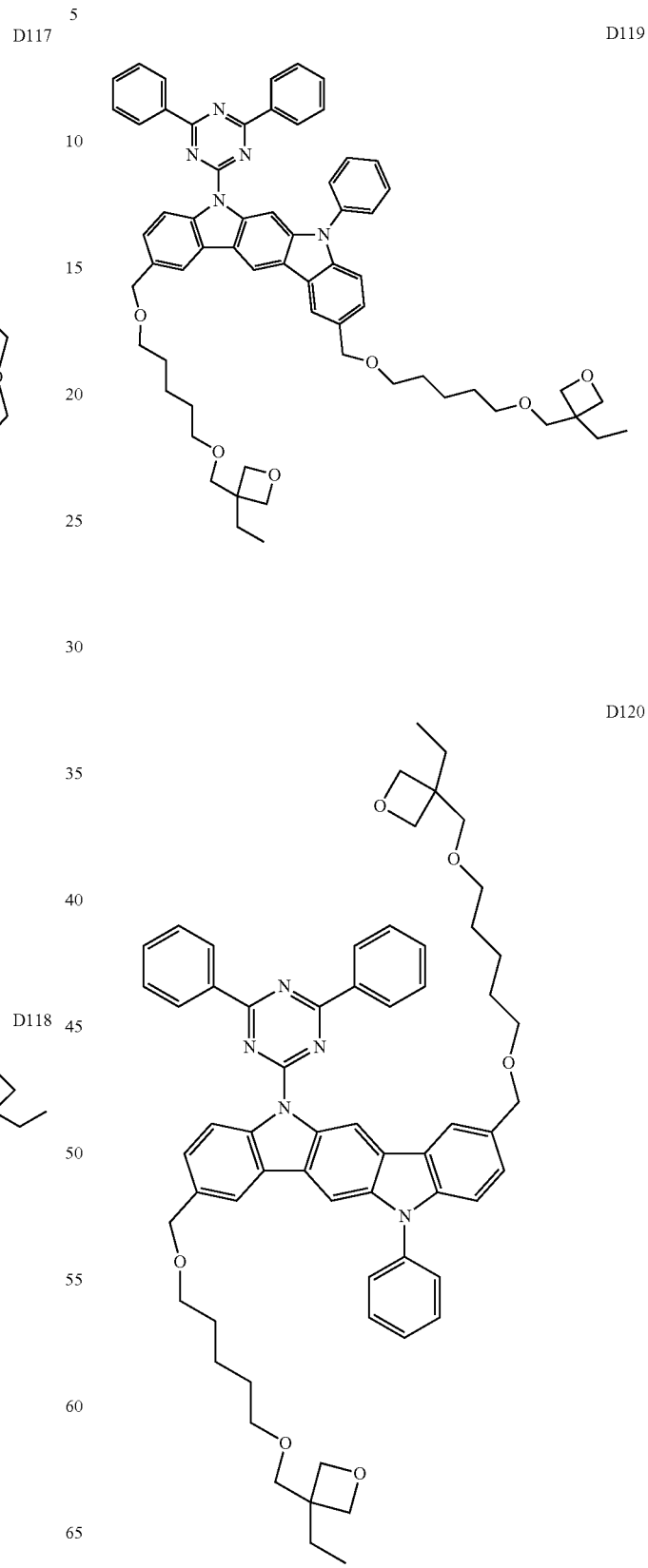
D118
D120

125
-continued
D121
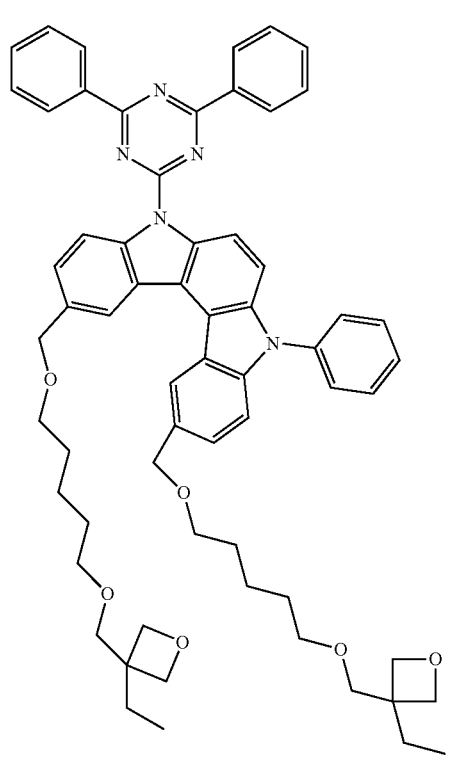
D122
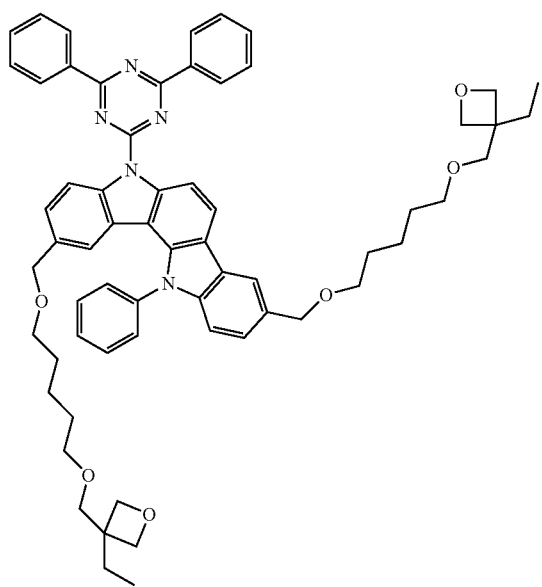
126
-continued
D123
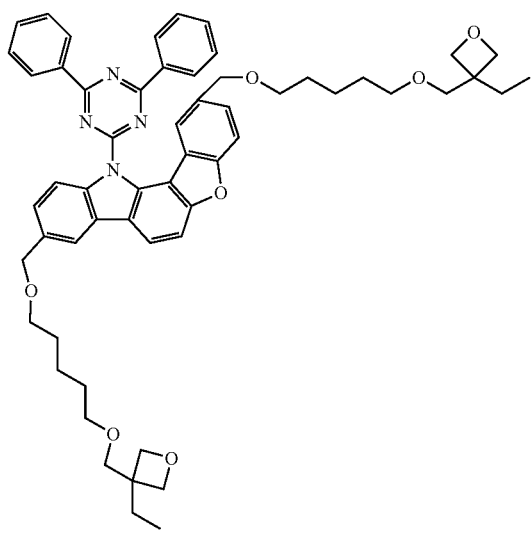
D124
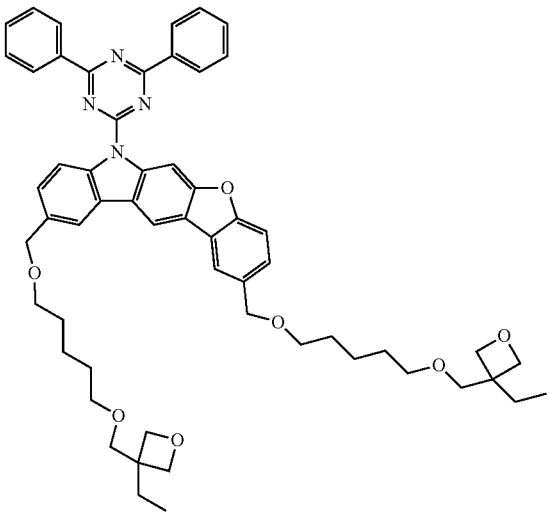

127
-continued
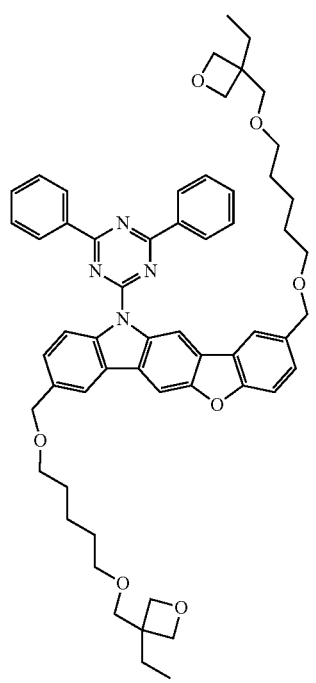
128
-continued
D125
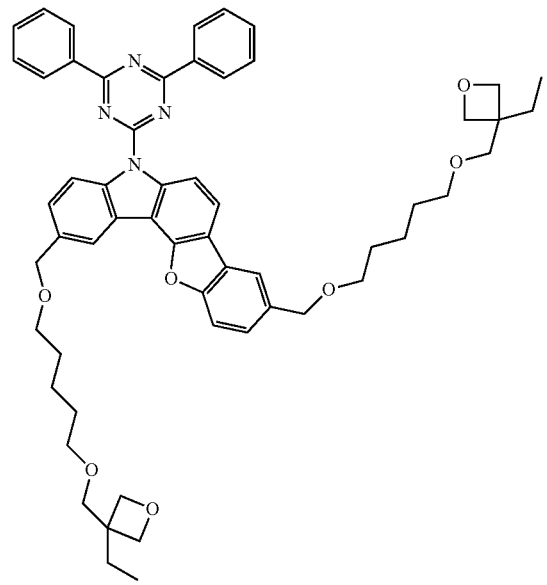
D126
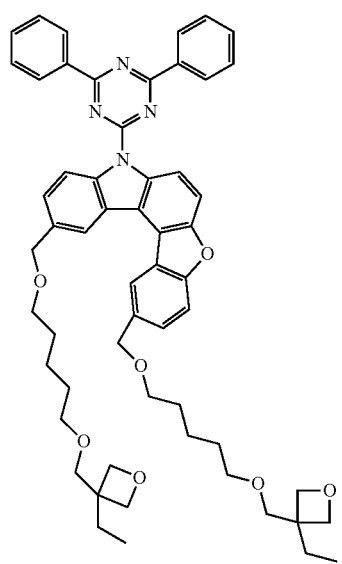
D127
D128
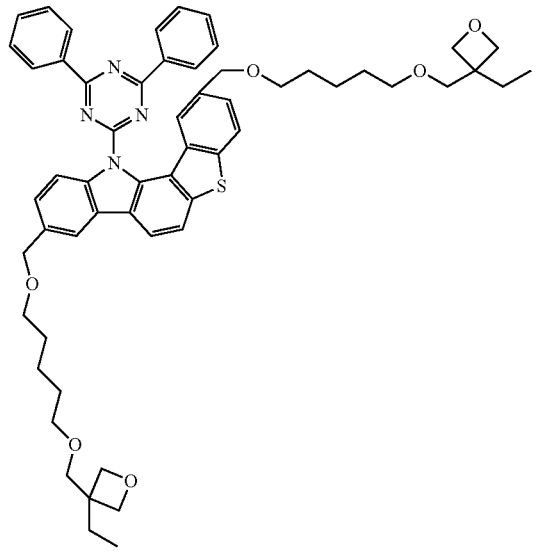

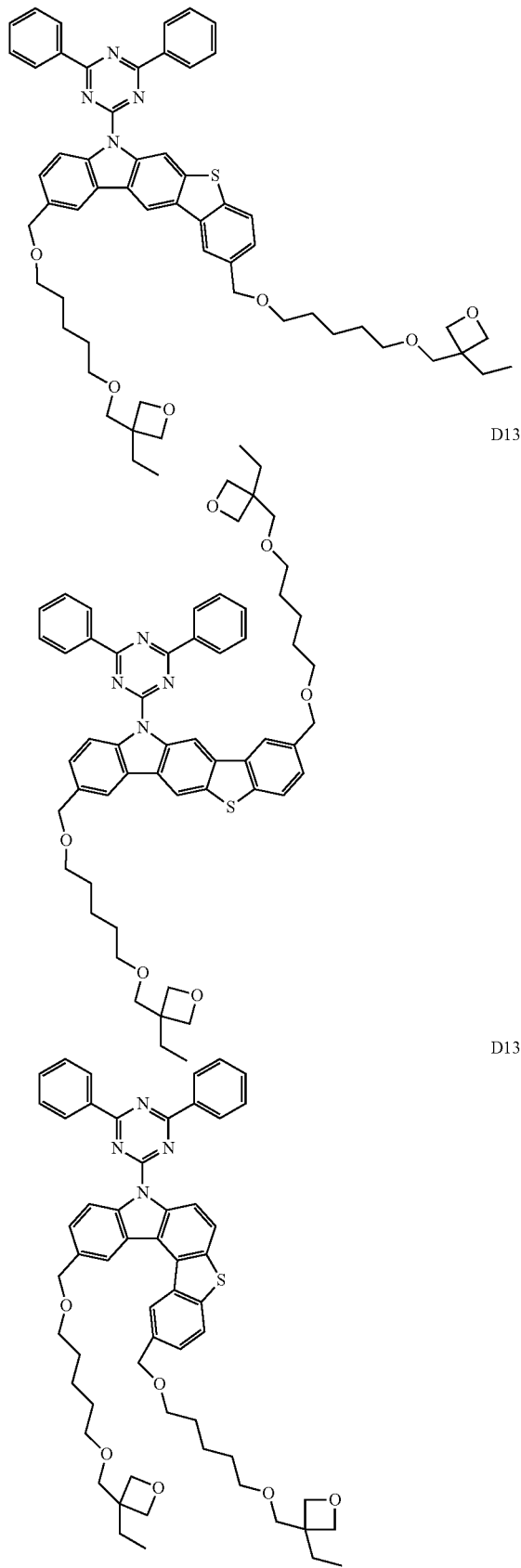
D129
D130
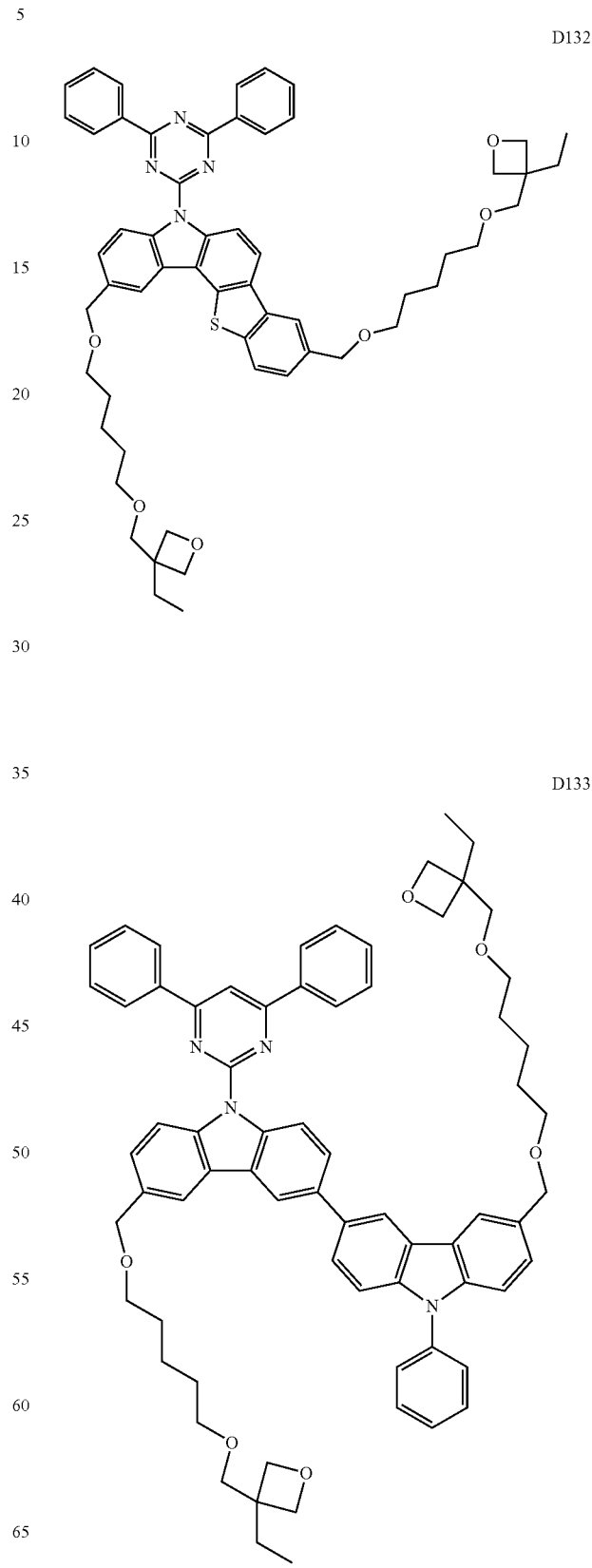
D132
D133

D134
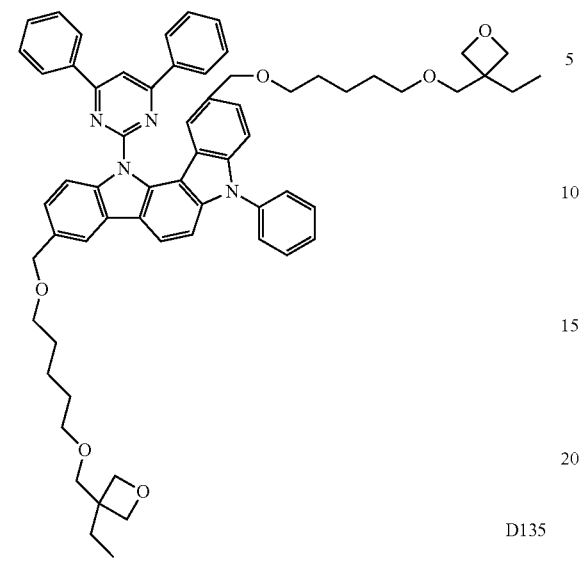
D135
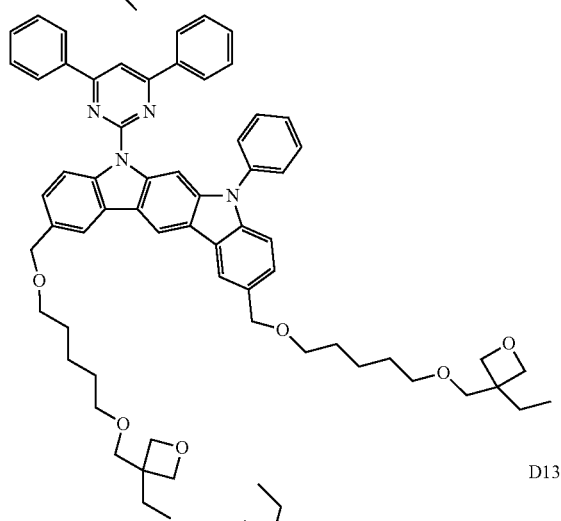
D136
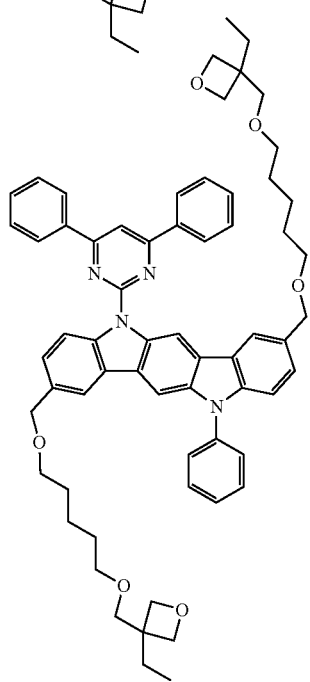
D137
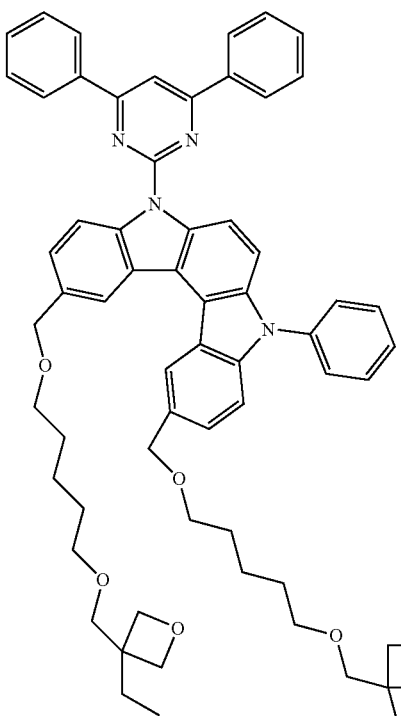
D138
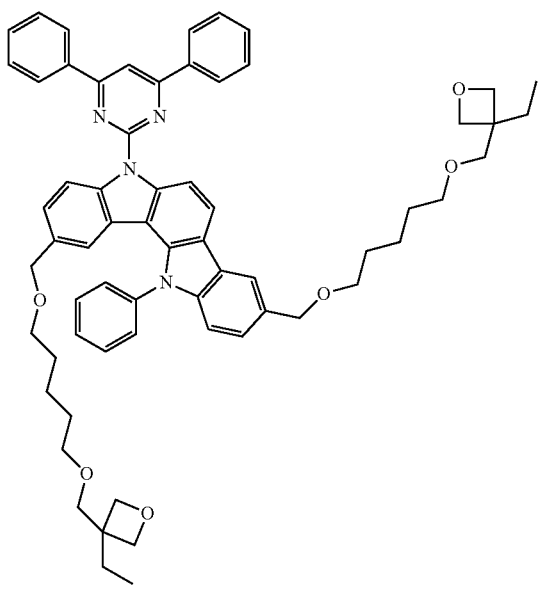

-continued
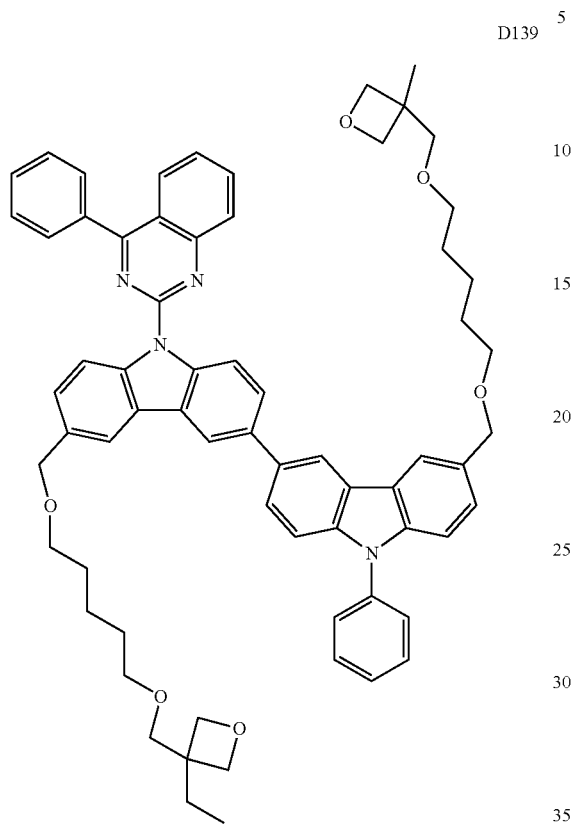
D139
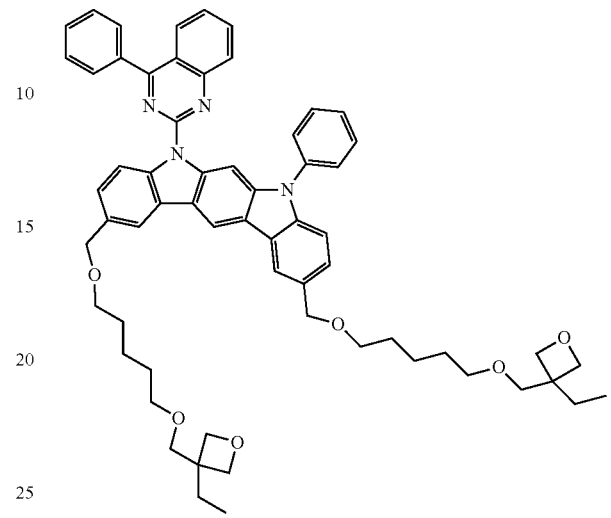
D141
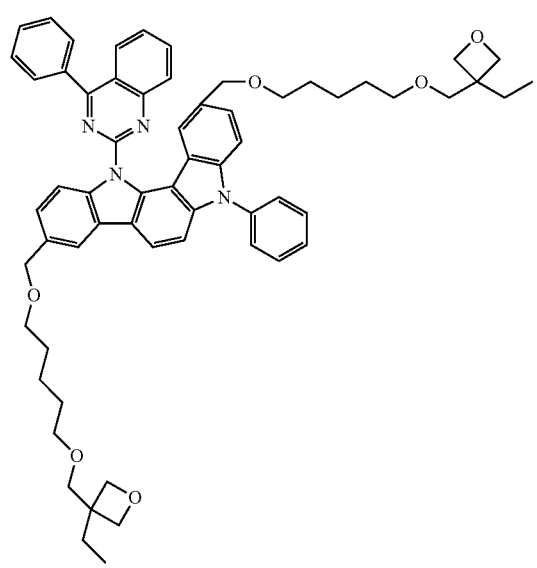
D140
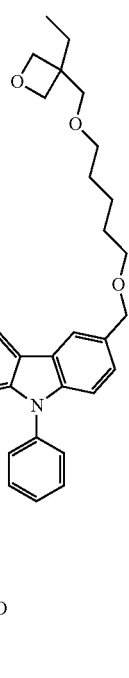
D142

135
-continued
D143
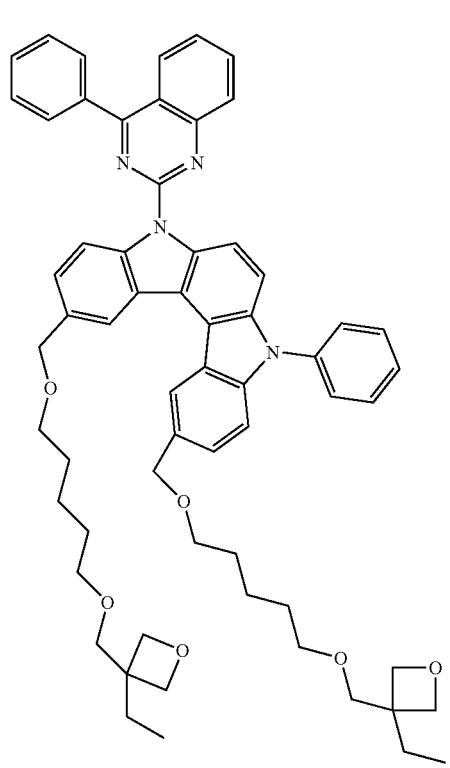
D144
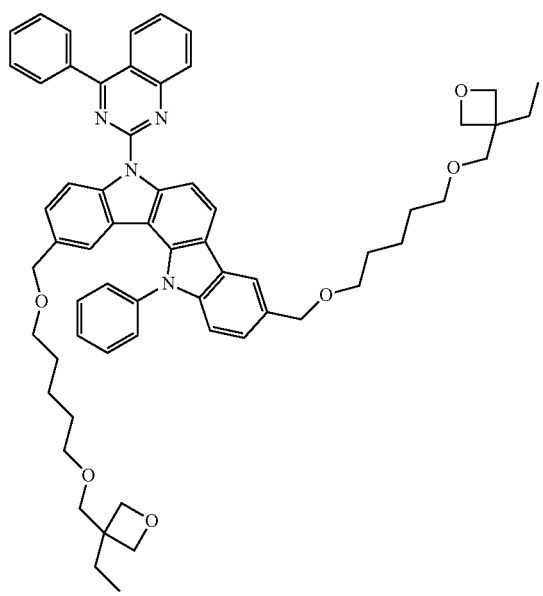
136
-continued
D145
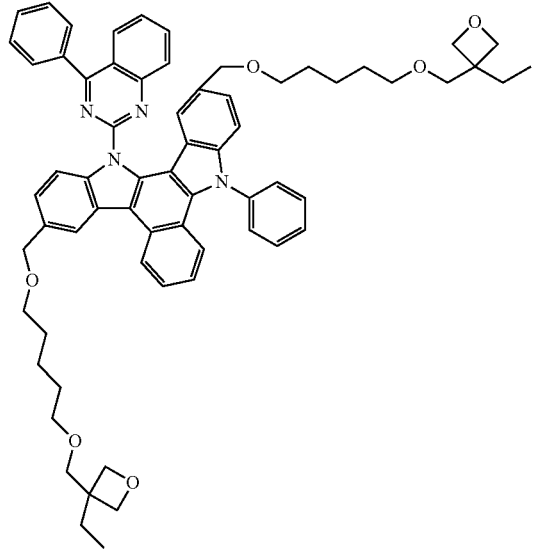
D146

137
-continued
138
-continued
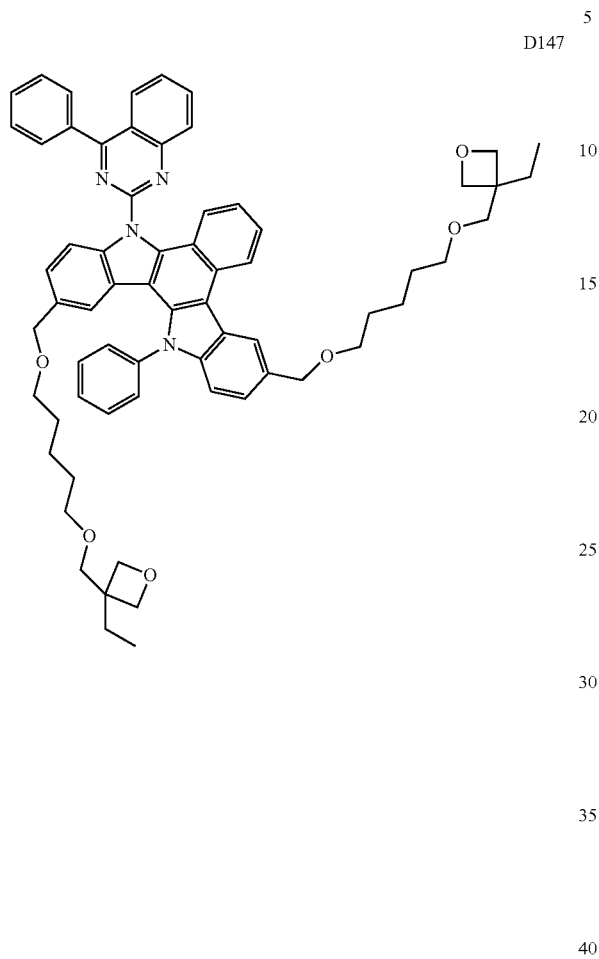
D147
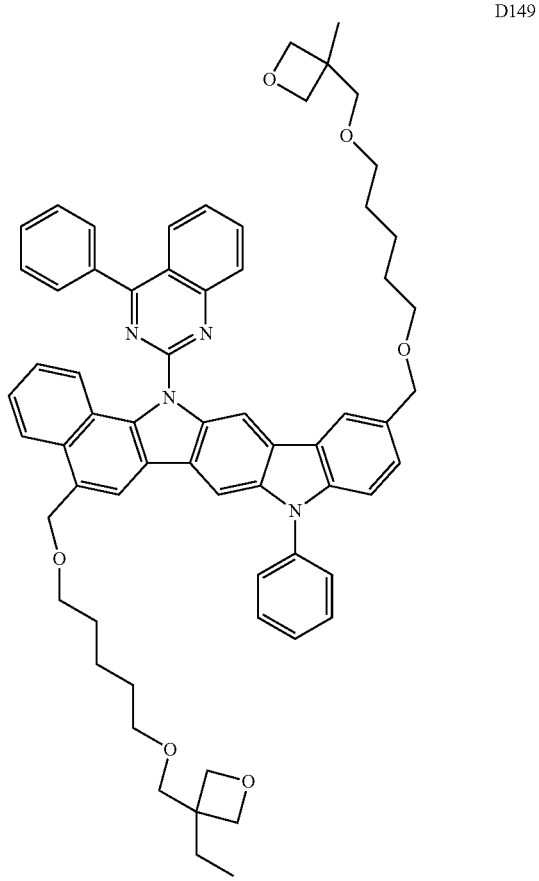
D149
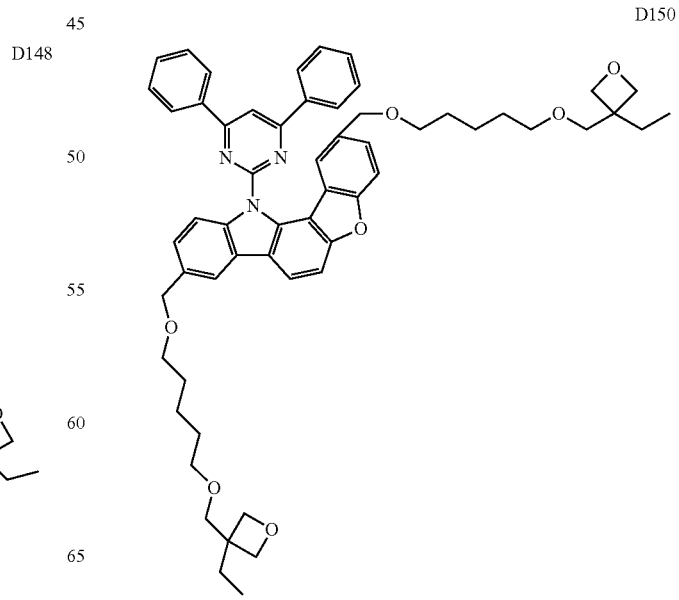
D148
D150

D151
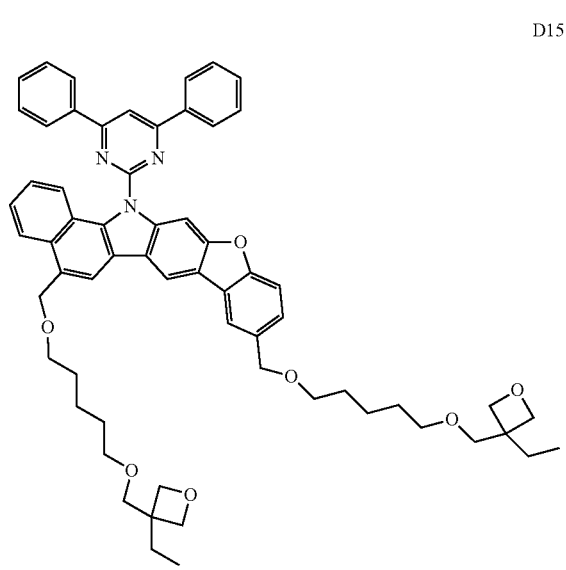
D153
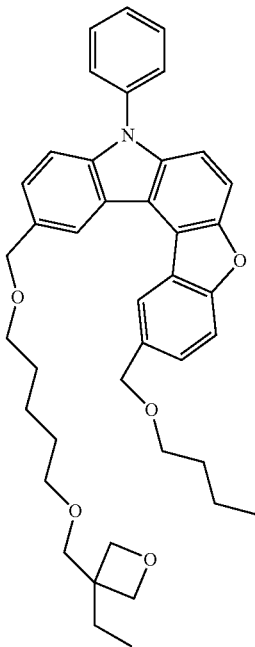
D152
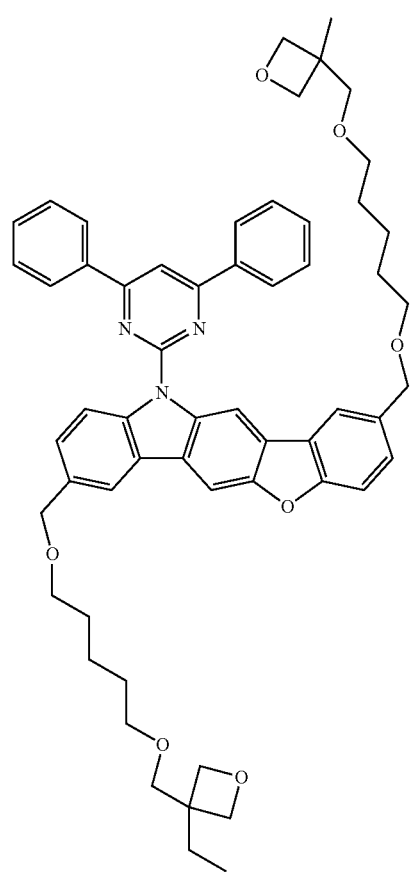
D154
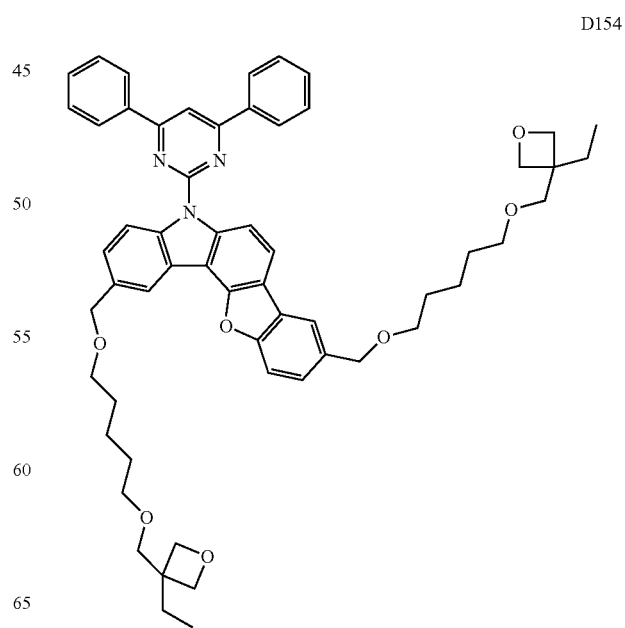

-continued
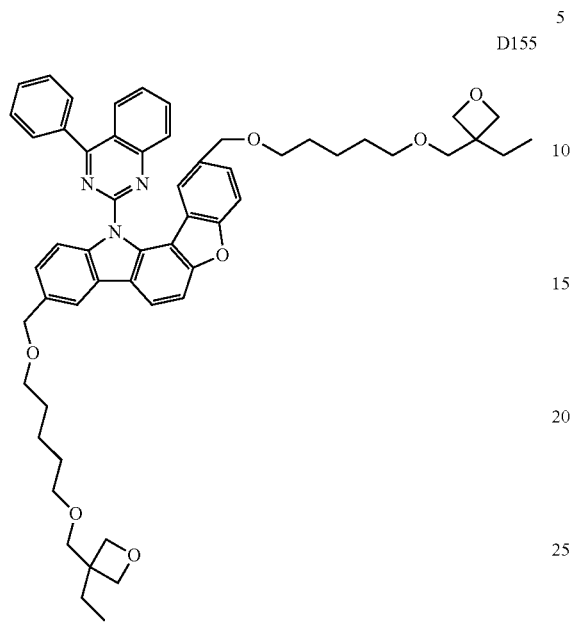
D155
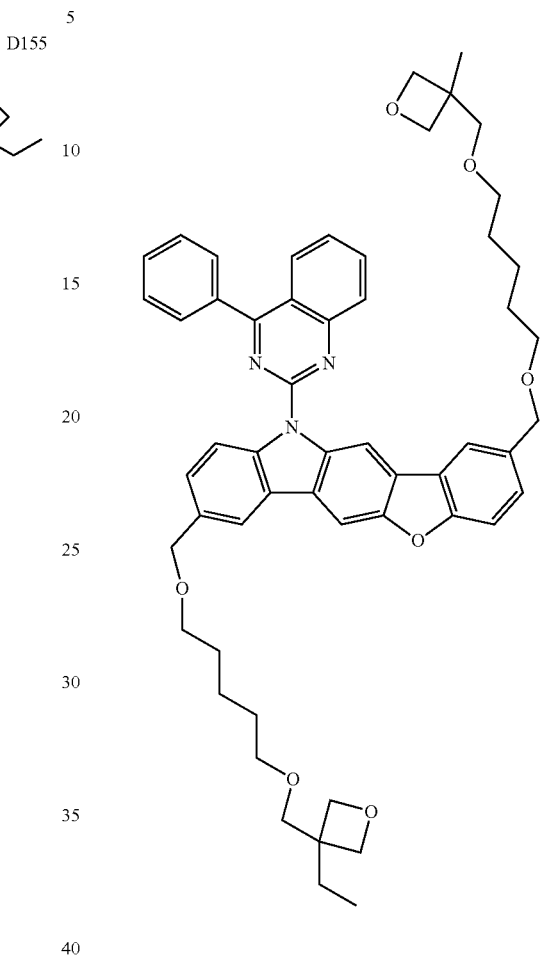
D157
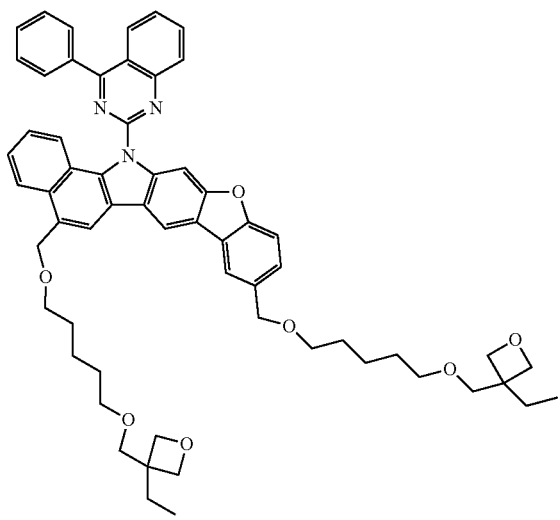
D156
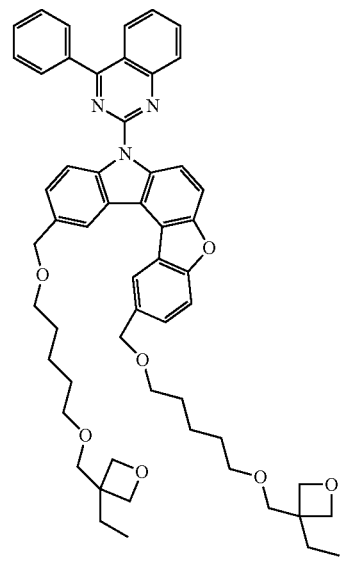
D158

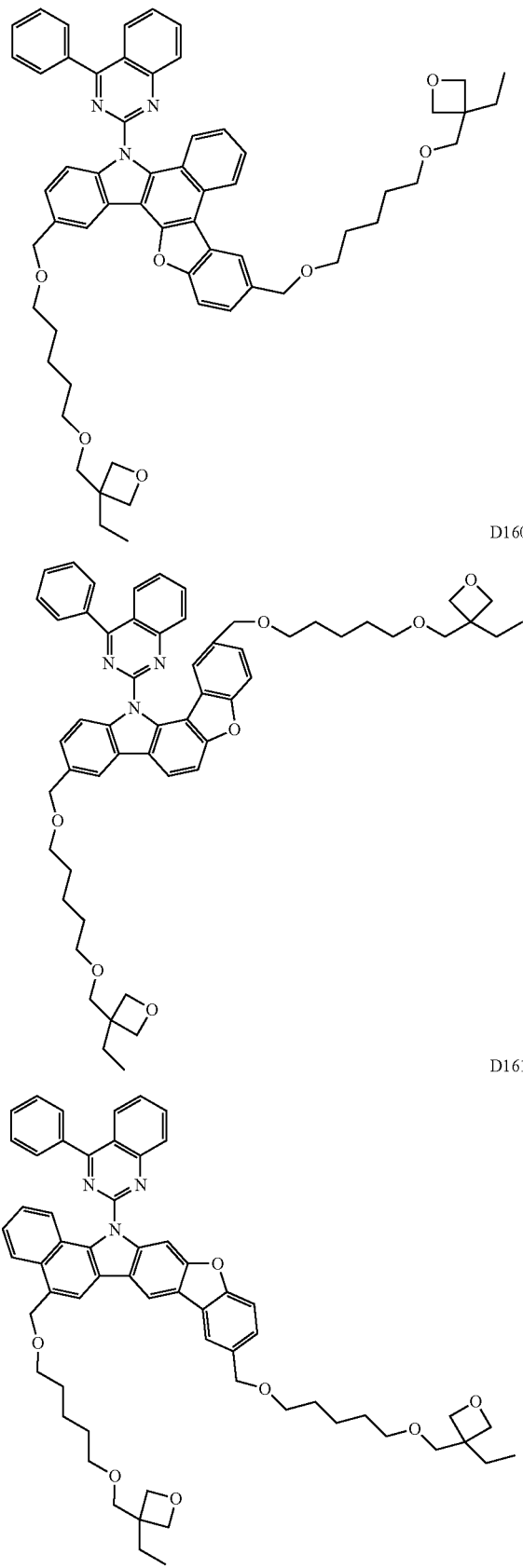
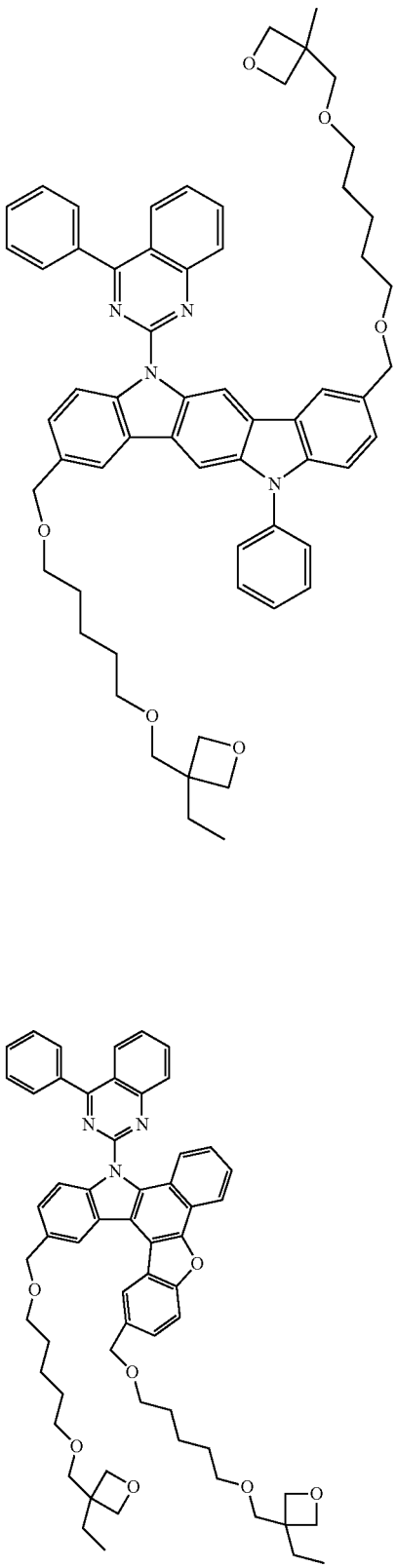

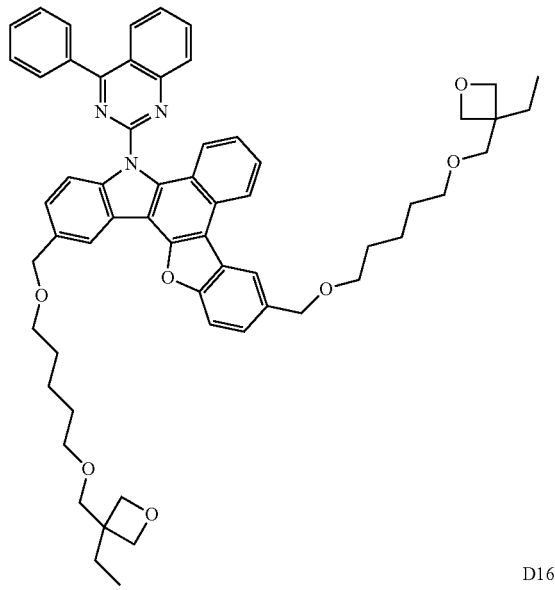
D164
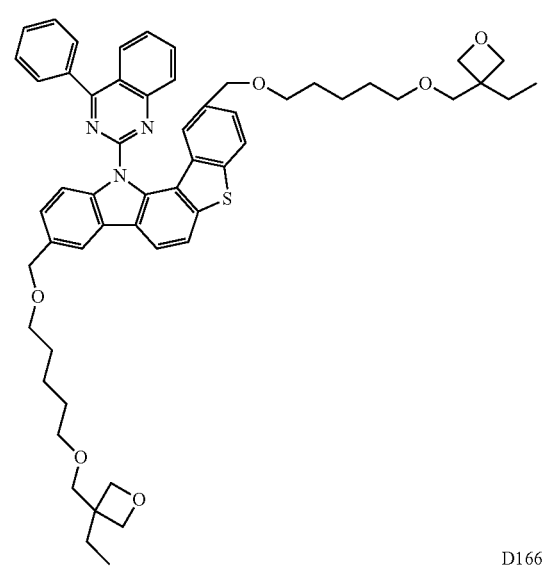
D165
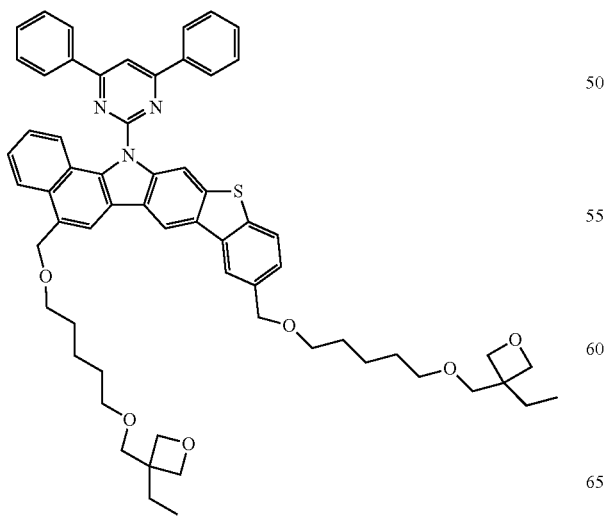
D166
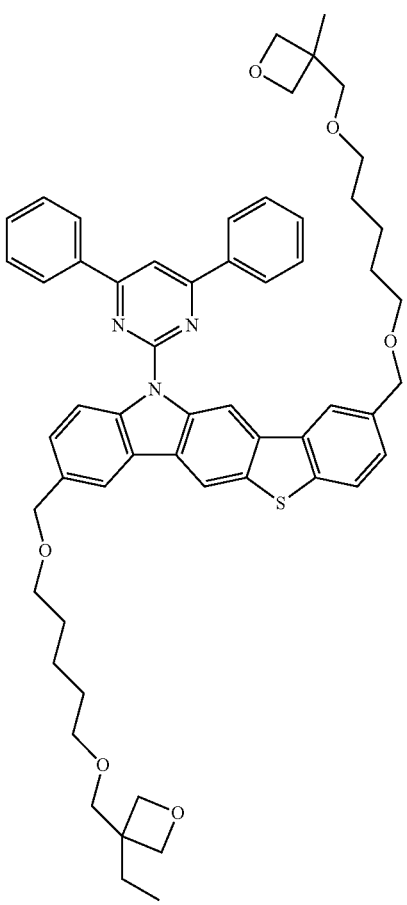
D167
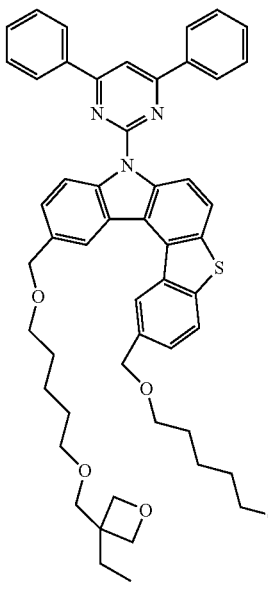
D168

147
-continued
148
-continued
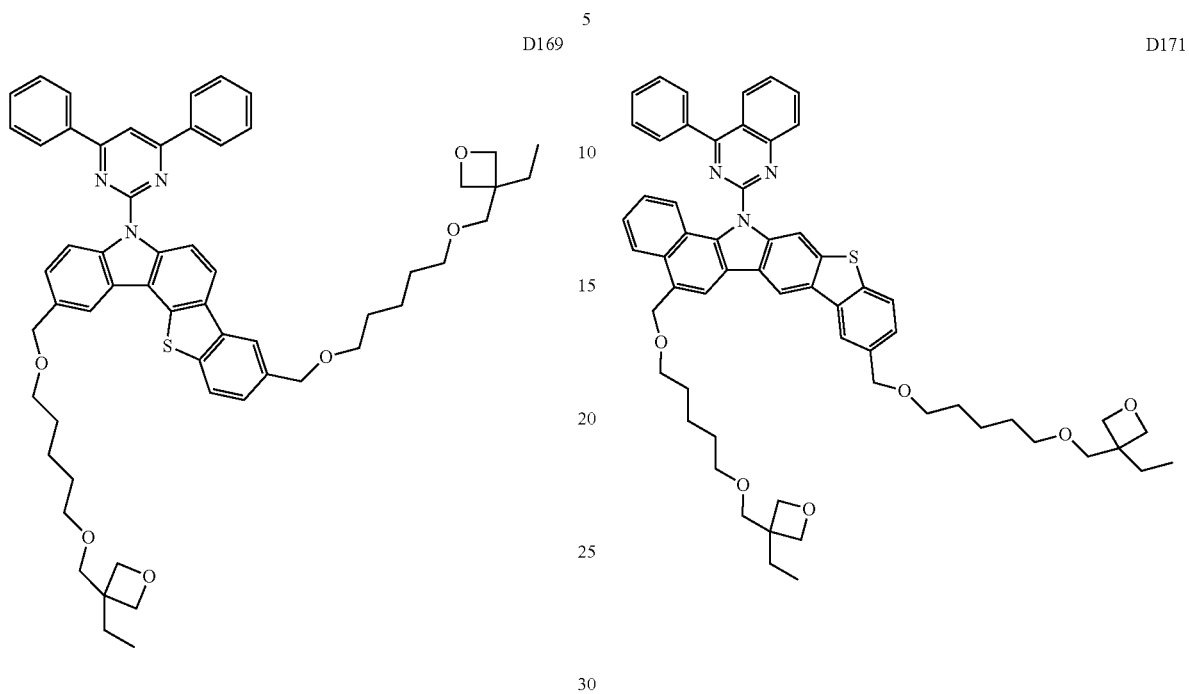
D169
D171
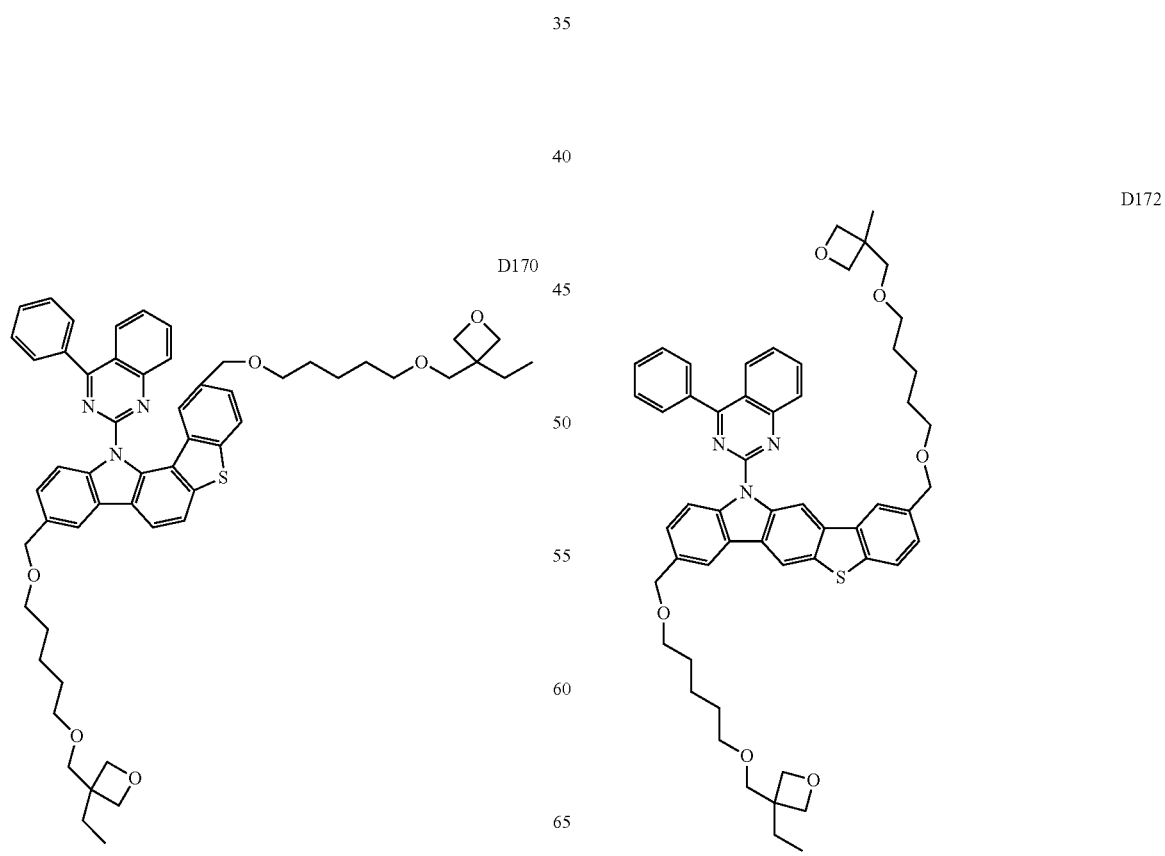
D170
D172

149
-continued
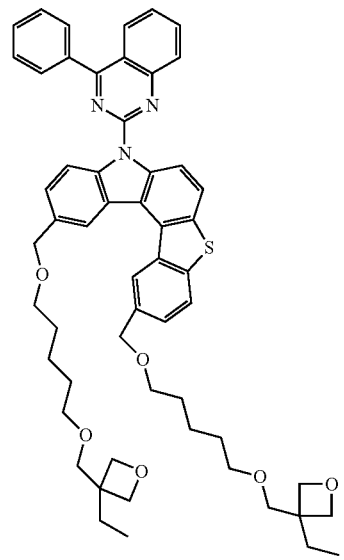
D173
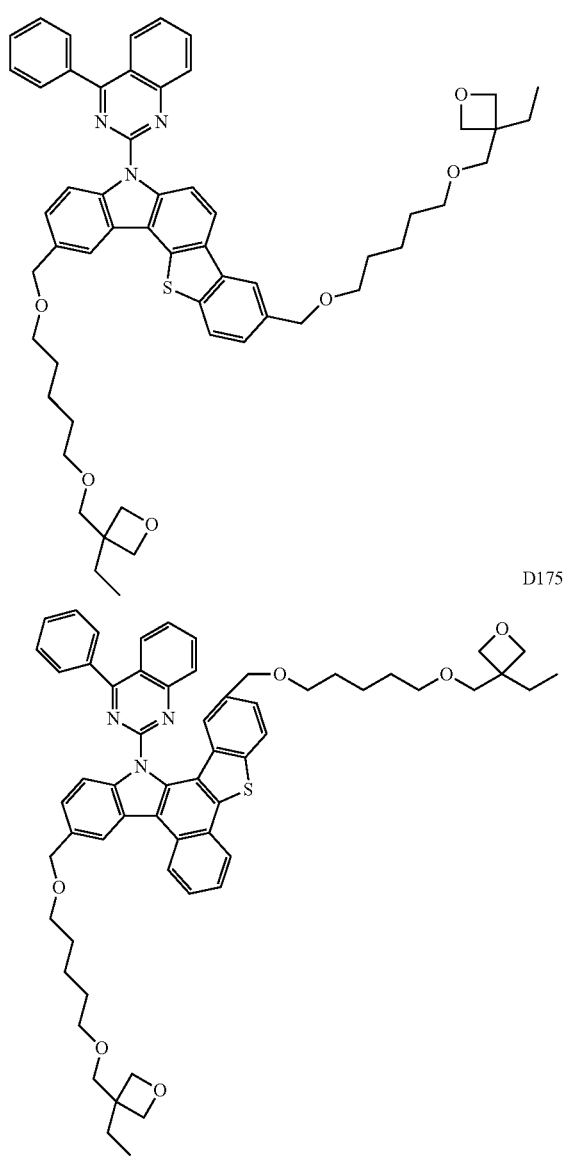
D174
D175
150
-continued
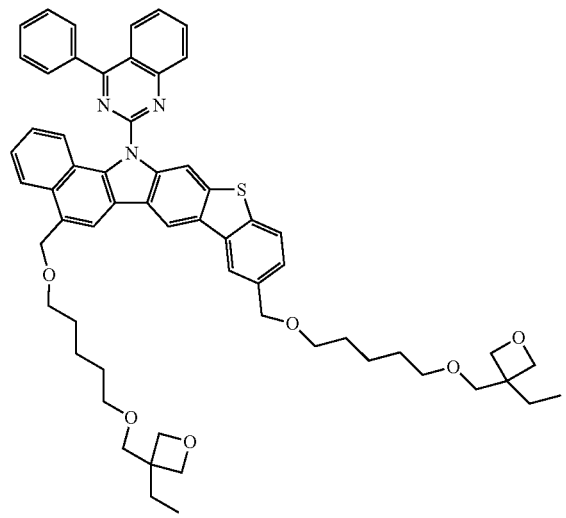
D176
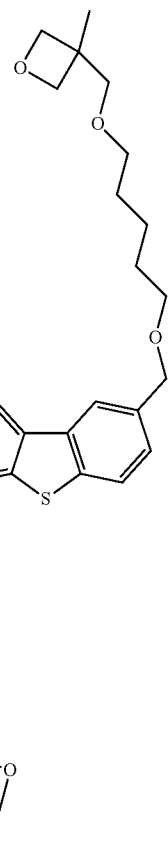
D177

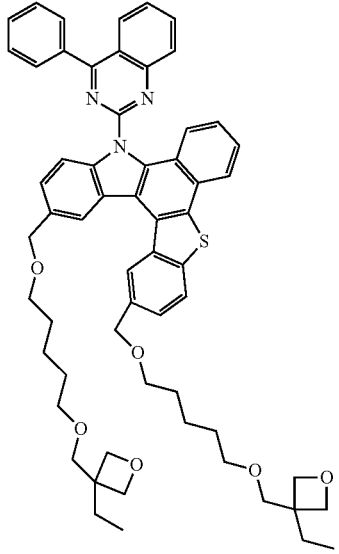
D178

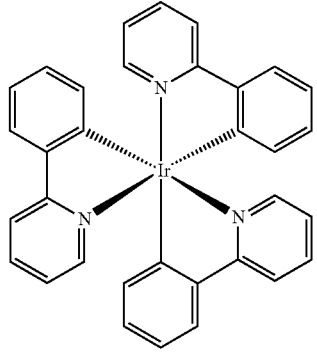
Formula E-3

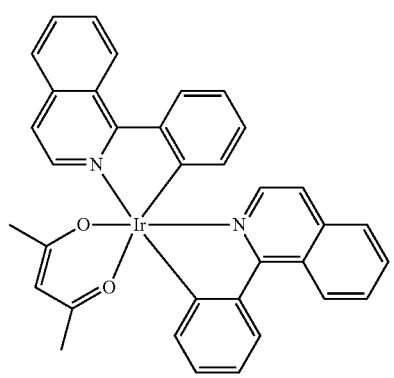
Formula E-4

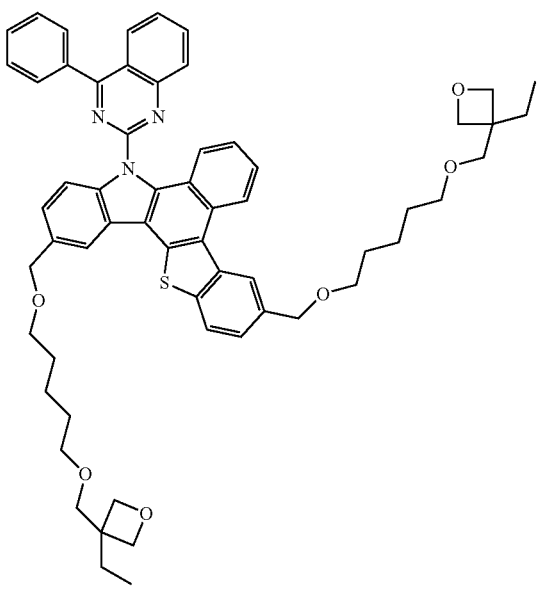
D179

The compounds of Formulae D-1 through D-16 and polymers thereof may be utilized as a host material for a red/green phosphorescent material (e.g., a red/green phosphorescent layer). In an exemplary embodiment where the composition for forming an organic film includes the compounds of Formulae D-1 through D-16, the composition for forming the organic film may further include a compound of Formula E-3 or E-4 below.

The composition for forming an organic film may include a solvent. The kind of the solvent is not particularly limited as long as it can properly disperse the compound of Formula 1. For example, the solvent may be methyl benzoate. In this example, the content of solids comprising the compound of Formula 1 may be about 1.0 weight percent (wt %) to 5.0 wt % with respect to the total weight of the composition for forming the organic film.

In some exemplary embodiments, the composition for forming an organic film includes the compound of Formula 1 and may further include an initiator compound. The content of the initiator compound may be about 0.5 wt % to 4.0 wt % with respect to the total weight of the composition for forming the organic film.

The initiator compound may be a cationic initiator compound. The cationic initiator compound may be a compound of any one of Formulae F-1 through F-3 below.

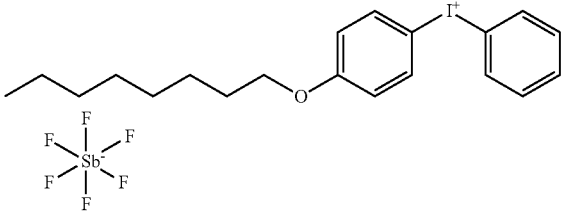
Formula F-1

Formula F-2

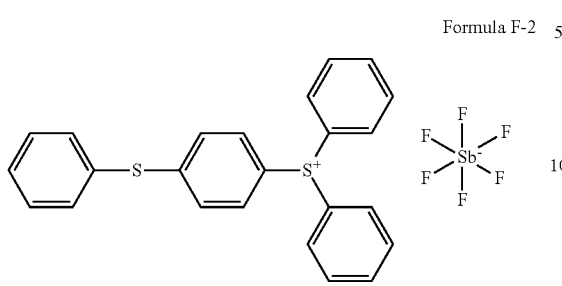

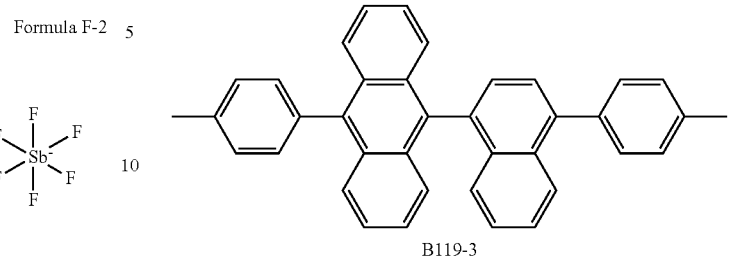

Formula F-3

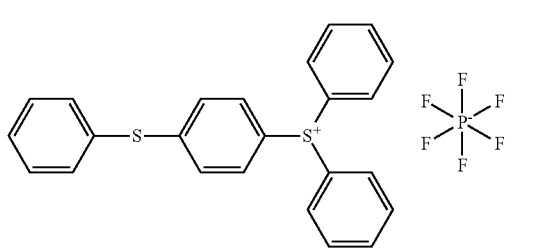

The preparation of the above-described compounds and composition will hereinafter be described in more detail.

Preparation Example 1: Synthesis of Compounds

Preparation Example 1-1: Synthesis of Compound B119

Synthesis of Intermediate B119-3

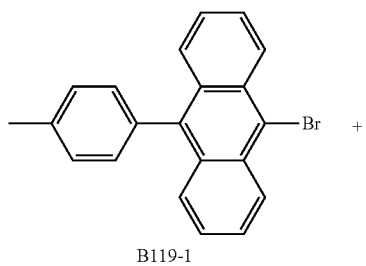

B119-1

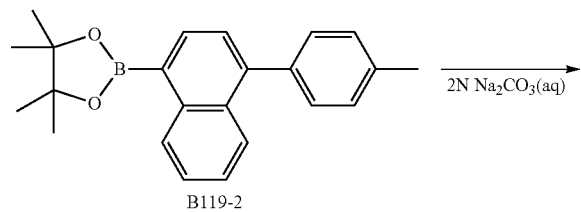

B119-2

3.60 g (10.46 mmol) of reactant B119-2 (4,4,5,5-tetramethyl-2-(4-(p-tolyl)naphthalen-1-yl)-1,3,2-dioxaborolane) and 0.216 g (0.188 mmol) of tetrakis(triphenylphosphine)palladium(0) were added to 3.63 g (10.46 mmol) of reactant B119-1 (9-bromo-10-(p-tolyl)anthracene) in a round flask, and the mixture was dissolved in 80 mL of tetrahydrofuran (THF). 40 mL of 2N aqueous sodium carbonate solution was added, and the mixture was refluxed for 24 hours. After cooled to room temperature, the mixture was poured into water, extracted with methylene chloride (MC), and dehydrated with $MgSC_4$, and the solvent was removed with a rotary evaporator. The resultant was purified utilizing column chromatography with $CHCl_3$ and was reprecipitated with methanol and THF to obtain 3.80 g of intermediate B119-3 (7.85 mmol, yield: 75%).

MS: m/z 484 [M]+

Synthesis of Intermediate B119-4

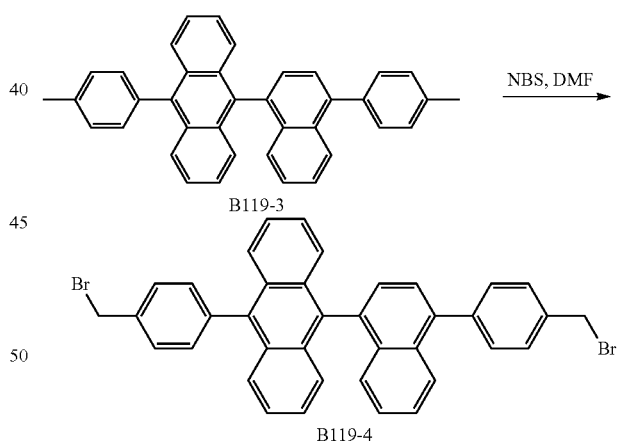

5.15 g (28.97 mmol) of N-bromosuccinimide (NBS) was slowly added to a solution a solution obtained by dissolving 6.84 g (14.13 mmol) of intermediate B119-3 (9-(p-tolyl)-10-(4-(p-tolyl)naphthalen-1-yl)anthracene) in 150 mL of dimethyl formamide (DMF). The mixture was reacted for 12 hours at room temperature. Then, the mixture was poured into brine and was extracted with MC. The extract was dehydrated with $MgSC_4$, and the solvent was removed with a rotary evaporator. The resultant was reprecipitated with methanol and THF to obtain 7.44 g of intermediate B119-4 (11.59 mmol, yield: 82%).

MS: m/z 642 [M]+

Synthesis of Compound B119

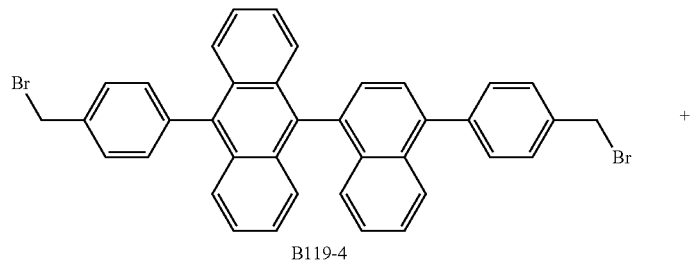
B119-4

+

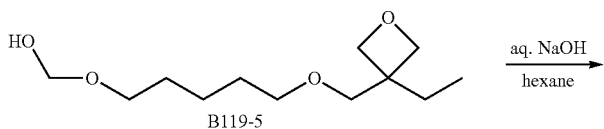
B119-5 → aq. NaOH / hexane

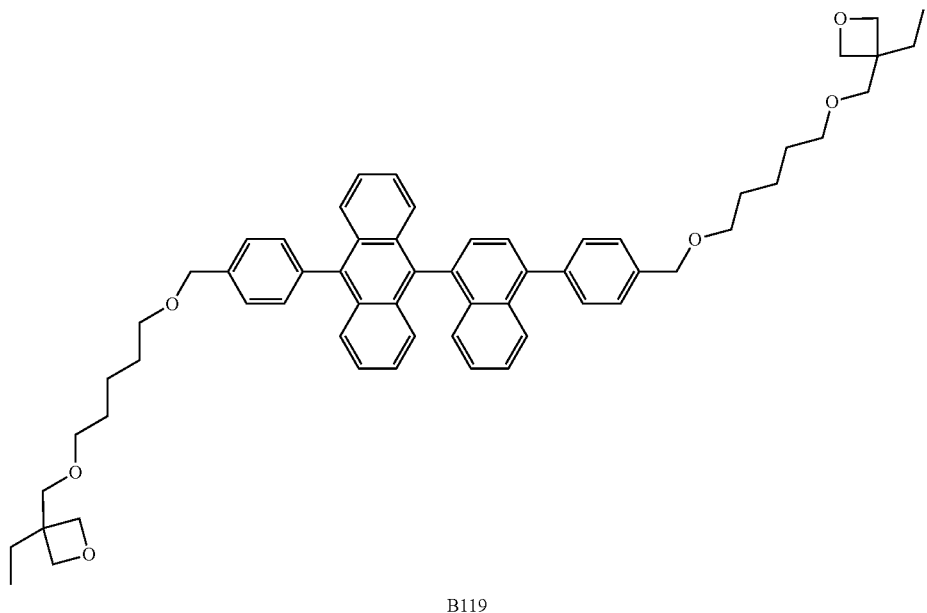
B119

6.96 g (30.00 mmol) of reactant B110-5 (((5-((3-ethyl-oxetan-3-yl)methoxy)pentyl)oxy)methanol) was added to 9.63 g (15.00 mmol) of intermediate B119-4 (9-(4-(bromomethyl)phenyl)-10-(4-(4-(bromomethyl)phenyl)naphthalen-1-yl)anthracene), 20 g of 50% aqueous NaOH, and a 100 ml hexane solution. The mixture was refluxed for 2 hours. The mixture was cooled to room temperature, poured into water, extracted with diethyl ether, and dehydrated with $MgSC_4$. The solvent was removed with a rotary evaporator. The resultant was reprecipitated with methanol and THF to obtain 10.35 g of compound B119 (11.70 mmol, yield: 78%).

MS: m/z 884 [M]+

157

Preparation Example 1-2: Synthesis of Compound C102

Synthesis of Intermediate C102-3

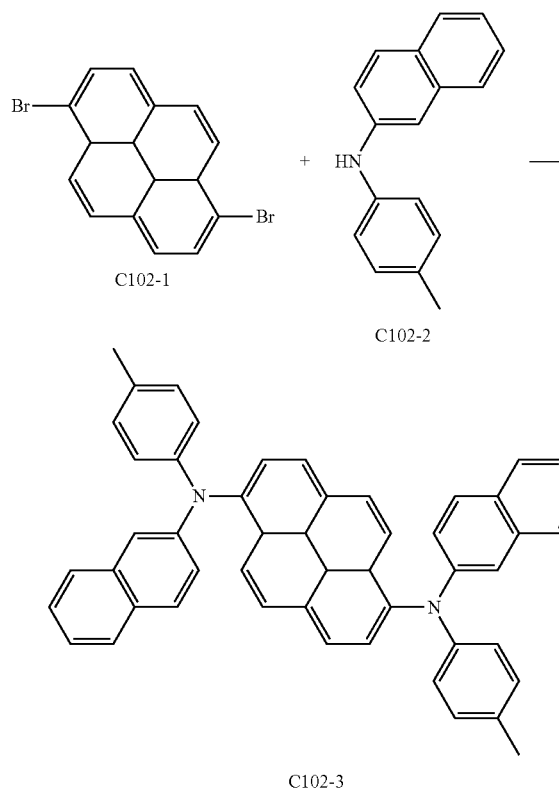

158

Synthesis of Intermediate C102-4

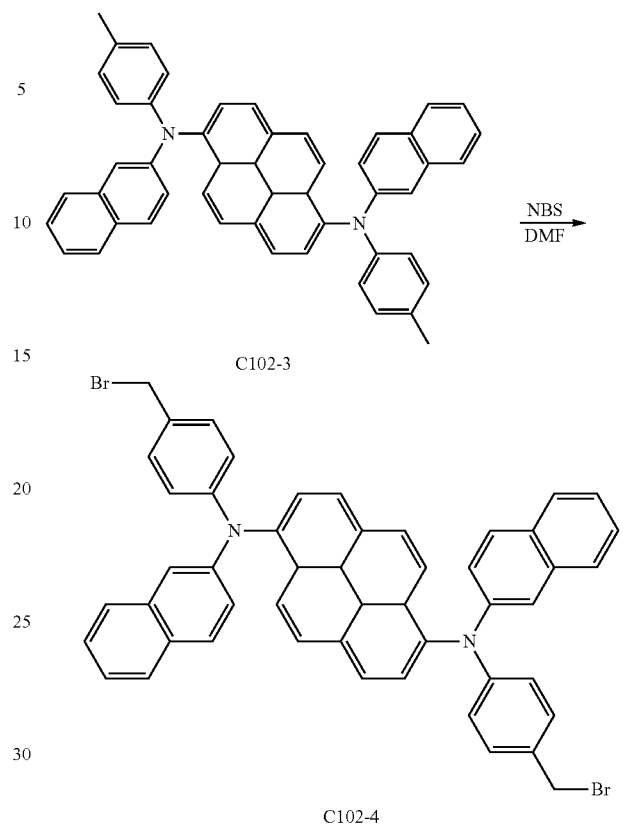

5.4 g (15 mmol) of reactant C102-1 (1,6-dibromopyrene), 9.32 g (40 mmol) of reactant C102-2 (N-(p-tolyl)naphthalen-2-amine), 0.2 g (0.7 mmol) of palladium acetate (Pd(OAc)2), 6.7 g of sodium tertiary butoxide, 6.7 g (69 mmol) of sodium tertiary butoxide, 0.14 g (0.7 mmol) of triturated butylphosphine, and 100 ml of toluene were added into a round flask and were reacted for 2 hours at 100° C. When the reaction was complete, the mixture was filtered, and the filtrate was concentrated and separated by column chromatography. The solid obtained by recrystallization utilizing toluene and methanol was filtered and dried to obtain 5.49 g of intermediate C102-3 (8.25 mmol, yield: 55%)

MS: m/z 664 [M]+

5.15 g (28.97 mmol) of NBS was slowly added to a solution obtained by dissolving 9.40 g (14.13 mmol) of intermediate C102-3 (N1,N6-di(naphthalen-2-yl)-N1,N6-di-p-tolylpyrene-1,6-diamine) in 150 ml of DMF. The mixture was reacted for 12 hours at room temperature, was poured into brine, and was extracted with MC. The extract was dehydrated with MgSC4, and the solvent was removed with a rotary evaporator. The resultant was reprecipitated with methanol and THF to obtain 8.72 g of intermediate C102-4 (10.60 mmol, yield: 75%).

MS: m/z 822 [M]+

Synthesis of Compound C102

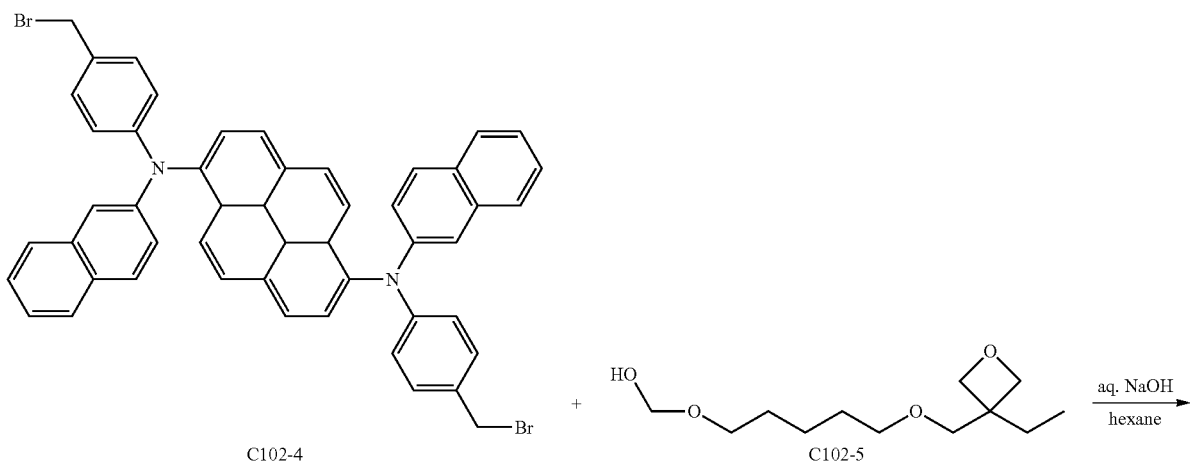

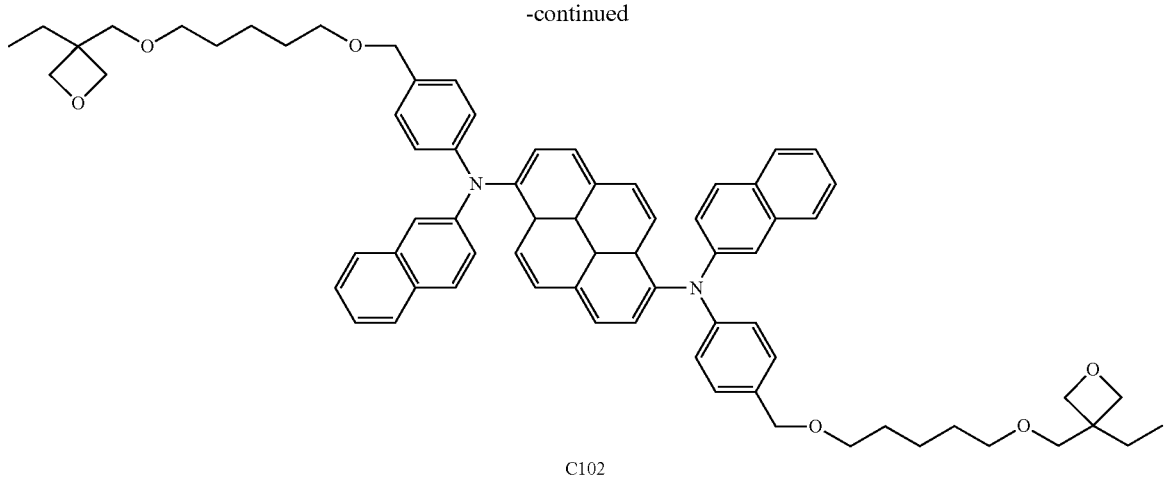

C102

6.96 g (30.00 mmol) of reactant C102-5 ((((5-((3-ethyl-oxetan-3-yl)methoxy)pentyl)oxy)methanol) was added to 12.35 g (15.00 mmol) of intermediate C102-4 (N1,N6-bis(4-(bromomethyl)phenyl)-N1,N6-di(naphthalen-2-yl)pyrene-1,6-diamine), 20 g of 50% aqueous NaOH, and a 100 ml hexane solution. The mixture was refluxed for 2 hours. The mixture was cooled to room temperature, poured into water, extracted with diethyl ether, and dehydrated with MgSO₄. The solvent was removed with a rotary evaporator. The resultant was reprecipitated with methanol and THF to obtain 11.97 g of compound C102 (11.25 mmol, yield: 75%).

MS: m/z 1064 [M]+

Preparation Example 2: Preparation of Composition for Forming Organic Film

Compositions for forming an organic film were prepared in accordance with the compositions shown in Tables 1 and 2 below.

The compound of Formula F-3 was utilized as an initiator compound, and methyl benzoate was utilized as a solvent.

The formulae of compounds B133 and B134 shown in Table 2 are as follows:

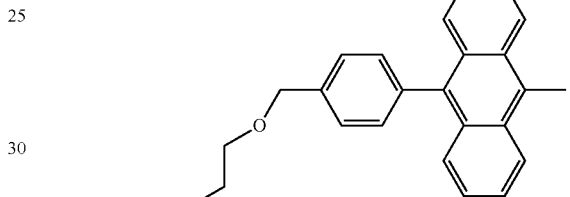

B133

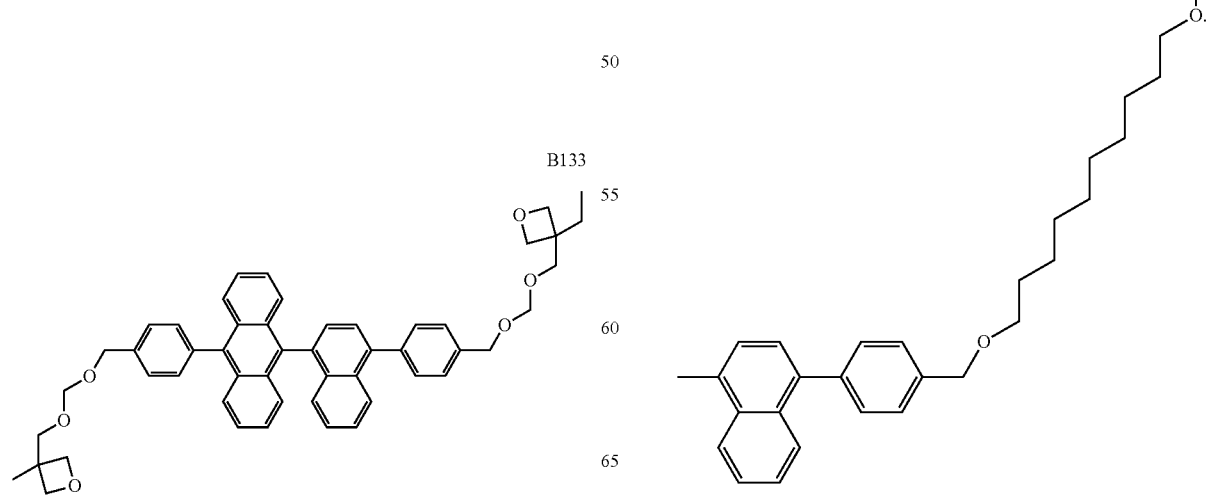

B134

TABLE 1

| Preparation Examples for Compositions for Forming Organic Film | Compounds | Compound Contents (wt %) | Initiator Compound Contents (wt %) |
|---|---|---|---|
| HIL-1 | A104 Formula E-1 | 2.5 | 1.0 |
| HIL-2 | A105 Formula E-1 | 2.5 | 1.0 |
| HIL-3 | A106 Formula E-1 | 2.5 | 1.0 |
| HIL-4 | A110 Formula E-1 | 2.5 | 1.0 |
| HIL-5 | A104 Formula E-2 | 2.5 | 1.0 |
| HIL-6 | A105 Formula E-2 | 2.5 | 1.0 |
| HIL-7 | A106 Formula E-2 | 2.5 | 1.0 |
| HIL-8 | A110 Formula E-2 | 2.5 | 1.0 |
| HTL-1 | A104 | 2.0 | 1.0 |
| HTL-2 | A105 | 2.0 | 1.0 |
| HTL-3 | A106 | 2.0 | 1.0 |
| HTL-4 | A110 | 2.0 | 1.0 |
| B EML-1 | B112 C102 | 3.0 | 1.0 |
| B EML-2 | B119 C102 | 3.0 | 1.0 |
| B EML-3 | B121 C102 | 3.0 | 1.0 |
| B EML-4 | B127 C102 | 3.0 | 1.0 |
| B EML-5 | B112 C104 | 3.0 | 1.0 |
| B EML-6 | B119 C104 | 3.0 | 1.0 |
| B EML-7 | B121 C104 | 3.0 | 1.0 |
| B EML-8 | B127 C104 | 3.0 | 1.0 |
| B EML-9 | B112 C116 | 3.0 | 1.0 |
| B EML-10 | B119 C116 | 3.0 | 1.0 |
| B EML-11 | B121 C116 | 3.0 | 1.0 |
| B EML-12 | B127 C116 | 3.0 | 1.0 |
| B EML-13 | B112 C123 | 3.0 | 1.0 |
| B EML-14 | B119 C123 | 3.0 | 1.0 |
| B EML-15 | B121 C123 | 3.0 | 1.0 |
| B EML-16 | B127 C123 | 3.0 | 1.0 |
| G EML-1 | D117 Formula E-3 | 3.0 | 1.0 |
| G EML-2 | D120 Formula E-3 | 3.0 | 1.0 |
| G EML-3 | D125 Formula E-3 | 3.0 | 1.0 |
| G EML-4 | D130 Formula E-3 | 3.0 | 1.0 |
| G EML-5 | D101 D117 Formula E-3 | 3.0 | 1.0 |
| G EML-6 | D101 D120 Formula E-3 | 3.0 | 1.0 |
| G EML-7 | D101 D125 Formula E-3 | 3.0 | 1.0 |
| G EML-8 | D101 D130 Formula E-3 | 3.0 | 1.0 |
| R EML-1 | D133 Formula E-4 | 3.0 | 1.0 |
| R EML-2 | D147 Formula E-4 | 3.0 | 1.0 |
| R EML-3 | D179 Formula E-4 | 3.0 | 1.0 |

TABLE 2

| Comparative Examples | Compounds | Compound Contents (wt %) | Initiator Compound Contents (wt %) |
|---|---|---|---|
| B EML-17 | B133 C104 | 3.0 | 1.0 |
| B EML-18 | B133 C104 | 3.0 | 5.0 |
| B EML-19 | B134 C104 | 3.0 | 1.0 |

Preparation Example 3: Fabrication of Organic Light-Emitting Element

Preparation Example 3-1

An ITO glass substrate (50 mm×50 mm, Samsung Corning's) was subjected to ultrasonic cleaning utilizing distilled water and isopropanol. Then, UV ozone cleaning was performed on the substrate for 30 minutes.

HIL-5 prepared in accordance with Preparation Example 2 was spin-coated on the cleaned substrate (i.e., the glass with the transparent electrode line adhered thereto) to form a film having a thickness of 60 nm, and was irradiated with ultraviolet light having a wavelength of 365 nm at a dose of 2 mJ/cm$^2$. Then, soft baking was performed at a temperature of 60° C. for 10 minutes, and the substrate was washed with methyl benzoate. Thereafter, hard baking was performed at a temperature of 150° C. for 30 minutes to form an organic film, i.e., a hole injection layer.

Thereafter, HTL-1 prepared in accordance with Preparation Example 2 was spin-coated on the hole injection layer to form a film having a thickness of 20 nm, and was irradiated with ultraviolet light having a wavelength of 365 nm at a dose of 2 mJ/cm$^2$. Then, soft baking was performed at 60° C. for 10 minutes, and the substrate was washed with methyl benzoate. Thereafter, hard baking was performed at a temperature of 150° C. for 30 minutes to form an organic film, i.e., a hole transport layer.

Thereafter, B EML-1 prepared in accordance with Preparation Example 2 was spin-coated on the hole transport layer to form a film having a thickness of 30 nm, and was irradiated with ultraviolet light having a wavelength of 365 nm at a dose of 2 mJ/cm$^2$. Then, soft baking was performed at 60° C. for 10 minutes, and the substrate was washed with methyl benzoate. Thereafter, hard baking was performed at a temperature of 140° C. for 30 minutes to form an organic film, i.e., a blue emission layer.

A compound of Formula G below was co-deposited with LiQ (8-Hydroxyquinolinolato-lithium) at a ratio of 5:5 on the blue emission layer to form an electron transport layer having a thickness of 20 nm.

LiQ was deposited on the electron transport layer to form an electron injection layer having a thickness of 1 nm, and then aluminum (Al) was deposited on the electron injection layer to form a cathode electrode having a thickness of 100 nm, thereby obtaining an organic light-emitting element. The deposition processes were performed utilizing Sunic System's Sunicel Plus 200.

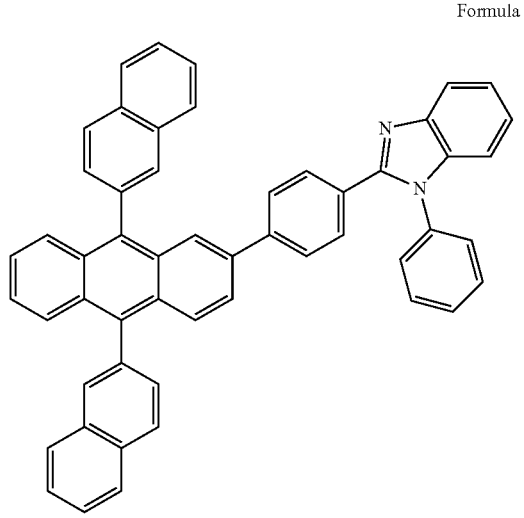

Formula G

Preparation Examples 3-2 Through 3-13

Organic light-emitting elements were fabricated utilizing compositions shown in Table 3 below and utilizing substantially the same method as the organic light-emitting element according to Preparation Example 3-1.

TABLE 3

|  | Hole Injection Layer | Hole Transport Layer | Emission Layer |
|---|---|---|---|
| Preparation Example 3-2 | HIL-7 | HTL-3 | B EML-5 |
| Preparation Example 3-3 | HIL-7 | HTL-3 | B EML-6 |
| Preparation Example 3-4 | HIL-7 | HTL-3 | B EML-7 |
| Preparation Example 3-5 | HIL-7 | HTL-3 | B EML-13 |
| Preparation Example 3-6 | HIL-7 | HTL-3 | B EML-14 |
| Preparation Example 3-7 | HIL-7 | HTL-3 | B EML-15 |
| Preparation Example 3-8 | HIL-5 | HTL-1 | G EML-5 |
| Preparation Example 3-9 | HIL-7 | HTL-3 | G EML-5 |
| Preparation Example 3-10 | HIL-7 | HTL-3 | G EML-6 |
| Preparation Example 3-11 | HIL-5 | HTL-1 | R EML-1 |
| Preparation Example 3-12 | HIL-7 | HTL-3 | R EML-1 |
| Preparation Example 3-13 | HIL-7 | HTL-3 | R EML-3 |

Comparative Example 3-1

An organic light-emitting element was fabricated in substantially the same manner as the organic light-emitting element according to Preparation Example 3-7, except that a blue emission layer was formed utilizing B EML-17.

Comparative Example 3-2

An organic light-emitting element was fabricated in substantially the same manner as the organic light-emitting element according to Preparation Example 3-7, except that a blue emission layer was formed by forming a film utilizing B EML-17 and irradiating the film with UV light at a dose of 100 mJ/cm$^2$.

Comparative Example 3-3

An organic light-emitting element was fabricated in substantially the same manner as the organic light-emitting element according to Preparation Example 3-7, except that a blue emission layer was formed utilizing B EML-18.

Comparative Example 3-4

An organic light-emitting element was fabricated in substantially the same manner as the organic light-emitting element according to Preparation Example 3-7, except that a blue emission layer was formed utilizing B EML-19.

Experimental Example

The driving voltage, efficiency, color purity, and lifespan of each of the organic light-emitting elements according to Preparation Examples 3-1 through 3-13 and Comparative Examples 3-1 through 3-4 were measured, and the results of the measurement are as shown in Table 4 below.

Specifically, color coordinates, luminance, and efficiency were measured by supplying power from a current voltmeter (Keithley SMU 236) and utilizing a spectrophotometer (PR650).

T95 lifespan denotes the amount of time (hr) that it takes for luminance to decline to 95% from its initial level of 100% under a current condition of 10 mA/cm$^2$.

TABLE 4

|  | Driving Voltage (V) | Efficiency (cd/A) | Color Coordinates | | T95 Lifespan (hr) |
|---|---|---|---|---|---|
|  |  |  | CIEx | CIEy |  |
| Preparation Example 3-1 | 4.5 | 6.2 | 0.15 | 0.13 | 110 |
| Preparation Example 3-2 | 4.1 | 6.9 | 0.15 | 0.13 | 145 |
| Preparation Example 3-3 | 4.2 | 6.7 | 0.15 | 0.13 | 135 |
| Preparation Example 3-4 | 4.0 | 7.0 | 0.15 | 0.13 | 125 |
| Preparation Example 3-5 | 4.2 | 7.2 | 0.15 | 0.11 | 160 |
| Preparation Example 3-6 | 4.1 | 7.5 | 0.15 | 0.11 | 140 |
| Preparation Example 3-7 | 4.3 | 6.9 | 0.14 | 0.11 | 155 |
| Preparation Example 3-8 | 4.8 | 28.5 | 0.28 | 0.61 | 220 |
| Preparation Example 3-9 | 4.3 | 29.2 | 0.28 | 0.61 | 255 |
| Preparation Example 3-10 | 4.1 | 29.5 | 0.28 | 0.61 | 270 |
| Preparation Example 3-11 | 4.7 | 13.2 | 0.64 | 0.35 | 640 |
| Preparation Example 3-12 | 4.3 | 14.0 | 0.64 | 0.35 | 710 |

TABLE 4-continued

| | Driving Voltage (V) | Efficiency (cd/A) | Color Coordinates | | T95 Lifespan (hr) |
| --- | --- | --- | --- | --- | --- |
| | | | CIEx | CIEy | |
| Preparation Example 3-13 | 4.2 | 14.3 | 0.64 | 0.35 | 730 |
| Comparative Example 3-1 | 5.2 | 5.3 | 0.14 | 0.11 | 50 |
| Comparative Example 3-2 | 4.6 | 4.8 | 0.14 | 0.11 | 30 |
| Comparative Example 3-3 | 4.8 | 5.4 | 0.14 | 0.11 | 70 |
| Comparative Example 3-4 | 4.5 | 6.5 | 0.14 | 0.11 | 85 |

Referring to Table 4, the organic light-emitting elements according to Preparation Examples 3-1 through 3-13 have a low driving voltage and at the same time, have a high efficiency and excellent color coordinates. Also, the organic light-emitting elements according to Preparation Examples 3-1 through 3-13 have a relatively long lifespan.

On the other hand, the organic light-emitting elements according to Comparative Examples 3-1 through 3-4 have a high driving voltage and a very short lifespan.

The results of the experiment conducted on the organic light-emitting elements according to Preparation Examples 3-1 through 3-13 and Comparative Examples 3-1 through 3-4 show that the compound of Formula 1 has excellent physical/chemical stability.

Display devices according to exemplary embodiments of the present disclosure and methods of manufacturing a display device according to exemplary embodiments of the present disclosure will hereinafter be described in more detail with reference to the accompanying drawings. Detailed descriptions of compounds and substituents that can be represented by the same formulae as those set forth hereinabove will not be repeated, which can be easily understood by a person skilled in the art.

Figure 2:
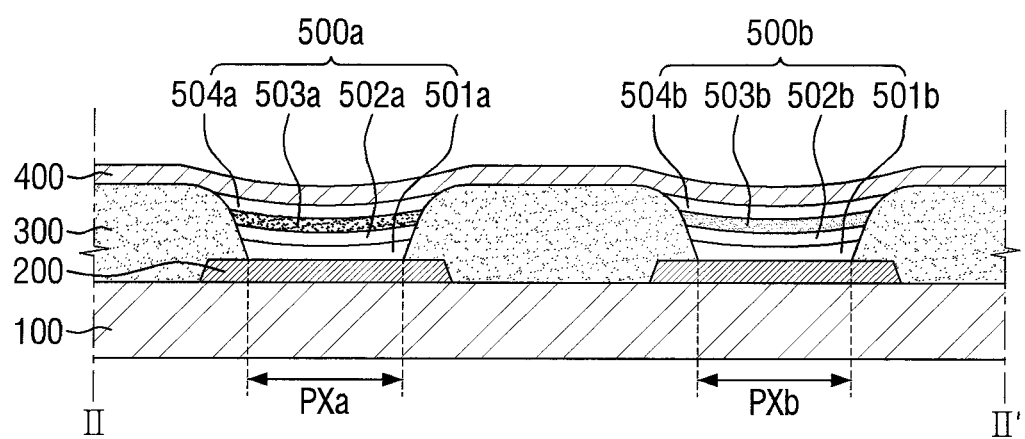
FIG. 2 is a cross-sectional view taken along the line II-II' of FIG. 1.
Figure 3:
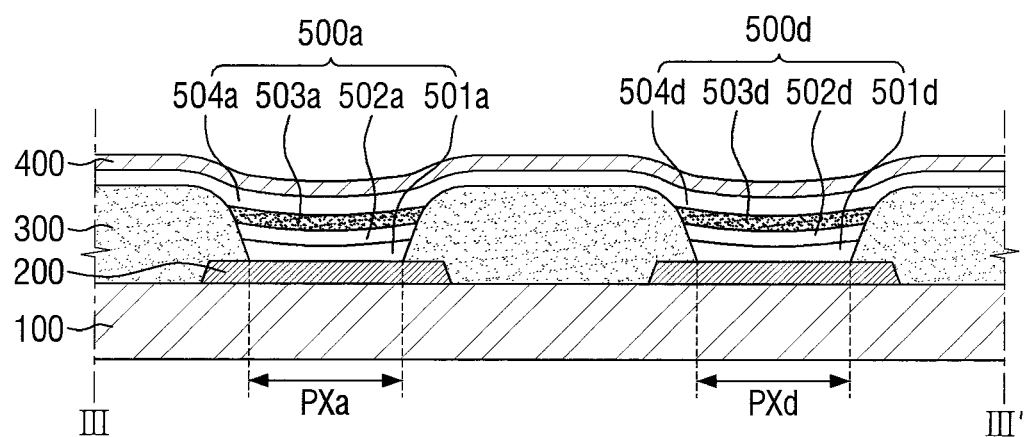
FIG. 3 is a cross-sectional view taken along the line of FIG. 1.

FIG. 1 is a plan view of a display device according to an exemplary embodiment of the present disclosure. FIG. 2 is a cross-sectional view taken along the line II-II' of FIG. 1. FIG. 3 is a cross-sectional view taken along the line of FIG. 1.

Referring to FIGS. 1 through 3, a plurality of pixels, which are arranged substantially in a matrix form on a plane, may be defined on a display device 1. In the description that follows, the term "pixel" refers to a single area defined, in a plan view, by dividing a display area for the display of a color, and a pixel can display a predetermined basic color. That is, a pixel may be a minimum (e.g., a smallest) unit of a display panel for displaying a color independently.

The plurality of pixels of the display device 1 include a first pixel PXa displaying a first color, a second pixel PXb displaying a second color having a longer peak wavelength than the first color, and a third pixel PXc displaying a third color having a longer peak wavelength than the second color. In one exemplary embodiment, the first pixel PXa, the second pixel PXb, and the third pixel PXc, which are illustrated as being sequentially arranged in a horizontal direction, may be repeatedly arranged one after another in the horizontal direction, forming a basic unit.

For example, the first pixel PXa may be a pixel displaying a blue color, the second pixel PXb may be a pixel displaying a green color, and the third pixel PXc may be a pixel displaying a red color. A fourth pixel PXd, which is adjacent to the first pixel PXa in a vertical direction, may be a pixel displaying the same color as the first pixel PXa.

The display device 1 includes a base 100, anode electrodes 200 and a cathode electrode 400, which are disposed on the base 100, and organic layers (500a, 500b, and 500d), which are interposed between the anode electrodes 200 and the cathode electrode 400.

The base 100 may provide a space in which to dispose organic light-emitting elements. Although not specifically illustrated, the base 100 may include switching transistors and driving transistors for driving the organic light-emitting elements.

The anode electrodes 200 may be disposed on the base 100. The anode electrodes 200 may be electrically connected to the driving transistors of the base 100. The anode electrodes 200 may have a higher work function than the cathode electrode 400. The anode electrodes 200 may be transparent electrodes, opaque electrodes, or stacks of transparent electrodes and opaque electrodes. Examples of the material of the transparent electrodes include indium tin oxide (ITO), indium zinc oxide (IZO), zinc oxide, indium oxide, etc., and examples of the material of the opaque electrodes include lithium (Li), aluminum (Al), magnesium (Mg), silver (Ag), nickel (Ni), chromium (Cr), etc. The anode electrodes 200 may be disposed in the plurality of pixels, respectively, and may be supplied with driving signals independently of one another. That is, the anode electrode may include a plurality of anode electrodes patterned according to the plurality of pixels.

The cathode electrode 400 may have a relatively lower work function than the anode electrodes 200. The cathode electrode 400 and the anode electrodes 200 may be disposed on opposite sides of the organic layers (500a, 500b, and 500d) and may drive the organic light-emitting elements together. The cathode electrode 400, like the anode electrodes 200, may be a transparent electrode, an opaque electrode, or a stack of the transparent electrodes and the opaque electrodes. The cathode electrode 400 may be disposed on substantially the entire surface of the base 100 without regard to the distinction between the plurality of pixels.

A bank 300 may be disposed on the base 100 and the anode electrodes 200. The bank 300 separates the plurality of pixels from one another. The bank 300 may at least partially overlap with the anode electrodes 200 and may have openings that at least partially expose the surfaces of the anode electrodes 200 therethrough. That is, the bank 300 may have openings that expose the anode electrodes 200 therethrough and may thus be substantially lattice-shaped in a plan view. The bank 300 may include an organic material such as a polyacrylic resin or a polyimide (PI) resin.

The organic layers (500a, 500b, and 500d) may be interposed between the anode electrodes 200 and the cathode electrode 400. A first organic layer 500a is disposed between the anode electrode 200 in the first pixel PXa and the cathode electrode 400, a second organic layer 500b is disposed between the anode electrode 200 in the second pixel PXb and the cathode electrode 400, and a third organic layer 500d may be disposed between the anode electrode 200 in the fourth pixel PXd and the cathode electrode 400. The first, second, and third organic layers 500a, 500b, and 500d will hereinafter be described in more detail.

The first organic layer 500a in the first pixel PXa may include a first hole injection layer 501a, a first hole transport layer 502a, a first emission layer 503a, and a first electron injection layer 504a. The second organic layer 500b in the second pixel PXb may include a second hole injection layer 501b, a second hole transport layer 502b, a second emission layer 503b, and a second electron injection layer 504b. The third organic layer 500d in the fourth pixel PXd may include a third hole injection layer 501d, a third hole transport layer 502d, a third emission layer 503d, and a third electron injection layer 504d.

The first, second, and third hole injection layers 501a, 501b, and 501d may facilitate the injection of holes from the anode electrodes 200. The first, second, and third hole injection layers 501a, 501b, and 501d may be disposed on the base 100 and the bank 300.

The first, second, and third hole injection layers 501a, 501b, and 501d may include the same material.

In one exemplary embodiment, the first, second, and third hole injection layers 501a, 501b, and 501d may include a polymer of a compound of Formula 1. For example, the first, second, and third hole injection layers 501a, 501b, and 501d may include a polymer of a compound of Formula A-1. In some exemplary embodiments, the first, second, and third hole injection layers 501a, 501b, and 501d may further include a compound of Formula E-1 or E-2.

The polymerization of compounds of Formula A-1 may occur at the terminal photo-polymerizable groups. Compounds of Formulae A-2 through A-8, which are specific examples of a compound of Formula A-1, and their respective substituents have already been described above, and detailed descriptions thereof will not be repeated.

In a non-limiting example, the first, second, and third hole injection layers 501a, 501b, and 501d may include a polymer main chain of (i.e., represented by) any one of Formulae 2A through 2C below.

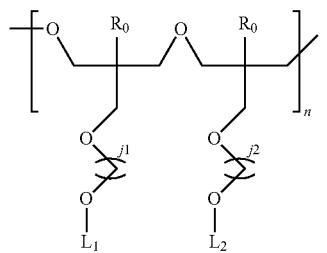

Formula 2A

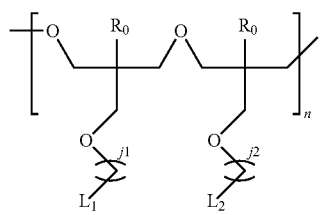

Formula 2B

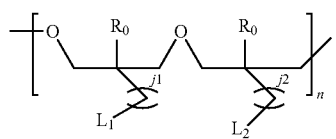

Formula 2C

In Formulae 2A, 2B, and 2C, $R_0$ may be a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; j1 and j2 may be each independently an integer of 2 to 9; and n, which defines the repeating unit of the polymer main chain, may be an integer of 1 to 100.

In Formulae 2A, 2B, and 2C, $L_1$ and $L_2$ may be parts originating from (e.g., branched from) the basic skeletons of the compounds of Formulae A-1 through A-8.

The first hole injection layer 501a in the first pixel PXa and the second hole injection layer 501b in the second pixel PXb may be physically spaced apart from each other. The first hole injection layer 501a in the first pixel PXa and the third hole injection layer 501d in the fourth pixel PXd may be physically spaced apart from each other. By physically separating the first, second, and third hole injection layers 501a, 501b, and 501d, which have conductivity, from one another, a lateral leakage current that may be formed between the plurality of pixels may be prevented.

The first, second, and third hole transport layers 502a, 502b, and 502d may facilitate the transfer of holes provided from the anode electrodes 200. The first, second, and third hole transport layers 502a, 502b, and 502d may be disposed on the hole injection layers 501a, 501b, and 501d and the bank 300.

The first, second, and third hole transport layers 502a, 502b, and 502d may include the same material.

In one exemplary embodiment, the first, second, and third hole transport layers 502a, 502b, and 502d may include a polymer of a compound of Formula 1. The polymerization of compounds of Formula A-1 may occur at the terminal photo-polymerizable groups. Compounds of Formulae A-2 through A-8, which are specific examples of a compound of Formula A-1, and their respective substituents have already been described above, and detailed descriptions thereof will not be repeated.

In a non-limiting example, the first, second, and third hole transport layers 502a, 502b, and 502d may include the polymer main chain of any one of Formulae 2A through 2C.

The first hole transport layer 502a in the first pixel PXa and the second hole transport layer 502b in the second pixel PXb may be physically spaced apart from each other. The first hole transport layer 502a in the first pixel PXa and the third hole transport layer 502d in the fourth pixel PXd may be physically spaced apart from each other.

The first, second, and third emission layers 503a, 503b, and 503d may generate light by recombining holes provided from the anode electrodes 200 and electrons provided from the cathode electrode 400. Specifically, as a result of the recombination of the holes and the electrons, excitons may be generated, and as the excitons relax from the excited state to the ground state, light may be emitted from the excitons. The first and third emission layers 503a and 503d may be, but are not limited to, blue emission layers, and the second emission layer 503b may be, but is not limited to, a green emission layer. The first, second, and third emission layers 503a, 503b, and 503d may be disposed on the first, second, and third hole transport layers 502a, 502b, and 502d and the bank 300.

In one exemplary embodiment, the first and third emission layers 503a and 503d may include a polymer of the compound of Formula 1. For example, the first and third emission layers 503a and 503d may include a polymer of compounds of Formula B-1, a polymer of compounds of Formula C-1, and/or a polymer (e.g., a copolymer) of a compound of Formula B-1 and a compound of Formula C-1. The polymerization of compounds of Formula B-1, the polymerization of compounds of Formula C-1, and/or the polymerization of a compound of Formula B-1 and a compound of Formula C-1 may occur at the terminal photo-polymerization groups. Compounds of Formulae B-1 through B-23 and C-1 through C-16, which are specific examples of a compound of Formula B-1 or C-1, and their respective substituents have already been described above, and detailed descriptions thereof will not be repeated.

The second emission layer 503b may include a polymer of the compound of Formula 1. For example, the second emission layer 503b may include a polymer of a compound of Formula D-1. The polymerization of compounds of Formula D-1 may occur at the terminal photo-polymerization groups. Compounds of Formulae D-1 through D-16, which are specific examples of a compound of Formula D-1, and their respective substituents have already been described above, and detailed descriptions thereof will not be provided.

In a non-limiting example, the first, second, and third emission layers 503a, 503b, and 503d may include a polymer main chain of any one of Formulae 2A through 2C.

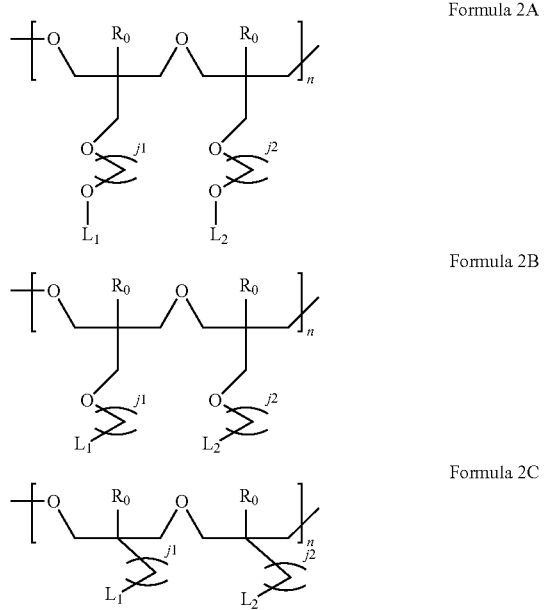

Formula 2A

Formula 2B

Formula 2C

In Formulae 2A, 2B, and 2C, $L_1$ and $L_2$ may be parts originating (e.g., branching) from the basic skeletons of the compounds of Formulae B-1 through B-23, C-1 through C-16, or D-1 through D-16.

The first emission layer 503a in the first pixel PXa and the second emission layer 503b in the second pixel PXb may be physically spaced apart from each other. The first emission layer 503a in the first pixel PXa and the third emission layer 503d in the fourth pixel PXd may be physically spaced apart from each other.

The first, second, and third electron injection layers 504a, 504b, and 504d may facilitate the injection of electrons from the cathode electrode 400. The first, second, and third electron injection layers 504a, 504b, and 504d may be disposed on the first, second, and third emission layers 503a, 503b, and 503d and the bank 300.

The first, second, and third electron injection layers 504a, 504b, and 504d may include the same material.

The first electron injection layer 504a in the first pixel PXa and the second electron injection layer 504b in the second pixel PXb may be physically spaced apart from each other. The first electron injection layer 504a in the first pixel PXa and the third electron injection layer 504d in the fourth pixel PXd may be physically connected to each other and may be formed in one integral body with each other.

Although not specifically illustrated, a functional layer such as an electron transfer layer may be further interposed between the first emission layer 503a and the first electron injection layer 504a, between the second emission layer 503b and the second electron injection layer 504b, or between the third emission layer 503d and the third electron injection layer 504d.

A display device according to another exemplary embodiment of the present disclosure will hereinafter be described in more detail.

Figure 4:
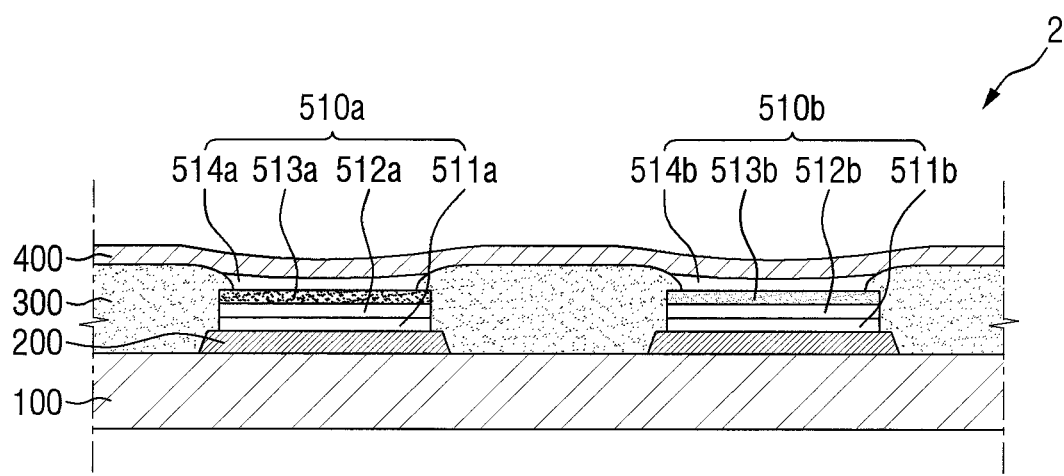
FIG. 4 is a cross-sectional view of a display device according to another exemplary embodiment of the present disclosure.

FIG. 4 is a cross-sectional view of a display device according to another exemplary embodiment of the present disclosure.

Referring to FIG. 4, a display device 2 differs from the display device 1 according to the exemplary embodiment of FIG. 1 in that a bank 300 is disposed on the first and second emission layers 513a and 513b.

In one exemplary embodiment, the first and second organic layers 510a and 510b may be disposed between anode electrodes 200 and a cathode electrode 400. The first organic layer 510a may be disposed in a first pixel displaying a blue color, and the second organic layer 510b may be disposed in a second pixel displaying a green color.

The first organic layer 510a may include a first hole injection layer 511a, a first hole transport layer 512a, the first emission layer 513a, and a first electron injection layer 514a. The first emission layer 513a may be, but is not limited to, a blue emission layer. The second organic layer 510b may include a second hole injection layer 511b, a second hole transport layer 512b, the second emission layer 513b, and a second electron injection layer 514b. The second emission layer 513b may be, but is not limited to, a green emission layer. The first and second organic layers 510a and 510b have been already described above with reference to FIGS. 1 through 3, and thus, detailed descriptions thereof will be omitted.

The bank 300 may be disposed on the first and second emission layers 513a and 513b. The bank 300 may at least partially overlap with the anode electrodes 200, the first hole injection layer 511a, the first hole transport layer 512a, the first emission layer 513a, the second hole injection layer 511b, the second hole transport layer 512b, and the second emission layer 513b and may have openings that at least partially expose the surfaces of the first and second emission layers 513a and 513b therethrough.

Methods of manufacturing a display device according to exemplary embodiments of the present disclosure will hereinafter be described in more detail.

FIGS. 5 through 14 are cross-sectional views illustrating a method of manufacturing a display device according to an exemplary embodiment of the present disclosure.

Figure 5:
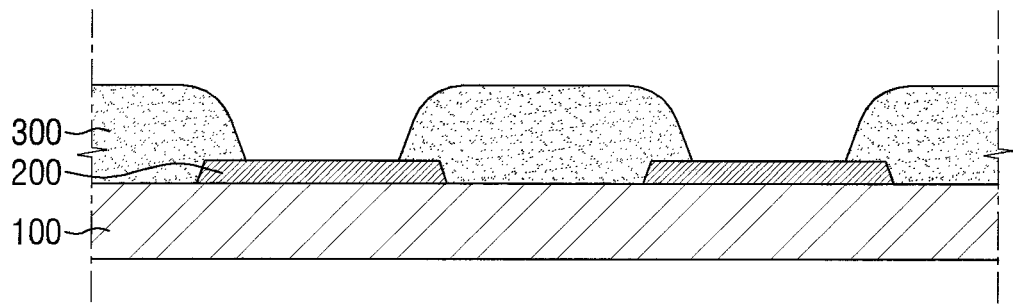
FIGS. 5 through 14 are cross-sectional views illustrating a method of manufacturing a display device according to an exemplary embodiment of the present disclosure.

Referring to FIG. 5, anode electrodes 200 and a bank 300 are formed on a base 100.

The anode electrodes 200 may be disposed on the base 100. The anode electrodes 200 may be electrically connected to driving transistors of the base 100. The anode electrodes 200 may be disposed in pixels, respectively, by forming an electrode layer and then patterning the electrode layer.

The bank 300 may be disposed on the anode electrodes 200. The bank 300 may have openings that at least partially expose the surfaces of the anode electrodes 200 therethrough. The bank 300 may be substantially lattice-shaped in a plan view.

The anode electrodes 200 and the bank 300 have already been described above with reference to FIG. 3, and detailed descriptions thereof will not be repeated.

Figure 6:
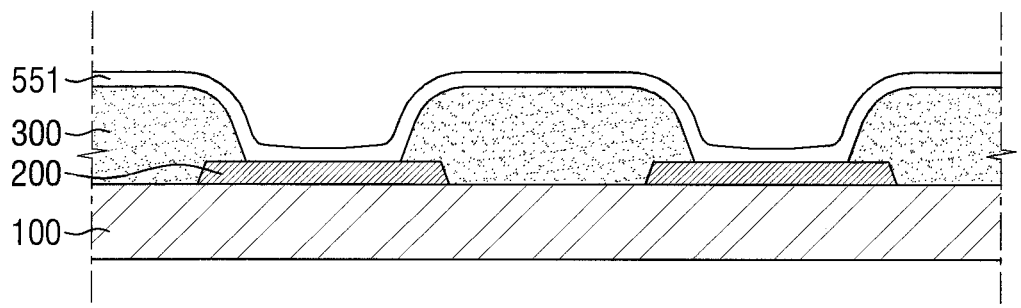

Thereafter, referring to FIG. 6, a first coating layer 551 is formed by coating the anode electrodes 200 and the bank 300 with a composition for forming an organic film. A coating method utilized to form the first coating layer 551 is not particularly limited, but for example, spin coating or slit coating may be utilized.

In one exemplary embodiment, the composition utilized to form the first coating layer 551 and the first coating layer 551 may include a compound of Formula 1. For example, the first coating layer 551 may include a compound of Formula A-1 and may further include a compound of Formula E-1 or E-2. Compounds of Formulae A-2 through A-8, which are specific examples of the compound of Formula A-1, and substituents thereof have been already described above, and detailed descriptions thereof will not be repeated.

Figure 7:
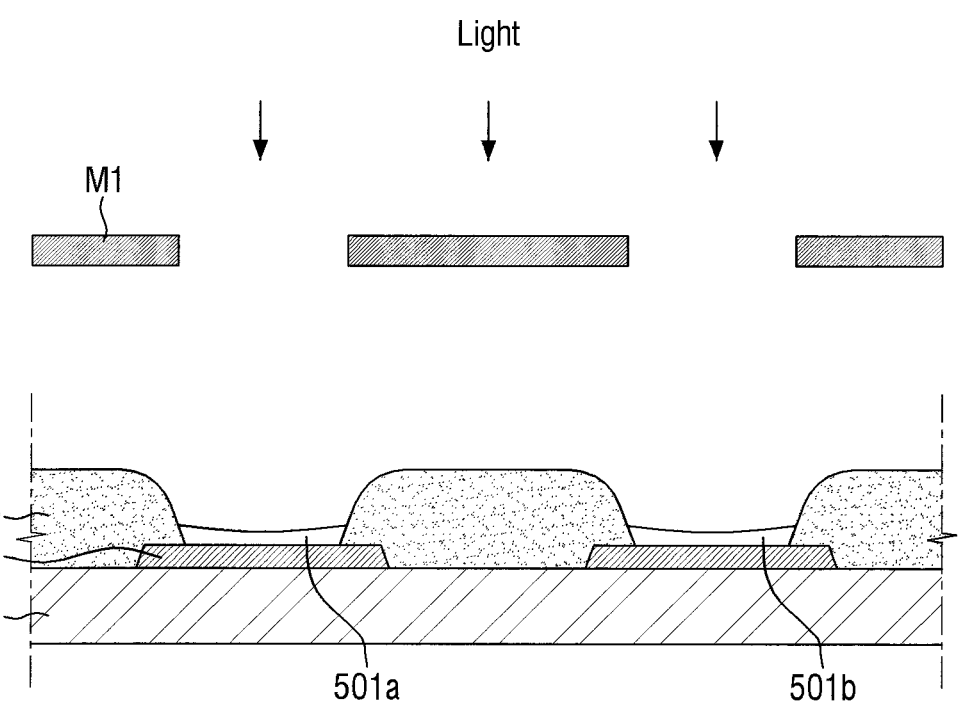

Thereafter, referring to FIG. 7, organic layer patterns are formed by patterning the first coating layer 551 of FIG. 6. An act of forming the organic layer patterns of FIG. 7 may be an act of forming the first and second hole injection layer patterns 501*a* and 501*b* in the first and second pixels, respectively, by patterning the first coating layer 551.

In one exemplary embodiment, the act of forming the organic layer patterns of FIG. 7 may include: placing a mask M1; partially exposing and curing the first coating layer 551 of FIG. 6 by applying light; and forming the first and second hole injection layer patterns 501*a* and 501*b*, which are exposed and cured, utilizing a developer.

The composition utilized to form the first coating layer 551 and the first coating layer 551 may include the compound of Formula A-1, which has a photo-polymerizable reacting group, and may thus have negative photosensitivity so that part thereof that is exposed to light may be photo-cured. Accordingly, the organic layer patterns of FIG. 7 can be precisely formed at any desired locations without the need of a complex process.

Figure 8:
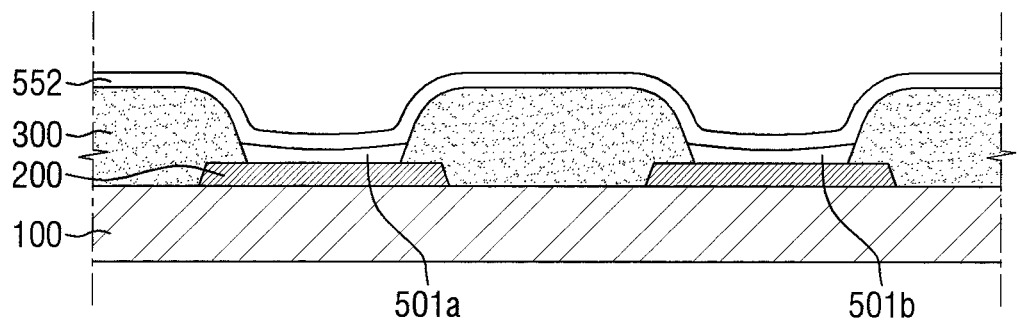

Thereafter, referring to FIG. 8, a second coating layer 552 is formed by coating the first and second hole injection layer patterns 501*a* and 501*b* with a composition for forming an organic layer.

In one exemplary embodiment, the composition utilized to form the second coating layer 552 and the second coating layer 552 may include the compound of Formula 1. For example, the second coating layer 552 may include the compound of Formula A-1. Compounds of Formulae A-2 through A-8, which are specific examples of the compound of Formula A-1, and their respective substituents have been already described above, and detailed descriptions thereof will not be repeated.

Figure 9:
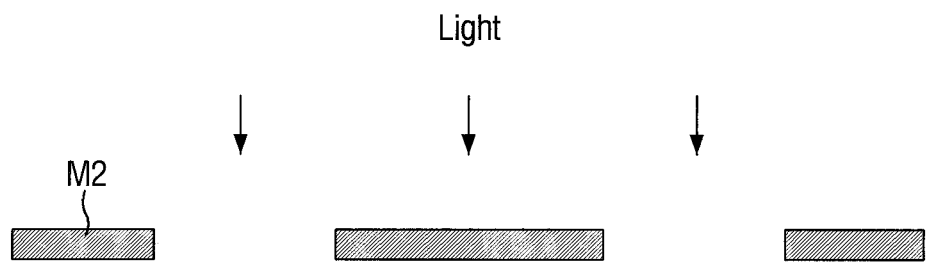
Figure 9:
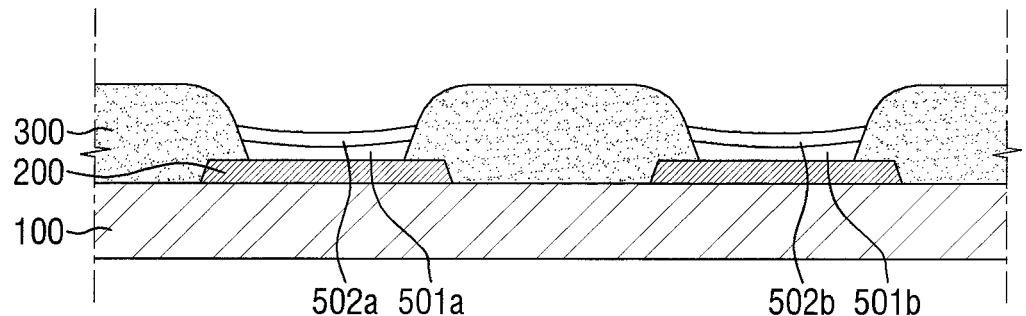

Thereafter, referring to FIG. 9, organic layer patterns are formed by patterning the second coating layer 552 of FIG. 8. An act of forming the organic layer patterns of FIG. 9 may be an act of forming the first and second hole transfer layer patterns 502*a* and 502*b* in the first and second pixels, respectively, by patterning the second coating layer 552.

In one exemplary embodiment, the act of forming the organic layer patterns of FIG. 9 may include: placing a mask M2; partially exposing and curing the second coating layer 552 of FIG. 8 by applying light; and forming the first and second hole transfer layer patterns 502*a* and 502*b*, which are exposed and cured, utilizing a developer.

The composition utilized to form the second coating layer 552 and the second coating layer 552 may include the compound of Formula A-1, which has a photo-polymerizable reacting group, and may thus have negative photosensitivity so that part thereof that is exposed to light may be photo-cured. Accordingly, the organic layer patterns of FIG. 9 can be precisely formed at any desired locations without the need of a complex process.

Figure 10:
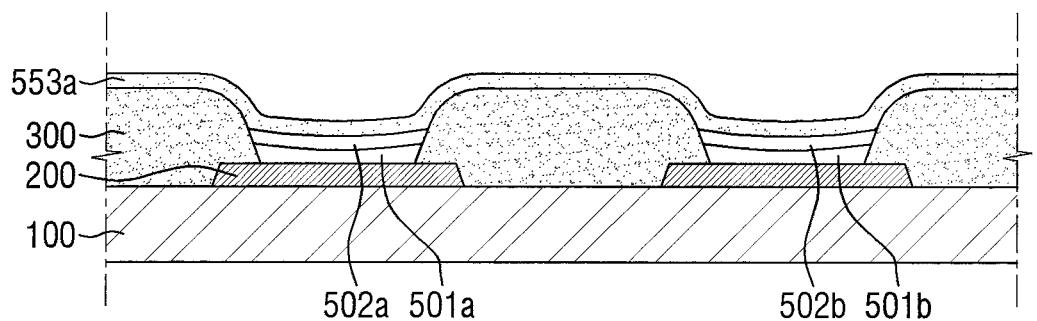

Thereafter, referring to FIG. 10, a third coating layer 553*a* is formed by coating the first and second hole transport layer patterns 502*a* and 502*b* with a composition for forming an organic film.

In one exemplary embodiment, the composition utilized to form the third coating layer 553*a* and the third coating layer 553*a* may include the compound of Formula 1. For example, the third coating layer 553*a* may include a compound of Formula B-1 and/or a compound of Formula C-1. Compounds of Formulae B-2 through B-23 and C-2 through C-16, which are specific examples of the compound of Formula B-1 or C-1, and their respective substituents have been already described above, and detailed descriptions thereof will not be repeated.

Figure 11:
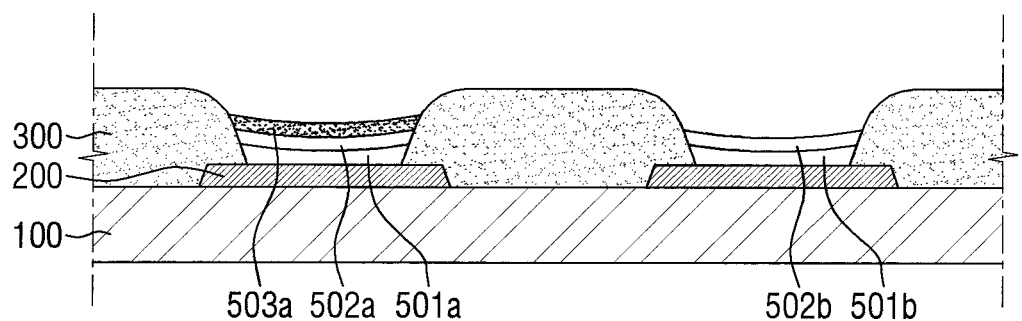

Thereafter, referring to FIG. 11, an organic layer pattern is formed by patterning the third coating layer 553*a* of FIG. 10. An act of forming the organic layer pattern of FIG. 11 may be an act of forming a first emission layer pattern 503*a* in the first pixel by patterning the third coating layer 553*a*.

In one exemplary embodiment, the act of forming the organic layer pattern of FIG. 11 may include: placing a mask M3; partially exposing and curing the third coating layer 553*a* of FIG. 10 by applying light; and forming the first emission layer pattern 503*a*, which is exposed and cured, utilizing a developer.

The composition utilized to form the third coating layer 553*a* and the third coating layer 553*a* may include the compound of Formula B-1, which has a photo-polymerizable reacting group, and/or the compound of Formula C-1, which also has a photo-polymerizable reacting group, and may thus have negative photosensitivity so that part thereof that is exposed to light may be photo-cured. Accordingly, the organic layer pattern of FIG. 11 can be precisely formed at any desired location without the need of a complex process.

Figure 12:
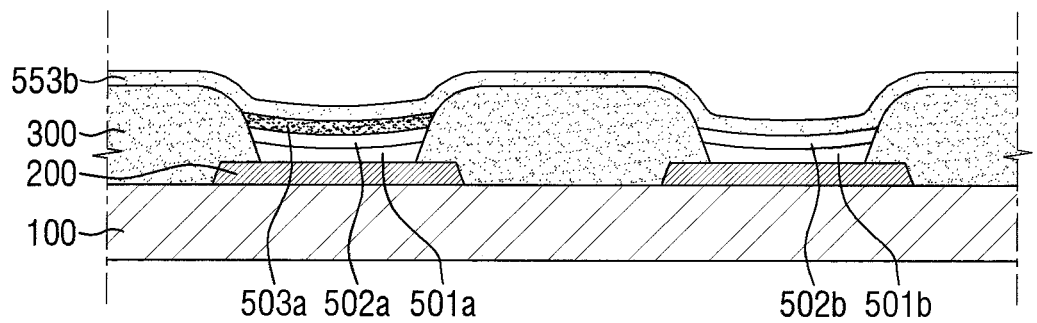

Thereafter, referring to FIG. 12, a fourth coating layer 553*b* is formed by coating the first emission layer pattern 503*a* and the second hole transport layer pattern 502*b* with a composition for forming an organic film.

In one exemplary embodiment, the composition utilized to form the fourth coating layer 553*b* and the fourth coating layer 553*b* may include the compound of Formula 1. For example, the fourth coating layer 553*b* may include a compound of Formula D-1 and may further include a compound of Formula E-3 or E-4. Compounds of Formulae D-2 through D-16, which are specific examples of the compound of Formula D-1, and their respective substituents have already been described above, and detailed descriptions thereof will not be repeated.

Figure 13:
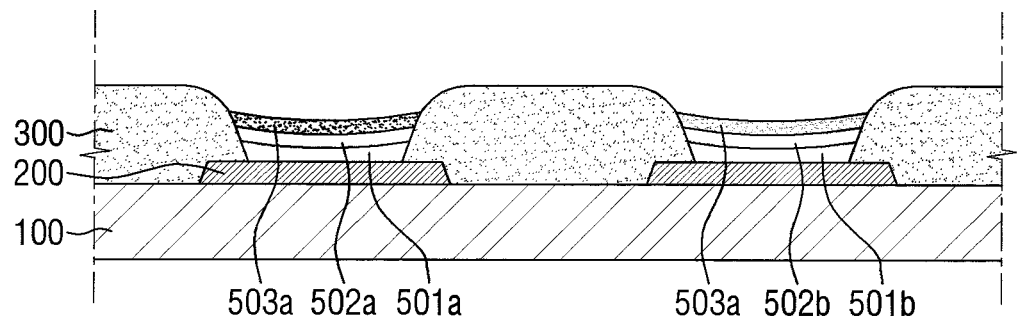

Thereafter, referring to FIG. 13, an organic layer pattern is formed by patterning the fourth coating layer 553*b* of FIG. 12. An act of forming the organic layer pattern of FIG. 13 may be an act of forming a second emission layer pattern 503*b* in the second pixel by patterning the fourth coating layer 553*b*.

In one exemplary embodiment, the act of forming the organic layer pattern of FIG. 13 may include placing a mask M4; partially exposing and curing the fourth coating layer 553*b* of FIG. 12 by applying light; and forming the second emission layer pattern 503*b*, which is exposed and cured, utilizing a developer.

The composition utilized to form the fourth coating layer 553*b* and the fourth coating layer 553*b* may include the compound of Formula D-1, which has a photo-polymerizable reacting group, and may thus have negative photosensitivity so that part thereof that is exposed may be photocured. Accordingly, the organic layer pattern of FIG. 13 can be precisely formed at any desired location without the need of a complex process.

Figure 14:
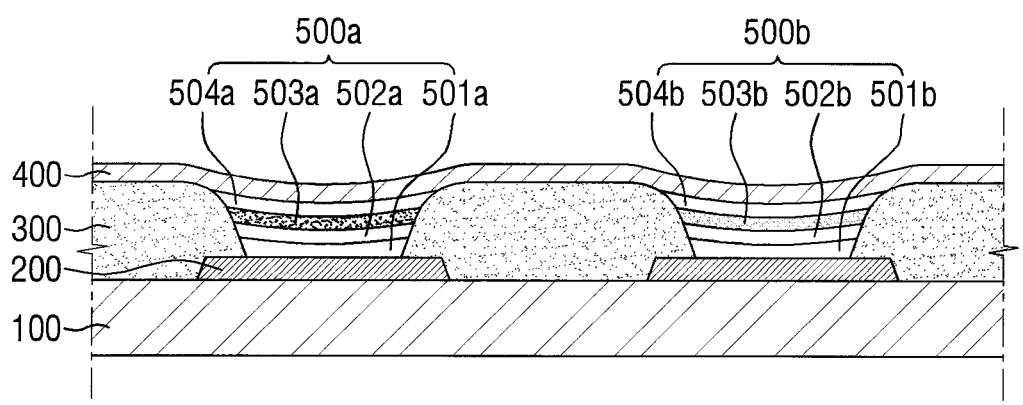

Thereafter, referring to FIG. 14, first and second electron injection layer patterns 504a and 504b are formed on the first and second emission layer patterns 503a and 503b, respectively, and a cathode electrode 400 is formed.

A method of manufacturing a display device according to another exemplary embodiment of the present disclosure will hereinafter be described in more detail.

FIGS. 15 through 18 are cross-sectional views illustrating a method of manufacturing a display device according to another exemplary embodiment of the present disclosure.

Figure 15:
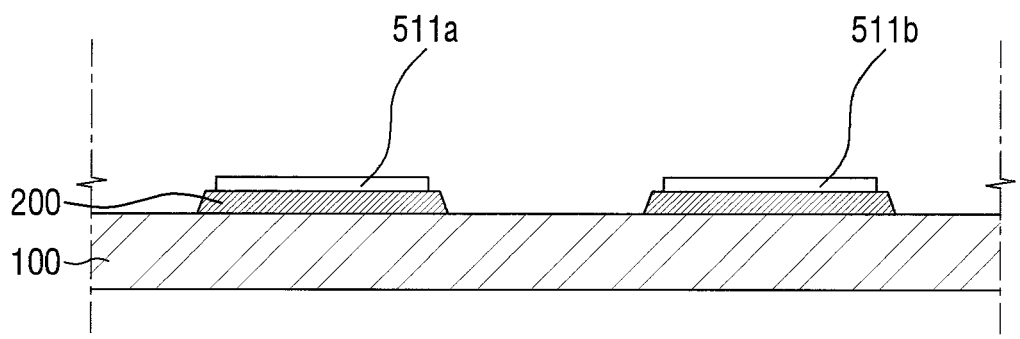
FIGS. 15 through 18 are cross-sectional views illustrating a method of manufacturing a display device according to another exemplary embodiment of the present disclosure.

Referring to FIG. 15, anode electrodes 200 and the first and second hole injection layer patterns 511a and 511b are formed on a base 100. The formation of the first and second hole injection layer patterns 511a and 511b has been already described above with reference to FIGS. 6 and 7, and a detailed description thereof will not be repeated.

Figure 16:
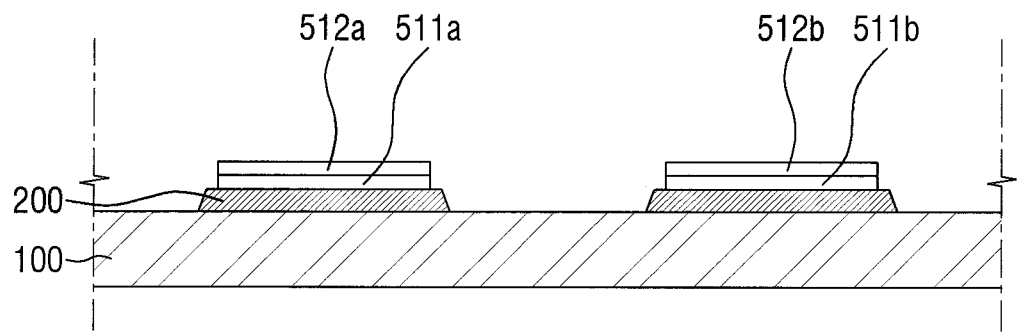

Thereafter, referring to FIG. 16, the first and second hole transport layer patterns 512a and 512b are formed on the first and second hole injection layer patterns 511a and 511b, respectively. The formation of the first and second hole transport layer patterns 512a and 512b has been already described above with reference to FIGS. 8 and 9, and a detailed description thereof will not be repeated.

Figure 17:
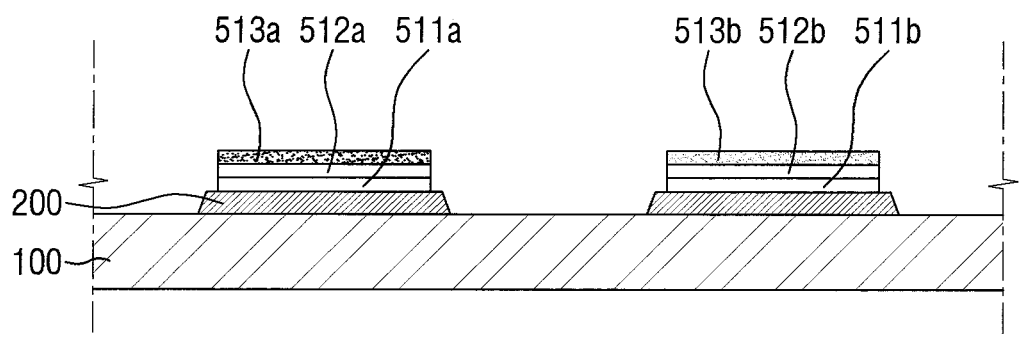
Figure 18:
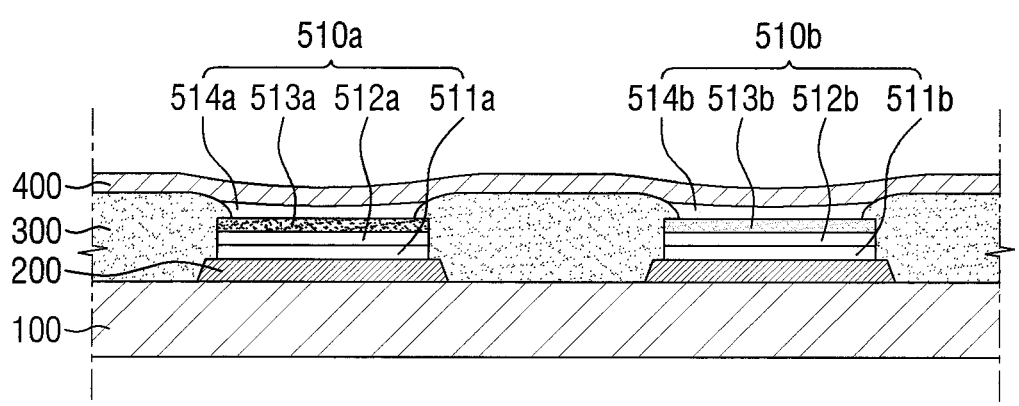

Thereafter, referring to FIG. 17, the first and second emission layer patterns 513a and 513b are formed on the first and second hole transport layer patterns 512a and 512b, respectively. The formation of the first and second emission layer patterns 513a and 513b has been already described above with reference to FIGS. 10 through 13, and a detailed description thereof will not be repeated.

Thereafter, a bank 300 is formed on the first and second emission layer patterns 513a and 513b, and the first and second electron injection layer patterns 514a and 514b are formed.

In one exemplary embodiment, the bank 300 may be formed to have openings that at least partially expose the surfaces of the first and second emission layer patterns 513a and 513b therethrough. The bank 300 may be substantially lattice-shaped in a plan view. The first and second electron injection layer patterns 514a and 514b may be disposed on the bank 300.

In another exemplary embodiment, the first hole injection layer pattern 511a, the first hole transport layer pattern 512a, and the first emission layer pattern 513a may be formed at the same time by patterning. That is, the first hole injection layer pattern 511a, the first hole transport layer pattern 512a, and the first emission layer pattern 513a may be formed at the same time by performing exposure and curing utilizing a single mask. In this case, the sides of the first hole injection layer pattern 511a, the sides of the first hole transport layer pattern 512a, and the sides of the first emission layer pattern 513a may all be aligned.

Similarly, the second hole injection layer pattern 511b, the second hole transport layer pattern 512b, and the second emission layer pattern 513b may be formed at the same time by patterning. That is, the second hole injection layer pattern 511b, the second hole transport layer pattern 512b, and the second emission layer pattern 513b may be formed at the same time by performing exposure and curing utilizing a single mask. In this case, the sides of the second hole injection layer pattern 511b, the sides of the second hole transport layer pattern 512b, and the sides of the second emission layer pattern 513b may all be aligned.

While the present invention has been particularly illustrated and described with reference to exemplary embodiments thereof, it will be understood by those of ordinary skill in the art that various changes in form and detail may be made therein without departing from the spirit and scope of the present invention as defined by the following claims, and equivalents thereof. The exemplary embodiments should be considered in a descriptive sense only and not for purposes of limitation.

What is claimed is:
1. A composition for forming an organic film, comprising:
a solvent; and
a compound of Formula 1:

$$Ar\text{-}(\text{-}R)_k \quad \quad \quad \text{Formula 1}$$

wherein in Formula 1,
Ar is

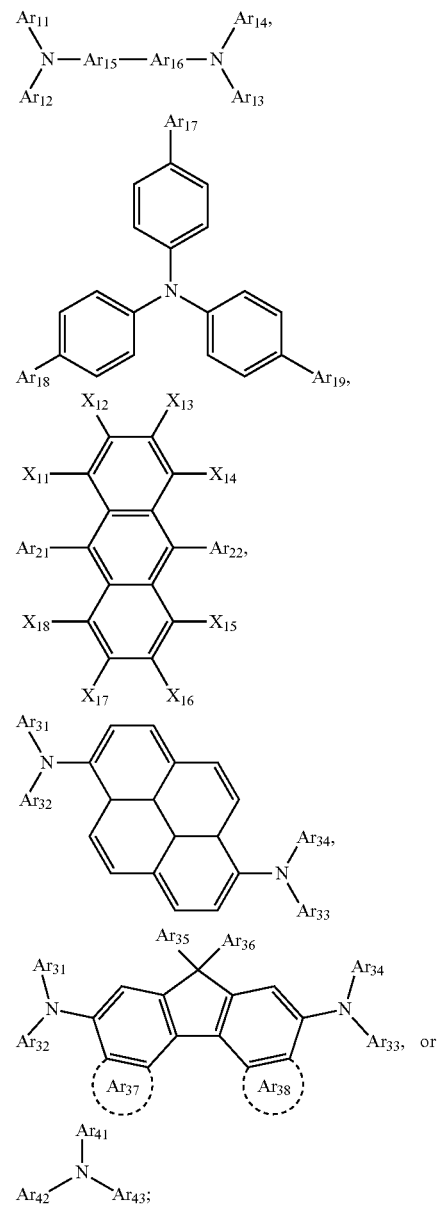

$Ar_{11}$, $Ar_{12}$, $Ar_{13}$ and $Ar_{14}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;

$Ar_{15}$ and $Ar_{16}$ are each independently a substituted or unsubstituted $C_{6-12}$ arylene group or a substituted or unsubstituted $C_{1-12}$ heteroarylene group;

two or more of $Ar_{11}$, $Ar_{12}$, and $Ar_{15}$ optionally form a ring together;

two or more of $Ar_{13}$, $Ar_{14}$, and $Ar_{16}$ optionally form a ring together;

$Ar_{17}$, $Ar_{18}$, and $Ar_{19}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;

$Ar_{21}$ and $Ar_{22}$ are each independently a substituted or unsubstituted $C_{6-60}$ arylene group or a substituted or unsubstituted $C_{1-60}$ heteroarylene group;

$X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group;

$Ar_{31}$, $Ar_{32}$, $Ar_{33}$, and $Ar_{34}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;

$Ar_{35}$ and $Ar_{36}$ are each independently a hydrogen atom or a substituted or unsubstituted $C_{6-10}$ aryl group or a substituted or unsubstituted $C_{1-10}$ heteroaryl group;

$Ar_{35}$ and $Ar_{36}$ optionally form a ring together;

$Ar_{37}$ and $Ar_{38}$ are each independently a substituted or unsubstituted $C_{6-20}$ fused ring;

$Ar_{41}$ is a substituted or unsubstituted $C_{6-60}$ aryl group or a substituted or unsubstituted $C_{3-60}$ heteroaryl group;

$Ar_{42}$ and $Ar_{43}$ are each independently a substituted or unsubstituted $C_{6-60}$ arylene group or a substituted or unsubstituted $C_{3-60}$ heteroarylene group;

$Ar_{42}$ and $Ar_{43}$ form a ring together;

at least one of $Ar_{11}$, $Ar_{12}$, $Ar_{13}$, and $Ar_{14}$, at least one of $Ar_{17}$, $Ar_{18}$, and $Ar_{19}$, at least one of $Ar_{21}$, and $Ar_{22}$, at least one of $Ar_{31}$, $Ar_{32}$, $Ar_{33}$, and $Ar_{34}$, and at least one of $Ar_{42}$, and $Ar_{43}$ are divalent arylene or divalent heteroarylene groups, R is bonded thereto;

R is

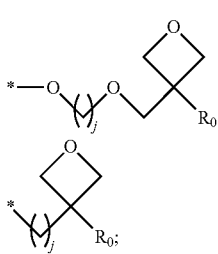 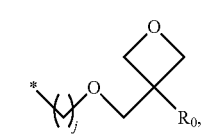 or

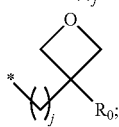

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group;

j is an integer between 2 and 9; and k is an integer between 2 and 4, wherein when the compound of Formula 1 is a compound represented by Formula A-2:

$R_{11}$ to $R_{14}$ are each independently a hydrogen atom or

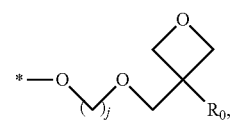

two or more of $R_{11}$, $R_{12}$, $R_{13}$, and $R_{14}$ are each independently

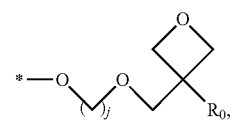

and j is an integer between 2-9; and wherein when two selected from $R_{11}$ to $R_{14}$ of Formula A-2 are each a hydrogen atom, and another two of $R_{11}$ to $R_{14}$ are each represented by

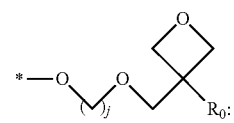

j is an integer between 2-5 or 7-9:

Formula A-2

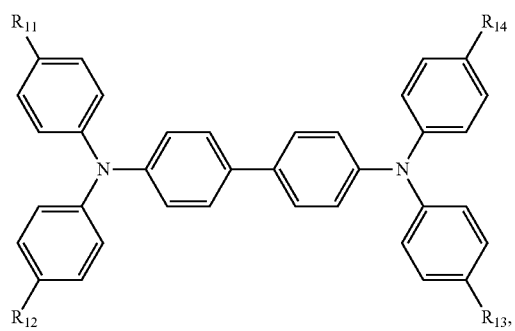

and wherein the compound of Formula 1 is contained in an amount of 1.0 weight percent (wt %) to 5.0 wt % with respect to a total weight of the composition for forming the organic film.

2. The composition of claim 1, wherein the compound of Formula 1 is a compound of Formula A-1, and the composition for forming the organic film further comprises a compound of Formula E-1 or E-2:

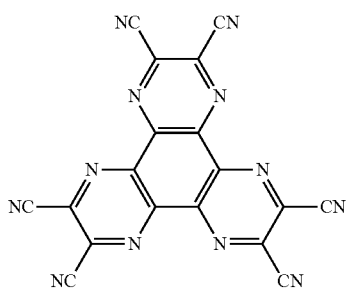

Formula A-1

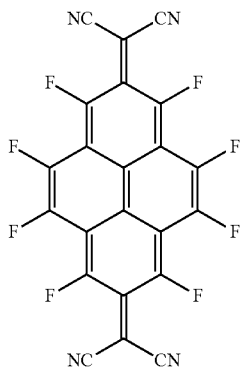

Formula E-1

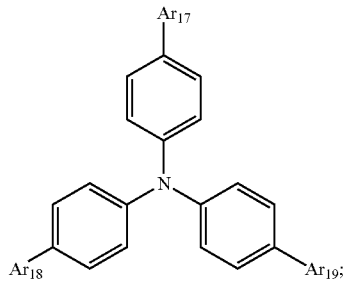

Formula E-2 wherein in Formula A-1, $Ar_1$ is

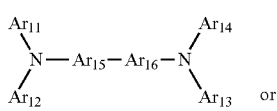

or

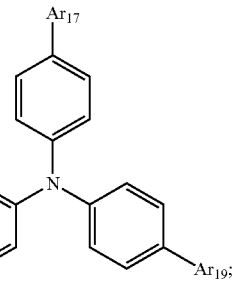

$Ar_{11}$, $Ar_{12}$, $Ar_{13}$, and $Ar_{14}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;

$Ar_{15}$ and $Ar_{16}$ are each independently a substituted or unsubstituted $C_{6-12}$ arylene group or a substituted or unsubstituted $C_{1-12}$ heteroarylene group;

two or more of $Ar_{11}$, $Ar_{12}$, and $Ar_{15}$ optionally form a ring together, two or more of $Ar_{13}$, $Ar_{14}$, and $Ar_{16}$ optionally form a ring together, $Ar_{17}$, $Ar_{18}$, and $Ar_{19}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;

at least one of $Ar_{11}$, $Ar_{12}$, $Ar_{13}$, and $Ar_{14}$, and at least one of $Ar_{17}$, $Ar_{18}$, and $Ar_{19}$ are divalent arylene or divalent heteroarylene groups, $R_1$ is bonded thereto;

$R_1$ is

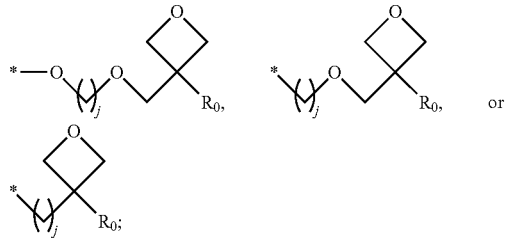

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group;

j is an integer between 2 and 9; and k1 is an integer between 2 and 4.

3. The composition of claim 2, wherein the compound of Formula A-1 is a compound of any one of Formulae A-2 through A-8:

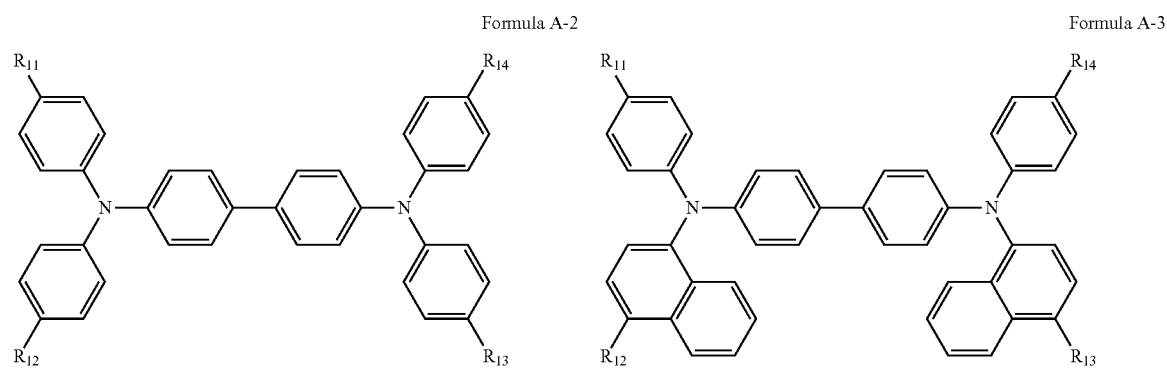
Formula A-2
Formula A-3
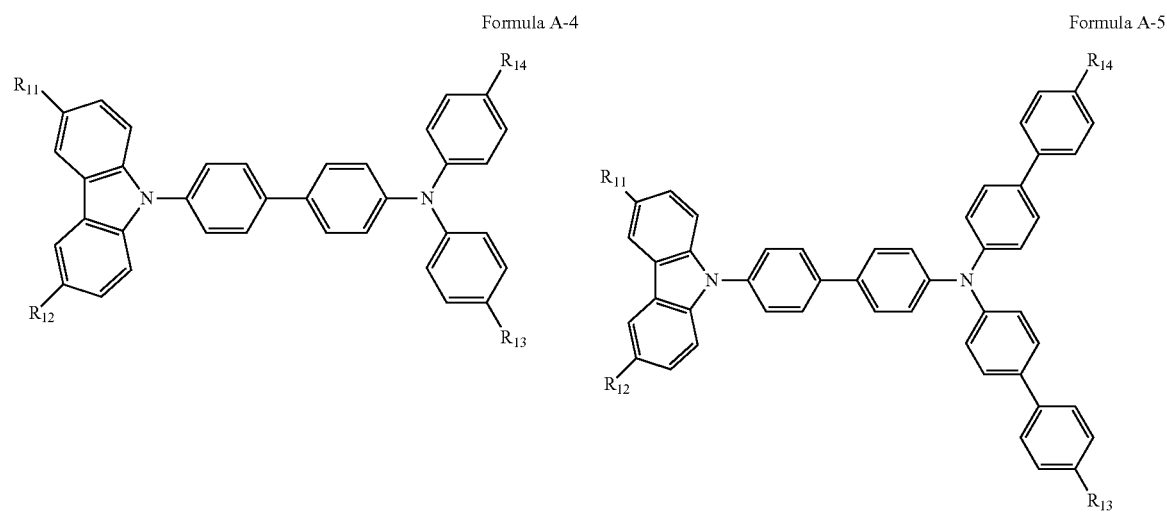
Formula A-4
Formula A-5
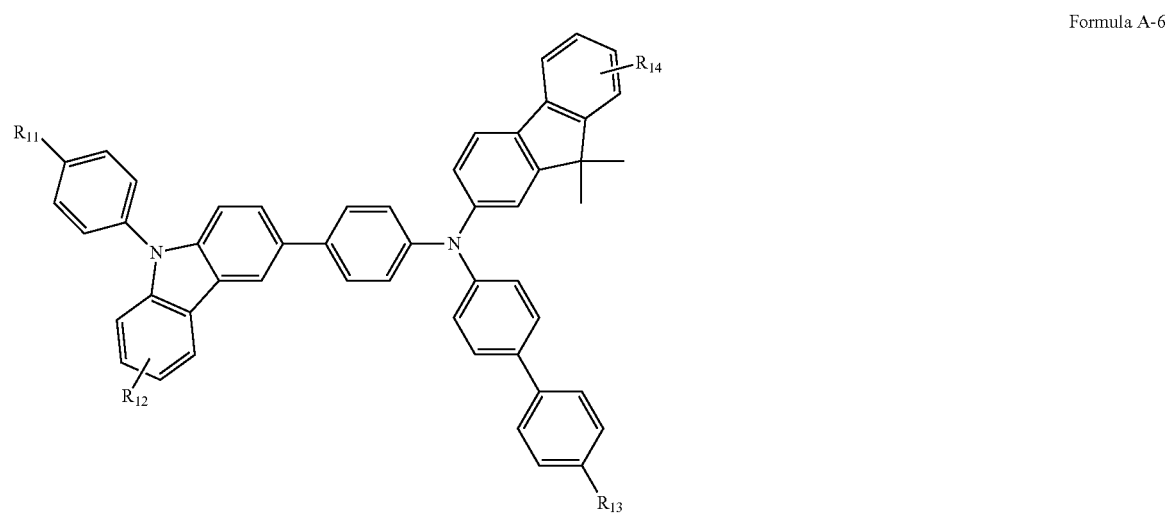
Formula A-6

-continued
Formula A-7
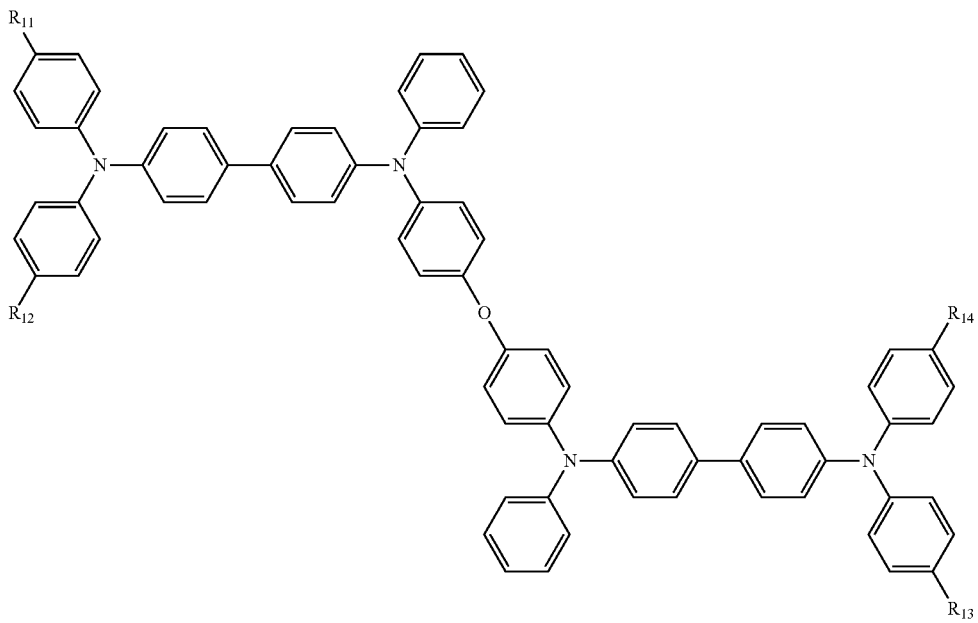
Formula A-8
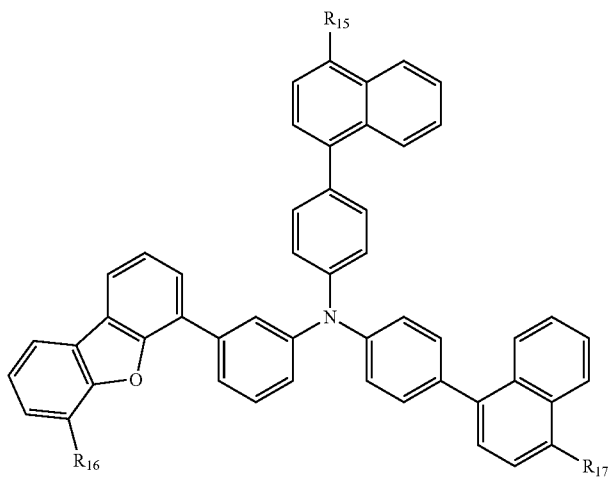
wherein in Formula A-2, $R_{11}$, $R_{12}$, $R_{13}$, $R_{14}$ and j are the same as defined in claim 1, and
wherein in Formulae A-3 through Formula A-8, $R_{11}$, $R_{12}$, $R_{13}$, $R_{14}$, $R_{15}$, $R_{16}$, and $R_{17}$ are each independently a hydrogen atom,
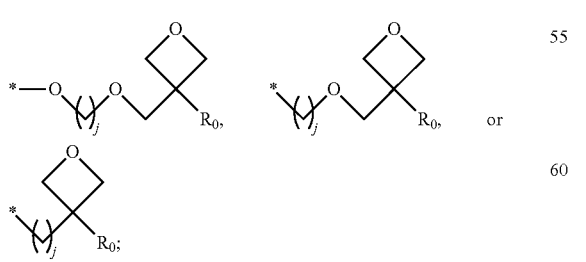
two or more of $R_{11}$, $R_{12}$, $R_{13}$, and $R_{14}$ are each independently
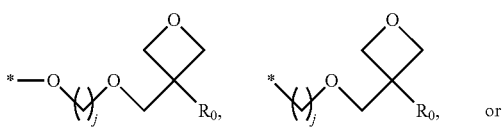
two or more of $R_{15}$, $R_{16}$, and $R_{17}$ are each independently
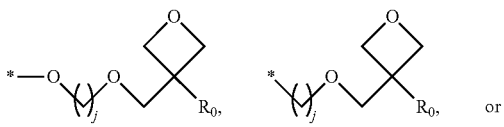

-continued

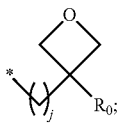

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9.

4. The composition of claim 1, wherein
the compound of Formula 1 is a compound of Formula B-1, and
the composition for forming the organic film comprises the compound of Formula B-1:

$$R_2-Ar_2-R_2' \quad \text{Formula B-1}$$

wherein in Formula B-1,
$Ar_2$ is

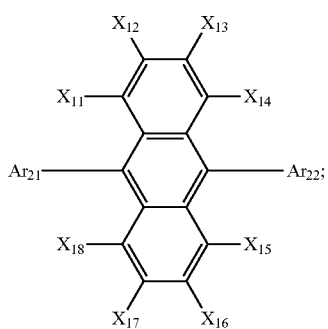

$Ar_{21}$ and $Ar_{22}$ are each independently a substituted or unsubstituted $C_{6-60}$ arylene group or a substituted or unsubstituted $C_{1-60}$ heteroarylene group;

$R_2$ and $R_2'$ are bonded to $Ar_{21}$ and $Ar_{22}$, respectively;

$X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group;

R2 and $R_2'$ are each independently

[structures shown]

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted C2-30 alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9.

5. The composition of claim 4, wherein the compound of Formula B-1 is a compound of any one of Formulae B-2 through B-23:

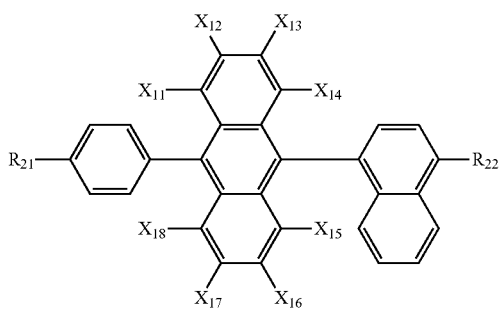

Formula B-2

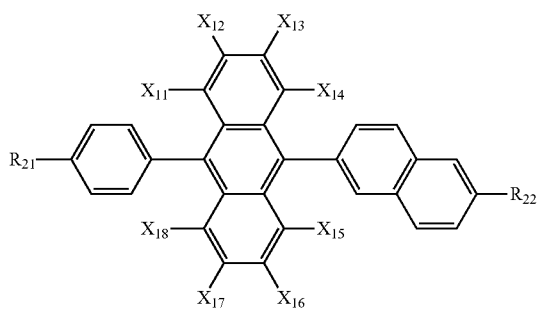

Formula B-3

Formula B-4
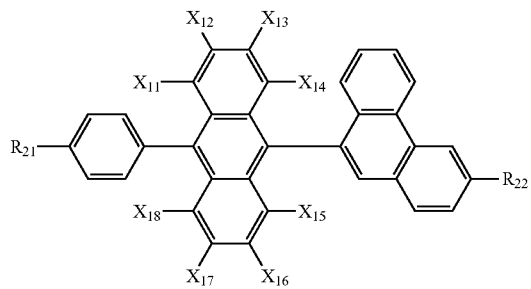
Formula B-5
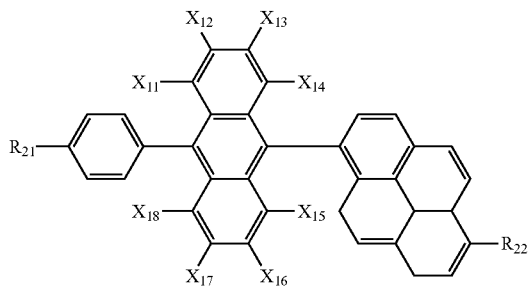
Formula B-6
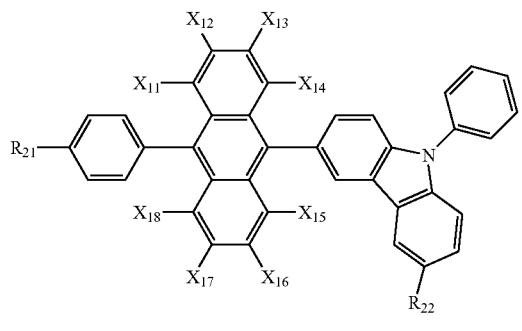
Formula B-7
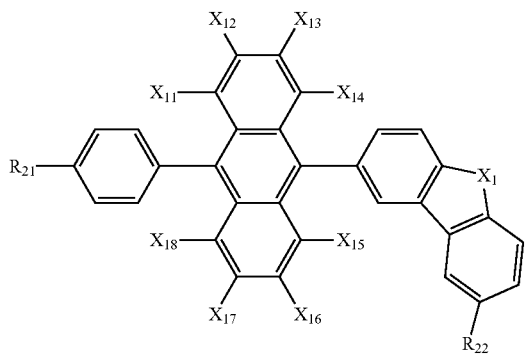
Formula B-8
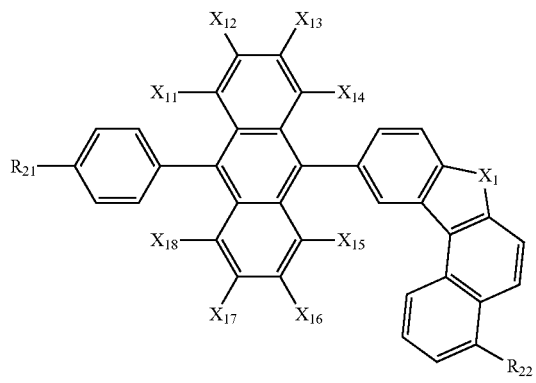
Formula B-9
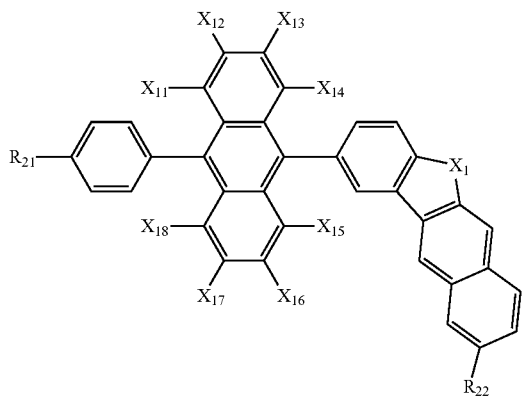
Formula B-10
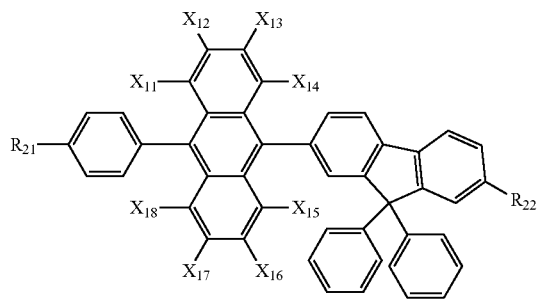
Formula B-11
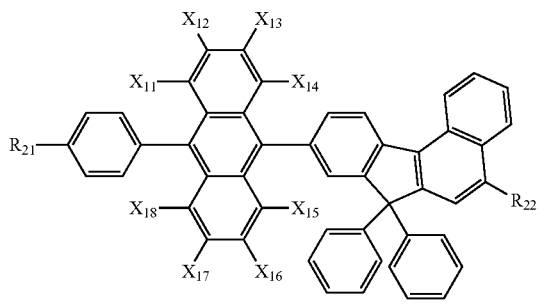

-continued
Formula B-12
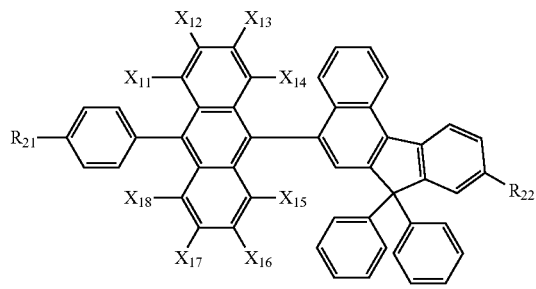
Formula B-13
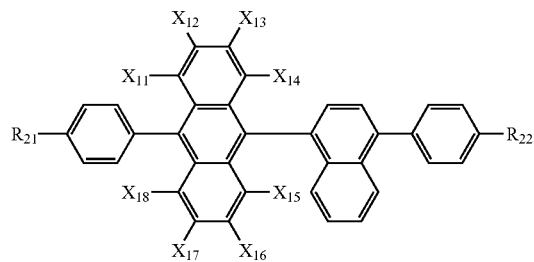
Formula B-14
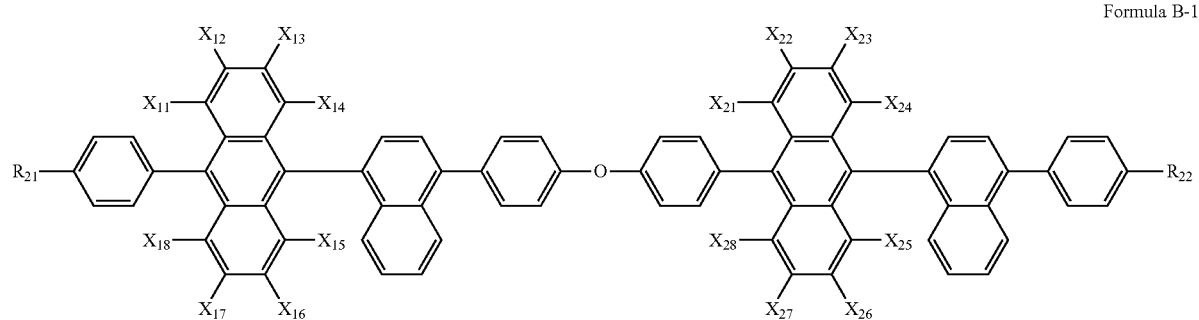
Formula B-15
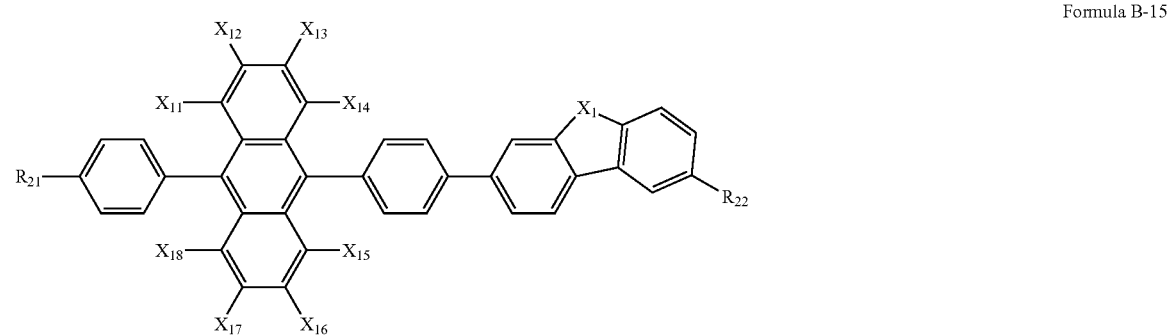
Formula B-16
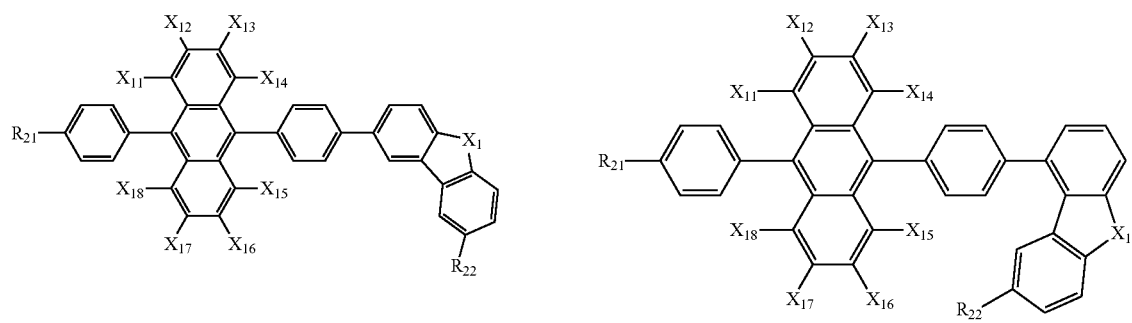
Formula B-17
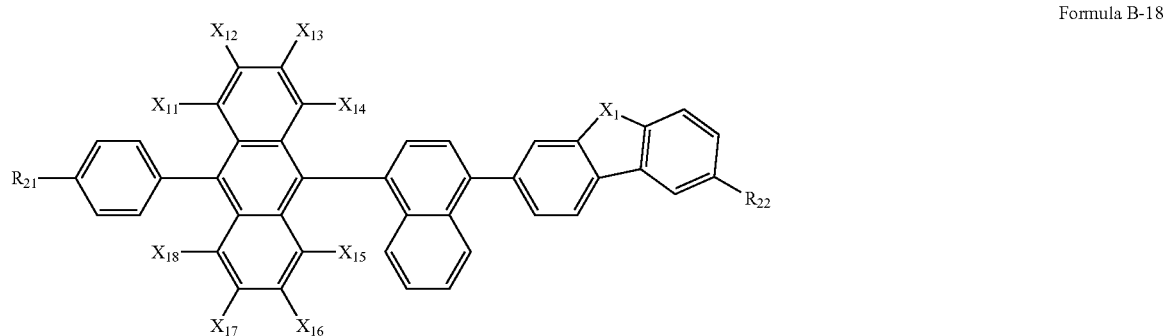
Formula B-18

-continued

Formula B-19

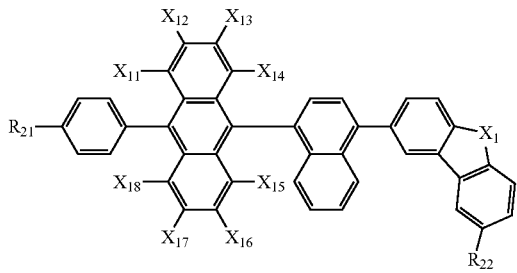

Formula B-20

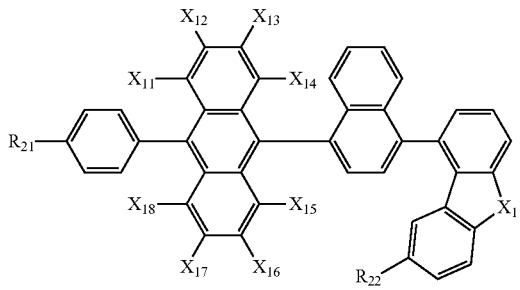

Formula B-21

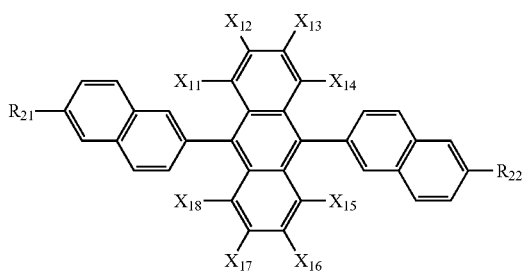

Formula B-22

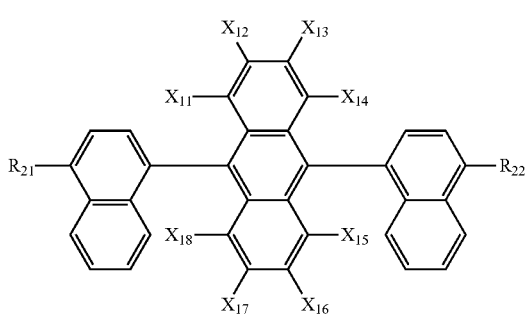

Formula B-23

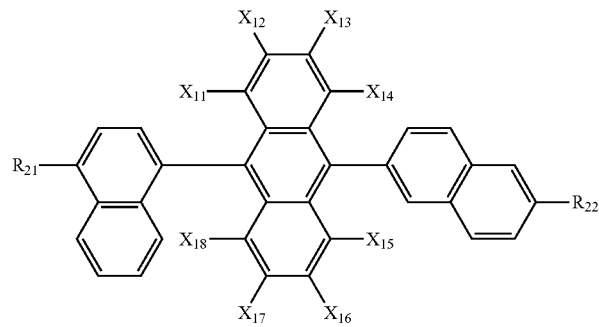

wherein in Formulae B-2 through B-23,
$R_{21}$ and $R_{22}$ are each independently

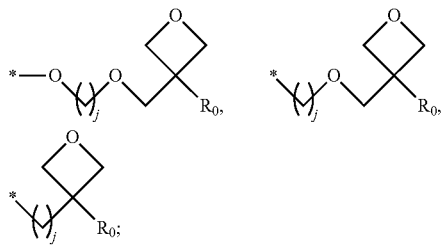

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group;

j is an integer between 2 and 9; and $X_{11}$, $X_{12}$, $X_{13}$, $X_{14}$, $X_{15}$, $X_{16}$, $X_{17}$, and $X_{18}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or an unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group, in Formulae B-7 through B-9 and B-15 through B-20,
$X_1$ is an oxygen atom or a sulfur atom; and
in Formula B-14,
$X_{21}$, $X_{22}$, $X_{23}$, $X_{24}$, $X_{25}$, $X_{26}$, $X_{27}$, and $X_{28}$ are each independently a hydrogen atom, a deuterium atom, a fluorine atom, a substituted or unsubstituted $C_{1-10}$ alkyl group, a substituted or unsubstituted $C_{3-10}$ cycloalkyl group, a substituted or unsubstituted $C_{1-20}$ alkoxy group, a substituted or unsubstituted $C_{3-30}$ alkylsilyl group, a substituted or unsubstituted $C_{6-30}$ aryl group, a substituted or unsubstituted $C_{6-20}$ aryloxy group, a substituted or unsubstituted $C_{8-30}$ arylsilyl group, or a substituted or unsubstituted $C_{5-30}$ heteroaryl group.

6. The composition of claim 5, further comprising:
a compound of Formula C-1:

 Formula C-1 wherein in Formula C-1
$Ar_3$ is

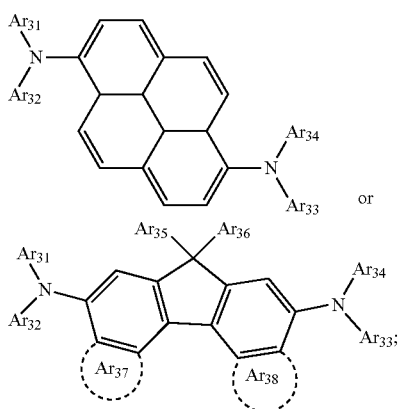

$Ar_{31}$, $Ar_{32}$, $Ar_{33}$, and $Ar_{34}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted C1-60 heteroarylene group;
at least one of $Ar_{31}$, $Ar_{32}$, $Ar_{33}$, and $Ar_{34}$ are divalent arylene or divalent heteroarylene groups, $R_3$ is bonded thereto,
$Ar_{35}$ and $Ar_{36}$ are each independently a hydrogen atom or a substituted or unsubstituted $C_{6-10}$ aryl group or a substituted or unsubstituted heteroaryl group;
$Ar_{35}$ and $Ar_{36}$ optionally form a ring together,
$Ar_{37}$ and $Ar_{38}$ are each independently a hydrogen atom, a substituted or unsubstituted $C_{6-20}$ fused ring;
$R_3$ is

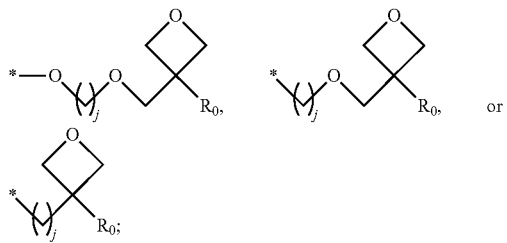

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group;

j is an integer between 2 and 9; and
k3 is an integer between 2 and 4.

7. The composition of claim 6, wherein the compound of Formula C-1 is a compound of any one of Formulae C-2 through C-16:

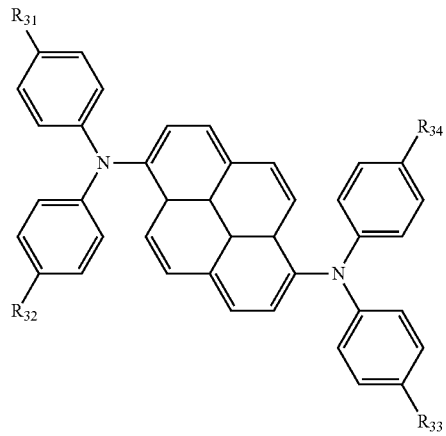

Formula C-2

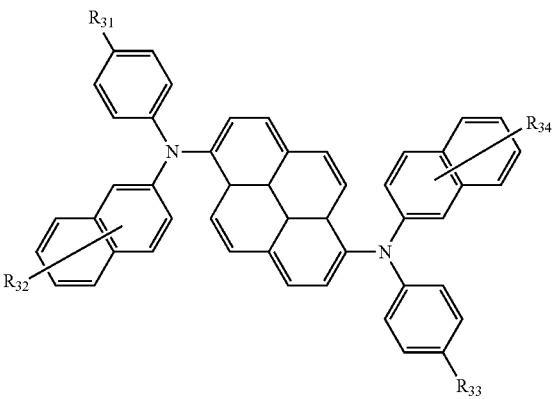

Formula C-3

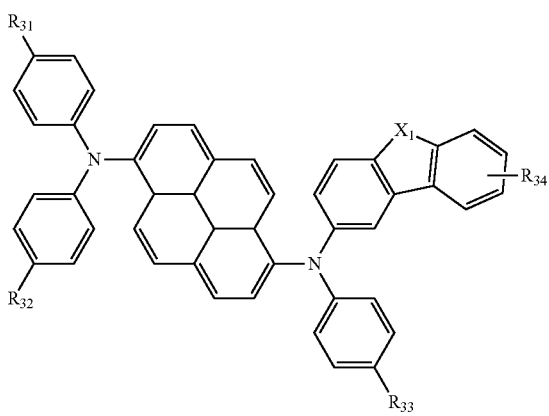

Formula C-4

Formula C-5
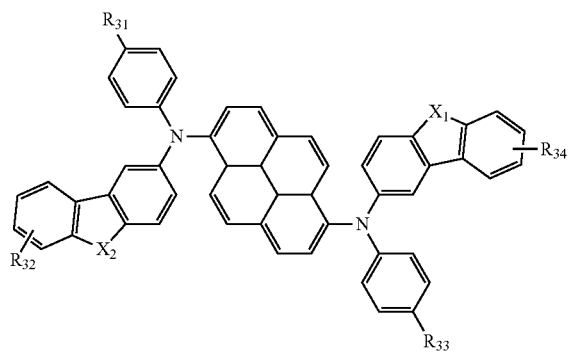
Formula C-6
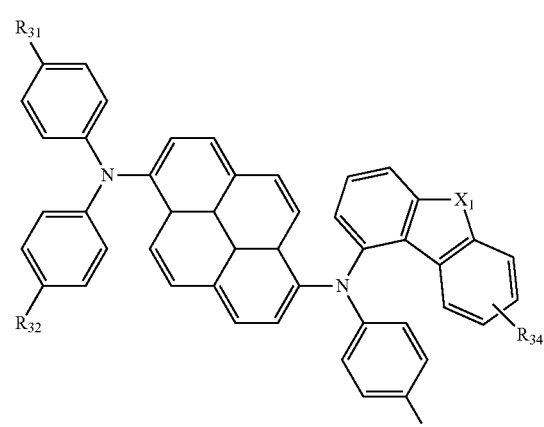
Formula C-7
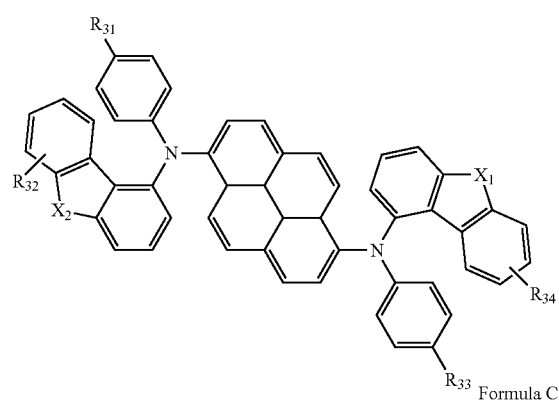
Formula C-8
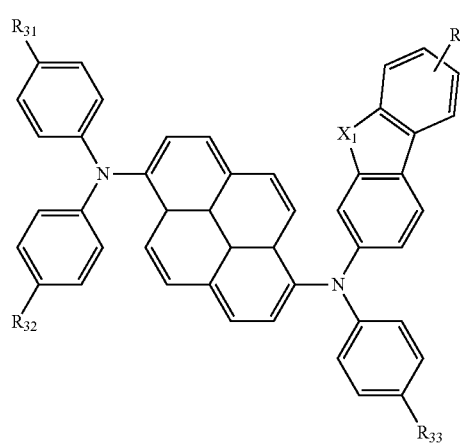
Formula C-9
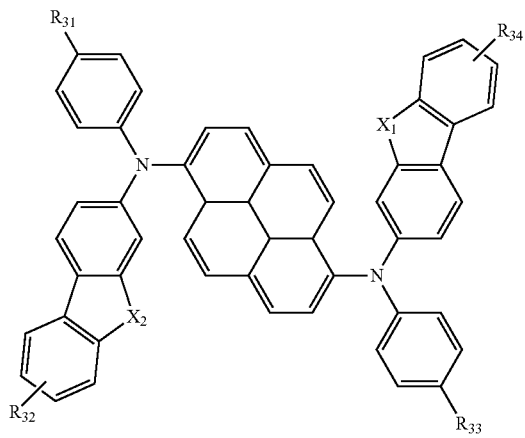
Formula C-10
Formula C-11
Formula C-12

Formula C-13

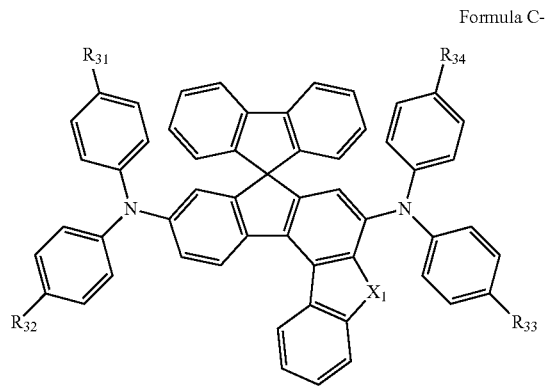

Formula C-14

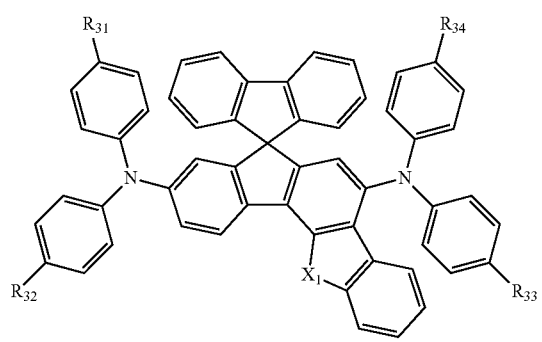

Formula C-15

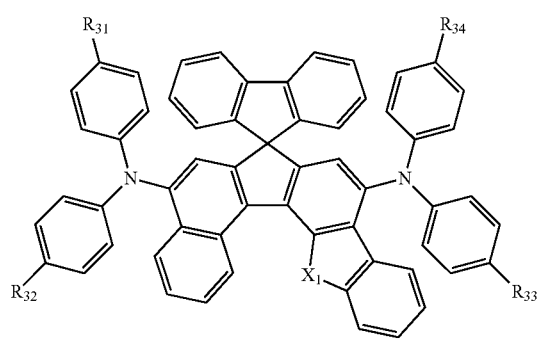

Formula C-16

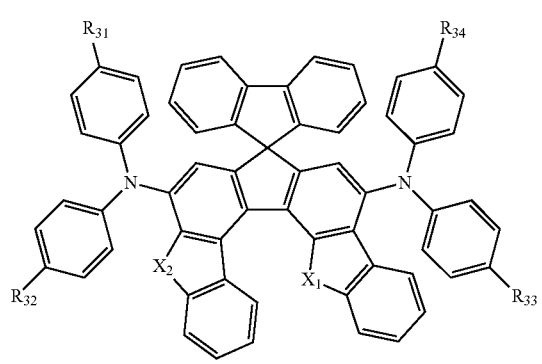

wherein in Formulae C-2 through Formula C-16, $R_{31}$, $R_{32}$, $R_{33}$, and $R_{34}$ are each independently a hydrogen atom,

*—O$\underset{j}{\overbrace{\phantom{xxx}}}$O$\underset{}{\overbrace{\phantom{xx}}}$⬜$R_0$, *$\underset{j}{\overbrace{\phantom{xxx}}}$O$\underset{}{\overbrace{\phantom{xx}}}$⬜$R_0$, or

*$\underset{j}{\overbrace{\phantom{xxx}}}$⬜$R_0$;

two or more of $R_{31}$, $R_{32}$, $R_{33}$, and $R_{34}$ are each independently

*—O$\underset{j}{\overbrace{\phantom{xxx}}}$O$\underset{}{\overbrace{\phantom{xx}}}$⬜$R_0$, *$\underset{j}{\overbrace{\phantom{xxx}}}$O$\underset{}{\overbrace{\phantom{xx}}}$⬜$R_0$, or

*$\underset{j}{\overbrace{\phantom{xxx}}}$⬜$R_0$;

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9; and in Formulae C-4 through C-9 and C-13 through C-16, $X_1$ and $X_2$ are each independently an oxygen atom or a sulfur atom.

8. A composition for forming an organic film, comprising:

a solvent;

a compound of Formula D-1; and a compound of Formula E-3 or E-4:

$R_4$—$Ar_4$—$R_4'$    Formula D-1

Formula E-3

[Ir complex structure]

-continued

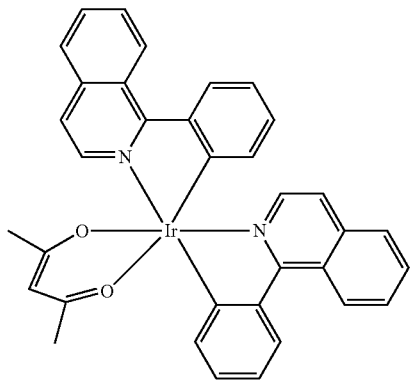

Formula E-4

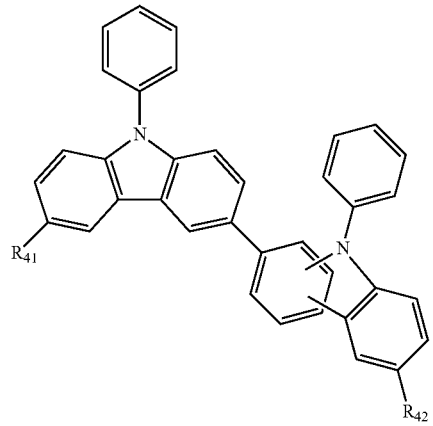

Formula D-2 wherein in Formula D-1,
Ar₄ is

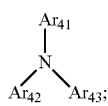

Ar₄₁ is a substituted or unsubstituted $C_{6-60}$ aryl group or a substituted or unsubstituted $C_{1-60}$ heteroaryl group;

Ar₄₂ and Ar₄₃ are each independently a substituted or unsubstituted $C_{6-60}$ arylene group or a substituted or unsubstituted $C_{1-60}$ heteroarylene group;

Ar₄₂ and Ar₄₃ form a ring together;

R₄ and R₄' are bonded to Ar₄₂ and Ar₄₃, respectively;

R₄ and R₄' are each independently

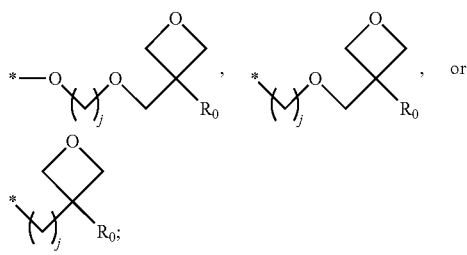

R₀ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group, and j is an integer between 2 and 9.

9. The composition of claim 8, wherein the compound of Formula D-1 is a compound of any one of Formulae D-2 through D-16:

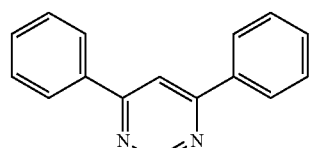

Formula D-3

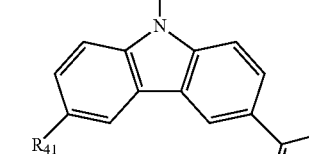

Formula D-4

Formula D-5
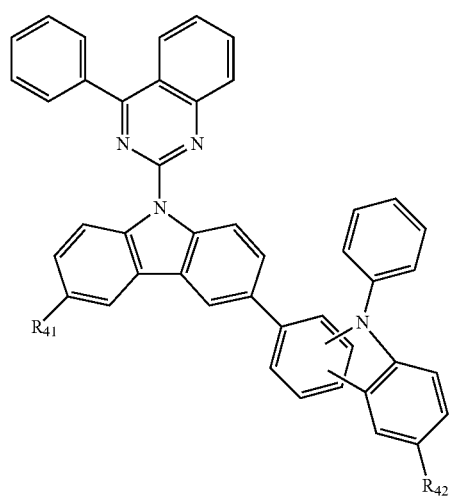
Formula D-6
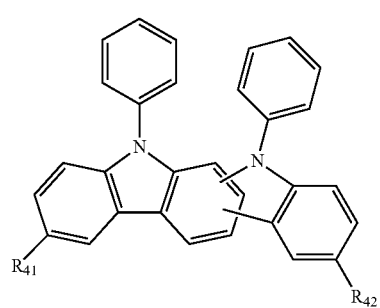
Formula D-7
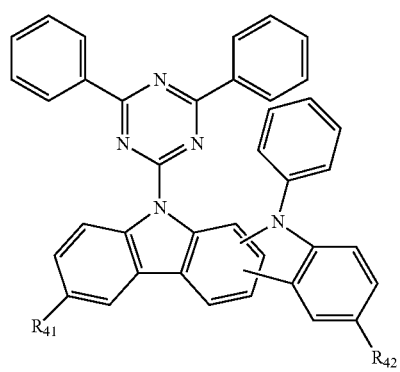
Formula D-8
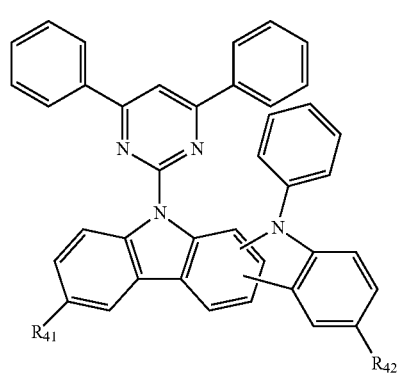
Formula D-9
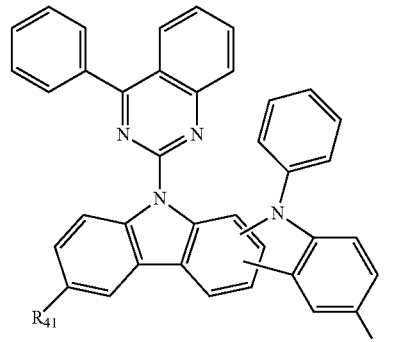
Formula D-10
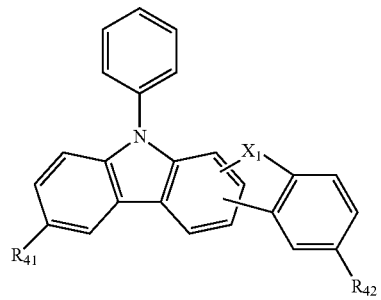
Formula D-11
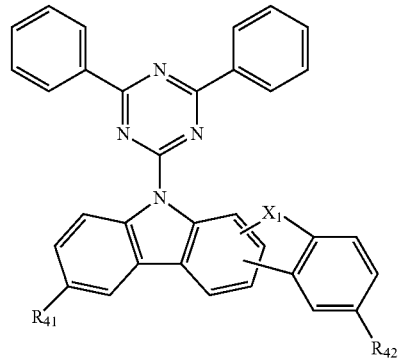
Formula D-12
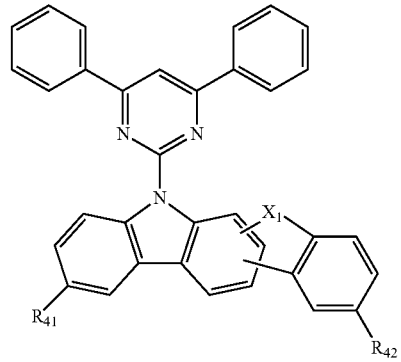

-continued

Formula D-13

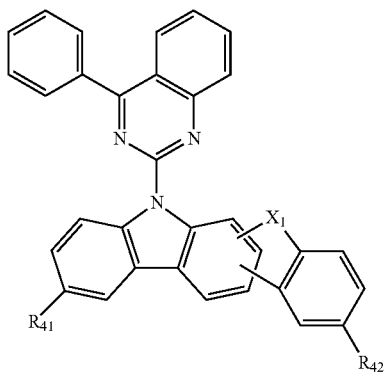

Formula D-14

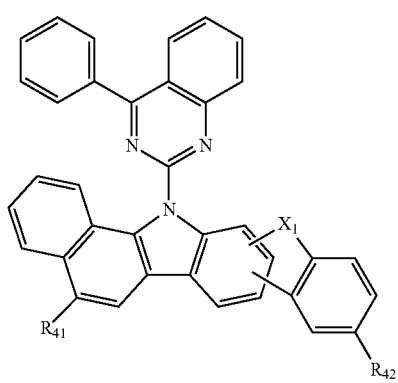

Formula D-15

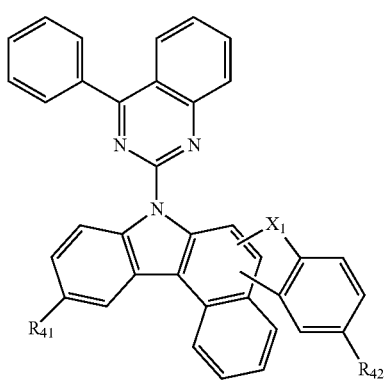

Formula D-16

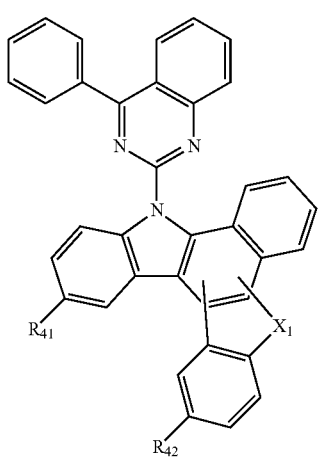

wherein in Formulae D-2 through D-16, $R_{41}$ and $R_{42}$ are each independently

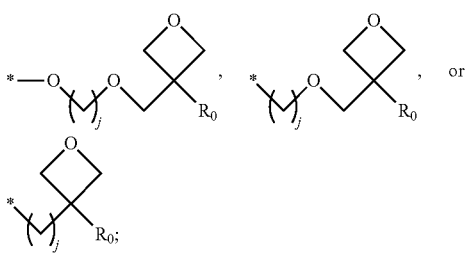

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group; and j is an integer between 2 and 9; and in Formulae D-10 through D-16, $X_1$ is an oxygen atom or a sulfur atom.

10. The composition of claim 1, further comprising:
an initiator compound,
wherein
the solvent is methyl benzoate,
the initiator compound is contained in an amount of about 0.5 wt % to 4.0 wt % with respect to the total weight of the composition for forming the organic film, and
the initiator compound comprises a compound of any one of Formulae F-1, F-2, and F-3:

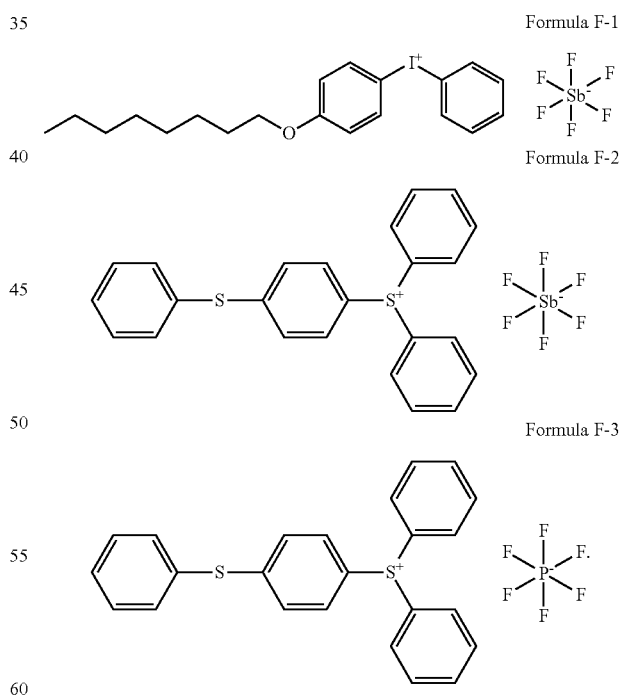

11. A display device, comprising:
a base;
anode electrodes on the base;
a cathode electrode on the anode electrodes; and
organic layers between the anode electrodes and the cathode electrode, wherein the organic layers comprise a polymer of a compound of Formula 1:

    Formula 1 wherein in Formula 1,
Ar is

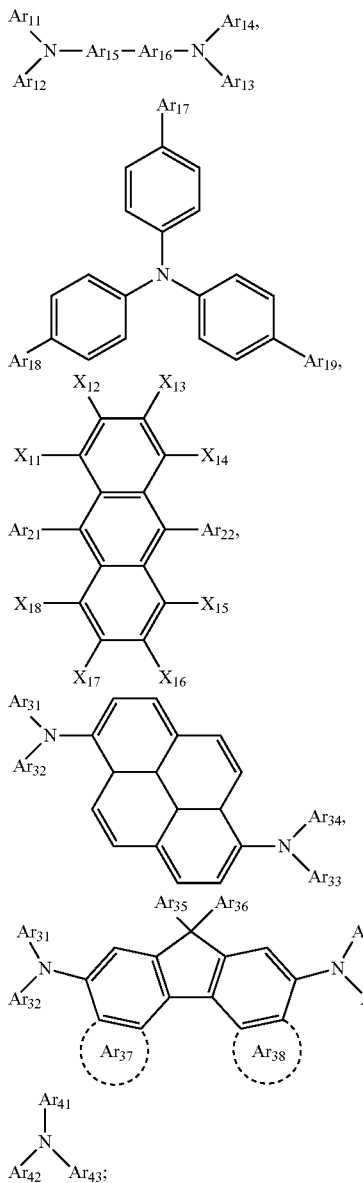

Ar$_{11}$, Ar$_{12}$, Ar$_{13}$, and Ar$_{14}$ are each independently a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group;

Ar$_{15}$ and Ar$_{16}$ are each independently a substituted or unsubstituted C$_{6-12}$ arylene group or a substituted or unsubstituted C$_{1-12}$ heteroarylene group;

two or more of Ar$_{11}$, Ar$_{12}$, and Ar$_{15}$ optionally form a ring together;

two or more of Ar$_{13}$, Ar$_{14}$, and Ar$_{16}$ optionally form a ring together;

Ar$_{17}$, Ar$_{18}$, and Ar$_{19}$ are each independently a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group;

Ar$_{21}$ and Ar$_{22}$ are each independently a substituted or unsubstituted C$_{6-60}$ arylene group or a substituted or unsubstituted C$_{1-60}$ heteroarylene group;

X$_{11}$, X$_{12}$, X$_{13}$, X$_{14}$, X$_{15}$, X$_{16}$, X$_{17}$, and X$_{18}$ are each independently a hydrogen atom, a deuterium atom, a fluorine atom, a substituted or unsubstituted C$_{1-10}$ alkyl group, a substituted or unsubstituted C$_{3-10}$ cycloalkyl group, a substituted or unsubstituted C$_{1-20}$ alkoxy group, a substituted or unsubstituted C$_{3-30}$ alkylsilyl group, a substituted or unsubstituted C$_{6-30}$ aryl group, a substituted or unsubstituted C$_{6-20}$ aryloxy group, a substituted or unsubstituted C$_{8-30}$ arylsilyl group, or a substituted or unsubstituted C$_{5-30}$ heteroaryl group;

Ar$_{31}$, Ar$_{32}$, Ar$_{33}$, and Ar$_{34}$ are each independently a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group;

Ar$_{35}$ and Ar$_{36}$ are each independently a hydrogen atom or a substituted or unsubstituted C$_{6-10}$ aryl group or a substituted or unsubstituted C$_{1-10}$ heteroaryl group;

Ar$_{35}$ and Ar$_{36}$ optionally form a ring together;

Ar$_{37}$ and Ar$_{38}$ are each independently a substituted or unsubstituted C$_{6-20}$ fused ring;

Ar$_{41}$ is a substituted or unsubstituted C$_{6-60}$ aryl group or a substituted or unsubstituted C$_{3-60}$ heteroaryl group;

Ar$_{42}$ and Ar$_{43}$ are each independently a substituted or unsubstituted C$_{6-60}$ arylene group or a substituted or unsubstituted C$_{1-60}$ heteroarylene group;

Ar$_{42}$ and Ar$_{43}$ form a ring together;

at least one of Ar$_{11}$, Ar$_{12}$, Ar$_{13}$, and Ar$_{14}$, at least one of Ar$_{17}$, Ar$_{18}$, and Ar$_{19}$, at least one of Ar$_{21}$, and Ar$_{22}$, at least one of Ar$_{31}$, Ar$_{32}$, Ar$_{33}$, and Ar$_{34}$, and at least one of Ar$_{42}$, and Ar$_{43}$ are divalent arylene or divalent heteroarylene groups, R is bonded thereto;

R is

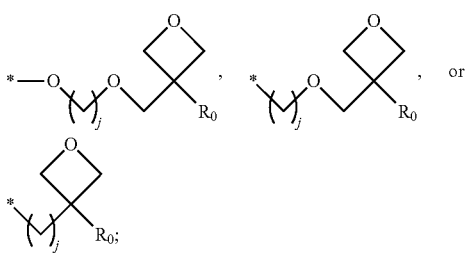

R$_0$ is a substituted or unsubstituted C$_{1-30}$ alkyl group, a substituted or unsubstituted C$_{3-30}$ cycloalkyl group, a substituted or unsubstituted C$_{3-30}$ heterocycloalkyl group, a substituted or unsubstituted C$_{2-30}$ alkenyl group, a substituted or unsubstituted C$_{2-30}$ alkynyl group, a substituted or unsubstituted C$_{6-30}$ aryl group, or a substituted or unsubstituted C$_{3-30}$ heteroaryl group;

j is an integer between 2 and 9; and k is an integer between 2 and 4, and wherein in the polymer, the compound of Formula 1 are connected through a reaction product of R, wherein when Ar is

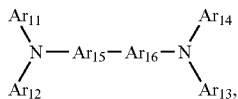

and when two or more of $Ar_{11}$, $Ar_{12}$, and $Ar_{15}$ form a ring together or when two or more of $Ar_{13}$, $Ar_{14}$, and $Ar_{16}$ form a ring together, R is

12. The display device of claim 11, wherein
the organic layers comprise a first organic layer between the anode electrodes and the cathode electrode, and
the first organic layer comprises a polymer of a compound of Formula A-1:

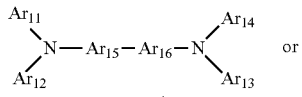      Formula C-1 wherein in Formula A-1,
$Ar_1$ is

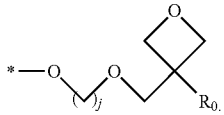 or

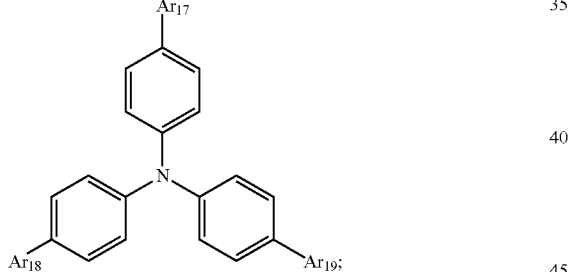

$Ar_{11}$, $Ar_{12}$, $Ar_{13}$, and $Ar_{14}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;
$Ar_{15}$ and $Ar_{16}$ are each independently a substituted or unsubstituted $C_{6-12}$ arylene group or a substituted or unsubstituted $C_{1-12}$ heteroarylene group;
two or more of $Ar_{11}$, $Ar_{12}$, and $Ar_{15}$ optionally form a ring together,
two or more of $Ar_{13}$, $Ar_{14}$, and $Ar_{16}$ optionally form a ring together,
$Ar_{17}$, $Ar_{18}$, and $Ar_{19}$ are each independently a substituted or unsubstituted $C_{6-60}$ aryl group, a substituted or unsubstituted $C_{6-60}$ arylene group, a substituted or unsubstituted $C_{1-60}$ heteroaryl group, or a substituted or unsubstituted $C_{1-60}$ heteroarylene group;
at least one of $Ar_{11}$, $Ar_{12}$, $Ar_{13}$, and $Ar_{14}$, and at least one of $Ar_{17}$, $Ar_{18}$, and $Ar_{19}$ are divalent arylene or divalent heteroarylene groups, $R_1$ is bonded thereto;

$R_1$ is

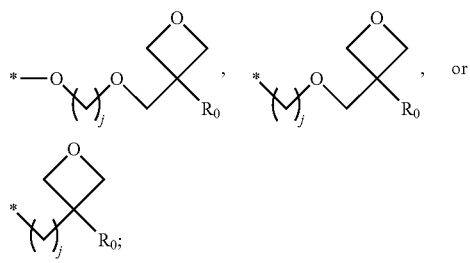

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group;
j is an integer between 2 and 9; and
k1 is an integer between 2 and 4,
wherein when Ar is

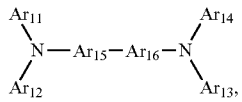

and when two or more of $Ar_{11}$, $Ar_{12}$, and $Ar_{15}$ form a ring together or when two or more of $Ar_{13}$, $Ar_{14}$, and $Ar_{16}$ form a ring together, R is

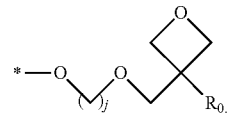

13. The display device of claim 12, wherein the display device comprises
a first pixel configured to display a first color,
a second pixel adjacent to the first pixel and configured to display a second color having a longer peak wavelength than the first color, and
a third pixel adjacent to the first pixel and configured to display the first color,
wherein the first organic layer in the first pixel is physically spaced apart from the first organic layer in the third pixel.

14. The display device of claim 13, wherein
the organic layers further comprise a second organic layer in the first pixel between the first organic layer and the cathode electrode, and the second organic layer comprises a polymer of compounds of Formulae B-2 and C-1:

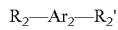 Formula B-1

 Formula C-1 wherein in Formula B-1,
Ar$_2$ is

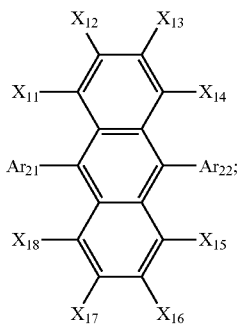

Ar$_{21}$ and Ar$_{22}$ are each independently a substituted or unsubstituted C$_{6-60}$ arylene group or a substituted or unsubstituted C$_{1-60}$ heteroarylene group;

R$_2$ and R$_2$' are bonded to Ar$_{21}$ and Ar$_{22}$, respectively;

X$_{11}$, X$_{12}$, X$_{13}$, X$_{14}$, X$_{15}$, X$_{16}$, X$_{17}$, and X$_{18}$ are each independently a hydrogen atom, a deuterium atom, a fluorine atom, a substituted or unsubstituted C$_{1-10}$ alkyl group, a substituted or unsubstituted C$_{3-10}$ cycloalkyl group, a substituted or unsubstituted C$_{1-20}$ alkoxy group, a substituted or unsubstituted C$_{3-30}$ alkylsilyl group, a substituted or an unsubstituted C$_{6-30}$ aryl group, a substituted or unsubstituted C$_{6-20}$ aryloxy group, a substituted or unsubstituted C$_{8-30}$ arylsilyl group, or a substituted or unsubstituted C$_{5-30}$ heteroaryl group;

R7 and R$_2$' are each independently

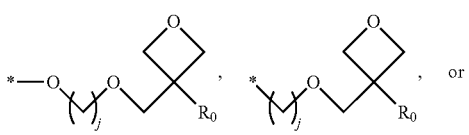

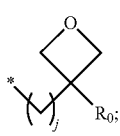

R$_0$ is a substituted or unsubstituted C$_{1-30}$ alkyl group, a substituted or unsubstituted C$_{3-30}$ cycloalkyl group, a substituted or unsubstituted C$_{3-30}$ heterocycloalkyl group, a substituted or unsubstituted C$_{2-30}$ alkenyl group, a substituted or unsubstituted C$_{2-30}$ alkynyl group, a substituted or unsubstituted C$_{6-30}$ aryl group, or a substituted or unsubstituted C$_{3-30}$ heteroaryl group;

j is an integer between 2 and 9; and in Formula C-1,
Ar$_3$ is

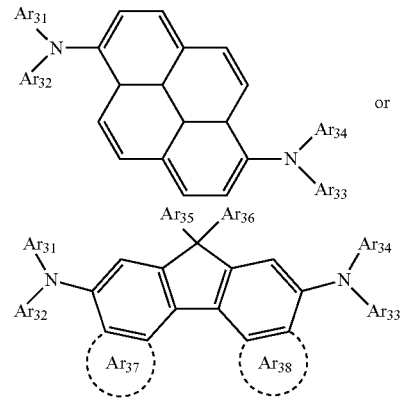

Ar$_{31}$, Ar$_{32}$, Ar$_{33}$, and Ar$_{34}$ are each independently a substituted or unsubstituted C$_{6-60}$ aryl group, a substituted or unsubstituted C$_{6-60}$ arylene group, a substituted or unsubstituted C$_{1-60}$ heteroaryl group, or a substituted or unsubstituted C$_{1-60}$ heteroarylene group;

at least one of Ar$_{31}$, Ar$_{32}$, Ar$_{33}$, and Ar$_{34}$ is a divalent arylene or divalent heteroarylene group, R$_3$ is bonded thereto, Ar$_{35}$ and Ar$_{36}$ are each independently a hydrogen atom or a substituted or unsubstituted C$_{6-10}$ aryl group or a substituted or unsubstituted heteroaryl group, Ar$_{35}$ and Ar$_{36}$ optionally form a ring together;

Ar$_{37}$ and Ar$_{38}$ are each independently a substituted or unsubstituted C$_{6-20}$ fused ring;

R$_3$ is

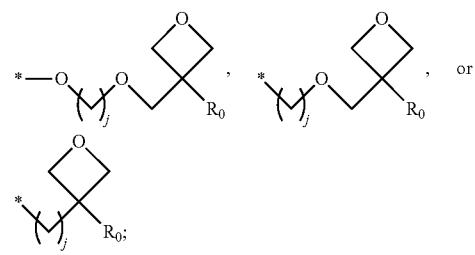

R$_0$ is a substituted or unsubstituted C$_{1-30}$ alkyl group, a substituted or unsubstituted C$_{3-30}$ cycloalkyl group, a substituted or unsubstituted C$_{3-30}$ heterocycloalkyl group, a substituted or unsubstituted C$_{2-30}$ alkenyl group, a substituted or unsubstituted C$_{2-30}$ alkynyl group, a substituted or unsubstituted C$_{6-30}$ aryl group, or a substituted or unsubstituted C$_{3-30}$ heteroaryl group, j is an integer between 2 and 9, and k3 is an integer between 2 and 4.

15. The display device of claim 14, wherein
the organic layers further comprise a third organic layer in the second pixel between the first organic layer and the cathode electrode, and the third organic layer comprises a polymer of a compound of Formula D-1:

$$R_4\text{—}Ar_4\text{—}R_4' \quad \text{Formula D-1}$$

wherein in Formula D-1,
$Ar_4$ is

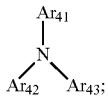

$Ar_{41}$ is a substituted or unsubstituted $C_{6-60}$ aryl group or a substituted or unsubstituted $C_{1-60}$ heteroaryl group;
$Ar_{42}$ and $Ar_{43}$ are each independently a substituted or unsubstituted $C_{6-60}$ arylene group or a substituted or unsubstituted $C_{1-60}$ heteroarylene group;
$Ar_{42}$ and $Ar_{43}$ form a ring together;
$R_4$ and $R_4'$ are bonded to $Ar_{42}$ and $Ar_{43}$, respectively;
$R_4$ and $R_4'$ are each independently

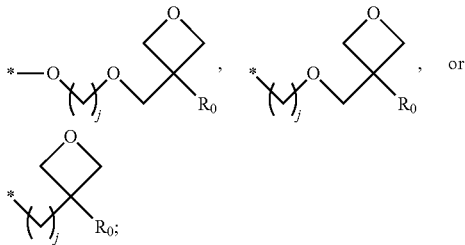

$R_0$ is a substituted or unsubstituted $C_{1-30}$ alkyl group, a substituted or unsubstituted $C_{3-30}$ cycloalkyl group, a substituted or unsubstituted $C_{3-30}$ heterocycloalkyl group, a substituted or unsubstituted $C_{2-30}$ alkenyl group, a substituted or unsubstituted $C_{2-30}$ alkynyl group, a substituted or unsubstituted $C_{6-30}$ aryl group, or a substituted or unsubstituted $C_{3-30}$ heteroaryl group, and j is an integer between 2 and 9.

16. The display device of claim 15, wherein
the organic layers further comprise a fourth organic layer between the second organic layer and the cathode electrode and between the third organic layer and the cathode electrode, and
the fourth organic layer in the first pixel is physically formed in one integral body with the fourth organic layer in the third pixel.

17. A method of manufacturing a display device, the method comprising:
forming a coating layer by coating a base with the composition of claim 1; and
forming organic layer patterns by patterning the coating layer.

18. The method of claim 17, wherein the forming of the organic layer patterns comprises:
placing a mask having openings over the coating layer,
partially exposing and curing the coating layer by applying light, and
developing the cured coating layer utilizing a developer.

19. The method of claim 18, further comprising, before the forming of the coating layer:
forming an electrode layer on the base; and
forming a bank having openings to expose a surface of the electrode layer.

20. The method of claim 18, further comprising, after the forming the organic layer patterns:
forming a bank having openings to expose the surfaces of the organic layer patterns.

* * * * *

UNITED STATES PATENT AND TRADEMARK OFFICE
CERTIFICATE OF CORRECTION

PATENT NO. : 11,515,481 B2
APPLICATION NO. : 15/863768
DATED : November 29, 2022
INVENTOR(S) : Se Hun Kim et al.

It is certified that error appears in the above-identified patent and that said Letters Patent is hereby corrected as shown below:

In the Claims

Column 174, Line 15 (Approx.), Claim 1, Formula 1 — After "$Ar\text{-}(\text{-}R)_k$" Insert -- , --

Column 175, Line 1, Claim 1 — Delete "$Ar_{13}$" and Insert -- $Ar_{13}$, --

Column 184, Line 16, (Approx.), Claim 4 — Delete "R2" and Insert -- $R_2$ --

Column 184, Line 38, Claim 4 — Delete "C2-30" and Insert -- $C_{2\text{-}30}$ --

Column 191, Lines 24-31 — Delete " 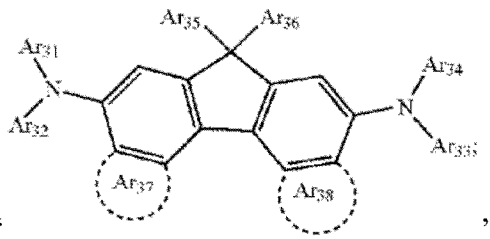 "

Signed and Sealed this
Twenty-ninth Day of August, 2023

Katherine Kelly Vidal
*Director of the United States Patent and Trademark Office*

CERTIFICATE OF CORRECTION (continued)
U.S. Pat. No. 11,515,481 B2

| | |
|---|---|
| (Approx.), Claim 6 | Insert -- 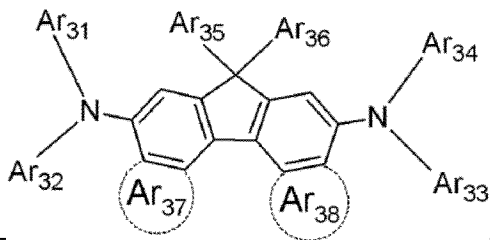 -- |
| Column 191, Line 37 (Approx.), Claim 6 | Delete "C1-60" and Insert -- $C_{1-60}$ -- |
| Column 191, Line 43 (Approx.), Claim 6 | After "unsubstituted" Insert -- $C_{1-10}$ -- |
| Column 196, Lines 54-67 | Delete " 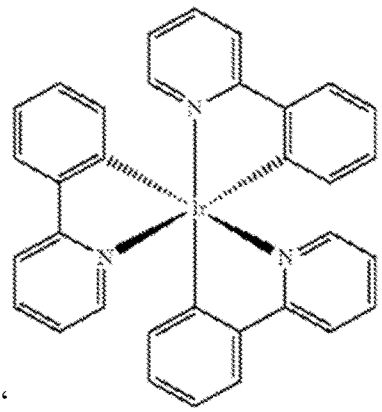 " |
| (Approx.), Claim 8, Formula E-3 | Insert -- 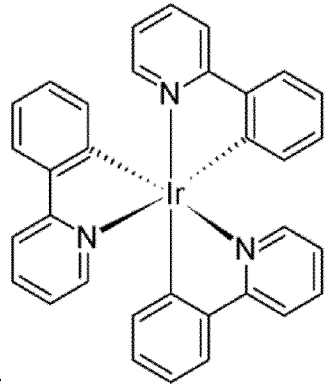 -- |
| Column 205, Line 26, Claim 12, Formula A-1 | Delete "$Ar_3\!\!-\!\!(R_3)_{k3}$ Formula C-1" Insert -- $Ar_1\!\!-\!\!(R_1\,)_{k1}$ Formula A-1 -- |
| Column 207, Line 42, Claim 14 | Delete "R7" and Insert -- $R_2$ -- |

| | |
|---|---|
| Column 208, Line 36, Claim 14 | After "unsubstituted" Insert -- $C_{1-10}$ -- |